(12) United States Patent
Benedict et al.

(10) Patent No.: US 7,579,456 B2
(45) Date of Patent: *Aug. 25, 2009

(54) APTAMER THERAPEUTICS USEFUL IN THE TREATMENT OF COMPLEMENT-RELATED DISORDERS

(75) Inventors: Claude Benedict, Cambridge, MA (US); David Epstein, Belmont, MA (US); Dilârâ McCauley, Cambridge, MA (US); Jeffrey Kurz, Arlington, MA (US); Markus Kurz, Newton, MA (US); Thomas Greene McCauley, Cambridge, MA (US); James Rottman, Sudbury, MA (US); Charles Wilson, Concord, MA (US)

(73) Assignee: Archemix Corp., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/354,657

(22) Filed: Feb. 14, 2006

(65) Prior Publication Data

US 2007/0048248 A1    Mar. 1, 2007

Related U.S. Application Data

(63) Continuation-in-part of application No. 11/058,134, filed on Feb. 14, 2005.

(60) Provisional application No. 60/608,048, filed on Sep. 7, 2004, provisional application No. 60/581,685, filed on Jun. 21, 2004, provisional application No. 60/547,747, filed on Feb. 25, 2004, provisional application No. 60/544,542, filed on Feb. 12, 2004.

(51) Int. Cl.
*C07H 21/04* (2006.01)
*G01N 33/551* (2006.01)

(52) U.S. Cl. ..................... 536/24.5; 436/524
(58) Field of Classification Search ................ 536/24.5; 436/524

See application file for complete search history.

(56) References Cited

U.S. PATENT DOCUMENTS

| | | | |
|---|---|---|---|
| 3,710,795 A | 1/1973 | Higuchi et al. | |
| 4,683,195 A | 7/1987 | Mullis | |
| 4,935,363 A | 6/1990 | Brown et al. | |
| 4,959,309 A | 9/1990 | Dattagupta et al. | |
| 5,070,010 A | 12/1991 | Hsu | |
| 5,262,564 A | 11/1993 | Kun et al. | |
| 5,270,163 A | 12/1993 | Gold et al. | |
| 5,338,671 A | 8/1994 | Scalice et al. | |
| 5,459,015 A | 10/1995 | Janjic et al. | |
| 5,475,096 A | 12/1995 | Gold et al. | |
| 5,496,938 A | 3/1996 | Gold et al. | |
| 5,503,978 A | 4/1996 | Schneider et al. | |
| 5,567,588 A | 10/1996 | Gold et al. | |
| 5,580,737 A | 12/1996 | Polisky et al. | |
| 5,635,615 A | 6/1997 | Allen et al. | |
| 5,637,459 A | 6/1997 | Burke et al. | |
| 5,648,214 A | 7/1997 | Nieuwlandt et al. | |
| 5,654,151 A | 8/1997 | Allen et al. | |
| 5,660,985 A | 8/1997 | Pieken et al. | |
| 5,668,264 A | 9/1997 | Janjic et al. | |
| 5,674,685 A | 10/1997 | Janjic et al. | |
| 5,683,867 A | 11/1997 | Biesecker et al. | |
| 5,705,337 A | 1/1998 | Gold et al. | |
| 5,707,796 A | 1/1998 | Gold et al. | |
| 5,723,323 A | 3/1998 | Kauffman et al. | |
| 5,763,173 A | 6/1998 | Gold et al. | |
| 5,789,157 A | 8/1998 | Jensen et al. | |
| 5,861,254 A | 1/1999 | Schneider et al. | |
| 6,011,020 A | 1/2000 | Gold et al. | |
| 6,013,443 A | 1/2000 | Heilig et al. | |
| 6,020,130 A | 2/2000 | Gold et al. | |
| 6,051,698 A | 4/2000 | Janjic et al. | |
| 6,229,002 B1 | 5/2001 | Janjic et al. | |
| 6,395,888 B1 | 5/2002 | Biesecker et al. | |
| 6,566,343 B2 | 5/2003 | Biesecker et al. | 514/44 |
| 6,573,299 B1 | 6/2003 | Petrus | 514/558 |
| 2004/0249130 A1 | 12/2004 | Stanton et al. | 530/350 |
| 2005/0214308 A1 | 9/2005 | Ashkenazi et al. | 424/178.1 |
| 2006/0018871 A1 | 1/2006 | Benedict et al. | 424/78.3 |

FOREIGN PATENT DOCUMENTS

| | | |
|---|---|---|
| EP | 0592035 B1 | 1/1996 |
| GB | 2 183 661 A | 6/1987 |
| WO | WO89/06694 | 7/1989 |
| WO | WO91/14436 | 10/1991 |
| WO | WO91/19813 | 12/1991 |
| WO | WO92/05285 | 4/1992 |
| WO | WO92/14842 | 9/1992 |
| WO | WO92/14843 | 9/1992 |
| WO | WO 98/18480 | 5/1998 |

OTHER PUBLICATIONS

Watson et al. (Antisense & Nucleic Acid Drug Development 10:63-75, 2000).*
Invitation to Pay Additional Fees for PCT/US06/05215, mailed Apr. 18, 2007.
Acosta et al., "Molecular basis for a link between complement and the vascular complications of diabetes", *PNAS* (2002) 97(10): 5450-5455.
Agrawal et al., "Mixed-backbone oligonucleotides as second generation antisense oligonucleotides: In vitro and in vivo studies", *Proc. Natl. Acad. Sci. USA* (1997) 94: 2620-2625.
Agrawal et al., "Novel enzymatic and immunological responses to oligonucleotides", *Tox. Lett.* (1995) 82/83: 431-434.
Albrecht et al., "C5a-Induced Gene Expression in Human Umbilical Vein Endotheilial Cells", *Am. J. Pathology* (2004) 164(3): 849-859.

(Continued)

*Primary Examiner*—Brian Whiteman
(74) *Attorney, Agent, or Firm*—Ivor R. Elrifi, Esq.; Mintz, Levin, Cohn, Ferris, Glovsky and Popeo, P.C.

(57) ABSTRACT

The invention provides nucleic acid therapeutics and methods for using these nucleic acid therapeutics in the treatment of complement-related disorders.

6 Claims, 60 Drawing Sheets

OTHER PUBLICATIONS

Allegretti et al., "Targeting C5a: Recent Advances in Drug Discovery", *Curr. Med. Chem.* (2005) 12: 217-236.

Altschul et al., "Basic Local Alignment Search Tool", *J. Mol. Biol.* (1990) 215: 403-410.

Altschul et al., "Gapped BLAST and PSI-BLAST: a new generation of protein database search programs", *Nuc. Acids Res.* (1997) 25(17): 3389-3402.

Andrake, "DNA polymerase of bacteriophage T4 is an autogenous translational repressor", *Proc. Natl. Acad. Sci. USA* (1988) 85: 7942-7946.

Baldwin et al., "Complement in Organ Transplantation: Contributions to Inflammation, Injury, and Rejection", *Transplantation* (1995) 59(6): 797-808.

Baudouin et al, "Immunohistopathologic Findings in Proliferative Diabetic Retinopathy", *Am. J. Ophthalmol.* (1988) 105: 383-388.

Bednar et al., "Activation of complement by tissue plasminogen activator, but not acute cerebral ischemia, in a rabbit model of thromboembolic stroke", *J. Neurosurg.* (1997) 86: 139-142.

Bhole, D. and Stahl, G.L., "Therapeutic potential of targeting the complement cascade in critical care medicine", *Crit. Care Med.* (2003) 31(1 Suppl.): S97-S104.

Biesecker et al., "Derivation of RNA aptamer inhibitors of human complement C5", *Immunopharmacology* (1999) 42: 219-230.

Biesecker, "Renal Localization of the Membrane Attack Complex in Systemic Lupus Erythematosus Nephritis", *J. Exp. Med.* (1981) 154: 1779-1794.

Brauer et al., "The Contribution of Terminal Complement Components to Acute and Hyperacute Allograft Rejection in the Rat", *Transplantation* (1995) 59(2): 288-293.

Brus et al., "Physiochemical and Biological Characterization of Polyethylenimine-graft-Poly(ethylene glycol) Block Copolymers as a Delivery System for Oligonucleotides and Ribozymes", *Bioconjugate Chem.* (2004) 15: 677-684.

Carey et al., "Sequence-specific interaction of R17 coat protein with its ribonucleic acid binding site", *Biochem.* (1983) 22: 2601-2610.

Chen et al., "Pharmacologic C5-Complement Suppression Reduces Blood Loss During On-Pump Cardiac Surgery", *J. Card. Surg.* (2005) 20: 35-41.

Chen et al., "Selection of high-affinity RNA ligands to reverse transcriptase: Inhibition of cDNA synthesis and RNase H activity", *Biochem.* (1994) 33: 8746-8756.

Cohen et al., "Interactions of hormonal steroids with nucleic acids: A specific requirement for guanine", *Proc. Natl. Acad. Sci. USA* (1969) 63: 458-464.

Cotton et al., "2'-O-methyl, 2'O-ethyl oligoribonucleotides and phosphorothioate oligodeoxyribonucleotides as inhibitors of the in vitro U7 snRNP-dependent mRNA processing event," *Nuc. Acids Res.* (1991) 19(10): 2629-2635.

Davis et al., "Identifying consensus patterns and secondary structure in SELEX sequence sets", *Methods in Enzymology* (1996) 267: 302-314.

Dehouck et al., "Blood-brain barrier in vitro—rapid evaluation of strategies for achieving drug targeting to the central nervous system", *Biol. Physiology of the Blood Brain Barrier*, (1996) Couraud and Scherman eds., 23: 143-146.

Ellington and Szostak, "Abstracts of papers presented at the 1990 meeting on RNA Processing", (1990) Cold Spring Harbor, NY, p. 84.

Evans et al., "In vitro and in vivo Inhibition of Complement Activity by a Single-Chain Fv Fragment Recognizing Human C5", *Mol. Immunol.* (1995) 32(16): 1183-1195.

Fitch et al., "Pharmacology and Biological Efficacy of a Recombinant, Humanized, Single-Chain Antibody C5 Complement Inhibitor in Patients Undergoing Coronary Artery Bypass Graft Surgery with Cardiopulmonary Bypass", *Circulation* (1999) 100: 2499-2506.

Fitzwater et al., "A SELEX primer", (1996) *Methods in Enzymology* 267: 275-301.

Froehler et al., "Synthesis of DNA via deoxynucleoside H-phosphonate intermediates," *Nuc. Acids Res.* (1986) 14(13): 5399-5467.

Froehler, "Deoxynucleoside H-Phosphonate Diester Intermediates in the Synthesis of Internucleotide Phosphate Analogues", *Tet. Lett.* (1986) 27(46): 5575-5578.

Gath et al., "The blood-CSF barrier in vitro", *Biol. and Physiology of the Blood Brain Barrier*, (1996) Couraud and Scherman eds., 25: 153-158.

Gong et al., "Tubing Loops as a Model for Cardiopulmonary Bypass Circuits: Both the Biomaterial and the Blood-Gas Phase Interfaces Induce Complement Activation in an In Vitro Model", *J. Clin. Immunol.* (1996) 16(4): 222-229.

Gerl et al., "Extensive Deposits of Complement C3d and C5b-9 in the Choriocapillaries of Eyes of Patients with Diabetic Retinopathy", *Invest. Opthalmol. Vis. Sci.* (2002) 43(4): 1104-1108.

Granger et al., "Pexeluzimab, an Anti-C5 complement Antibody, as Adjunctive Therapy to Primary Percutaneous Coronary Intervention in Acute Myocardial Infarction", *Circulation* (2003) 108: 1184-1190.

Green et al., "Nuclease-resistant nucleic acid ligands to vascular permeability factor/vascular endothelial growth factor", *Chemistry & Biology* (1995) 2: 683-695.

Greenwald et al., "Higly Water Soluble Taxol Derivatives: 7-Polythylene Glycol Carbamates and Carbonates", *J. Org. Chem.* (1995) 60: 331-336.

Hangen et al., "Complement Levels in Septic Primates Treated with Anti-C5a Antibodies", *J. Surg. Res.* (1989) 46: 195-199.

Hansen et al., "Association Between Mannose-Binding Lectin and Vascular Complications in Type-1 Diabetes", *Diabetes* (2004) 53: 1570-1576.

Harris et al., "Effect of Pegylation on Pharmaceuticals", *Nature* (2003) 2: 214-221.

Haviland et al., "Structure of the Murine Fifth Complement Component (C5) Gene", *J. Biol. Chem.* (1991) 266(18): 11818-11825.

Henry et al., "Activation of the Alternative Pathway of Complement by a Phosphorothioate Oligonucleotide: Potential Mechanism of Action", *J. Pharm. Exp. Ther.* (1997) 281(2): 810-816.

Hirose et al., "Rapid Synthesis of Trideoxyribonucleotide Blocks", *Tet. Lett.* (1978) 28: 2449-2452.

Hobbs et al., "Polynucleotides Containing 2'-Amino-2'-deoxyribose and 2'-Azido-2'-deoxyribose", *Biochemistry* (1973) 12(25): 5138-5145.

Homeister and Lucchesi. "Complement Activation and Inhibition in Myocardial Ischemia and Reperfusion Injury" *Annu. Rev. Pharmacol. Toxicol.* (1994) 34: 17-40.

Joyce and Inoue, "A novel technique for the rapid preparation of mutant RNAs", *Nuc.Acids Res.* (1998) 17: 711-722.

Joyce, "Amplification, mutation and selection of catalytic RNA: Catalysis, Splicing, Evolution", (1989) Marlene Belfort & David Shub, editors, Elsevier, Amsterdam pp. 83-87.

Kacian et al., "A replicating RNA molecule suitable for a detailed analysis of extracellular evolution and replication", *Proc. Natl. Acad. Sci USA* (1972) 69: 3038-3042.

Kadonaga et al., "Affinity purification of sequence-specific DNA binding proteins", *Proc. Natl. Acad. Sci. USA* (1986) 83: 5889-5893.

Kandimalla et al., "Effects of Phosphorothioate Oligodeoxyribonucleotide and Oligoribonucleotides on Human Complement and Coagulation", *Bio. Med. Chem. Lett.* (1998) 8: 2103-2108.

Kellogg et al., "Taqstart antibody™: 'Hot start' PCR facilitated by a neutralizing monoclonal antibody directed against taq DNA polymerase", *BioTechniques* (1994) 16(6): 1134-1137.

Kinzler and Vogelstein, "Whole genome PCR: Application to the identification of sequences bound by gene regulatory proteins", *Nuc. Acids Res.* (1989) 17: 3645-3653.

Kinzler and Vogelstein, "The *GLI* gene encodes a nuclear protein which binds specific sequences in the human genome", *Mol. Cell. Biol.* (1989) 10: 634-642.

Kramer et al., "Evolution in vitro: Sequence and phenotype of a mutant RNA resistant to ethidium bromide", *J. Mol. Biol.* (1974) 89: 719-736.

Kroshus et al., "Complement Inhibition with an Anti-C5 Monoclonal Antibody Prevents Acute Cardiac Tissue Injury in an Ex Vivo Model of Pig-to-Human Xenotranplantation", *Transplantation* (1995) 60(11): 1194-1202.

Lestienne et al., "Inhibition of human leucocyte elastase by polynucleotides", *Biochimie* (1983) 65: 49-52.

Levisohn and Spiegelman, "The cloning of a self-replicating RNA molecule", *PNAS USA* (1968) 60: 866-872.

Levisohn and Spiegelman, "Further extracellular Darwinian experiments with replicating RNA molecules: diverse variants isolated under different selective conditions", *PNAS USA* (1969) 63: 805-811.

Ma and Ptashne, "A new class of yeast transcriptional activators", *Cell* (1987) 51: 113-119.

Mahaffey et al., "Effect of Pexelizumab, an Anti-C5 Complement Antibody, as Adjunctive Therapy to Fibrinolysis in Acute Myocardial Infarction", *Circulation* (2003) 108: 1176-1183.

Makrides et al., "Therapeutic Inhibition of the Complement System", *Pharmacol. Rev.* (1998) 50(1): 59-87.

Maniatis et al., "Molecular Cloning: A Laboratory Manual", (1982) Cold Spring Harbor, NY p. 118.

Maniatis et al., "Regulation of inducible and tissue-specific gene expression", *Science* (1987) 236: 1237-1245.

Matis and Rollins, "Complement-specific antibodies: Designing novel anti-inflammatories" *Nature Medicine* (1995) 1(8): 839-842.

McGinnis and Madden, "BLAST: at the core of a powerful and diverse set of sequence analysis tools", *Nuc. Acids Res.* (2004) 32: W20-W25.

Miele et al., "Autocatalytic replication of a recombinant RNA", *J. Mol. Biol.* (1983) 171: 281-295.

Mills et al., "An extracellular Darwinian experiment with a self-duplicating nucleic acid molecule", *Proc. Natl. Acad. Sci. USA* (1967) 58: 217-220.

Mills et al., "Complete nucleotide sequence of a replicating RNA molecule", *Science* (1973) 180: 916-927.

Min et al., "Search for the optimal sequence of the ribosome binding site by random oligonucleotide-directed mutagenisis" *Nuc. Acids Res.* (1988) 16: 5075-5088.

Morgan, "Role of Complement in Inflammation and Injury in the Nervous System", *Exp. Clin. Immunogenet.* (1997) 14: 19-23.

Muesing et al., "Nucleic acid structure and expression of the human AIDS/lymphadenopathy retrovirus", *Nature* (1985) 313: 450-458.

Mulligan et al., "Requirement and Role of C5a in Acute Lung Inflammatory Injury in Rats", *J. Clin. Invest.* (1996) 98(2): 503-512.

Nangaku, "Renal microvascular injury induced by antibody to glomerular endothelial cells is mediated by C5b-9", *Kidney Int.* (1997) 52: 1570-1580.

Needleman and Wunsch, "A General Method Applicable to the Search for Similarities in the Amino Acid Sequence of Two Proteins", *J. Mol. Biol.* (1970) 48: 443-453.

Nilsson et al., "Compstatin Inhibits Complement and Cellular Activation in Whole Blood in Two Models of Extracorporeal Circulation", *Blood* (1998) 92(5): 1661-1667.

Oliphant and Struhl, "The use of random-sequence oligonucleotides for determining consensus sequences", *Methods in Enzymology* (1987) 155: 568-582.

Oliphant and Struhl, "Defining the consensus sequences of E. coli promoter elements by random selection", *Nuc. Acids Res.* (1988) 16: 7673-7683.

Oliphant et al., "Cloning of random-sequence oligodeoxynucleotides", *Gene* (1986) 44: 177-183.

Oliphant et al., "Defining the sequence specificity of DNA-binding proteins by selecting binding sites from random-sequence oligonucleotides: analysis of yeast GCN4 protein", *Mol. Cell. Biol.* (1989) 9: 2944-2949.

Orgel, "Selection in vitro", *Proc. R. Soc. Lon.* (1979) B205: 435-442.

Ou et al., "DNA amplification for direct detection of HIV-1 in DNA of peripheral blood mononuclear cells", *Science* (1988) 239: 295-297.

Padilla and Sousa, "A Y639F/H784A T7 RNA polymerase double mutant displays superior properties for synthesizing RNAs with non-canonical NTPs", *Nuc. Acids Res.* (2002) 30(24): e138.

Pearson and Lipman, "Improved tools for biological sequence comparison", *Proc. Natl. Acad. Sci. USA* (1988) 85: 2444-2448.

Pietersz et al., "A 16-mer peptide (RQIKIWFQNRRMKWKK) from antennapedia preferentially targets the Class I pathway", *Vaccine* (2001) 19: 1397-1405.

Planck et al., "Activation of the Complement System by Synthetic DNA Complexes: A Potential Barrier for Intravenous Gene Delivery", *Human Gene Therapy* (1996) 7: 1437-1446.

Peng et al., "Role of C5 in the development of airway inflammation, airway hyperresponsiveness, and ongoing airway response", *J. Clin. Invest.* (2005) 115(6): 1590-1600.

Rinder et al., "Blockade of C5a and C5b-9 Generation Inhibits Leukocyte and Platelet Activation during Extracorporeal Circulation", *J. Clin. Invest.* (1995) 96: 1564-1572.

Rothbard et al., "Conjugation of arginine oligomers to cyclosporin A facilitates topical delivery and inhibition of inflammation", *Nature Medicine* (2000) 6(11): 1253-1257.

Rothbard et al., "Arginine-Rich Molecular Transporters for Drug Delivery: Role of Backbone Spacing in Cellular Uptake", *J. Med. Chem.* (2002) 45: 3612-3618.

Roberts et al., "Chemistry for peptide and protein PEGylation", *Advanced Drug Delivery Rev.* (2002) 54: 459-476.

Robertson and Joyce, "Selection in vitro of an RNA enzyme that specifically cleaves single-stranded DNA", *Nature* (1990) 344: 467-468.

Romaniuk et al., "RNA binding site of R17 coat protein", *Biochem.* (1987) 26: 1563-1568.

Rothboard et al., "Conjugation of arginine oligomers to cyclosporing A facilitates topical delivery and inhibition of inflammation", *Nature Medicine* (2000) 6: 1253-1257.

Rothbard et al., "Arginine-rich molecular transporters for drug delivery: role of backbone spacing in cellular uptake", *J. Med. Chem.* (2002) 45(17): 3612-3618.

Saffhill et al., "In vitro selection of bacteriophage Qβ ribonucleic acid variants resistant to ethidium bromide", *J. Mol. Biol.* (1970) 51: 531-539.

Sambrook et al., "Molecular Cloning: A Laboratory Manual", (1989) Cold Spring Harbor, NY, pp. 8.9-8.10.

Shernan et al., "Impact of Pexelizumab, an Anti-C5 Complement Antibody, on Total Mortality and Adverse Cardiovascular Outcomes in Cardiac Surgical Patients Undergoing Cardiopulmonary Bypass", *Ann. Throac. Surg.* (2004) 77: 942-950.

Singleton et al., "Dictionary of Microbiol. and Molecular Biology", (1991) Wiley & Sons, New York, NY, 2nd ed. p. 493.

Sohn et al., "Chronic Low Level Complement Activation within the Eye is Controlled by Intraocular Complement Regulatory Proteins", *IOVS* (2000) 41(11): 3492-3502.

Sood et al., "A rapid and convenient synthesis of poly-thymidylic acid by the modified triester approach", *Nuc. Acids Res.* (1977) 4(8): 2757-2765.

Sproat et al., "New synthetic routes to synthons suitable for 2'-O-allyloligoribonucleotide assemby", *Nuc. Acids Res.* (1991) 19(4): 733-738.

Spycher and Nydegger, "Participation of the Blood Platelet in Immune Reactions Due to Platelet-Complement Interaction", *Infusionsther Transfusionsmed* (1995) 22: 36-43.

Sun et al., "Target sequence-specific inhibition of HIV-1 replication by ribozymes directed to tat RNA", *Nuc. Acids Res.* (1995) 23(15): 2909-2913.

Szostak, J.W., "Structure and Activity of Ribozymes" in "Redesigning the Molecules of Life", (1988) Springer-Verlag Berline Heidelberg, pp. 87-113.

Takahashi et al., "Recent Advances in the Immunology of Xenotransplantation", *Immunologic Research* (1997) 16/3: 273-297.

Tanchou et al., "Monoclonal antibody-mediated inhibition of RNA binding and annealing activities of HIV type 1 nucleocapsid protein", *Aids Research and Human Retroviruses* (1994) 10: 983-993.

Thiesen and Bach, "Target detection assay (TDA): A versatile procedure to determine DNA binding sites as demonstrated on SPI protein", *Nuc. Acids Res.* (1990) 18: 3203-3209.

Thomas et al., "Inhibition of Complement Activity by Humanized Anti-C5 Antibody and Single-Chain Fv", *Molecular Immunology* (1996) 33(17/18): 1389-1401.

Tucker et al., "Detection and plasma pharmacokinetics of an anti-vascular endothelial growth factor oligonucleotide-aptamer (NX1838) in rhesus monkeys", *J. Chromatography B* (1999) 732: 203-212.

Uhlenbeck et al., "Interaction of R17 coat protein with its RNA binding site for translational repression", *J. Biomolecular Structure and Dynamics* (1983) 1: 539-552.

Vakeva et al., "Myocardial Infarction and Apoptosis After Myocardial Infarction Ischemia and Reperfusion: Role of the Terminal Complement Components and Inhibition by Anti-C5 Therapy", *Circulation* (1998) 97: 2259-2267.

Vives et al., "A Truncated HIV-1 Tat Protein Basic Domain Rapidly Translocates Through the Plasma Membrane and Accumulates in the Cell Nucleus", *J. Bio. Chem.* (1997) 272(25): 16010-16017.

Wang et al., "Complement Inhibition with an Anti-C5 Monoclonal Antibody Prevents Hyperacute Rejection in a Xenograft Heart Transplantation Model". *Transplantation* (1999) 68(11): 1643-1651.

Ward, "Role Complement in Lung Inflammatory Injury", *Am. J. Pathol.* (1996) 149(4): 1079-1086.

Watson et al., "Molecular Biology of the Gene", (1987) Benjamin/Cummings Publishing Co., Inc. California, pp. 267, 295, 323, 361, 394, 396, 397 and 405.

Whiss, "Pexeluzimab Alexion", *Curr. Opin. Invest. Drugs* (2002) 3(6): 870-874.

Wurzner et al., "Inhibition of Terminal Complement Complex Formation and Cell Lysis by Monoclonal Antibodies", *Complement Inflamm.* (1991) 8: 328-340.

Yu et al., "Hybrid Oligonucleotides: Synthesis, Biophysical Properties, Stability Studies, and Biological Activity", *Bio. Med. Chem.* (1996) 4(10): 1685-1692.

Zhang et al., "Early complement activation and decreased levels of glycosylphosphatidylinositol-anchored complement inhibitors in human and experimental diabetic retinopathy", *Diabetes* (2002) 51: 3499-3504.

\* cited by examiner (SEQ ID NO: 1)

ARC330 (SEQ ID NO: 2)

ARC186 (SEQ ID NO: 4)

Figure 6
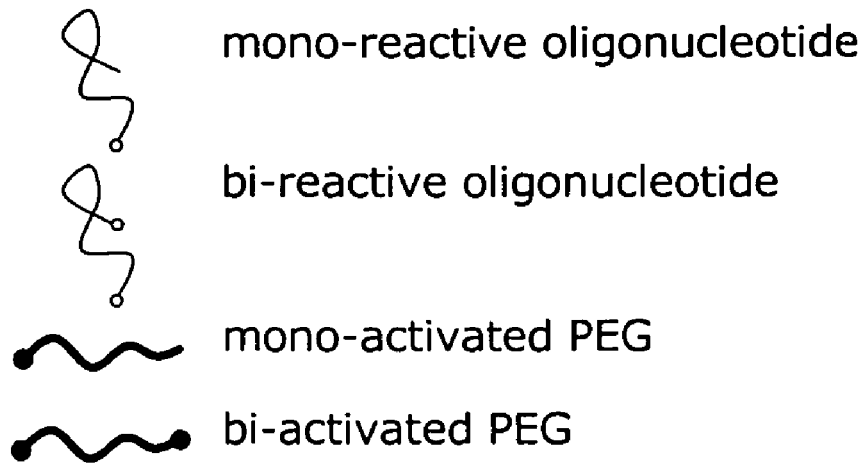
standard PEGylation
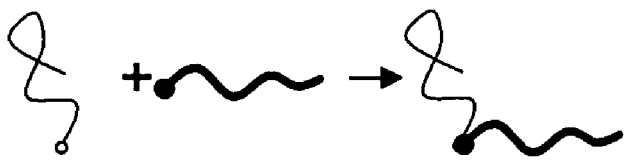
multiple PEGylation
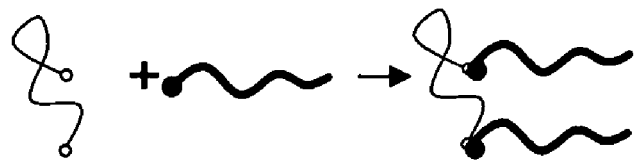
dimerization via PEGylation
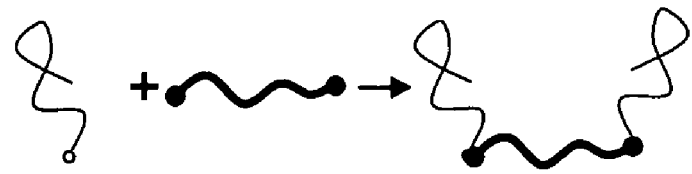

| ARC# | PEG modification | IC50 (nM) |
|---|---|---|
| 186 | No PEG | 0.5 ± 0.1 |
| 657 | ARC186+20 kDa | 0.6 ± 0.1 |
| 658 | ARC186+30 kDa | 0.5 ± 0.1 |
| 187 | 40 kDa branched 1,3 bis(mPEG-[20 kDa])-propyl-2-(4'-butamide) | 0.6 ± 0.2 |

| ARC# | PEG modification | IC50 (nM) |
|---|---|---|
| 187 | 40K branched 1,3 bis(mPEG-[20 kDa])-propyl-2-(4'-butamide) | 0.38 ± 0.03 |
| 1537 | 40K Dow linear | 0.39 ± 0.06 |
| 1730 | 2 x 20K linear | 0.48 ± 0.04 |
| 1905 | 40K branched 2,3 bis(mPEG-[20 kDa])-propyl-1-carbamoyl | 0.40 ± 0.03 |

Aptamer =
CmGfCfCGfCmGmGfUfCfUfCmAmGmGfCGfCfUmGmAmGfUfCfUmGmAmGfUfUf
UAfCfCfUmGfCmG-3T (SEQ ID NO 4)

ARC187 (SEQ ID NO: 5)

Aptamer =
CmGfCfCGfCmGmGfUfCfUfCmAmGmGfCGfCfUmGmAmGfUfCfUmGmAmGfUfUf
UAfCfCfUmGfCmG-3T (SEQ ID NO 4)

ARC1905 (SEQ ID NO: 67)

Figure 23

| Group | # mice | Test Article | Dose | | Measurements |
|---|---|---|---|---|---|
| | | | Conc (nM) | Perfusion rate mL/min | |
| 1 | 5 | No aptamer | 0 | 3 | Heart rate, rhythm, left ventricular pressure |
| 3 | 3 | Irrelevant aptamer at 50X molar ratio | 1500 | 3 | Heart rate, rhythm, left ventricular pressure |
| 4 | 3 | ARC186 at molar equivalence | 30 | 3 | Heart rate, rhythm, left ventricular pressure |
| 5 | 5 | ARC186 at 10X molar ratio | 300 | 3 | Heart rate, rhythm, left ventricular pressure |
| 6 | 4 | ARC186 at 50X molar ratio | 1500 | 3 | Heart rate, rhythm, left ventricular pressure |

Figure 31

| Animal | Treatment | Irrelevant | C3b | C5b-9 |
|---|---|---|---|---|
| 1-001 (1/26) | None | neg | Pos | pos |
| 1-002 (1-26) | None | neg | Pos | pos |
| 1-001 | None | neg | Pos | pos |
| 1-002 | None | neg | Pos | pos |
| 1-003 | None | neg | Pos | pos |
| 3-001 | Irrelevant aptamer 50X molar | neg | Pos | pos |
| 3-002 | Irrelevant aptamer 50X molar | neg | Pos | pos |
| 3-003 | Irrelevant aptamer 50X molar | neg | Pos | pos |
| 4-001 | C5 aptamer molar equivalence | neg | Pos | pos |
| 4-002 | C5 aptamer molar equivalence | neg | Pos | pos |
| 4-003 | C5 aptamer molar equivalence | neg | Pos | pos |
| 5-001 | C5 aptamer 10X molar equivalence | neg | Pos | neg |
| 5-002 | C5 aptamer 10X molar equivalence | neg | Pos | neg |
| 5-003 | C5 aptamer 10X molar equivalence | neg | Pos | neg |
| 5-004 | C5 aptamer 10X molar equivalence | neg | Pos | neg |
| 5-005 | C5 aptamer 10X molar equivalence | neg | Pos | neg |
| 6-001 | C5 aptamer 50X molar equivalence | neg | Pos | neg |
| 6-002 | C5 aptamer 50X molar equivalence | neg | Pos | neg |
| 6-003 | C5 aptamer 50X molar equivalence | neg | Pos | neg |
| 6-004 | C5 aptamer 50X molar equivalence | neg | Pos | neg |

Figure 32

| Animal | Compound | Serum | Molar ratio | Increased EDP | Failure (Y or No) | Time to failure |
|---|---|---|---|---|---|---|
| 1-001 | ARC658 | Human | 0 | Y | Y | 4 min 30 sec |
| 1-002 | ARC658 | Human | 0 | Y | Y | 4 min 38 sec |
| 1-003 | ARC658 | Human | 0 | Y | Y | 3 min 20 sec |
| 1-004 | ARC658 | Human | 0 | Y | Y | 12 min 24 sec |
| 1-005 | ARC658 | Human | 0 | Y | N | NA |
| 1-006 | ARC658 | Human | 0 | Y | Y | 8 min 30 sec |
| 1a-001 | ARC658 | Human | 0.5 | Y | Y | 7 min 22 sec |
| 1a-002 | ARC658 | Human | 0.5 | Y | Y | 7 min 30 sec |
| 1a-003 | ARC658 | Human | 0.5 | Y | Y | 8 min 13 sec |
| 2-001 | ARC658 | Human | 1 | N | N | NA |
| 2-002 | ARC658 | Human | 1 | N | N | NA |
| 2-003 | ARC658 | Human | 1 | N | N | NA |
| 2-004 | ARC658 | Human | 1 | N | N | NA |
| 3-001 | ARC658 | Human | 3 | N | N | NA |
| 3-002 | ARC658 | Human | 3 | N | N | NA |
| 3-003 | ARC658 | Human | 3 | N | N | NA |
| 6-001 | ARC658 | Primate | 0 | Y | Y | 2 min 30 sec |
| 6-002 | ARC658 | Primate | 0 | Y | Y | 2 min 47 sec |
| 6-003 | ARC658 | Primate | 0 | Y | Y | 3 min 30 sec |
| 6-004 | ARC658 | Primate | 0 | Y | Y | 1 min 28 sec |
| 6a-001 | ARC658 | Primate | 3 | Y | Y | 5 min 2 sec |
| 6a-002 | ARC658 | Primate | 3 | Y | Y | 4 min 30 sec |
| 6a-003 | ARC658 | Primate | 3 | Y | Y | 3 min 43 sec |
| 6a-004 | ARC658 | Primate | 3 | Y | Y | 8 min 0 sec |
| 7-001 | ARC658 | Primate | 10 | Y | N | NA |
| 7-002 | ARC658 | Primate | 10 | Y | N | NA |
| 7-003 | ARC658 | Primate | 10 | Y | Y | 9 min 15 sec |
| 7-004 | ARC658 | Primate | 10 | Y | N | NA |
| 9-001 | ARC658 | Primate | 20 | Y | Y | 12 min 50 sec |
| 11-001 | ARC658 | Primate | 30 | Y | N | NA |
| 11-002 | ARC658 | Primate | 30 | Y | Y | 10 min 0 sec |
| 11-003 | ARC658 | Primate | 30 | Y | N | NA |
| 13-001 | ARC658 | Primate | 50 | N | N | NA |
| 13-002 | ARC658 | Primate | 50 | N | N | NA |
| 13-003 | ARC658 | Primate | 50 | N | N | NA |

Figure 34

| Group Number | Number of Animals | Test Article | Dosage Level (mg/kg) | Dose Volume (mL/kg) | Dosing Regimen | Sample Collection |
|---|---|---|---|---|---|---|
| 1 | 3 | ARC657 20 kDa PEG | 10 | 1 | Intravenous bolus on Day 1 | t= pre-dose, 0.5, 1, 2, 4, 8, 16, 24, 32, 48 hrs |
| 2 | 3 | ARC658 30 kDa PEG | 10 | 1 | Intravenous bolus on Day 1 | t= pre-dose, 0.5, 1, 2, 4, 8, 16, 24, 32, 48 hrs |
| 3 | 3 | ARC187 40 kDa PEG | 10 | 1 | Intravenous bolus on Day 1 | t= pre-dose, 0.5, 1, 2, 4, 8, 16, 24, 32, 48 hrs |

Figure 35

| PK of Anti-C5 Aptamer -PEG Conjugates in Sprague-Dawley Rat | | | | | | |
|---|---|---|---|---|---|---|
| Aptamer | ARC657 | | ARC658 | | ARC187 | |
| PEG Group | 20 kDa | | 30 kDa | | 40 kDa | |
| | MEAN | STDEV | MEAN | STDEV | MEAN | STDEV |
| time (hrs) | Cp ($\mu$M) | Cp ($\mu$M) | Cp ($\mu$M) | Cp ($\mu$M) | Cp ($\mu$M) | Cp ($\mu$M) |
| 0 | 0.00 | 0.00 | 0.00 | 0.00 | 0.00 | 0.00 |
| 0.5 | 12.77 | 2.67 | 2.97 | 0.62 | 6.52 | 1.77 |
| 1 | 13.38 | 2.08 | 4.09 | 1.44 | 7.94 | 1.08 |
| 2 | 6.63 | 1.87 | 3.40 | 0.66 | 6.57 | 1.56 |
| 4 | 2.38 | 0.87 | 2.22 | 0.39 | 4.56 | 0.54 |
| 8 | 0.72 | 0.18 | 2.87 | 1.84 | 1.53 | 0.57 |
| 12 | 0.31 | 0.03 | 0.60 | 0.09 | 1.45 | 0.17 |
| 24 | < LLOQ | < LLOQ | 0.47 | 0.17 | 0.73 | 0.03 |
| 32 | < LLOQ | < LLOQ | < LLOQ | < LLOQ | 0.49 | 0.01 |
| 48 | < LLOQ | < LLOQ | < LLOQ | < LLOQ | 0.27 | 0.02 |

Figure 37

| Species | Dose (mg/kg) | Admin Route | PEG Group | $C_{max}$ (µg/ml) | $AUC_{0-\infty}$ (µg·hr/mL) | $t_{1/2}$ (α) (hr) | $t_{1/2}$ (β) (hr) | Cl (mL/min·kg) | $V_{ss}$ (mL/kg) |
|---|---|---|---|---|---|---|---|---|---|
| rat | 10 | IV | 20kD | 169.97 | 458 | - | 2.05 | 0.36 | 65 |
| rat | 10 | IV | 30kD | 52.00 | 497 | - | 7.40 | 0.34 | 220 |
| rat | 10 | IV | 40kD | 100.85 | 886 | - | 15.00 | 0.19 | 188 |

| Group No. | No. Animals | Test Article | Dose (mg/kg) | Dose (mL/kg) | Dose Route | Sample Collection |
|---|---|---|---|---|---|---|
| 1 | 33F | ARC187 | 10 | 4 | IV | t=pre-dose, 0.5, 1, 2, 4, 8, 16, 24, 32, 48, 72 hrs |
| 2 | 33F | ARC1905 | 10 | 4 | IV | t=pre-dose, 0.5, 1, 2, 4, 8, 16, 24, 32, 48, 72 hrs |

Figure 38C

| Noncompartmental PK analysis (NCA) | | | |
|---|---|---|---|
| Attribute | Unit | ARC1905 | ARC187 |
| Cmax | µM | 12 | 10 |
| AUC0-∞ | µM·hr | 88 | 89 |
| MRT0-∞ | hr | 11 | 11 |
| CL | mL/min·kg | 0.15 | 0.15 |
| Vss | mL/kg | 95 | 96 |
| K10 | 1/hr | 0.151 | 0.121 |
| t1/2 (K10) | hr | 5 | 6 |

Figure 39

| Aptamer | Pre | 1hr | 3hr | 6hr |
|---|---|---|---|---|
| ARC657 | No | Yes | Yes | Yes |
| ARC658 | No | Yes | Yes | Yes |
| ARC187 | No | Yes | Yes | Yes |

Figure 40

| Group Number | Number of Animals | Test Article | Dosage Level (mg/kg) | Dose Volume (mL/kg) | Dosing Regimen | Sample Collection |
|---|---|---|---|---|---|---|
| 1 | 1 | ARC657 20 kDa PEG | 30 | 3 | Intravenous bolus on Day 1 | t= pre-dose, 1, 5, 10, 15, and 30 minutes and at 1, 2, 4, 6, 8, 12, 24, 48, 72, 96, and 192 hrs |
| 2 | 1 | ARC658 30 kDa PEG | 30 | 3 | Intravenous bolus on Day 1 | t= pre-dose, 1, 5, 10, 15, and 30 minutes and at 1, 2, 4, 6, 8, 12, 24, 48, 72, 96, and 192 hrs |
| 3 | 1 | ARC187 40 kDa PEG | 30 | 3 | Intravenous bolus on Day 1 | t= pre-dose, 1, 5, 10, 15, and 30 minutes and at 1, 2, 4, 6, 8, 12, 24, 48, 72, 96, and 192 hrs |

Figure 41

| PK of Anti-C5 Aptamer -PEG Conjugates in Cynomolgus Macaque | | | |
|---|---|---|---|
| Aptamer | ARC657 | ARC658 | ARC187 |
| PEG Group | 20 kDa | 30 kDa | 40 kDa |
| | MEAN | MEAN | MEAN |
| time (hrs) | $C_p$ (μM) | $C_p$ (μM) | $C_p$ (μM) |
| 0 | 0.00 | 0.00 | 0.00 |
| 0.08 | 16.41 | 21.99 | 18.00 |
| 0.25 | 16.64 | 22.67 | 17.26 |
| 0.5 | 19.38 | 26.16 | 24.17 |
| 1 | 19.36 | 27.08 | 21.79 |
| 4 | 7.73 | 14.16 | 21.69 |
| 8 | 2.03 | 6.02 | 16.68 |
| 12 | 1.10 | 3.04 | 13.11 |
| 24 | 0.36 | 0.95 | 7.24 |
| 48 | 0.15 | 0.42 | 2.30 |
| 72 | 0.07 | 0.25 | 0.96 |
| 96 | 0.03 | 0.23 | 0.54 |
| 192 | 0.01 | 0.04 | 0.14 |

Figure 42

| Species | Dose (mg/kg) | Admin Route | PEG Group | $C_{max}$ (μg/ml) | $AUC_{0-\infty}$ (μg·hr/mL) | $t_{1/2}$ (α) (hr) | $t_{1/2}$ (β) (hr) | Cl (mL/min kg) | $V_{ss}$ (mL/kg) |
|---|---|---|---|---|---|---|---|---|---|
| primate | 30 | IV | 20kD | 293 | 1191 | 2.35 | 31.80 | 0.41 | 273 |
| primate | 30 | IV | 30kD | 385 | 2484 | 3.33 | 40.08 | 0.20 | 233 |
| primate | 30 | IV | 40kD | 316 | 6752 | 12.38 | 60.11 | 0.07 | 141 |

Figure 43
Figure 43a [sC5b-9] vs time
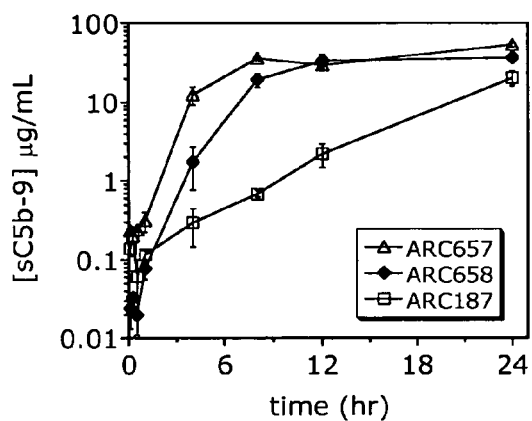
Figure 43b [sC5b-9] vs [aptamer]
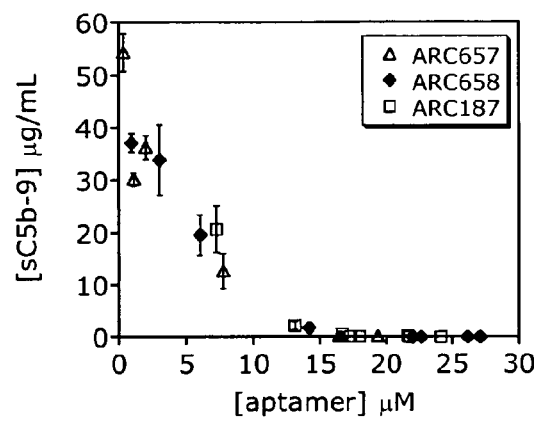
Figure 43c [C5a] vs time
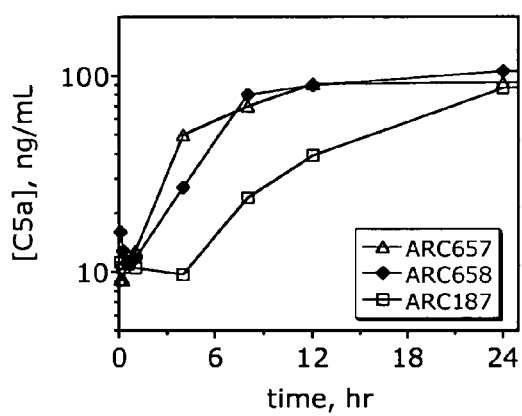
Figure 43d [C5a] vs [aptamer]
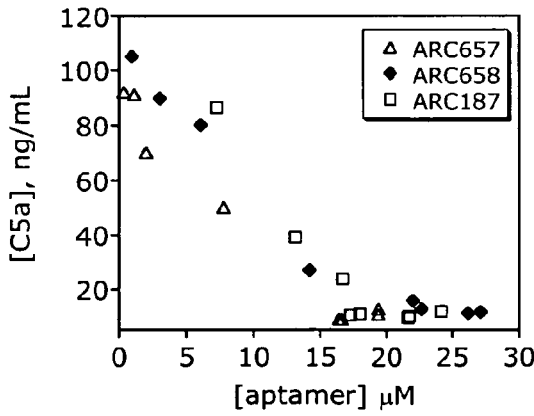

Figure 44

| Group Number | Number of Animals | Test Article | Dosage Level (mg/kg) | Dose Volume (mL/kg) | Dosing Regimen | Sample Collection |
|---|---|---|---|---|---|---|
| 1 | 4 | ARC658 30 kDa PEG | 30 | 3 | Intravenous bolus on Day 1 | t= pre-dose, 5, 10, 15, and 30 minutes and at 1, 2, 4, 6, 8, 12, 24, 48, 72, 96, 144 and 192 hrs |
| 2 | 4 | ARC187 40 kDa PEG | 30 | 3 | Intravenous bolus on Day 1 | t= pre-dose, 5, 10, 15, and 30 minutes and at 1, 2, 4, 6, 8, 12, 24, 48, 72, 96, 144 and 192 hrs |

Figure 46
| Species | Dose (mg/kg) | Admin Route | PEG Group | $C_{max}$ (μM) | $AUC_{0-\infty}$ (μg·hr/mL) | $t_{1/2}$ (α) (hr) | $t_{1/2}$ (β) (hr) | Cl (mL/min·kg) | $V_{ss}$ (mL/kg) |
|---|---|---|---|---|---|---|---|---|---|
| primate | 30 | IV | 30kD | 519 | 3059 | 2.35 | 30.45 | 0.16 | 213 |
| primate | 30 | IV | 40kD | 609 | 8061 | 4.48 | 53.13 | 0.06 | 168 |
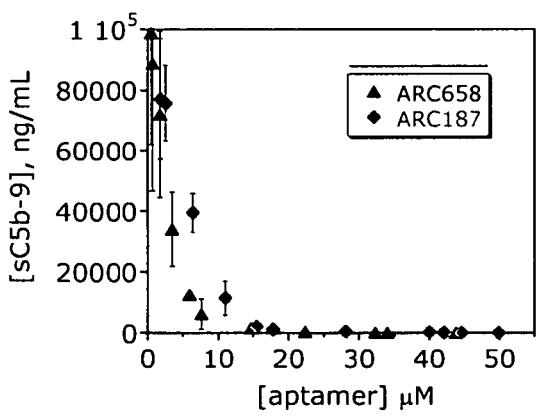
Figure 47
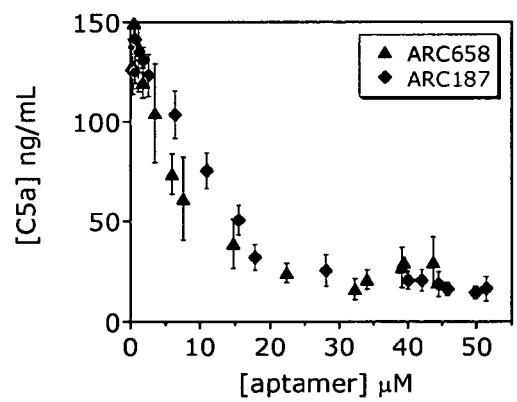
Figure 48

Figure 49

| Gr. No. | No. of Animals | Test Article | Dosage Level (mg/kg) | Dose Conc. (mg/mL) | Dose Volume (mL/kg) | Dosing Regimen | Last Day on Test |
|---|---|---|---|---|---|---|---|
| 1 | 3 | ARC187 | 1 mg/kg IV bolus and 0.0013 mg/kg/min IV infusion | 10 | 0.1 mL/kg, IV bolus and 0.1872 mL/kg/day, IV infusion | IV bolus and 48 hour infusion on Day 1 | Day 8 |

Figure 50

| Species | Dose (mg/kg) | Admin Route | PEG Group | $C_{max}$ (µg/ml) | $AUC_{0-\infty}$ (µg·hr/mL) | $t_{1/2}$ (α) (hr) | $t_{1/2}$ (β) (hr) | Cl (mL/min·kg) | $V_{ss}$ (mL/kg) |
|---|---|---|---|---|---|---|---|---|---|
| primate | 30 | IV | 40kD | 610 | 8061 | 4.48 | 53.13 | 0.06 | 168 |

| Aptamer | PEG Group | Mol. Wt. (oligo) | Mol. Wt. (total) | $t_{1/2}$ (α) (hr) | $t_{1/2}$ (β) (hr) | Total (oligo) Dose for 1.5 µM (g) |
|---|---|---|---|---|---|---|
| ARC187 | 40 kDa | 12,703 | 52,703 | 4.48 | 53.13 | 0.40 |

Figure 55

| treatment | ACT (seconds) | | |
|---|---|---|---|
| | Donor 1[a] | Donor 2[b] | Donor 3[b] |
| baseline | 133 ± 30 | 145 ± 12 | 138 ± 1 |
| + heparin | 842 ± 95 | 519 ± 16 | 450 ± 15 |
| + heparin & ARC187 | nd | 618 ± 55 | 492 ± 28 |
| + heparin & protamine | 160 ± 11 | 155 ± 6 | 159 ± 9 |
| + heparin, protamine & ARC187 | 200 ± 5 | 172 ± 1 | 169 ± 8 |

[a]5 U/mL heparin; [b]4 U/mL heparin; nd, not determined

| Serum Species | ARC1905 IC$_{50}$ (nM) | ARC127 IC$_{50}$ (nM) |
|---|---|---|
| Human | 0.349 ±0.0898 | >10,000 NA |
| Cynomolgus Monkey | 3.69 ±0.603 | >10,000 NA |
| Rat | 2700 ±470 | ~10,000 NA |

| Aptamer | IC$_{50}$ (nM) | IC$_{90}$ (nM) | IC$_{99}$ (nM) |
|---|---|---|---|
| Human | 196 ±13.9 | 442 ±23.2 | 1090 ±198.0 |
| Cynomolgus Macaque | 536 ±54.7 | 1810 ±405.8 | 6900 ±2600 |
| cyno/human ratio | 2.73 ±0.339 | 4.1 ±0.94 | 6.4 ±2.65 |

| Donor | $IC_{50}$ (nM) | $IC_{90}$ (nM) | $IC_{99}$ (nM) |
|---|---|---|---|
| Mean of 5 donors | 119 | 268 | 694 |
| SD | 28.6 | 39.2 | 240.9 |

APTAMER THERAPEUTICS USEFUL IN THE TREATMENT OF COMPLEMENT-RELATED DISORDERS

REFERENCE TO RELATED APPLICATIONS

This non-provisional patent application is a continuation-in-part of U.S. patent application Ser. No. 11/058,134, filed Feb. 14, 2005, (pending) which claims priority under 35 U.S.C. § 119(e) to the following provisional patent applications: U.S. Provisional Patent Application Ser. No. 60/544,542, filed Feb. 12, 2004, U.S. Provisional Patent Application Ser. No. 60/547,747, filed Feb. 25, 2004, U.S. Provisional Patent Application Ser. No. 60/581,685, filed Jun. 21, 2004, and U.S. Provisional Patent Application Ser. No. 60/608,048, filed Sep. 7, 2004, each of which is herein incorporated by reference in its entirety.

FIELD OF THE INVENTION

The invention relates generally to the field of nucleic acids and more particularly to aptamers capable of binding to the C5 protein of the complement system, useful as therapeutics in and diagnostics in complement-related cardiac, inflammatory, and auto-immune disorders, ischemic reperfusion injury and/or other diseases or disorders in which C5 mediated complement activation has been implicated. The invention further relates to materials and methods for the administration of aptamers capable of binding to the C5 complement system protein.

BACKGROUND OF THE INVENTION

Aptamers are nucleic acid molecules having specific binding affinity to molecules through interactions other than classic Watson-Crick base pairing.

Aptamers, like peptides generated by phage display or monoclonal antibodies ("MAbs"), are capable of specifically binding to selected targets and modulating the target's activity, e.g., through binding aptamers may block their target's ability to function. Created by an in vitro selection process from pools of random sequence oligonucleotides, aptamers have been generated for over 100 proteins including growth factors, transcription factors, enzymes, immunoglobulins, and receptors. A typical aptamer is 10-15 kDa in size (30-45 nucleotides), binds its target with sub-nanomolar affinity, and discriminates against closely related targets (e.g., aptamers will typically not bind other proteins from the same gene family). A series of structural studies have shown that aptamers are capable of using the same types of binding interactions (e.g., hydrogen bonding, electrostatic complementarity, hydrophobic contacts, steric exclusion) that drive affinity and specificity in antibody-antigen complexes.

Aptamers have a number of desirable characteristics for use as therapeutics and diagnostics including high specificity and affinity, biological efficacy, and excellent pharmacokinetic properties. In addition, they offer specific competitive advantages over antibodies and other protein biologics, for example:

1) Speed and control. Aptamers are produced by an entirely in vitro process, allowing for the rapid generation of initial leads, including therapeutic leads. In vitro selection allows the specificity and affinity of the aptamer to be tightly controlled and allows the generation of leads, including leads against both toxic and non-immunogenic targets.

2) Toxicity and Immunogenicity. Aptamers as a class have demonstrated little or no toxicity or immunogenicity. In chronic dosing of rats or woodchucks with high levels of aptamer (10 mg/kg daily for 90 days), no toxicity is observed by any clinical, cellular, or biochemical measure. Whereas the efficacy of many monoclonal antibodies can be severely limited by immune response to antibodies themselves, it is extremely difficult to elicit antibodies to aptamers most likely because aptamers cannot be presented by T-cells via the MHC and the immune response is generally trained not to recognize nucleic acid fragments.

3) Administration. Whereas most currently approved antibody therapeutics are administered by intravenous infusion (typically over 2-4 hours), aptamers can be administered by subcutaneous injection (aptamer bioavailability via subcutaneous administration is >80% in monkey studies (Tucker et al., J. Chromatography B. 732: 203-212, 1999)). This difference is primarily due to the comparatively low solubility and thus large volumes necessary for most therapeutic MAbs. With good solubility (>150 mg/mL) and comparatively low molecular weight (aptamer: 10-50 kDa; antibody: 150 kDa), a weekly dose of aptamer may be delivered by injection in a volume of less than 0.5 mL. In addition, the small size of aptamers allows them to penetrate into areas of conformational constrictions that do not allow for antibodies or antibody fragments to penetrate, presenting yet another advantage of aptamer-based therapeutics or prophylaxis.

4) Scalability and cost. Therapeutic aptamers are chemically synthesized and consequently can be readily scaled as needed to meet production demand. Whereas difficulties in scaling production are currently limiting the availability of some biologics and the capital cost of a large-scale protein production plant is enormous, a single large-scale oligonucleotide synthesizer can produce upwards of 100 kg/year and requires a relatively modest initial investment. The current cost of goods for aptamer synthesis at the kilogram scale is estimated at $500/g, comparable to that for highly optimized antibodies. Continuing improvements in process development are expected to lower the cost of goods to <$100/g in five years.

5) Stability. Therapeutic aptamers are chemically robust. They are intrinsically adapted to regain activity following exposure to factors such as heat and denaturants and can be stored for extended periods (>1 yr) at room temperature as lyophilized powders.

The Complement System

The complement system comprises a set of at least 20 plasma and membrane proteins that act together in a regulated cascade system to attack extracellular forms of pathogens (e.g., bacterium). The complement system includes two distinct enzymatic activation cascades, the classical and alternative pathways (FIG. 1), and a non-enzymatic pathway known as the membrane attack pathway.

The first enzymatically activated cascade, known as the classical pathway, comprises several components, C1, C4, C2, C3 and C5 (listed by order in the pathway). Initiation of the classical pathway of the complement system occurs following binding and activation of the first complement component (C1) by both immune and non-immune activators. C1 comprises a calcium-dependent complex of components C1q, C1r and C1s, and is activated through binding of the C1q component. C1q contains six identical subunits and each subunit comprises three chains (the A, B and C chains). Each chain has a globular head region that is connected to a collagen-like tail. Binding and activation of C1q by antigen-antibody complexes occurs through the C1q head group region. Numerous non-antibody C1q activators, including proteins, lipids and nucleic acids, bind and activate C1q through a distinct site on the collagen-like stalk region. The C1qrs complex then catalyzes the activation of complement components C4 and C2, forming the C4bC2a complex which functions as a C3 convertase.

The second enzymatically activated cascade, known as the alternative pathway, is a rapid, antibody-independent route for complement system activation and amplification. The alternative pathway comprises several components, C3, Factor B, and Factor D (listed by order in the pathway). Activation of the alternative pathway occurs when C3b, a proteolytic cleavage form of C3, is bound to an activating surface agent such as a bacterium. Factor B is then bound to C3b, and cleaved by Factor D to yield the active enzyme, Ba. The enzyme Ba then cleaves more C3 to generate more C3b, producing extensive deposition of C3b-Ba complexes on the activating surface.

Thus, both the classical and alternate complement pathways produce C3 convertases that split factor C3 into C3a and C3b. At this point, both C3 convertases further assemble into C5 convertases (C4b2a3b and C3b3bBb). These complexes subsequently cleave complement component C5 into two components: the C5a polypeptide (9 kDa) and the C5b polypeptide (170 kDa). The C5a polypeptide binds to a 7 transmembrane G-protein coupled receptor, which was originally associated with leukocytes and is now known to be expressed on a variety of tissues including hepatocytes and neurons. The C5a molecule is the primary chemotactic component of the human complement system and can trigger a variety of biological responses including leukocyte chemotaxis, smooth muscle contraction, activation of intracellular signal transduction pathways, neutrophil-endothelial adhesion, cytokine and lipid mediator release and oxidant formation.

The larger C5b fragment binds sequentially to later components of the complement cascade, C6, C7, C8 and C9 to form the C5b-9 membrane attack complex ("MAC"). The C5b-9 MAC can directly lyse erythrocytes, and in greater quantities, it is lytic for leukocytes and damaging to tissues such as muscle, epithelial and endothelial cells. In sublytic amounts, the MAC can stimulate upregulation of adhesion molecules, intracellular calcium increase and cytokine release. In addition, the C5b-9 MAC can stimulate cells such as endothelial cells and platelets without causing cell lysis. The non-lytic effects of C5a and the C5b-9 MAC are sometimes quite similar.

Although the complement system has an important role in the maintenance of health, it has the potential to cause or contribute to disease. For example, the complement system has been implicated in side effects relating to coronary artery bypass graft ("CABG") surgery, numerous renal, rheumatological, neurological, dermatological, hematological, vascular/pulmonary, allergy, infectious, and biocompatibility/shock diseases and/or conditions, and diabetic retinopathy. The complement system is not necessarily the only cause of a disease state, but it may be one of several factors that contribute to pathogenesis.

In Fitch et al., Circ. 100:2499-506 (1999), the effects of the anti-C5 single-chain antibody fragment Pexelizumab on patients undergoing coronary artery bypass graft surgery with cardiopulmonary bypass ("CPB") was tested. Individual patients were administered Pexelizumab in a 10 minute, single-bolus dose just prior to CPB at 0.5 mg/kg, 1.0 mg/kg and 2.0 mg/kg. Blood samples were removed and tested for complement activity at pre-dose, 5 min post-dose, after 5 min at 28° C., after initiation of rewarming, after 5 min at 37° C., and up to 7 days after CPB. Pharmacodynamic analysis demonstrated significant dose-dependent inhibition of complement hemolytic activity for up to 14 hours at a dosage of 2 mg/kg, and the generation of proinflammatory complement byproducts (sC5b-9) was effectively inhibited in a dose-dependent fashion. As previously mentioned, however, antibody therapeutics have certain limitations.

Accordingly, it would be beneficial to have novel inhibitors of the complement system for use as therapeutics and diagnostics in the treatment of complement-related disorders.

BRIEF DESCRIPTION OF THE DRAWINGS

FIG. 6 is an illustration depicting various strategies for synthesis of high molecular weight PEG-nucleic acid conjugates.

FIG. 23 is a table outlining the experimental design of the first isolated perfused heart study.

FIG. 31 is a table showing the immunohistochemistry staining results for the isolated perfused mouse heart study.

FIG. 32 is a table showing the molar ratio of ARC658 (SEQ ID NO: 62) necessary, in human or primate serum, to protect the heart from C5b-mediated damage.

FIG. 34 is a table showing the experimental design of the pharmacokinetic study conducted Sprague-Dawley rats as described in Example 5.

FIG. 35 is a table showing mean plasma concentration of ARC657 (SEQ ID NO: 61), ARC658 (SEQ ID NO: 62) or ARC187 (SEQ ID NO: 5) versus time in Sprague-Dawley rats.

FIG. 37 is a table showing the noncompartmental analysis of the concentration versus time data depicted in FIGS. 35 and 36.

FIG. 38C is a table showing the noncompartmental analysis of the concentration versus time data depicted in FIG. 38B.

FIG. 39 is a table showing detection of the listed aptamers in mouse heart tissue following intravenous administration.

FIG. 40 is a table showing the experimental design of animal Study 1, described in Example 5E.

FIG. 41 is a table showing aptamer plasma concentration versus time following intravenous bolus administration of aptamer to cynomolgus macaques.

FIG. 42 is a table listing the pharmacokinetic parameters for ARC657 (SEQ ID NO: 61), ARC658 (SEQ ID NO: 62) and ARC187 (SEQ ID NO: 5) administered intravenously to cynomolgus macaque in Study 1.

FIGS. 43(a) and 43(c) are graphs depicting plasma concentrations of sC5b-9 and C5a over time following intravenous administration of the anti-C5 aptamers ARC657 (SEQ ID NO: 61), ARC658 (SEQ ID NO: 62), or ARC187 (SEQ ID NO: 5) to cynomolgus macaques; FIGS. 43(b) and 43(d) are graphs depicting plasma concentrations of sC5b-9 and C5a versus concentration of anti-C5 aptamers, ARC657 (SEQ ID NO: 61), ARC658 (SEQ ID NO: 62), or ARC187 (SEQ ID NO: 5).

FIG. 44 is a table showing the experimental design of Study 2, described in Example 5F.

FIG. 46 is a table showing the two compartmental analysis of the concentration versus time data following intravenous bolus aptamer administration to cynomolgus macaque.

FIG. 47 is a graph depicting C5b-9 concentration versus ARC187 (SEQ ID NO: 5) or ARC658 (SEQ ID NO: 62) concentration in the presence of zymosan in cynomolgus plasma.

FIG. 48 is a graph depicting C5a concentration versus ARC187 (SEQ ID NO: 5) or ARC658 (SEQ ID NO: 62) concentration in the presence of zymosan in cynomolgus plasma.

FIG. 49 is a table summarizing the PK-PD study of ARC187 (SEQ ID NO: 5) during and after IV bolus plus infusion administration to cynomolgus macaques.

FIG. 50 is a table summarizing the pharmacokinetic parameters for ARC187 (SEQ ID NO: 5) in cynomolgus macaques after IV bolus administration.

FIG. 55 is a table summarizing the in vitro effects of ARC187 (SEQ ID NO: 5) on anti-coagulation activity of heparin, and procoagulation activity of protamine.

SUMMARY OF THE INVENTION

Figure 1:
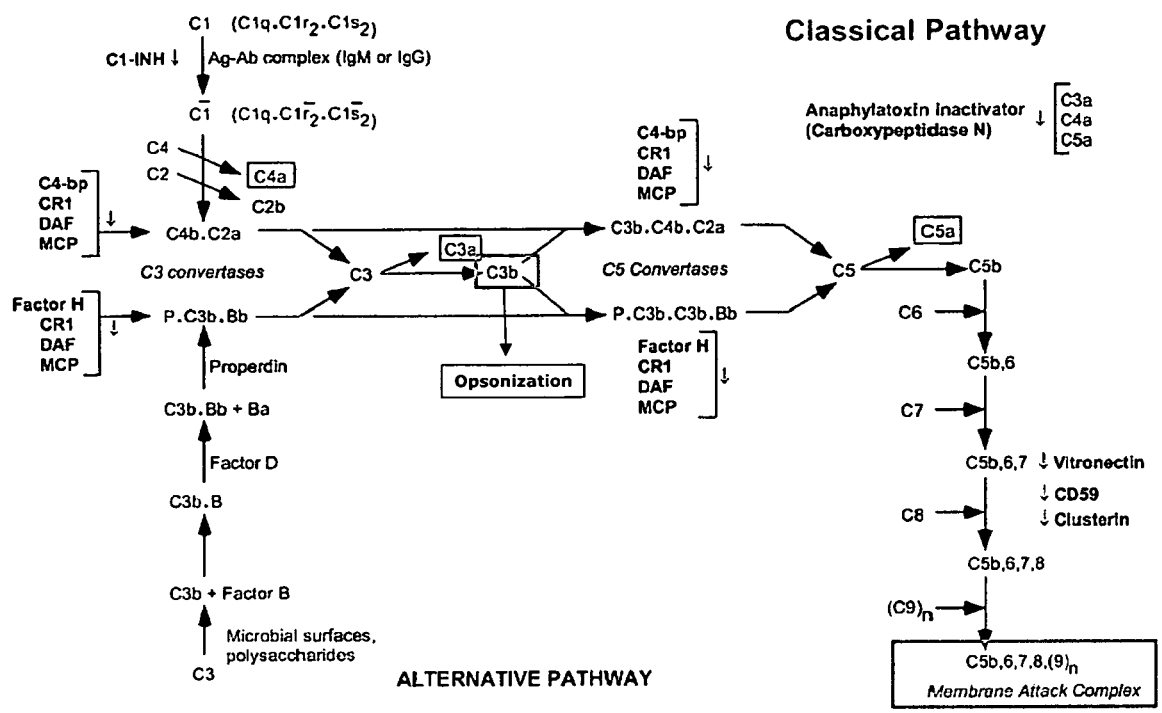
FIG. 1 is an illustration depicting the classical and alternative pathways of the complement system.

The present invention provides materials and methods for the treatment, prevention and amelioration of complement related disease. In one embodiment, an aptamer comprising a nucleotide sequence according to ARC186 (SEQ ID NO: 4) conjugated to a PEG moiety is provided. In particular embodiments, this ARC186 aptamer/PEG conjugate comprises substantially the same binding affinity for C5 complement protein as an aptamer consisting of the sequence according to SEQ ID NO: 4 but lacking the PEG moiety. Substantially the same binding affinity as used herein means no more than about a 2 to ten fold difference, preferably no more than a 2 to five fold difference in dissociation constants as measured by dot blot analysis. In some embodiments the dissociation constants are measured by competition dot blot analysis as described in Example 1A below. In some embodiments, the polyethylene glycol moiety comprises a molecular weight greater than 10 kDA, particularly a molecular weight of 20 kDA, more particularly 30 kDa and more particularly 40 kDa. In some embodiments, the PEG moiety is conjugated to the 5' end of ARC186 (SEQ ID NO:4). In some embodiments the aptamer/PEG conjugate comprises a half life, preferably the terminal half life in a two compartment model as determined by the method described in Example 5E below, of at least 15 hours, preferably at least 24 hours, more preferably at least 48 hours in primate. In some embodiments the aptamer/PEG conjugate comprises a half life, preferably the terminal half life in a two compartment model, of at least 10, preferably at least 15 hours in rat. In some embodiments, the PEG conjugated to the 5' end of ARC186 (SEQ ID NO: 4) is a 40 kDa PEG. In particular embodiments the 40 kDa PEG is a branched PEG. In some embodiments the branched 40 kDa PEG is 1,3-bis(mPEG-[20 kDa])-propyl-2-(4'-butamide). In other embodiments the branched 40 kDa PEG is 2,3-bis (mPEG-[20 kDa])-propyl-1-carbamoyl.

In embodiments where the branched 40 kDa PEG is 1,3-bis(mPEG-[20 kDa])-propyl-2-(4'-butamide), an aptamer having the structure set forth below is provided:

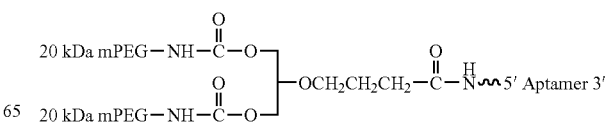

where,

`````` indicates a linker

Aptamer = (SEQ ID NO: 4)
fCmGfCfCGfCmGmGfUfCfUfCmAmGmGfCGfCfUmGmAmGfUfCfUmG mAmGfUfUfUAfCfCfUmGfCmG-3T, wherein fC and fU=2'-fluoro nucleotides, and mG and mA=2'-OMe nucleotides and all other nucleotides are 2'-OH and 3T indicates an inverted deoxy thymidine.

In embodiments where the branched 40 kDa PEG is 2,3-bis(mPEG-[20 kDa])-propyl-1-carbamoyl, an aptamer having the structure set forth below is provided:

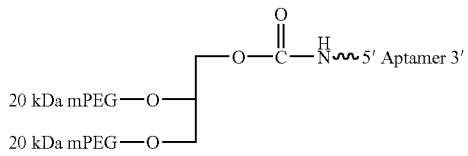

where,

`````` indicates a linker

Aptamer = (SEQ ID NO: 4)
fCmGfCfCGfCmGmGfUfCfUfCmAmGmGfCGfCfUmGmAmGfUfCfUmG mAmGfUfUfUAfCfCfUmGfCmG-3T, wherein fC and fU=2'-fluoro nucleotides, and mG and mA=2'-OMe nucleotides and all other nucleotides are 2'-OH and 3T indicates an inverted deoxy thymidine.

In some embodiments of this aspect of the invention the linker is an alkyl linker. In particular embodiments, the alkyl linker comprises 2 to 18 consecutive CH$_2$ groups. In preferred embodiments, the alkyl linker comprises 2 to 12 consecutive CH$_2$ groups. In particularly preferred embodiments the alkyl linker comprises 3 to 6 consecutive CH$_2$ groups.

In a particular embodiment an aptamer, ARC187 (SEQ ID NO: 5), having the structure set forth below is provided:

where

Aptamer = (SEQ ID NO: 4)
fCmGfCfCGfCmGmGfUfCfUfCmAmGmGfCGfCfUmGmAmGfUfCfUmG mAmGfUfUfUAfCfCfUmGfCmG-3T wherein fC and fU=2'-fluoro nucleotides, and mG and mA=2'-OMe nucleotides and all other nucleotides are 2'-OH and where 3T indicates an inverted deoxy thymidine.

In another embodiment an aptamer, ARC1905 (SEQ ID NO: 67), having the structure set forth below is provided:

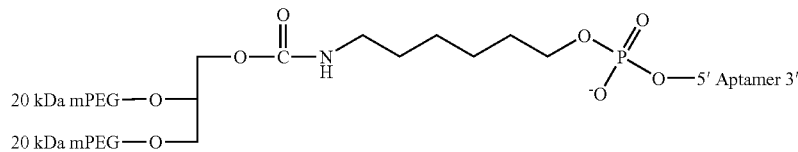

where

Aptamer = (SEQ ID NO: 4)
fCmGfCfCGfCmGmGfUfCfUfCmAmGmGfCGfCfUmGmAmGfUfCfUmG mAmGfUfUfUAfCfCfUmGfCmG-3T wherein fC and fU=2'-fluoro nucleotides, and mG and mA=2'-OMe nucleotides and all other nucleotides are 2'-OH and where 3T indicates and inverted deoxy thymidine.

In another aspect, the invention provides pharmaceutical compositions. In one embodiment, a pharmaceutical composition comprising a therapeutically effective amount of ARC187 (SEQ ID NO: 5) or ARC1905 (SEQ ID NO: 67) or a salt thereof is provided. The pharmaceutical composition of the invention may comprise a pharmaceutically acceptable carrier or diluent. In this aspect, the invention provides a pharmaceutical composition comprising a therapeutically effective amount of an aptamer that inhibits C5 complement protein cleavage in vivo or a salt thereof and a pharmaceutically acceptable carrier or diluent. In this aspect of the invention an ARC187 (SEQ ID NO: 5) or ARC1905 (SEQ ID NO: 67) pharmaceutical composition for use in the treatment, prevention or amelioration of disease in vivo is provided. Also, in this aspect of the invention ARC187 (SEQ ID NO: 5) or ARC1905 (SEQ ID NO: 67) for the use in the preparation of a pharmaceutical composition are provided.

In another aspect of the invention, methods of treatment are provided. In one embodiment, the method of the invention comprises treating, preventing or ameliorating a disease

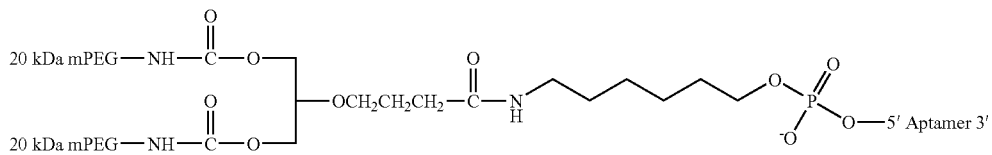

mediated by C5 complement protein, and/or it's derivatives C5a and C5b-9, the method including administering a pharmaceutical composition comprising ARC187 (SEQ ID NO: 5) or ARC1905 (SEQ ID NO: 67) or a salt thereof to a vertebrate. In some embodiments, the method comprises administering the pharmaceutical composition of the invention to a mammal. In some embodiments, the mammal is a human.

In some embodiments, the C5 complement protein, C5a and/or C5b-9-mediated disease to be treated is acute ischemic diseases (myocardial infarction, stroke, ischemic/reperfusion injury); acute inflammatory diseases (infectious disease, septicemia, shock, acute/hyperacute transplant rejection); chronic inflammatory and/or immune-mediated diseases (allergy, asthma, rheumatoid arthritis, and other rheumatological diseases, multiple sclerosis and other neurological diseases, psoriasis and other dermatological diseases, myasthenia gravis, systemic lupus erythematosus (SLE), sub-acute/chronic transplant rejection, glomerulonephritis and other renal diseases). In some embodiments, the C5 complement protein, C5a and/or C5b-9 mediated diseases to be treated include complement activation associated with dialysis or circumstances in which blood is passed over and/or through synthetic tubing and/or foreign material. In some embodiments, the C5 complement protein, C5a and/or C5b-9-mediated disease to be treated is selected from the group consisting of myocardial injury relating to CABG surgery, myocardial injury relating to balloon angioplasty and myocardial injury relating to restenosis. In some embodiments, C5 complement protein, C5a and/or C5b-9-mediated disorder to be treated is selected from the group consisting of: myocardial injury relating to CABG surgery, myocardial injury relating to balloon angioplasty, myocardial injury relating to restenosis, complement protein mediated complications relating to CABG surgery, complement protein mediated complications relating to percutaneous coronary intervention, paroxysmal nocturnal hemoglobinuria, acute transplant rejection, hyperacute transplant rejection, sub-acute transplant rejection, and chronic transplant rejection. In some embodiments the C5 complement protein C5a and/or C5b-9-mediated disease to be treated is complications relating to CABG surgery. In a particular embodiment, the disease to be treated is myocardial injury relating to CABG surgery In some embodiments, the method of the invention includes administering the pharmaceutical composition comprising ARC187 (SEQ ID NO: 5) or ARC1905 (SEQ ID NO: 67) to achieve an aptamer plasma concentration that is about 0.5 to about 10 times that of the endogenous C5 complement protein. In some embodiments, the pharmaceutical ARC187 (SEQ ID NO: 5) or ARC1905 (SEQ ID NO: 67) aptamer compositions are administered to achieve an aptamer plasma concentration that is about 0.75 to about 5 times, 0.75 to about 3 times, and 1.5 to about 2 times that of the endogenous C5 complement protein while in other embodiments the aptamer composition is administered to achieve a concentration equivalent to that of the endogenous complement protein. In some embodiments, the pharmaceutical composition of the invention comprising ARC187 (SEQ ID NO: 5) or ARC1905 (SEQ ID NO: 67) is administered to achieve an aptamer plasma concentration of about 5 µM, about 4 µM, about 3 µM, about 2 µM, about 1.5 µM, about 1 µM or of about 500 nM.

Any combination of route, duration, and rate of administration may be used that is sufficient to achieve the aptamer plasma concentrations of the invention. In some embodiments the pharmaceutical composition is administered intravenously. In some embodiments, the pharmaceutical composition is administered as a bolus and/or via continuous infusion.

In particular embodiments of treating, preventing and/or ameliorating complications related to CABG surgery, particularly myocardial injury related to CABG surgery, the method of the invention comprises administering the pharmaceutical composition prior to surgery and continuing administration at least 24 hours, in some embodiments about 48 hours or in some embodiments about 72 hours. In a particular embodiment of this aspect of the invention, a plasma aptamer concentration of about two times the endogenous complement protein concentration is achieved by administration of an intravenous bolus of about 0.75 to 1.25, preferably of about 1 mg of aptamer per kg of the patient to be treated in advance of, simultaneously with or after intravenous infusion of a lower dose of aptamer wherein mg does not include the weight of the conjugated PEG. In some embodiments the lower dose will be infused at a rate selected from the range of 0.001 to 0.005 mg/kg/min wherein mg does not include the weight of the conjugated PEG. In a particular embodiment, the lower dose will be infused at a rate of about 0.0013 mg/kg/min. In still other embodiments of this aspect of the invention, where the aptamer/conjugate comprises a sufficiently long half life, the aptamer pharmaceutical composition may be administered once or twice daily as an intravenous bolus dose.

In another aspect of the invention, diagnostic methods are provided. In one embodiment, the diagnostic method comprises contacting the ARC187 (SEQ ID NO: 5) or ARC1905 (SEQ ID NO: 67) with a composition suspected of comprising C5 complement protein or a variant thereof, and detecting the presence or absence of C5 complement protein or a variant thereof. In some embodiments the complement protein or variant are vertebrate, particularly mammalian, and more particularly human. The present invention provides an ARC187 (SEQ ID NO: 5) or ARC1905 (SEQ ID NO: 67) composition for use as an in vitro or in vivo diagnostic.

In another aspect of the invention, an aptamer comprising a nucleotide sequence selected from the group consisting of: ARC330 (SEQ ID NO: 2) and ARC188-189, ARC250, ARC296-297, ARC331-334, ARC411-440, ARC457-459, ARC473, ARC522-525, ARC532, ARC543-544, ARC550-554, ARC657-658, ARC672, ARC706, ARC1537, ARC1730, (SEQ ID NOS: 6 to SEQ NO: 66) is provided. In another embodiment any one of ARC330 (SEQ ID NO: 2) and ARC188-189, ARC250, ARC296-297, ARC331-334, ARC411-440, ARC457-459, ARC473, ARC522-525, ARC532, ARC543-544, ARC550-554, ARC657-658, ARC672, ARC706, ARC1537, ARC1730, (SEQ ID NOS: 6 to SEQ NO: 66) for use in the preparation of a pharmaceutical composition is provided. In this aspect, the invention provides a pharmaceutical composition comprising a therapeutically effective amount of an aptamer that inhibits C5 complement protein cleavage in vivo or a salt thereof and a pharmaceutically acceptable carrier or diluent.

In a particular embodiment, an aptamer comprising a nucleotide sequence according to SEQ ID NO: 1 is provided. In a particular embodiment, an aptamer comprising a nucleotide sequence selected from the group consisting of SEQ ID NO: 61, SEQ ID NO: 62, and SEQ ID NO: 64 to SEQ ID NO: 66 is provided. In some embodiments, where the aptamer comprises a nucleotide sequence selected from the group consisting of SEQ ID NO: 61, SEQ ID NO: 62, and SEQ ID NO: 64 to SEQ ID NO: 66, the aptamer comprises substantially the same binding affinity for C5 complement protein as an aptamer consisting of the sequence according to SEQ ID NO: 4 but lacking a PEG moiety.

In some embodiments wherein the aptamer comprises a nucleotide sequence selected from the group consisting of SEQ ID NO: 61, SEQ ID NO: 62, and SEQ ID NO: 64 to SEQ ID NO: 66, the aptamer comprises a half life, preferably the terminal half life in a two compartment model as determined in Example 5E below, of at least 15, preferably at least 30 hours in primate. In some embodiments wherein the aptamer comprises a nucleotide sequence selected from the group consisting of SEQ ID NO: 61, SEQ ID NO: 62, and SEQ ID NO: 64 to SEQ ID NO: 66, the aptamer comprises a half life, preferably the terminal half life in a two compartment model, of at least 1 and a half, preferably at least seven hours in rat.

In some embodiments of this aspect of the invention, wherein the aptamer comprises a nucleotide sequence selected from the group consisting of SEQ ID NO: 61, SEQ ID NO: 62, and SEQ ID NO: 64 to SEQ ID NO: 66, the aptamer is synthesized with a 5' linker as follows: H₂N~~~~5' Aptamer 3', wherein "~~~~" denotes the linker. In some embodiments the linker is an alkyl linker as follows:

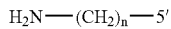

H₂N—(CH₂)ₙ—5'

Aptamer 3' wherein n=2 to 18, preferably n=2-12, more preferably n=3 to 6, more preferably n=6, and wherein

```
Aptamer =
                                          (SEQ ID NO: 4)
fCmGfCfCGfCmGmGfUfCfUfCmAmGmGfCGfCfUmGmAmGfUfCfUmG mAmGfUfUfUAfCfCfUmGfCmG-3T,
``` wherein fC and fU=2'-fluoro nucleotides, and mG and mA=2'-OMe nucleotides and all other nucleotides are 2'-OH and where 3T indicates an inverted deoxy thymidine. The resulting amine-modified aptamer may be conjugated to a PEG moiety selected from the group consisting of a 10 kDa PEG, 20 kDa PEG, 30 kDa PEG and 40 kDa linear PEG. In some embodiments, a pharmaceutical composition comprising a therapeutically effective amount of an aptamer comprising a nucleotide sequence selected from the group consisting of: SEQ ID NO: 1, SEQ ID NO: 2 and SEQ ID NO: 6 to SEQ NO: 66, particularly from the group consisting of SEQ ID NO: 61, SEQ ID NO: 62, and SEQ ID NO: 64 to SEQ ID NO: 66 or a salt thereof is provided. The pharmaceutical composition of the invention may comprise a pharmaceutically acceptable carrier or diluent. In this aspect of the invention a pharmaceutical composition for use in the treatment, prevention or amelioration of disease in vivo, comprising an aptamer which comprises a nucleotide sequence selected from the group consisting of: SEQ ID NO: 2 and SEQ ID NO: 6 to SEQ NO: 66, particularly from the group consisting of SEQ ID NO: 61, SEQ ID NO: 62, and SEQ ID NO: 64 to SEQ ID NO: 66 is provided.

In another embodiment, a method of treating, preventing or ameliorating a disease mediated by C5 complement protein is provided, comprising administering a pharmaceutical composition comprising an aptamer or a salt thereof, where the aptamer comprises a nucleotide sequence selected from the group consisting of: SEQ ID NO: 2 and SEQ ID NO: 6 to SEQ NO: 66, particularly from the group consisting of SEQ ID NO: 61, SEQ ID NO: 62, and SEQ ID NO: 64 to SEQ ID NO: 66 to a vertebrate. In some embodiments of this aspect of the invention, the method comprises administering the pharmaceutical composition of the invention to a mammal, preferably a human.

In some embodiments, the C5 complement protein, C5a and/or C5b-9-mediated disease to be treated is acute ischemic diseases (myocardial infarction, stroke, ischemic/reperfusion injury); acute inflammatory diseases (infectious disease, septicemia, shock, acute/hyperacute transplant rejection); chronic inflammatory and/or immune-mediated diseases (allergy, asthma, rheumatoid arthritis, and other rheumatological diseases, multiple sclerosis and other neurological diseases, psoriasis and other dermatological diseases, myasthenia gravis, systemic lupus erythematosus (SLE), subacute/chronic transplant rejection, glomerulonephritis and other renal diseases). In some embodiments, the C5 complement protein, C5a and/or C5b-9 mediated diseases to be treated include complement activation associated with dialysis or circumstances in which blood is passed over and/or through synthetic tubing and/or foreign material. In some embodiments, the C5 complement protein C5a and/or C5b-9-mediated disease to be treated is selected from the group consisting of myocardial injury relating to CABG surgery, myocardial injury relating to balloon angioplasty and myocardial injury relating to restenosis. In some embodiments, C5 complement protein, C5a and/or C5b-9-mediated disorder to be treated is selected from the group consisting of: myocardial injury relating to CABG surgery, myocardial injury relating to balloon angioplasty, myocardial injury relating to restenosis, complement protein mediated complications relating to CABG surgery, complement protein mediated complications relating to percutaneous coronary intervention, paroxysmal nocturnal hemoglobinuria, acute transplant rejection, hyperacute transplant rejection, subacute transplant rejection, and chronic transplant rejection. In some embodiments the C5 complement protein C5a and/or C5b-9-mediated disease to be treated is complications relating to CABG surgery. In a particular embodiment, the disease to be treated is myocardial injury relating to CABG surgery.

In some embodiments, the method of the invention includes administering the pharmaceutical composition comprising an aptamer having a nucleotide sequence selected from the group consisting of: SEQ ID NO: 2 and SEQ ID NO: 6 to SEQ NO: 66, particularly from the group consisting of SEQ ID NO: 61, SEQ ID NO: 62, and SEQ ID NO: 64 to SEQ ID NO: 66, to a patient to achieve an aptamer plasma concentration that is about 0.5 to about 10 times that of the endogenous C5 complement protein. In some embodiments, the pharmaceutical aptamer compositions are administered to achieve an aptamer plasma concentration that is about 0.75 to about 5 times, 0.75 to about 3 times, and 1.5 to about 2 times that of the endogenous C5 complement protein while in other embodiments the aptamer composition is administered to achieve a concentration equivalent to that of the endogenous complement protein. In some embodiments, the pharmaceutical composition of the invention administered to achieve an aptamer plasma concentration of about 5 µM, about 4 µM, about 3 µM, about 2 µM, about 1.5 µM, about 1 µM or of about 500 nM.

Any combination of route, duration, and rate of administration may be used that is sufficient to achieve the aptamer plasma concentrations of the invention. In some embodiments the pharmaceutical composition is administered intravenously. In some embodiments, the pharmaceutical composition is administered as a bolus and/or via continuous infusion.

In particular embodiments of treating, preventing and/or ameliorating complications related to CABG surgery, particularly myocardial injury related to CABG surgery, the method of the invention comprises administering the pharmaceutical composition prior to surgery and continuing administration at least 24 hours, in some embodiments about 48 hours or in some embodiments about 72 hours. In a particular embodiment of this aspect of the invention, the desired aptamer plasma concentration, e.g., two times the endogenous complement protein concentration in some embodiments, is achieved by administration of an intravenous bolus to the patient to be treated in advance of, simultaneously with, or after intravenous infusion of a lower dose of aptamer. In still other embodiments of this aspect of the invention, where the aptamer/conjugate comprises a sufficiently long half life, the aptamer pharmaceutical composition may be administered once or twice daily as an intravenous bolus dose.

In another aspect of the invention diagnostic methods are provided. In one embodiment, the diagnostic method comprises contacting a composition suspected of comprising C5 complement protein or a variant thereof with an aptamer comprising a nucleotide sequence selected from the group consisting of: SEQ ID NO: 2 and SEQ ID NO: 6 to SEQ NO 66, particularly from the group consisting of SEQ ID NO: 61, SEQ ID NO: 62, and SEQ ID NO: 64 to SEQ ID NO: 66, and detecting the presence or absence of C5 complement protein or a variant thereof. In some embodiments the complement protein or variant is vertebrate, particularly mammalian, and more particularly human. The present invention provides an aptamer composition having an aptamer comprising a nucleotide sequence selected from the group consisting of: SEQ ID NO: 2 and SEQ ID NO: 6 to SEQ NO 66 for use as an in vitro or in vivo diagnostic. In the present invention, an aptamer comprising a nucleotide sequence selected from the group consisting of: SEQ ID NO: 2 and SEQ ID NO: 6 to SEQ NO 66 for use in the preparation of a pharmaceutical composition is provided.

In another aspect of the invention, an aptamer comprising a nucleotide sequence that is 80% identical to any one of the sequences selected from the group consisting of SEQ ID NOS: 75 to 81, SEQ ID NO: 83, and SEQ ID NOS: 88 to 98 is provided. In some embodiments, an aptamer comprising a nucleotide sequence that is 80% identical to the unique region of any one of the sequences selected from the group consisting of SEQ ID NOS: 75 to 81 and SEQ ID NOS: 88 to 98 is provided. In another embodiment an aptamer comprising a nucleotide sequence that is 90% identical to any one of the sequences selected from the group consisting of SEQ ID NOS: 75 to 81, SEQ ID NO: 83, and SEQ ID NOS: 88 to 98 is provided. In a particular embodiment, an aptamer comprising a nucleotide sequence that is 90% identical to the unique region of any one of the sequences selected from the group consisting of SEQ ID NOS: 75 to 81 and SEQ ID NOS: 88 to 98 is provided. In yet another embodiment, an aptamer comprising a nucleotide sequence of 40 contiguous nucleotides identical to 40 contiguous nucleotides included in any one of the sequences selected from the group consisting of SEQ ID NOS: 75 to 81 and SEQ ID NOS: 88 to 98 is provided. In another embodiment, an aptamer comprising a nucleotide sequence of 30 contiguous nucleotides identical to 30 contiguous nucleotides included in any one of the sequences selected from the group consisting of SEQ ID NOS: 75 to 81, SEQ ID NO: 83 and SEQ ID NOS: 88 to 98 is provided. In yet another embodiment, an aptamer that binds specifically to C5 complement protein comprising a nucleotide sequence of 10 contiguous nucleotides identical to 10 contiguous nucleotides included in any one of the sequences selected from the group consisting of SEQ ID NOS: 75 to 81, SEQ ID NO: 83 and SEQ ID NOS: 88 to 98 is provided. In a preferred embodiment an aptamer comprising a nucleotide sequence according to any one of the nucleotide sequences selected from the group consisting of: SEQ ID NOS: 75 to 81, SEQ ID NO: 83 and SEQ ID NOS: 88 to 98, is provided.

In some embodiments, the aptamers of this aspect of the invention described immediately above may further comprise a chemical modification selected from the group consisting: of a chemical substitution at a sugar position; a chemical substitution at a phosphate position; and a chemical substitution at a base position of the nucleic acid sequence. In some embodiments the modification is selected from the group consisting of: incorporation of a modified nucleotide; 3' capping, conjugation to a high molecular weight, non-immunogenic compound; conjugation to a lipophilic compound; and modification of the phosphate back bone.

In preferred embodiments of this aspect of the invention, the aptamer modulates a function of a C5 complement protein or a variant thereof. In particularly preferred embodiments, the aptamer inhibits a function of C5 complement protein or a variant thereof, preferably in vivo, more preferably in vivo in humans. In one embodiment of this aspect of the invention, the function modulated, preferably inhibited, by the aptamer is C5 complement protein cleavage.

In some embodiments of another aspect, the invention provides a pharmaceutical composition comprising a therapeutically effective amount of an aptamer that blocks C5 complement protein cleavage in vivo or a salt thereof and a pharmaceutically acceptable carrier or diluent.

In some embodiments, a pharmaceutical composition comprising a therapeutically effective amount of an aptamer comprising a nucleotide sequence 80% identical to, preferably 90% identical to a nucleotide sequence selected from the group consisting of SEQ ID NOS: 75 to 81, SEQ ID NO: 83 and SEQ ID NOS: 88 to 98 or a salt thereof is provided. In some embodiments, a pharmaceutical composition comprising a therapeutically effective amount of an aptamer comprising a nucleotide sequence 80% identical to, preferably 90% identical to the unique region of a nucleotide sequence selected from the group consisting of SEQ ID NOS: 75 to 81, SEQ ID NO: 83 and SEQ ID NOS: 88 to 98 or a salt thereof is provided. In other embodiments, a pharmaceutical composition comprising a therapeutically effective amount of an aptamer having 40, 30 or 10 contiguous nucleotides identical to 40, 30 or 10 nucleotides, respectively, to a nucleotide sequence selected from the group consisting of SEQ ID NOS: 75 to 81, SEQ ID NO: 83 and SEQ ID NOS: 88 to 98 is provided. The pharmaceutical composition of the invention may comprise a pharmaceutically acceptable carrier or diluent. In this aspect of the invention a pharmaceutical composition is provided for use in the treatment, prevention or amelioration of disease in vivo, where the pharmaceutical composition comprises an aptamer having a nucleotide sequence selected from the group consisting of: SEQ ID NOS: 3 to 4, SEQ ID NOS: 75 to 81, SEQ ID NO: 83 and SEQ ID NOS: 88 to 98 or a salt thereof. In this aspect, an aptamer having a nucleotide sequence selected from the group consisting of: SEQ ID NOS: 3 to 4, SEQ ID NOS: 75 to 81, SEQ ID NO: 83 and SEQ ID NOS: 88 to 98 for use in the preparation of a pharmaceutical composition is provided. In this aspect, the invention provides a pharmaceutical composition comprising a therapeutically effective amount of an aptamer that inhibits C5 complement protein cleavage in vivo or a salt thereof and a pharmaceutically acceptable carrier or diluent. In this aspect of the In some embodiments, the C5 complement protein, C5a and/or C5b-9-mediated disease to be treated is acute ischemic diseases (myocardial infarction, stroke, ischemic/reperfusion injury); acute inflammatory diseases (infectious disease, septicemia, shock, acute/hyperacute transplant rejection); chronic inflammatory and/or immune-mediated diseases (allergy, asthma, rheumatoid arthritis, and other rheumatological diseases, multiple sclerosis and other neurological diseases, psoriasis and other dermatological diseases, myasthenia gravis, systemic lupus erythematosus (SLE), subacute/chronic transplant rejection, glomerulonephritis and other renal diseases). In some embodiments, the C5 complement protein, C5a and/or C5b-9 mediated diseases to be treated include complement activation associated with dialysis or circumstances in which blood is passed over and/or through synthetic tubing and/or foreign material. In some embodiments, the C5 complement protein C5a and/or C5b-9-mediated disease to be treated is selected from the group consisting of myocardial injury relating to CABG surgery, myocardial injury relating to balloon angioplasty and myocardial injury relating to restenosis. In some embodiments, C5 complement protein, C5a and/or C5b-9-mediated disorder to be treated is selected from the group consisting of: myocardial injury relating to CABG surgery, myocardial injury relating to balloon angioplasty, myocardial injury relating to restenosis, complement protein mediated complications relating to CABG surgery, complement protein mediated complications relating to percutaneous coronary intervention, paroxysmal nocturnal hemoglobinuria, acute transplant rejection, hyperacute transplant rejection, subacute transplant rejection, and chronic transplant rejection. In some embodiments the C5 complement protein C5a and/or C5b-9-mediated disease to be treated is complications relating to CABG surgery. In a particular embodiment, the disease to be treated is myocardial injury relating to CABG surgery.

In some embodiments, the method of the invention includes administering the pharmaceutical composition comprising an aptamer having a nucleotide sequence selected from the group consisting of:, SEQ ID NOS: 3 to 4, SEQ ID NOS: 75 to 81, SEQ ID NO: 83 and SEQ ID NOS: 88 to 98, to a patient to achieve an aptamer plasma concentration that is about 0.5 to about 10 times that of the endogenous C5 complement protein. In some embodiments, the pharmaceutical aptamer compositions are administered to achieve an aptamer plasma concentration that is about 0.75 to about 5 times, 0.75 to about 3 times, and 1.5 to about 2 times that of the endogenous C5 complement protein while in other embodiments the aptamer composition is administered to achieve a concentration equivalent to that of the endogenous complement protein. In some embodiments, the pharmaceutical composition of the invention administered to achieve an aptamer plasma concentration of about 5 µM, about 4 µM, about 3 µM, about 2 µM, about 1.5 µM, about 1 µM or of about 500 nM.

Any combination of route, duration, and rate of administration may be used that is sufficient to achieve the aptamer plasma concentrations of the invention. In some embodiments the pharmaceutical composition is administered intravenously. In some embodiments, the pharmaceutical composition is administered as a bolus and/or via continuous infusion.

In particular embodiments of treating, preventing and/or ameliorating complications related to CABG surgery, particularly myocardial injury related to CABG surgery, the method of the invention comprises administering the pharmaceutical composition prior to surgery and continuing administration at least 24 hours, in some embodiments about 48 hours or in some embodiments about 72 hours. In a particular embodiment of this aspect of the invention, the desired aptamer plasma concentration, e.g., two times the endogenous complement protein concentration in some embodiments, is achieved by administration of an intravenous bolus to the patient to be treated in advance of, simultaneously with or after intravenous infusion of a lower dose of aptamer. In still other embodiments of this aspect of the invention, where the aptamer/conjugate comprises a sufficiently long half life, the aptamer pharmaceutical composition may be administered once or twice daily as an intravenous bolus dose.

In another embodiment, a diagnostic method is provided, the method comprising contacting a composition suspected of comprising C5 complement protein or a variant thereof with an aptamer comprising a nucleotide sequence selected from the group consisting of: SEQ ID NOS: 75 to 81, SEQ ID NO: 83 and SEQ ID NOS: 88 to 98 and detecting the presence or absence of C5 complement protein or a variant thereof. In some embodiments the complement protein or variant is vertebrate, particularly mammalian, and more particularly human. The present invention provides an aptamer composition having an aptamer comprising a nucleotide sequence selected from the group consisting of: SEQ ID NOS: 75 to 81, SEQ ID NO: 83 and SEQ ID NOS: 88 to 98 for use as an in vitro or in vivo diagnostic.

In some embodiments, an aptamer comprising a nucleotide sequence consisting essentially of a nucleotide sequence selected from the group consisting of SEQ ID NO: 68 and 69 is provided. In some embodiments, an aptamer comprising a nucleotide sequence consisting of a nucleotide sequence selected from the group consisting of SEQ ID NO: 68 and 69 is provided. In some embodiments of this aspect of the invention, the aptamers may be used in a diagnostic method.

DETAILED DESCRIPTION OF THE INVENTION

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description. In the specification, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present Specification will control.

The SELEX™ Method

Figure 2:
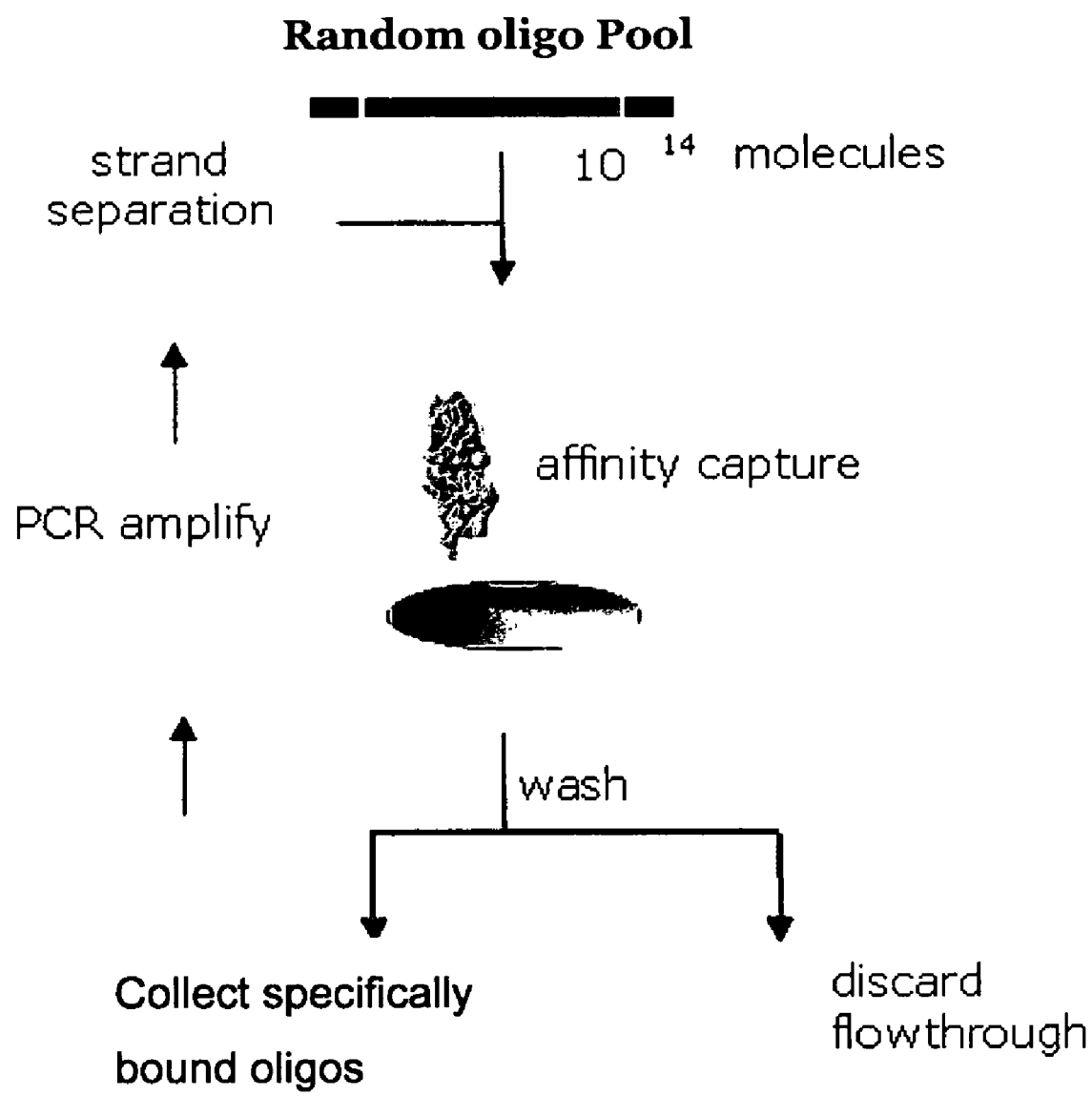
FIG. 2 is a schematic representation of the in vitro aptamer selection (SELEX™) process from pools of random sequence oligonucleotides.

A suitable method for generating an aptamer is with the process entitled "Systematic Evolution of Ligands by Exponential Enrichment" ("SELEX™") generally depicted in FIG. 2. The SELEX™ process is a method for the in vitro evolution of nucleic acid molecules with highly specific binding to target molecules and is described in, e.g., U.S. patent application Ser. No. 07/536,428, filed Jun. 11, 1990, now abandoned, U.S. Pat. No. 5,475,096 entitled "Nucleic Acid Ligands", and U.S. Pat. No. 5,270,163 (see also WO 91/19813) entitled "Nucleic Acid Ligands". Each SELEX™-identified nucleic acid ligand, i.e., each aptamer, is a specific ligand of a given target compound or molecule. The SELEX™ process is based on the unique insight that nucleic acids have sufficient capacity for forming a variety of two- and three-dimensional structures and sufficient chemical versatility available within their monomers to act as ligands (i.e., form specific binding pairs) with virtually any chemical compound, whether monomeric or polymeric. Molecules of any size or composition can serve as targets.

SELEX™ relies as a starting point upon a large library or pool of single stranded oligonucleotides comprising randomized sequences. The oligonucleotides can be modified or unmodified DNA, RNA, or DNA/RNA hybrids. In some examples, the pool comprises 100% random or partially random oligonucleotides. In other examples, the pool comprises random or partially random oligonucleotides containing at least one fixed and/or conserved sequence incorporated within randomized sequence. In other examples, the pool comprises random or partially random oligonucleotides containing at least one fixed and/or conserved sequence at its 5' and/or 3' end which may comprise a sequence shared by all the molecules of the oligonucleotide pool. Fixed sequences are sequences such as hybridization sites for PCR primers, promoter sequences for RNA polymerases (e.g., T3, T4, T7, and SP6), restriction sites, or homopolymeric sequences, such as poly A or poly T tracts, catalytic cores, sites for selective binding to affinity columns, and other sequences to facilitate cloning and/or sequencing of an oligonucleotide of interest. Conserved sequences are sequences, other than the previously described fixed sequences, shared by a number of aptamers that bind to the same target.

The oligonucleotides of the pool preferably include a randomized sequence portion as well as fixed sequences necessary for efficient amplification. Typically the oligonucleotides of the starting pool contain fixed 5' and 3' terminal sequences which flank an internal region of 30-50 random nucleotides. The randomized nucleotides can be produced in a number of ways including chemical synthesis and size selection from randomly cleaved cellular nucleic acids. Sequence variation in test nucleic acids can also be introduced or increased by mutagenesis before or during the selection/amplification iterations.

The random sequence portion of the oligonucleotide can be of any length and can comprise ribonucleotides and/or deoxyribonucleotides and can include modified or non-natural nucleotides or nucleotide analogs. See, e.g., U.S. Pat. No. 5,958,691; U.S. Pat. No. 5,660,985; U.S. Pat. No. 5,958,691; U.S. Pat. No. 5,698,687; U.S. Pat. No. 5,817,635; U.S. Pat. No. 5,672,695, and PCT Publication WO 92/07065. Random oligonucleotides can be synthesized from phosphodiester-linked nucleotides using solid phase oligonucleotide synthesis techniques well known in the art. See, e.g., Froehler et al., Nucl. Acid Res. 14:5399-5467 (1986) and Froehler et al., Tet. Lett. 27:5575-5578 (1986). Random oligonucleotides can also be synthesized using solution phase methods such as triester synthesis methods. See, e.g., Sood et al., Nucl. Acid Res. 4:2557 (1977) and Hirose et al., Tet. Lett., 28:2449 (1978). Typical syntheses carried out on automated DNA synthesis equipment yield $10^{14}$-$10^{16}$ individual molecules, a number sufficient for most SELEX™ experiments. Sufficiently large regions of random sequence in the sequence design increases the likelihood that each synthesized molecule is likely to represent a unique sequence.

The starting library of oligonucleotides may be generated by automated chemical synthesis on a DNA synthesizer. To synthesize randomized sequences, mixtures of all four nucleotides are added at each nucleotide addition step during the synthesis process, allowing for random incorporation of nucleotides. As stated above, in one embodiment, random oligonucleotides comprise entirely random sequences; however, in other embodiments, random oligonucleotides can comprise stretches of nonrandom or partially random sequences. Partially random sequences can be created by adding the four nucleotides in different molar ratios at each addition step.

The starting library of oligonucleotides may be either RNA or DNA. In those instances where an RNA library is to be used as the starting library it is typically generated by transcribing a DNA library in vitro using T7 RNA polymerase or modified T7 RNA polymerases and purified. The RNA or DNA library is then mixed with the target under conditions favorable for binding and subjected to step-wise iterations of binding, partitioning and amplification, using the same general selection scheme, to achieve virtually any desired criterion of binding affinity and selectivity. More specifically, starting with a mixture containing the starting pool of nucleic acids, the SELEX™ method includes steps of: (a) contacting the mixture with the target under conditions favorable for binding; (b) partitioning unbound nucleic acids from those nucleic acids which have bound specifically to target molecules; (c) dissociating the nucleic acid-target complexes; (d) amplifying the nucleic acids dissociated from the nucleic acid-target complexes to yield a ligand-enriched mixture of nucleic acids; and (e) reiterating the steps of binding, partitioning, dissociating and amplifying through as many cycles as desired to yield highly specific, high affinity nucleic acid ligands to the target molecule. In those instances where RNA aptamers are being selected, the SELEX™ method further comprises the steps of: (i) reverse transcribing the nucleic acids dissociated from the nucleic acid-target complexes before amplification in step (d); and (ii) transcribing the amplified nucleic acids from step (d) before restarting the process.

Within a nucleic acid mixture containing a large number of possible sequences and structures, there is a wide range of binding affinities for a given target. A nucleic acid mixture comprising, for example, a 20 nucleotide randomized segment can have $4^{20}$ candidate possibilities. Those which have the higher affinity constants for the target are most likely to bind to the target. After partitioning, dissociation and amplification, a second nucleic acid mixture is generated, enriched for the higher binding affinity candidates. Additional rounds of selection progressively favor the best ligands until the resulting nucleic acid mixture is predominantly composed of only one or a few sequences. These can then be cloned, sequenced and individually tested for binding affinity as pure ligands or aptamers.

Cycles of selection and amplification are repeated until a desired goal is achieved. In the most general case, selection/amplification is continued until no significant improvement in binding strength is achieved on repetition of the cycle. The method is typically used to sample approximately $10^{14}$ different nucleic acid species but may be used to sample as many as about $10^{18}$ different nucleic acid species. Generally, nucleic acid aptamer molecules are selected in a 5 to 20 cycle procedure. In one embodiment, heterogeneity is introduced only in the initial selection stages and does not occur throughout the replicating process.

In one embodiment of SELEX™, the selection process is so efficient at isolating those nucleic acid ligands that bind most strongly to the selected target, that only one cycle of selection and amplification is required. Such an efficient selection may occur, for example, in a chromatographic-type process wherein the ability of nucleic acids to associate with targets bound on a column operates in such a manner that the column is sufficiently able to allow separation and isolation of the highest affinity nucleic acid ligands.

In many cases, it is not necessarily desirable to perform the iterative steps of SELEX™ until a single nucleic acid ligand is identified. The target-specific nucleic acid ligand solution may include a family of nucleic acid structures or motifs that have a number of conserved sequences and a number of sequences which can be substituted or added without significantly affecting the affinity of the nucleic acid ligands to the target. By terminating the SELEX™ process prior to completion, it is possible to determine the sequence of a number of members of the nucleic acid ligand solution family.

A variety of nucleic acid primary, secondary and tertiary structures are known to exist. The structures or motifs that have been shown most commonly to be involved in non-Watson-Crick type interactions are referred to as hairpin loops, symmetric and asymmetric bulges, pseudoknots and myriad combinations of the same. Almost all known cases of such motifs suggest that they can be formed in a nucleic acid sequence of no more than 30 nucleotides. For this reason, it is often preferred that SELEX™ procedures with contiguous randomized segments be initiated with nucleic acid sequences containing a randomized segment of between about 20 to about 50 nucleotides and in some embodiments of about 30 to about 40 nucleotides. In one example, the 5'-fixed:random:3'-fixed sequence comprises a random sequence of about 30 to about 50 nucleotides.

The core SELEX™ method has been modified to achieve a number of specific objectives. For example, U.S. Pat. No. 5,707,796 describes the use of SELEX™ in conjunction with gel electrophoresis to select nucleic acid molecules with specific structural characteristics, such as bent DNA. U.S. Pat. No. 5,763,177 describes SELEX™ based methods for selecting nucleic acid ligands containing photoreactive groups capable of binding and/or photocrosslinking to and/or photo-inactivating a target molecule. U.S. Pat. No. 5,567,588 and U.S. Pat. No. 5,861,254 describe SELEX™ based methods which achieve highly efficient partitioning between oligonucleotides having high and low affinity for a target molecule. U.S. Pat. No. 5,496,938 describes methods for obtaining improved nucleic acid ligands after the SELEX™ process has been performed. U.S. Pat. No. 5,705,337 describes methods for covalently linking a ligand to its target.

SELEX™ can also be used to obtain nucleic acid ligands that bind to more than one site on the target molecule, and to obtain nucleic acid ligands that include non-nucleic acid species that bind to specific sites on the target. SELEX™ provides means for isolating and identifying nucleic acid ligands which bind to any envisionable target, including large and small biomolecules such as nucleic acid-binding proteins and proteins not known to bind nucleic acids as part of their biological function as well as cofactors and other small molecules. For example, U.S. Pat. No. 5,580,737 discloses nucleic acid sequences identified through SELEX™ which are capable of binding with high affinity to caffeine and the closely related analog, theophylline.

Counter-SELEX™ is a method for improving the specificity of nucleic acid ligands to a target molecule by eliminating nucleic acid ligand sequences with cross-reactivity to one or more non-target molecules. Counter-SELEX™ is comprised of the steps of: (a) preparing a candidate mixture of nucleic acids; (b) contacting the candidate mixture with the target, wherein nucleic acids having an increased affinity to the target relative to the candidate mixture may be partitioned from the remainder of the candidate mixture; (c) partitioning the increased affinity nucleic acids from the remainder of the candidate mixture; (d) dissociating the increased affinity nucleic acids from the target; e) contacting the increased affinity nucleic acids with one or more non-target molecules such that nucleic acid ligands with specific affinity for the non-target molecule(s) are removed; and f) amplifying the nucleic acids with specific affinity only to the target molecule to yield a mixture of nucleic acids enriched for nucleic acid sequences with a relatively higher affinity and specificity for binding to the target molecule. As described above for SELEX™, cycles of selection and amplification are repeated as necessary until a desired goal is achieved.

One potential problem encountered in the use of nucleic acids as therapeutics and vaccines is that oligonucleotides in their phosphodiester form may be quickly degraded in body fluids by intracellular and extracellular enzymes such as endonucleases and exonucleases before the desired effect is manifest. The SELEX™ method thus encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX™-identified nucleic acid ligands containing modified nucleotides are described, e.g., in U.S. Pat. No. 5,660,985, which describes oligonucleotides containing nucleotide derivatives chemically modified at the 2' position of ribose, 5 position of pyrimidines, and 8 position of purines, U.S. Pat. No. 5,756,703 which describes oligonucleotides containing various 2'-modified pyrimidines, and U.S. Pat. No. 5,580,737 which describes highly specific nucleic acid ligands containing one or more nucleotides modified with 2'-amino (2'-$NH_2$), 2'-fluoro (2'-F), and/or 2'-OMe (2'-OMe) substituents.

Modifications of the nucleic acid ligands contemplated in this invention include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole. Modifications to generate oligonucleotide populations which are resistant to nucleases can also include one or more substitute internucleotide linkages, altered sugars, altered bases, or combinations thereof. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, and unusual base-pairing combinations such as the isobases isocytidine and isoguanidine. Modifications can also include 3' and 5' modifications such as capping.

In one embodiment, oligonucleotides are provided in which the P(O)O group is replaced by P(O)S ("thioate"), P(S)S ("dithioate"), P(O)$NR_2$ ("amidate"), P(O)R, P(O)OR', CO or $CH_2$ ("formacetal") or 3'-amine (—NH—$CH_2$—$CH_2$—), wherein each R or R' is independently H or substituted or unsubstituted alkyl. Linkage groups can be attached to adjacent nucleotides through an —O—, —N—, or —S— linkage. Not all linkages in the oligonucleotide are required to be identical. As used herein, the term phosphorothioate encompasses one or more non-bridging oxygen atoms in a phosphodiester bond replaced by one or more sulfur atoms.

In further embodiments, the oligonucleotides comprise modified sugar groups, for example, one or more of the hydroxyl groups is replaced with halogen, aliphatic groups, or functionalized as ethers or amines. In one embodiment, the 2'-position of the furanose residue is substituted by any of an OMe, O-alkyl, O-allyl, S-alkyl, S-allyl, or halo group. Methods of synthesis of 2'-modified sugars are described, e.g., in Sproat, et al., Nucl. Acid Res. 19:733-738 (1991); Cotten, et al., Nucl. Acid Res. 19:2629-2635 (1991); and Hobbs, et al., Biochemistry 12:5138-5145 (1973). Other modifications are known to one of ordinary skill in the art. Such modifications may be pre-SELEX™ process modifications or post-SELEX™ process modifications (modification of previously identified unmodified ligands) or may be made by incorporation into the SELEX process.

Pre-SELEX process modifications or those made by incorporation into the SELEX process yield nucleic acid ligands with both specificity for their SELEX™ target and improved stability, e.g., in vivo stability. Post-SELEX™ process modifications made to nucleic acid ligands may result in improved stability, e.g., in vivo stability without adversely affecting the binding capacity of the nucleic acid ligand.

The SELEX™ method encompasses combining selected oligonucleotides with other selected oligonucleotides and non-oligonucleotide functional units as described in U.S. Pat. No. 5,637,459 and U.S. Pat. No. 5,683,867. The SELEX™ method further encompasses combining selected nucleic acid ligands with lipophilic or non-immunogenic high molecular weight compounds in a diagnostic or therapeutic complex, as described, e.g., in U.S. Pat. No. 6,011,020, U.S. Pat. No. 6,051,698, and PCT Publication No. WO 98/18480. These patents and applications teach the combination of a broad array of shapes and other properties, with the efficient amplification and replication properties of oligonucleotides, and with the desirable properties of other molecules.

The identification of nucleic acid ligands to small, flexible peptides via the SELEX™ method has also been explored. Small peptides have flexible structures and usually exist in solution in an equilibrium of multiple conformers, and thus it was initially thought that binding affinities may be limited by the conformational entropy lost upon binding a flexible peptide. However, the feasibility of identifying nucleic acid ligands to small peptides in solution was demonstrated in U.S. Pat. No. 5,648,214. In this patent, high affinity RNA nucleic acid ligands to substance P, an 11 amino acid peptide, were identified.

The aptamers with specificity and binding affinity to the target(s) of the present invention are typically selected by the SELEX™ process as described herein. As part of the SELEX™ process, the sequences selected to bind to the target are then optionally minimized to determine the minimal sequence having the desired binding affinity. The selected sequences and/or the minimized sequences are optionally optimized by performing random or directed mutagenesis of the sequence to increase binding affinity or alternatively to determine which positions in the sequence are essential for binding activity. Additionally, selections can be performed with sequences incorporating modified nucleotides to stabilize the aptamer molecules against degradation in vivo.

2'Modified SELEX™

In order for an aptamer to be suitable for use as a therapeutic, it is preferably inexpensive to synthesize, safe and stable in vivo. Wild-type RNA and DNA aptamers are typically not stable in vivo because of their susceptibility to degradation by nucleases. Resistance to nuclease degradation can be greatly increased by the incorporation of modifying groups at the 2'-position.

Fluoro and amino groups have been successfully incorporated into oligonucleotide libraries from which aptamers have been subsequently selected. However, these modifications greatly increase the cost of synthesis of the resultant aptamer, and may introduce safety concerns in some cases because of the possibility that the modified nucleotides could be recycled into host DNA by degradation of the modified oligonucleotides and subsequent use of the nucleotides as substrates for DNA synthesis.

Aptamers that contain 2'-OMe ("2'-OMe") nucleotides, as provided in some embodiments herein, overcome many of these drawbacks. Oligonucleotides containing 2'-OMe nucleotides are nuclease-resistant and inexpensive to synthesize. Although 2'-OMe nucleotides are ubiquitous in biological systems, natural polymerases do not accept 2'-O-methyl NTPs as substrates under physiological conditions, thus there are no safety concerns over the recycling of 2'-OMe nucleotides into host DNA. The SELEX™ method used to generate 2'-modified aptamers is described, e.g., in U.S. Provisional Patent Application Ser. No. 60/430,761, filed Dec. 3, 2002, U.S. Provisional Patent Application Ser. No. 60/487,474, filed Jul. 15, 2003, U.S. Provisional Patent Application Ser. No. 60/517,039, filed Nov. 4, 2003, U.S. patent application Ser. No. 10/729,581, filed Dec. 3, 2003 (pending), and U.S. patent application Ser. No. 10/873,856, filed Jun. 21, 2004 (pending), entitled "Method for in vitro Selection of 2'-OMe Substituted Nucleic Acids", each of which is herein incorporated by reference in its entirety.

The present invention includes aptamers that bind to and modulate the function of complement protein C5 which contain modified nucleotides (e.g., nucleotides which have a modification at the 2'position) to make the oligonucleotide more stable than the unmodified oligonucleotide to enzymatic and chemical degradation as well as thermal and physical degradation. Although there are several examples of 2'-OMe containing aptamers in the literature (see, e.g., Green et al., Current Biology 2, 683-695, 1995) these were generated by the in vitro selection of libraries of modified transcripts in which the C and U residues were 2'-fluoro (2'-F) substituted and the A and G residues were 2'-OH. Once functional sequences were identified then each A and G residue was tested for tolerance to 2'-OMe substitution, and the aptamer was re-synthesized having all A and G residues which tolerated 2'-OMe substitution as 2'-OMe residues. Most of the A and G residues of aptamers generated in this two-step fashion tolerate substitution with 2'-OMe residues, although, on average, approximately 20% do not. Consequently, aptamers generated using this method tend to contain from two to four 2'-OH residues, and stability and cost of synthesis are compromised as a result. By incorporating modified nucleotides into the transcription reaction which generate stabilized oligonucleotides used in oligonucleotide pools from which aptamers are selected and enriched by SELEX™ (and/or any of its variations and improvements, including those described herein), the methods of the present invention eliminate the need for stabilizing the selected aptamer oligonucleotides (e.g., by resynthesizing the aptamer oligonucleotides with modified nucleotides).

In one embodiment, the present invention provides aptamers comprising combinations of 2'-OH, 2'-F, 2'-deoxy, and 2'-OMe modifications of the ATP, GTP, CTP, TTP, and UTP nucleotides. In another embodiment, the present invention provides aptamers comprising combinations of 2'-OH, 2'-F, 2'-deoxy, 2'-OMe, 2'-$NH_2$, and 2'-methoxyethyl modifications of the ATP, GTP, CTP, TTP, and UTP nucleotides. In another embodiment, the present invention provides aptamers comprising $5^6$ combinations of 2'-OH, 2'-F, 2'-deoxy, 2'-OMe, 2'-$NH_2$, and 2'-methoxyethyl modifications of the ATP, GTP, CTP, TTP, and UTP nucleotides.

2' modified aptamers of the invention are created using modified polymerases, e.g., a modified T7 polymerase, having a rate of incorporation of modified nucleotides having bulky substituents at the furanose 2' position that is higher than that of wild-type polymerases. For example, a single mutant T7 polymerase (Y639F) in which the tyrosine residue at position 639 has been changed to phenylalanine readily utilizes 2'deoxy, 2'amino-, and 2'fluoro-nucleotide triphosphates (NTPs) as substrates and has been widely used to synthesize modified RNAs for a variety of applications. However, this mutant T7 polymerase reportedly can not readily utilize (i.e., incorporate) NTPs with bulky 2'-substituents such as 2'-OMe or 2'-azido (2'-N$_3$) substituents. For incorporation of bulky 2' substituents, a double T7 polymerase mutant (Y639F/H784A) having the histidine at position 784 changed to an alanine residue in addition to the Y639F mutation has been described and has been used in limited circumstances to incorporate modified pyrimidine NTPs. See Padilla, R. and Sousa, R., Nucleic Acids Res., 2002, 30(24): 138. A single mutant T7 polymerase (H784A) having the histidine at position 784 changed to an alanine residue has also been described. Padilla et al., Nucleic Acids Research, 2002, 30: 138. In both the Y639F/H784A double mutant and H784A single mutant T7 polymerases, the change to a smaller amino acid residue such as alanine allows for the incorporation of bulkier nucleotide substrates, e.g., 2'-O methyl substituted nucleotides.

Generally, it has been found that under the conditions disclosed herein, the Y693F single mutant can be used for the incorporation of all 2'-OMe substituted NTPs except GTP and the Y639F/H784A double mutant can be used for the incorporation of all 2'-OMe substituted NTPs including GTP. It is expected that the H784A single mutant possesses properties similar to the Y639F and the Y639F/H784A mutants when used under the conditions disclosed herein.

2'-modified oligonucleotides may be synthesized entirely of modified nucleotides, or with a subset of modified nucleotides. The modifications can be the same or different. All nucleotides may be modified, and all may contain the same modification. All nucleotides may be modified, but contain different modifications, e.g., all nucleotides containing the same base may have one type of modification, while nucleotides containing other bases may have different types of modification. All purine nucleotides may have one type of modification (or are unmodified), while all pyrimidine nucleotides have another, different type of modification (or are unmodified). In this way, transcripts, or pools of transcripts are generated using any combination of modifications, including for example, ribonucleotides (2'-OH), deoxyribonucleotides (2'-deoxy), 2'-F, and 2'-OMe nucleotides. A transcription mixture containing 2'-OMe C and U and 2'-OH A and G is referred to as a "rRmY" mixture and aptamers selected therefrom are referred to as "rRmY" aptamers. A transcription mixture containing deoxy A and G and 2'-OMe U and C is referred to as a "dRmY" mixture and aptamers selected therefrom are referred to as "dRmY" aptamers. A transcription mixture containing 2'-OMe A, C, and U, and 2'-OH G is referred to as a "rGmH" mixture and aptamers selected therefrom are referred to as "rGmH" aptamers. A transcription mixture alternately containing 2'-OMe A, C, U and G and 2'-OMe A, U and C and 2'-F G is referred to as a "alternating mixture' and aptamers selected therefrom are referred to as "alternating mixture" aptamers. A transcription mixture containing 2'-OMe A, U, C, and G, where up to 10% of the G's are ribonucleotides is referred to as a "r/mGmH" mixture and aptamers selected therefrom are referred to as "r/mGmH" aptamers. A transcription mixture containing 2'-OMe A, U, and C, and 2'-F G is referred to as a "fGmH" mixture and aptamers selected therefrom are referred to as "fGmH" aptamers. A transcription mixture containing 2'-OMe A, U, and C, and deoxy G is referred to as a "dGmH" mixture and aptamers selected therefrom are referred to as "dGmH" aptamers. A transcription mixture containing deoxy A, and 2'-OMe C, G and U is referred to as a "dAmB" mixture and aptamers selected therefrom are referred to as "dAmB" aptamers, and a transcription mixture containing all 2'-OH nucleotides is referred to as a "rN" mixture and aptamers selected therefrom are referred to as "rN" or "rRrY" aptamers. A "mRmY" aptamer is one containing all 2'-OMe nucleotides and is usually derived from a r/mGmH oligonucleotide by post-SELEX replacement, when possible, of any 2'-OH Gs with 2'-OMe Gs.

A preferred embodiment includes any combination of 2'-OH, 2'-deoxy and 2'-OMe nucleotides. A more preferred embodiment includes any combination of 2'-deoxy and 2'-OMe nucleotides. An even more preferred embodiment is with any combination of 2'-deoxy and 2'-OMe nucleotides in which the pyrimidines are 2'-OMe (such as dRmY, mRmY or dGmH).

Incorporation of modified nucleotides into the aptamers of the invention is accomplished before (pre-) the selection process (e.g., a pre-SELEX™ process modification). Optionally, aptamers of the invention in which modified nucleotides have been incorporated by pre-SELEX™ process modification can be further modified by post-SELEX™ process modification (i.e., a post-SELEX™ process modification after a pre-SELEX™ modification). Pre-SELEX™ process modifications yield modified nucleic acid ligands with specificity for the SELEX™ target and also improved in vivo stability. Post-SELEX™ process modifications, i.e., modification (e.g., truncation, deletion, substitution or additional nucleotide modifications of previously identified ligands having nucleotides incorporated by pre-SELEX™ process modification) can result in a further improvement of in vivo stability without adversely affecting the binding capacity of the nucleic acid ligand having nucleotides incorporated by pre-SELEX™ process modification.

To generate pools of 2'-modified (e.g., 2'-OMe) RNA transcripts in conditions under which a polymerase accepts 2'-modified NTPs the preferred polymerase is the Y693F/H784A double mutant or the Y693F single mutant. Other polymerases, particularly those that exhibit a high tolerance for bulky 2'-substituents, may also be used in the present invention. Such polymerases can be screened for this capability by assaying their ability to incorporate modified nucleotides under the transcription conditions disclosed herein.

A number of factors have been determined to be important for the transcription conditions useful in the methods disclosed herein. For example, increases in the yields of modified transcript are observed when a leader sequence is incorporated into the 5' end of a fixed sequence at the 5' end of the DNA transcription template, such that at least about the first 6 residues of the resultant transcript are all purines.

Another important factor in obtaining transcripts incorporating modified nucleotides is the presence or concentration of 2'-OH GTP. Transcription can be divided into two phases: the first phase is initiation, during which an NTP is added to the 3'-hydroxyl end of GTP (or another substituted guanosine) to yield a dinucleotide which is then extended by about 10-12 nucleotides; the second phase is elongation, during which transcription proceeds beyond the addition of the first about 10-12 nucleotides. It has been found that small amounts of 2'-OH GTP added to a transcription mixture containing an excess of 2'-OMe GTP are sufficient to enable the polymerase to initiate transcription using 2'-OH GTP, but once transcription enters the elongation phase the reduced discrimination between 2'-OMe and 2'-OH GTP, and the excess of 2'-OMe GTP over 2'-OH GTP allows the incorporation of principally the 2'-OMe GTP.

Another important factor in the incorporation of 2'-OMe substituted nucleotides into transcripts is the use of both divalent magnesium and manganese in the transcription mixture. Different combinations of concentrations of magnesium chloride and manganese chloride have been found to affect yields of 2'-OMe transcripts, the optimum concentration of the magnesium and manganese chloride being dependent on the concentration in the transcription reaction mixture of NTPs which complex divalent metal ions. To obtain the greatest yields of maximally 2' substituted OMe transcripts (i.e., all A, C, and U and about 90% of G nucleotides), concentrations of approximately 5 mM magnesium chloride and 1.5 mM manganese chloride are preferred when each NTP is present at a concentration of 0.5 mM. When the concentration of each NTP is 1.0 mM, concentrations of approximately 6.5 mM magnesium chloride and 2.0 mM manganese chloride are preferred. When the concentration of each NTP is 2.0 mM, concentrations of approximately 9.6 mM magnesium chloride and 2.9 mM manganese chloride are preferred. In any case, departures from these concentrations of up to two-fold still give significant amounts of modified transcripts.

Priming transcription with GMP or guanosine is also important. This effect results from the specificity of the polymerase for the initiating nucleotide. As a result, the 5'-terminal nucleotide of any transcript generated in this fashion is likely to be 2'-OH G. The preferred concentration of GMP (or guanosine) is 0.5 mM and even more preferably 1 mM. It has also been found that including PEG, preferably PEG-8000, in the transcription reaction is useful to maximize incorporation of modified nucleotides.

For maximum incorporation of 2'-OMe ATP (100%), UTP (100%), CTP (100%) and GTP (~90%) ("r/mGmH") into transcripts the following conditions are preferred: HEPES buffer 200 mM, DTT 40 mM, spermidine 2 mM, PEG-8000 10% (w/v), Triton X-100 0.01% (w/v), $MgCl_2$ 5 mM (6.5 mM where the concentration of each 2'-OMe NTP is 1.0 mM), $MnCl_2$ 1.5 mM (2.0 mM where the concentration of each 2'-OMe NTP is 1.0 mM), 2'-OMe NTP (each) 500 µM (more preferably, 1.0 mM), 2'-OH GTP 30 µM, 2'-OH GMP 500 µM, pH 7.5, Y639F/H784A T7 RNA Polymerase 15 units/ml, inorganic pyrophosphatase 5 units/ml, and an all-purine leader sequence of at least 8 nucleotides long. As used herein, one unit of the Y639F/H784A mutant T7 RNA polymerase (or any other mutant T7 RNA polymerase specified herein) is defined as the amount of enzyme required to incorporate 1 nmole of 2'-OMe NTPs into transcripts under the r/mGmH conditions. As used herein, one unit of inorganic pyrophosphatase is defined as the amount of enzyme that will liberate 1.0 mole of inorganic orthophosphate per minute at pH 7.2 and 25° C.

For maximum incorporation (100%) of 2'-OMe ATP, UTP and CTP ("rGmH") into transcripts the following conditions are preferred: HEPES buffer 200 mM, DTT 40 mM, spermidine 2 mM, PEG-8000 10% (w/v), Triton X-100 0.01% (w/v), $MgCl_2$ 5 mM (9.6 mM where the concentration of each 2'-OMe NTP is 2.0 mM), $MnCl_2$ 1.5 mM (2.9 mM where the concentration of each 2'-OMe NTP is 2.0 mM), 2'-OMe NTP (each) 500 µM (more preferably, 2.0 mM), pH 7.5, Y639F T7 RNA Polymerase 15 units/ml, inorganic pyrophosphatase 5 units/ml, and an all-purine leader sequence of at least 8 nucleotides long.

For maximum incorporation (100%) of 2'-OMe UTP and CTP ("rRmY") into transcripts the following conditions are preferred: HEPES buffer 200 mM, DTT 40 mM, spermidine 2 mM, PEG-8000 10% (w/v), Triton X-100 0.01% (w/v), $MgCl_2$ 5 mM (9.6 mM where the concentration of each 2'-OMe NTP is 2.0 mM), $MnCl_2$ 1.5 mM (2.9 mM where the concentration of each 2'-OMe NTP is 2.0 mM), 2'-OMe NTP (each) 500 µM (more preferably, 2.0 mM), pH 7.5, Y639F/H784A T7 RNA Polymerase 15 units/ml, inorganic pyrophosphatase 5 units/ml, and an all-purine leader sequence of at least 8 nucleotides long.

For maximum incorporation (100%) of deoxy ATP and GTP and 2'-OMe UTP and CTP ("dRmY") into transcripts the following conditions are preferred: HEPES buffer 200 mM, DTT 40 mM, spermine 2 mM, spermidine 2 mM, PEG-8000 10% (w/v), Triton X-100 0.01% (w/v), $MgCl_2$ 9.6 mM, $MnCl_2$ 2.9 mM, 2'-OMe NTP (each) 2.0 mM, pH 7.5, Y639F T7 RNA Polymerase 15 units/ml, inorganic pyrophosphatase 5 units/ml, and an all-purine leader sequence of at least 8 nucleotides long.

For maximum incorporation (100%) of 2'-OMe ATP, UTP and CTP and 2'-F GTP ("fGmH") into transcripts the following conditions are preferred: HEPES buffer 200 mM, DTT 40 mM, spermidine 2 mM, PEG-8000 10% (w/v), Triton X-100 0.01% (w/v), $MgCl_2$ 9.6 mM, $MnCl_2$ 2.9 mM, 2'-OMe NTP (each) 2.0 mM, pH 7.5, Y639F T7 RNA Polymerase 15 units/ ml, inorganic pyrophosphatase 5 units/ml, and an all-purine leader sequence of at least 8 nucleotides long.

For maximum incorporation (100%) of deoxy ATP and 2'-OMe UTP, GTP and CTP ("dAmB") into transcripts the following conditions are preferred: HEPES buffer 200 mM, DTT 40 mM, spermidine 2 mM, PEG-8000 10% (w/v), Triton X-100 0.01% (w/v), $MgCl_2$ 9.6 mM, $MnCl_2$ 2.9 mM, 2'-OMe NTP (each) 2.0 mM, pH 7.5, Y639F T7 RNA Polymerase 15 units/ml, inorganic pyrophosphatase 5 units/ml, and an all-purine leader sequence of at least 8 nucleotides long.

For each of the above (a) transcription is preferably performed at a temperature of from about 20° C. to about 50° C., preferably from about 30° C. to 45° C., and more preferably at about 37° C. for a period of at least two hours and (b) 50-300 nM of a double stranded DNA transcription template is used (200 nM template is used in round 1 to increase diversity (300 nM template is used in dRmY transcriptions)), and for subsequent rounds approximately 50 nM, a 1/10 dilution of an optimized PCR reaction, using conditions described herein, is used). The preferred DNA transcription templates are described below (where ARC254 and ARC256 transcribe under all 2'-OMe conditions and ARC255 transcribes under rRmY conditions).

```
ARC254 (SEQ ID NO: 99):
5'-CATCGATGCTAGTCGTAACGATCCNNNNNNNNNNNNNNNNNNNNNNN

NNNNNNNNCGAGAACGTTCTCTCCTCTCCCTATAGTGAGTCGTATTA-3'

ARC255 (SEQ ID NO: 100):
5'-CATGCATCGCGACTGACTAGCCGNNNNNNNNNNNNNNNNNNNNNNNN

NNNNNNNGTAGAACGTTCTCTCCTCTCCCTATAGTGAGTCGTATTA-3'

ARC256 (SEQ ID NO: 101):
5'-CATCGATCGATCGATCGACAGCGNNNNNNNNNNNNNNNNNNNNNNNN

NNNNNNNGTAGAACGTTCTCTCCTCTCCCTATAGTGAGTCGTATTA-3'
```

Under rN transcription conditions of the present invention, the transcription reaction mixture comprises 2'-OH adenosine triphosphates (ATP), 2'-OH guanosine triphosphates (GTP), 2'-OH cytidine triphosphates (CTP), and 2'-OH uridine triphosphates (UTP). The modified oligonucleotides produced using the rN transcription mixtures of the present invention comprise substantially all 2'-OH adenosine, 2'-OH guanosine, 2'-OH cytidine, and 2'-OH uridine. In a preferred embodiment of rN transcription, the resulting modified oligonucleotides comprise a sequence where at least 80% of all adenosine nucleotides are 2'-OH adenosine, at least 80% of all guanosine nucleotides are 2'-OH guanosine, at least 80% of all cytidine nucleotides are 2'-OH cytidine, and at least 80% of all uridine nucleotides are 2'-OH uridine. In a more preferred embodiment of rN transcription, the resulting modified oligonucleotides of the present invention comprise a sequence where at least 90% of all adenosine nucleotides are 2'-OH adenosine, at least 90% of all guanosine nucleotides are 2'-OH guanosine, at least 90% of all cytidine nucleotides are 2'-OH cytidine, and at least 90% of all uridine nucleotides are 2'-OH uridine. In a most preferred embodiment of rN transcription, the modified oligonucleotides of the present invention comprise a sequence where 100% of all adenosine nucleotides are 2'-OH adenosine, 100% of all guanosine nucleotides are 2'-OH guanosine, 100% of all cytidine nucleotides are 2'-OH cytidine, and 100% of all uridine nucleotides are 2'-OH uridine.

Under rRmY transcription conditions of the present invention, the transcription reaction mixture comprises 2'-OH adenosine triphosphates, 2'-OH guanosine triphosphates, 2'-OMe cytidine triphosphates, and 2'-OMe uridine triphosphates. The modified oligonucleotides produced using the rRmY transcription mixtures of the present invention comprise substantially all 2'-OH adenosine, 2'-OH guanosine, 2'-OMe cytidine and 2'-OMe uridine. In a preferred embodiment, the resulting modified oligonucleotides comprise a sequence where at least 80% of all adenosine nucleotides are 2'-OH adenosine, at least 80% of all guanosine nucleotides are 2'-OH guanosine, at least 80% of all cytidine nucleotides are 2'-OMe cytidine and at least 80% of all uridine nucleotides are 2'-OMe uridine. In a more preferred embodiment, the resulting modified oligonucleotides comprise a sequence where at least 90% of all adenosine nucleotides are 2'-OH adenosine, at least 90% of all guanosine nucleotides are 2'-OH guanosine, at least 90% of all cytidine nucleotides are 2'-OMe cytidine and at least 90% of all uridine nucleotides are 2'-OMe uridine In a most preferred embodiment, the resulting modified oligonucleotides comprise a sequence where 100% of all adenosine nucleotides are 2'-OH adenosine, 100% of all guanosine nucleotides are 2'-OH guanosine, 100% of all cytidine nucleotides are 2'-OMe cytidine and 100% of all uridine nucleotides are 2'-OMe uridine.

Under dRmY transcription conditions of the present invention, the transcription reaction mixture comprises 2'-deoxy adenosine triphosphates, 2'-deoxy guanosine triphosphates, 2'-O-methyl cytidine triphosphates, and 2'-O-methyl uridine triphosphates. The modified oligonucleotides produced using the dRmY transcription conditions of the present invention comprise substantially all 2'-deoxy adenosine, 2'-deoxy guanosine, 2'-O-methyl cytidine, and 2'-O-methyl uridine. In a preferred embodiment, the resulting modified oligonucleotides of the present invention comprise a sequence where at least 80% of all adenosine nucleotides are 2'-deoxy adenosine, at least 80% of all guanosine nucleotides are 2'-deoxy guanosine, at least 80% of all cytidine nucleotides are 2'-O-methyl cytidine, and at least 80% of all uridine nucleotides are 2'-O-methyl uridine. In a more preferred embodiment, the resulting modified oligonucleotides of the present invention comprise a sequence where at least 90% of all adenosine nucleotides are 2'-deoxy adenosine, at least 90% of all guanosine nucleotides are 2'-deoxy guanosine, at least 90% of all cytidine nucleotides are 2'-O-methyl cytidine, and at least 90% of all uridine nucleotides are 2'-O-methyl uridine. In a most preferred embodiment, the resulting modified oligonucleotides of the present invention comprise a sequence where 100% of all adenosine nucleotides are 2'-deoxy adenosine, 100% of all guanosine nucleotides are 2'-deoxy guanosine, 100% of all cytidine nucleotides are 2'-O-methyl cytidine, and 100% of all uridine nucleotides are 2'-O-methyl uridine.

Under rGmH transcription conditions of the present invention, the transcription reaction mixture comprises 2'-OH guanosine triphosphates, 2'-OMe cytidine triphosphates, 2'-OMe uridine triphosphates, and 2'-OMe adenosine triphosphates. The modified oligonucleotides produced using the rGmH transcription mixtures of the present invention comprise substantially all 2'-OH guanosine, 2'-OMe cytidine, 2'-OMe uridine, and 2'-OMe adenosine. In a preferred embodiment, the resulting modified oligonucleotides comprise a sequence where at least 80% of all guanosine nucleotides are 2'-OH guanosine, at least 80% of all cytidine nucleotides are 2'-OMe cytidine, at least 80% of all uridine nucleotides are 2'-OMe uridine, and at least 80% of all adenosine nucleotides are 2'-OMe adenosine. In a more preferred embodiment, the resulting modified oligonucleotides comprise a sequence where at least 90% of all guanosine nucleotides are 2'-OH guanosine, at least 90% of all cytidine nucleotides are 2'-OMe cytidine, at least 90% of all uridine nucleotides are 2'-OMe uridine, and at least 90% of all adenosine nucleotides are 2'-OMe adenosine. In a most preferred embodiment, the resulting modified oligonucleotides comprise a sequence where 100% of all guanosine nucleotides are 2'-OH guanosine, 100% of all cytidine nucleotides are 2'-OMe cytidine, 100% of all uridine nucleotides are 2'-OMe uridine, and 100% of all adenosine nucleotides are 2'-OMe adenosine.

Under r/mGmH transcription conditions of the present invention, the transcription reaction mixture comprises 2'-OMe adenosine triphosphate, 2'-OMe cytidine triphosphate, 2'-OMe guanosine triphosphate, 2'-OMe uridine triphosphate and 2'-OH guanosine triphosphate. The resulting modified oligonucleotides produced using the r/mGmH transcription mixtures of the present invention comprise substantially all 2'-OMe adenosine, 2'-OMe cytidine, 2'-OMe guanosine, and 2'-OMe uridine, wherein the population of guanosine nucleotides has a maximum of about 10% 2'-OH guanosine. In a preferred embodiment, the resulting r/mGmH modified oligonucleotides of the present invention comprise a sequence where at least 80% of all adenosine nucleotides are 2'-OMe adenosine, at least 80% of all cytidine nucleotides are 2'-OMe cytidine, at least 80% of all guanosine nucleotides are 2'-OMe guanosine, at least 80% of all uridine nucleotides are 2'-OMe uridine, and no more than about 10% of all guanosine nucleotides are 2'-OH guanosine. In a more preferred embodiment, the resulting modified oligonucleotides comprise a sequence where at least 90% of all adenosine nucleotides are 2'-OMe adenosine, at least 90% of all cytidine nucleotides are 2'-OMe cytidine, at least 90% of all guanosine nucleotides are 2'-OMe guanosine, at least 90% of all uridine nucleotides are 2'-OMe uridine, and no more than about 10% of all guanosine nucleotides are 2'-OH guanosine. In a most preferred embodiment, the resulting modified oligonucleotides comprise a sequence where 100% of all adenosine nucleotides are 2'-OMe adenosine, 100% of all cytidine nucleotides are 2'-OMe cytidine, 90% of all guanosine nucleotides are 2'-OMe guanosine, and 100% of all uridine nucleotides are 2'-OMe uridine, and no more than about 10% of all guanosine nucleotides are 2'-OH guanosine.

Under fGmH transcription conditions of the present invention, the transcription reaction mixture comprises 2'-OMe adenosine triphosphates, 2'-OMe uridine triphosphates, 2'-OMe cytidine triphosphates, and 2'-F guanosine triphosphates. The modified oligonucleotides produced using the fGmH transcription conditions of the present invention comprise substantially all 2'-OMe adenosine, 2'-OMe uridine, 2'-OMe cytidine, and 2'-F guanosine. In a preferred embodiment, the resulting modified oligonucleotides comprise a sequence where at least 80% of all adenosine nucleotides are 2'-OMe adenosine, at least 80% of all uridine nucleotides are 2'-OMe uridine, at least 80% of all cytidine nucleotides are 2'-OMe cytidine, and at least 80% of all guanosine nucleotides are 2'-F guanosine. In a more preferred embodiment, the resulting modified oligonucleotides comprise a sequence where at least 90% of all adenosine nucleotides are 2'-OMe adenosine, at least 90% of all uridine nucleotides are 2'-OMe uridine, at least 90% of all cytidine nucleotides are 2'-OMe cytidine, and at least 90% of all guanosine nucleotides are 2'-F guanosine. In a most preferred embodiment, the resulting modified oligonucleotides comprise a sequence where 100% of all adenosine nucleotides are 2'-OMe adenosine, 100% of all uridine nucleotides are 2'-OMe uridine, 100% of all cytidine nucleotides are 2'-OMe cytidine, and 100% of all guanosine nucleotides are 2'-F guanosine.

Under dAmB transcription conditions of the present invention, the transcription reaction mixture comprises 2'-deoxy adenosine triphosphates, 2'-OMe cytidine triphosphates, 2'-OMe guanosine triphosphates, and 2'-OMe uridine triphosphates. The modified oligonucleotides produced using the dAmB transcription mixtures of the present invention comprise substantially all 2'-deoxy adenosine, 2'-OMe cytidine, 2'-OMe guanosine, and 2'-OMe uridine. In a preferred embodiment, the resulting modified oligonucleotides comprise a sequence where at least 80% of all adenosine nucleotides are 2'-deoxy adenosine, at least 80% of all cytidine nucleotides are 2'-OMe cytidine, at least 80% of all guanosine nucleotides are 2'-OMe guanosine, and at least 80% of all uridine nucleotides are 2'-OMe uridine. In a more preferred embodiment, the resulting modified oligonucleotides comprise a sequence where at least 90% of all adenosine nucleotides are 2'-deoxy adenosine, at least 90% of all cytidine nucleotides are 2'-OMe cytidine, at least 90% of all guanosine nucleotides are 2'-OMe guanosine, and at least 90% of all uridine nucleotides are 2'-OMe uridine. In a most preferred embodiment, the resulting modified oligonucleotides of the present invention comprise a sequence where 100% of all adenosine nucleotides are 2'-deoxy adenosine, 100% of all cytidine nucleotides are 2'-OMe cytidine, 100% of all guanosine nucleotides are 2'-OMe guanosine, and 100% of all uridine nucleotides are 2'-OMe uridine.

In each case, the transcription products can then be used as the library in the SELEX™ process to identify aptamers and/or to determine a conserved motif of sequences that have binding specificity to a given target. The resulting sequences are already stabilized, eliminating this step from the process to arrive at a stabilized aptamer sequence and giving a more highly stabilized aptamer as a result. Another advantage of the 2'-OMe SELEX™ process is that the resulting sequences are likely to have fewer 2'-OH nucleotides required in the sequence, possibly none. To the extent 2'OH nucleotides remain they can be removed by performing post-SELEX modifications.

As described below, lower but still useful yields of transcripts fully incorporating 2' substituted nucleotides can be obtained under conditions other than the optimized conditions described above. For example, variations to the above transcription conditions include:

The HEPES buffer concentration can range from 0 to 1 M. The present invention also contemplates the use of other buffering agents having a pKa between 5 and 10 including, for example, Tris(hydroxymethyl)aminomethane.

The DTT concentration can range from 0 to 400 mM. The methods of the present invention also provide for the use of other reducing agents including, for example, mercaptoethanol.

The spermidine and/or spermine concentration can range from 0 to 20 mM.

The PEG-8000 concentration can range from 0 to 50% (w/v). The methods of the present invention also provide for the use of other hydrophilic polymer including, for example, other molecular weight PEG or other polyalkylene glycols.

The Triton X-100 concentration can range from 0 to 0.1% (w/v). The methods of the present invention also provide for the use of other non-ionic detergents including, for example, other detergents, including other Triton-X detergents.

The $MgCl_2$ concentration can range from 0.5 mM to 50 mM. The $MnCl_2$ concentration can range from 0.15 mM to 15 mM. Both $MgCl_2$ and $MnCl_2$ must be present within the ranges described and in a preferred embodiment are present in about a 10 to about 3 ratio of $MgCl_2$:$MnCl_2$, preferably, the ratio is about 3-5:1, more preferably, the ratio is about 3-4:1.

The 2'-OMe NTP concentration (each NTP) can range from 5 µM to 5 mM.

The 2'-OH GTP concentration can range from 0 µM to 300 µM.

The 2'-OH GMP concentration can range from 0 to 5 mM.

The pH can range from pH 6 to pH 9. The methods of the present invention can be practiced within the pH range of activity of most polymerases that incorporate modified nucleotides. In addition, the methods of the present invention provide for the optional use of chelating agents in the transcription reaction condition including, for example, EDTA, EGTA, and DTT.

The selected aptamers having the highest affinity and specific binding as demonstrated by biological assays as described in the examples below are suitable therapeutics for treating conditions in which the C5 complement protein is involved in pathogenesis.

Aptamers with Binding Affinity to Complement System Protein C5

Although the complement system has an important role in the maintenance of health, it has the potential to cause or contribute to disease. Thus, it is desirable to develop inhibitors of the complement system for therapeutic use. It is particularly desirable to develop inhibitors of complement protein C5 because it is a component of both the classical and alternative pathways of complement activation cascades (Matis and Rollins (1995) Nature Medicine 1(8):839-842). Accordingly, inhibition of C5 can prevent complement-mediated damage caused by either pathway. Some complement system proteins, such as C1q and C3, are important in the normal defense mechanisms against microorganisms and in the clearance of immune components and damaged tissue; however, C5 is relatively unimportant for these functions. Thus, C5 function can be inhibited for short or long periods of time without compromising the protective role of the complement system.

A therapeutic C5 inhibitor is also desirable because inhibiting cleavage of C5 prevents the generation of two potentially damaging complement activities. First, inhibiting the generation of C5a from the cleavage of C5 eliminates the major complement chemotactic and vasoactive activity. Second, inhibiting the generation of C5b from the cleavage of C5 blocks assembly of the cytolytic C5b-9 membrane attack complex ("MAC"). Inhibition of C5 cleavage blocks both the C5a and the C5b effects on leukocytes and on tissue such as endothelial cells (Ward (1996) Am. J. Pathol. 149:1079).

Both C5a and the MAC have been implicated in acute and chronic inflammation associated with human disease, and their role in disease states has been confirmed in animal models. C5a is required for complement and neutrophil dependent lung vascular injury (Ward (1997) J. Lab. Clin. Med. 129:400; Mulligan et al., (1998) J. Clin. Invest. 98:503), and is associated with neutrophil and platelet activation in shock and in burn injury (Schmid et al., (1997) Shock 8:119). The MAC mediates muscle injury in acute autoimmune myasthenia gravis (Biesecker and Gomez (1989) J. Immunol. 142:2654), organ rejection in transplantation (Baldwin et al., (1995) Transplantation 59:797; Brauer et al., (1995) Transplantation 59:288; Takahashi et al., (1997) Immunol. Res. 16:273), and renal injury in autoimmune glomerulonephritis (Biesecker (1981) J. Exp. Med. 39:1779; Nangaku (1997) Kidney Int. 52:1570). Both C5a and the MAC are implicated in acute myocardial ischemia (Homeister and Lucchesi (1994) Annu. Rev. Pharmacol. Toxicol. 34:17), acute (Bednar et al., (1997) J. Neurosurg. 86:139) and chronic CNS injury (Morgan (1997) Exp. Clin. Immunogenet. 14:19), leukocyte activation during extracorporeal circulation (Sun et al., (1995) Nucleic Acids Res. 23:2909; Spycher and Nydegger (1995) Infushionsther. Transfusionsmed. 22:36) and in tissue injury associated with autoimmune diseases including arthritis and lupus (Wang et al., (1996) Immunology 93:8563).

Complement activation has also been implicated in diabetic retinopathy, and can compound or initiate retinal vascular damage (Zhang et al., (2002) Diabetes 51:3499). Low level constitutive complement activation normally occurs in the non-diabetic eye, evidenced by the presence of MAC and complement regulatory proteins in the eyes of non-diabetic rats, indicating that complement dysregulation occurs in diabetic patients (Sohn et al., (2000) IOVS 41:3492). In addition, C5b-9 deposition has been detected in retinal vessels from diabetic human donors where absent from non-diabetic human donors (Zhang et al.), reduced expression of CD55 and CD59 is shown in diabetic retinas (Zhang et al.), and glycated CD59 is present in urine from diabetic patients, but not non-diabetic patients (Acosta et al., (2002) PNAS 97, 5450-5455). Additionally, the complement and vascular system is known to be activated in type I diabetes. See, e.g. Hansen, T. K et al., Diabetes, 53: 1570-1576 (2004). C5a activates endothelial cells via interaction with the immune and complement systems. See, e.g., Albrecht, E. A. et al., Am J Pathology, 164: 849-859 (2004). The vascular system is activated in ocular diseases including diabetic retinopathy. See, e.g. Gert, V. B. et al., Invest Opthalmol Vis Sci, 43: 1104-1108 (2002). The complement system is also activated in diabetic retinopathy. See, See, e.g. Gert, V. B. et al., Invest Opthalmol Vis Sci, 43: 1104-1108 (2002) and Badouin, C et al., Am J Opthalmol, 105:383-388 (1988).

In some embodiments, the materials of the present invention comprise a series of nucleic acid aptamers of about 15 to about 60 nucleotides in length which bind specifically to complement protein C5 and which functionally modulate, e.g., block, the activity of complement protein C5 in in vivo and/or cell-based assays.

Aptamers that are capable of specifically binding and modulating complement protein C5 are set forth herein. These aptamers provide a low-toxicity, safe, and effective modality of treating, ameliorating and/or preventing a variety of complement-related diseases or disorders including, for example, complement-related heart disorders (e.g., myocardial injury; C5 mediated complement complications relating to coronary artery bypass graft (CABG) surgery such as post-operative bleeding, systemic neutrophil and leukocyte activation, increased risk of myocardial infarction, and increased cognitive dysfunction; restenosis; and C5 mediated complement complications relating to percutaneous coronary intervention), ischemia-reperfusion injury (e.g., myocardial infarction, stroke, frostbite), complement-related inflammatory disorders (e.g., asthma, arthritis, sepsis, and rejection after organ transplantation), and complement-related autoimmune disorders (e.g., myasthenia gravis, systemic lupus erythematosus (SLE)). Other indications for which C5 inhibition is desirable include, for example, lung inflammation (Mulligan et al. (1998) J. Clin. Invest. 98:503), extracorporeal complement activation (Rinder et al. (1995) J. Clin. Invest. 96:1564), antibody-mediated complement activation (Biesecker et al. (1989) J. Immunol. 142:2654), glomerulonephritis and other renal diseases, ocular indications such as C5 mediated ocular tissue damage, e.g. diabetic retinopathy, and paroxysmal nocturnal hemoglobinuria. These aptamers may also be used in diagnostics.

These aptamers may include modifications as described herein including, e.g., conjugation to lipophilic or high molecular weight compounds (e.g., PEG), incorporation of a capping moiety, incorporation of modified nucleotides, and modifications to the phosphate back bone.

In one embodiment of the invention an isolated, non-naturally occurring aptamer that binds to the C5 complement protein is provided. In some embodiments, the isolated, non-naturally occurring aptamer has a dissociation constant ("$K_d$") for C5 complement protein of less than 100 µM, less than 1 µM, less than 500 nM, less than 100 nM, less than 50 nM, less than 1 nM, less than 500 pM, less than 100 pM, less than 50 pM. In some embodiments of the invention, the dissociation constant is determined by dot blot titration as described in Example 1 below.

In another embodiment, the aptamer of the invention modulates a function of the C5 complement protein. In another embodiment, the aptamer of the invention inhibits a C5 function while in another embodiment the aptamer stimulates a function of C5. A C5 complement protein variant as used herein encompasses variants that perform essentially the same function as a C5 complement protein function. A C5 complement protein variant preferably comprises substantially the same structure and in some embodiments comprises 80% sequence identity, more preferably 90% sequence identity, and more preferably 95% sequence identity to the amino acid sequence of the C5 complement protein comprising the amino acid sequence below (SEQ ID NO: 102) (cited in Haviland et al., J. Immunol. 1991 Jan. 1; 146(1):362-8).:

```
  1 mgllgilcfl iflgktwgqe qtyvisapki frvgaseniv iqvygyteaf datisiksyp 61 dkkfsyssgh vhlssenkfq nsailtiqpk qlpggqnpvs yvylevvskh fskskrmpit 121 ydngflfiht dkpvytpdqs vkvrvyslnd dlkpakretv ltfidpegse vdmveeidhi 181 giisfpdfki psnprygmwt ikakykedfs ttgtayfevk eyvlphfsvs iepeynfigy 241 knfknfeiti karyfynkvv teadvyitfg iredlkddqk emmqtamqnt mlingiaqvt 301 fdsetavkel syysledlnn kylyiavtvi estggfseea eipgikyvls pyklnlvatp
```

-continued

```
 361  lflkpgipyp  ikvqvkdsld  qlvggvpvtl  naqtidvnqe  tsdldpsksv  trvddgvasf
 421  vlnlpsgvtv  lefnvktdap  dlpeenqare  gyraiayssl  sqsylyidwt  dnhkallvge
 481  hlniivtpks  pyidkithyn  ylilskgkii  hfgtrekfsd  asyqsinipv  tqnmvpssrl
 541  lvyyivtgeq  taelvsdsvw  lnieekcgnq  lqvhlspdad  ayspgqtvsl  nmatgmdswv
 601  alaavdsavy  gvqrgakkpl  ervfqfleks  dlgcgagggl  nnanvfhlag  ltfltnanad
 661  dsqendepck  eilrprrtlq  kkieeiaaky  khsvvkkccy  dgacvnndet  ceqraarisl
 721  gprcikafte  ccvvasqlra  nishkdmqlg  rlhmktllpv  skpeirsyfp  eswlwevhlv
 781  prrkqlqfal  pdslttweiq  gvgisntgic  vadtvkakvf  kdvflemnip  ysvvrgeqiq
 841  lkgtvynyrt  sgmqfcvkms  avegictses  pvidhqgtks  skcvrqkveg  ssshlvtftv
 901  lpleiglhni  nfsletwfgk  eilvktlrvv  pegvkresys  gvtldprgiy  gtisrrkefp
 961  yripldlvpk  teikrilsvk  gllvgeilsa  vlsqeginil  thlpkgsaea  elmsvvpvfy
1021  vfhyletgnh  wnifhsdpli  ekqklkkklk  egmlsimsyr  nadysysvwk  ggsastwlta
1081  falrvlgqvn  kyveqnqnsi  cnsllwlven  yqldngsfke  nsqyqpiklq  gtlpvearen
1141  slyltaftvi  girkafdicp  lvkidtalik  adnfllentl  paqstftlai  sayalslgdk
1201  thpqfrsivs  alkrealvkg  nppiyrfwkd  nlqhkdssvp  ntgtarmvet  tayalltsln
1261  lkdinyvnpv  ikwlseeqry  gggfystqdt  inaiegltey  sllvkqlrls  mdidvsykhk
1321  galhnykmtd  knflgrpvev  llnddlivst  gfgsglatvh  vttvvhktst  seevcsfylk
1381  idtqdieash  yrgygnsdyk  rivacasykp  sreesssgss  havmdislpt  gisaneedlk
1441  alvegvdqlf  tdyqikdghv  ilqlnsipss  dflcvrfrif  elfevgflsp  atftvyeyhr
1501  pdkqctmfys  tsnikiqkvc  egaackcvea  dcgqmqeeld  ltisaetrkq  tackpeiaya
1561  ykvsitsitv  envfvkykat  lldiyktgea  vaekdseitf  ikkvtctnae  lvkgrqylim
1621  gkealqikyn  fsfryiypld  sltwieywpr  dttcsscqaf  lanldefaed  iflngc
```

In some embodiments of the invention, the sequence identity of target variants is determined using BLAST as described below. The terms "sequence identity" in the context of tow or more nucleic acid or protein sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted, e.g., by the local homology algorithm of Smith & Waterman, Adv. Appl. Math. 2: 482 (1981), by the homology alignment algorithm of Needleman & Wunsch, J. Mol. Biol. 48: 443 (1970), by the search for similarity method of Pearson & Lipman, Proc. Nat'l. Acad. Sci. USA 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of an algorithm that is suitable for determining percent sequence identity is the algorithm used in the basic local alignment search tool (hereinafter "BLAST"), see, e.g. Altschul et al., J. Mol. Biol. 215: 403-410 (1990) and Altschul et al., Nucleic Acids Res., 15: 3389-3402 (1997). Software for performing BLAST analyses is publicly available through the National Center for Biotechnology Information (hereinafter "NCBI"). The default parameters used in determining sequence identity using the software available from NCBI, e.g., BLASTN (for nucleotide sequences) and BLASTP (for amino acid sequences) are described in McGinnis et al., Nucleic Acids Res., 32: W20-W25 (2004).

In another embodiment of the invention, the aptamer has substantially the same ability to bind C5 complement protein as that of an aptamer comprising any one of: SEQ ID NOS 1-2, 5-67, 75-81, 83 or 88-98 is provided. In another embodiment of the invention, the aptamer has substantially the same structure and ability to bind C5 complement protein as that of an aptamer comprising any one of: SEQ ID NOS 1-2, 5-67, 75-81, 83 or 88-98. In another embodiment, the aptamers of the invention have a sequence, including any chemical modifications, according to any one of SEQ ID NOS: 2, 5-67, 75-81, 83 or 88-98. In another embodiment, the aptamers of the invention are used as an active ingredient in pharmaceutical compositions. In another embodiment, the aptamers or compositions comprising the aptamers of the invention are used to treat a variety of complement-related diseases or disorders including any one selected from the group consisting of: complement-related heart disorders (e.g., myocardial injury; C5 mediated complement complications relating to coronary artery bypass graft (CABG) such as post-operative bleeding, systemic neutrophil and leukocyte activation, increased risk of myocardial infarction and increased cognitive dysfunction; restenosis; and C5 mediated complement complications relating to percutaneous coronary intervention), ischemia-reperfusion injury (e.g., myocardial infarction, stroke, frostbite), complement-related inflammatory disorders (e.g., asthma, arthritis, sepsis, and rejection after organ transplantation), and complement-related autoimmune disorders (e.g., myasthenia gravis, systemic lupus erythematosus (SLE), lung inflammation, extracorporeal complement activation, antibody-mediated complement activation and ocular indications such complement mediated ocular tissue damage such as diabetic retinopathy.

Figure 3A:
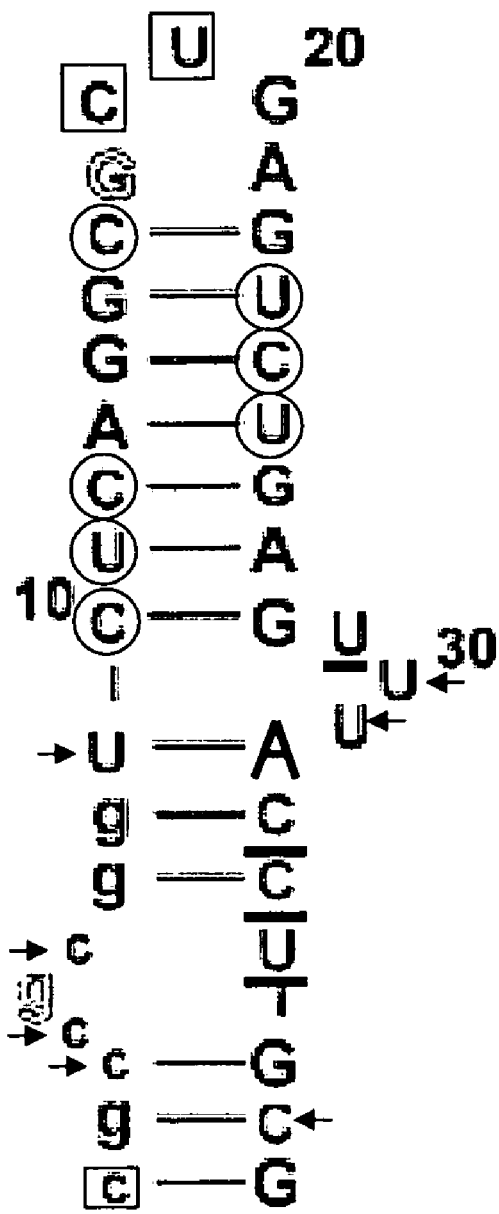
FIG. 3A is an illustration depicting the nucleotide sequence and secondary structure of an anti-C5 aptamer (SEQ ID NO: 1), in which the underlined residues are either 2'-H pyrimidine residues or 2'-fluoro pyrimidine residues, the boxed residues are either 2'-fluoro pyrimidine residues or 2'-OMe pyrimidine residues, and the residues indicated by an arrow (→) represent residues that must contain a 2'-fluoro modification.
Figure 3B:
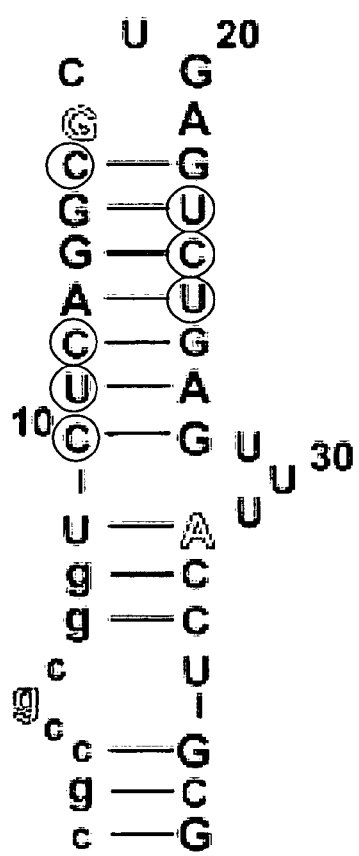
FIG. 3B is an illustration depicting the nucleotide sequence and secondary structure of the ARC330 anti-C5 aptamer (SEQ ID NO: 2), in which the circled residues are 2'-H residues, the pyrimidine residues are 2'-fluoro substituted, and the majority of purine residues are 2'-OMe substituted, except for the three 2'-OH purine residues shown in outline.

In one embodiment, the anti-C5 aptamers of the invention include a mixture of 2'-fluoro modified nucleotides, 2'-OMe modified nucleotides ("2'-OMe") and 2'-OH purine residues. A descriptive generic sequence (SEQ ID NO: 1) for a modified anti-C5 aptamer is shown below in Table 1, and the structure is shown in FIG. 3A. The vast majority of purines (A and G) have been modified to 2'-OMe, excluding only two G residues which remain 2'-OH (residues shown in outline). The circled residues represent a subset of pyrimidines that can be simultaneously modified to 2'-H without substantially altering the anti-C5 activity of the aptamer (see ARC330 in Table 1 below (SEQ ID NO: 2, FIG. 3B)). The underlined residues shown in FIG. 3A represent pyrimidine residues that can contain either a 2'-fluoro or a 2'-H modification (but not 2'-OMe), while the boxed residues represent pyrimidine residues that can contain either a 2'-fluoro or a 2-OMe modification (but not 2'-H). The residues indicated with an arrow (→) must contain a 2'-fluoro modification. Without a 2'-fluoro modification at the residues indicated by an arrow (→), resulting hemolytic activity of the resulting aptamer is substantially decreased. In a preferred embodiment, an anti-C5 aptamer of the invention comprises a nucleotide sequence according to SEQ ID NO: 1.

Figure 3C:
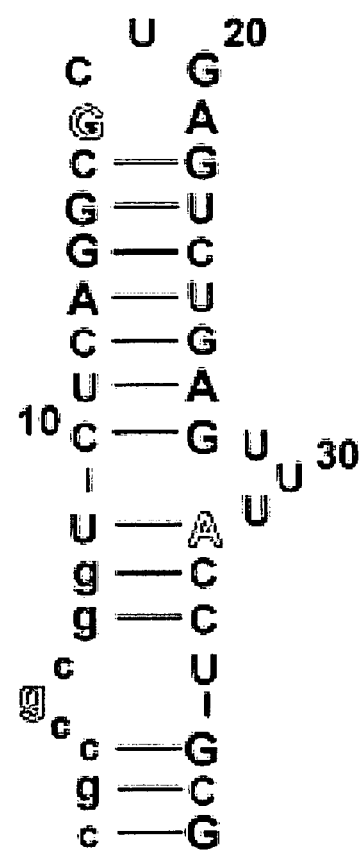
FIG. 3C is an illustration depicting the nucleotide sequence and secondary structure of the ARC186 anti-C5 aptamer (SEQ ID NO: 4) in which all 21 pyrimidine residues have 2'-fluoro modifications and the majority of purines (14 residues) have 2'-OMe modifications, except for the three 2'-OH purine residues shown in outline.

An example of an anti-C5 aptamer according to the invention is ARC186 (SEQ ID NO: 4) which is shown in FIG. 3C and described in U.S. Pat. No. 6,395,888 which is herein incorporated by reference in its entirety. All 21 pyrimidine residues of ARC186 have 2'-fluoro modifications. The majority of purines (14 residues) have 2'-OMe modifications, except for three 2'-OH purine residues (shown in outline in FIG. 3C). The anti-C5 aptamers of the invention can also include different mixtures of 2'-fluoro and 2'-H modifications. For example, another anti-C5 aptamer of the invention is the ARC330 (SEQ ID NO: 2) shown in FIG. 3B. ARC330 SEQ ID NO: 2) contains seven 2'-H modifications (circled residues in FIG. 3B), 14 pyrimidine residues with 2'-fluoro modifications, 14 purine residues with 2'-OMe modifications, and three 2'-OH purine residues (shown in outline in FIG. 3B).

Other combinations of aptamers containing a mixture of 2'-fluoro modifications, 2'-OMe modifications, 2'-OH purine residues, and conjugation to non-immunogenic, high molecular weight compounds (e.g., PEG) of varying size, each of which were derived from ARC186 (SEQ ID NO: 4), are described in Table 1 below. The invention comprises aptamers as described in Table 1 below. The invention also comprises aptamers as described below but lacking the indicated 3' cap (e.g., inverted deoxythymidine cap) and/or aptamers indicated below but comprising a 3' cap (e.g., inverted dT) where a 3' cap is not indicated.

Unless indicated otherwise, the nucleotide sequences in Table 1 below are listed in the 5' to 3' direction. For each of the individual sequences in Table 1, all 2'-OMe purine or pyrimidine modifications are indicated by an "m" preceding the corresponding nucleotide; all 2'-fluoro pyrimidine modifications are indicated by an "f" preceding the corresponding nucleotide; all purine or pyrimidine deoxy modifications are indicated by a "d" preceding the corresponding nucleotide; and any purine or pyrimidine appearing without an "m", "f", or "d" preceding the nucleotide indicates a 2'-OH residue. Further a "3T" indicates an inverted deoxy thymidine, "NH" indicates a hexylamine linker, "NH$_2$" indicates a hexylamine terminal group, "PEG" indicates a polyethylene glycol group having the indicated molecular weight, and "biotin" indicates an aptamer having biotin conjugated to the 5' end.

TABLE 1

SEQ ID NO: 1
$X_1X_2fCfCrGfCX_3X_4fUX_5X_6X_7X_8X_9X_{10}X_{11}rGX_{12}X_{13}X_{14}X_{15}$
$X_{16}X_{17}X_{18}X_{19}X_{20}X_{21}X_{22}X_{23}fUfUX_{24}X_{25}X_{26}X_{27}X_{28}fCX_{29}$

ARC330

(SEQ ID NO: 2)
fCmGfCfCGfCmGmGfUdCTdCmAmGmGdCGfCfUmGmAmGTdCTmGmAm
GfUfUfUAfCfCfUmGfCmG

ARC185

(SEQ ID NO: 3)
GAfCGAfUGfCGGfUfCfUfCAfUGfCGfUfCGAGfUGfUGAGfUfUfUA
fCfCfUfCGfUfC

ARC186

(SEQ ID NO: 4)
fCmGfCfCGfCmGmGfUfCfUfCmAmGmGfCGfCfUmGmAmGfUfCfUmG
mAmGfUfUfUAfCfCfUmGfCmG-3T

ARC187

(SEQ ID NO: 5)
40kDa PEG-- NH-fCmGfCfCGfCmGmGfUfCfUfCmAmGmGfCGfCf
UmGmAmGfUfCfUmGmAmGfUfUfUAfCfCfUmGfCmG-3T

ARC188

(SEQ ID NO: 6)
AGGAfCGAfUGfCGGfUfCfUfCAfUGfCGfUfCGAGfUGfUGAGfUfUf
UAfCfCfUfUfCGfUfC

ARC189

(SEQ ID NO: 7)
AGfCmGfCfCGfCmGmGfUfCfUfCmAmGmGfCGfCfUmGmAmGfUfCfU
mGmAmGfUfUfUAfCfCfUmGfCmG

ARC250

(SEQ ID NO: 8)
GGfCGfCfCGfCGGfUfCfUfCAGGfCGfCfUGAGfUfCfUGAGfUfUfU
AfCfCfUGfCG

ARC296

(SEQ ID NO: 9)
fCmGfCfCGfCmGmGfUdCTdCmAmGmGdCGfCfUmGmAmGTdCTmGmAm
GfUfUfUAdCdCfUmGfCmG-3T

ARC297

(SEQ ID NO: 10)
mCmGmCfCGfCmGmGfUdCTdCmAmGmGdCGfCfUmGmAmGTdCTmGmAm
GfUfUfUAdCdCfUmGmCmG-3T

TABLE 1-continued

ARC331

(SEQ ID NO: 11)
dCmGdCfCGfCmGmGfUdCTdCmAmGmGdCGfCfUmGmAmGTdCTmGmAm
GfUfUfUAfCfCfUmGdCmG

ARC332

(SEQ ID NO: 12)
dCmGfCfCGfCmGmGfUdCTdCmAmGmGdCGfCfUmGmAmGTdCTmGmAm
GfUfUfUAfCfCfUmGfCmG

ARC333

(SEQ ID NO: 13)
fCmGdCfCGfCmGmGfUdCTdCmAmGmGdCGfCfUmGmAmGTdCTmGmAm
GfUfUfUAfCfCfUmGfCmG

ARC334

(SEQ ID NO: 14)
fCmGfCfCGfCmGmGfUdCTdCmAmGmGdCGfCfUmGmAmGTdCTmGmAm
GfUfUfUAfCfCfUmGdCmG

ARC411

(SEQ ID NO: 15)
fCmGmCfCGfCmGmGfUdCTdCmAmGmGdCGfCfUmGmAmGTdCTmGmAm
GfUfUfUAfCfCfUmGfCmG

ARC412

(SEQ ID NO: 16)
fCmGfCfCGfCmGmGfUdCTdCmAmGmGdCGfCfUmGmAmGTdCTmGmAm
GfUfUfUAfCfCfUmGmCmG

ARC413

(SEQ ID NO: 17)
mCmGfCfCGfCmGmGfUdCTdCmAmGmGdCGfCfUmGmAmGTdCTmGmAm
GfUfUfUAfCfCfUmGfCmG

ARC414

(SEQ ID NO: 18)
mCmGmCfCGfCmGmGfUdCTdCmAmGmGdCGfCfUmGmAmGTdCTmGmAm
GfUfUfUAfCfCfUmGmCmG

ARC415

(SEQ ID NO: 19)
fCmGfCdCGfCmGmGfUdCTdCmAmGmGdCGfCfUmGmAmGTdCTmGmAm
GfUfUfUAfCfCfUmGfCmG

ARC416

(SEQ ID NO: 20)
fCmGfCfCGdCmGmGfUdCTdCmAmGmGdCGfCfUmGmAmGTdCTmGmAm
GfUfUfUAfCfCfUmGfCmG

ARC417

(SEQ ID NO: 21)
fCmGfCdCGdCmGmGfUdCTdCmAmGmGdCGfCfUmGmAmGTdCTmGmAm
GfUfUfUAfCfCfUmGfCmG

ARC418

(SEQ ID NO: 22)
fCmGfCfCGfCmGmGfUdCTdCmAmGmGdCGdCfUmGmAmGTdCTmGmAm
GfUfUfUAfCfCfUmGfCmG

ARC419

(SEQ ID NO: 23)
fCmGfCfCGfCmGmGfUdCTdCmAmGmGdCGfCTmGmAmGTdCTmGmAmG
fUfUfUAfCfCfUmGfCmG

ARC420

(SEQ ID NO: 24)
fCmGfCfCGfCmGmGfUdCTdCmAmGmGdCGdCTmGmAmGTdCTmGmAmG
fUfUfUAfCfCfUmGfCmG

ARC421

(SEQ ID NO: 25)
fCmGfCfCGfCmGmfUdCTdCmAmGmGdCGUmGmAmGTdCTmGmAmGTfU
fUAfCfCfUmGfCmG

ARC422

(SEQ ID NO: 26)
fCmGfCfCGfCmGmGfUdCTdCmAmGmGdCGfCUmGmAmGTdCTmGmAmG
fUTfUAfCfCfUmGfCmG

ARC423

(SEQ ID NO: 27)
fCmGfCfCGfCmGmGfUdCTdCmAmGmGdCGfCfUmGmAmGTdCTmGmAm
GfUfUTAfCfCfUmGfCmG

ARC424

(SEQ ID NO: 28)
fCmGfCfCGfCmGmGfUdCTdGmAmGmGdCGfCfUmGmAmGTdCTmGmAm
GTTTAfCfCfUmGfCmG

ARC425

(SEQ ID NO: 29)
fCmGfCfCGfCmGmGfUdCTdCmAmGmGdCGfCfUmGmAmGTdCTmGmAm
GfUfUfUAfCfCTmGfCmG

ARC426

(SEQ ID NO: 30)
fCmGfCfCGfCmGmGmUdCTdCmAmGmGdCGfCfUmGmAmGTdCTmGmAm
GfUfUfUAdCdCfUmGfCmG

ARC427

(SEQ ID NO: 31)
fCmGfCmCGfCmGmGfUdCTdCmAmGmGdCGfCfUmGmAmGTdCTmGmAm
GfUfUfUAfCfCfUmGfCmG

ARC428

(SEQ ID NO: 32)
fCmGfCfCGmCmGmGfUdCTdCmAmGmGdCGfCfUmGmAmGTdGTmGmAm
GfUfUfUAfCfCfUmGfCmG

ARC429

(SEQ ID NO: 33)
fCmGfCmCGmCmGmGfUdCTdCmAmGmGdCGfCfUmGmAmGTdCTmGmAm
GfUfUfUAfCfCUmGfCmG

ARC430

(SEQ ID NO: 34)
fCmGfCfCGfCmGmGfUdCfUdCmAmGmGdCGmCfUmGmAmGfUdCfUmG
mAmGfUfUfUAfCfCfUmGfCmG

ARC431

(SEQ ID NO: 35)
fCmGfCfCGfCmGmGfUdCfUdCmAmGmGdGGfCmUmGmAmGfUdCfUmG
mAmGfUfUfUAfCfCfUmGfCm

ARC432

(SEQ ID NO: 36)
fCmGfCfCGfCmGmGfUdCfUdCmAmGmGdCGmCmUmGmAmGfUdCfUmG
mAmGfUfUfUAfCfCfUmGfCmG

TABLE 1-continued

ARC433

(SEQ ID NO: 37)
fCmGfCfCGfCmGmGfUdCTdCmAmGmGdCGfCfUmGmAmGTdCTmGmAm
GmUfUfUAfCfCfUmGfCmG

ARC434

(SEQ ID NO: 38)
fCmGfCfCGfCmGmGfUdCTdCmAmGmGdCGfCfUmGmAmGTdCTmGmAm
GfUmUfUAfCfCfUmGfCmG

ARC435

(SEQ ID NO: 39)
fCmGfCfCGfCmGmGfUdCTdCmAmGmGdCGfCfUmGmAmGTdCTmGmAm
GfUfUmUAfCfCfUmGfCmG

ARC436

(SEQ ID NO: 40)
fCmGfCfCGfCmGmGfUdCTdCmAmGmGdCGfCfUmGmAmGTdCTmGmAm
GmUmUmUAfCfCfUmGfCmG

ARC437

(SEQ ID NO: 41)
fCmGfCfCGfCmGmGfUdCTdCmAmGmGdCGfCfUmGmAmGTdCTmGmAm
GfUfUfUAfCfCmUmGfCmG

ARC438

(SEQ ID NO: 42)
fCmGfCfCdGfCmGmGfUdCTdCmAmGmGdCGfCfUmGmAmGTdCTmGmA
mGfUfUfUAfCfCfUmGfCmG

ARC439

(SEQ ID NO: 43)
fCmGfCfCGfCmGmGfUdCTdCmAmGmGdCdGfCfUmGmAmGTdCTmGmA
mGfUfUfUAfCfCfUmGfCmG

ARC440

(SEQ ID NO: 44)
fCmGfCfCGfCmGmGfUdCTdCmAmGmGdCGfCfUmGmAmGTdCTmGmAm
GfUfUfUdAfCfCfUmGfCmG

ARC457

(SEQ ID NO: 45)
mGfCmGfUfCGfCmGmGfUdCTdCmAmGmGdCGfCfUmGmAmGTdCTmGm
AmGfUfUfUAfCfCfUmAfCmGmC

ARC458

(SEQ ID NO: 46)
mGmGmGfCGfCmGmGfUdCTdCmAmGmGdCGfCfUmGmAmGTdCTmGmAm
GfUfUfUAfCfCfUmCmCmC

ARC459

(SEQ ID NO: 47)
mGfCmGfCfCGfCmGmGfUdCTdCmAmGmGdCGfCfUmGmAmGTdCTmGm
AmGfUfUfUAfCfCfUmGfCmGmC

ARC473

(SEQ ID NO: 48)
mGmGmAfCmGfCfCGfCmGmGfUfCfUfCmAmGmGfCGfCfUmGmAmGfU
fCfUmGmAmGfUfUfUAfCfCfUmGfCmGfUfCfU-3T

ARC522

(SEQ ID NO: 49)
mGmGfCmGfCfCGfCmGmGfUdCTdCmAmGmGdCGmCmUmGmAmGTdCT
GmAmGTfUfUAdCdCTmGfCmGmCmC

ARC523

(SEQ ID NO: 50)
mGmGmCmGfCfCGfCmGmGfUdCTdCmAmGmGdCGmCmUmGmAmGTdCTm
GmAmGTTTAdCdCTmGdCmGmCmC

ARC524

(SEQ ID NO: 51)
mGmGmCmGdCdCGdCmGmGTdCTdCmAmGmGdCGmCmUmGmAmGTdCTmG
mAmGTTTmAdCdCTmGdCmGmCmC

ARC525

(SEQ ID NO: 52)
mGmGmCmGdCdCGdCmGmGTdCmUmCmAmGmGdCGmCmUmGmAmGmUmCm
UmGmAmGTTTmAdCdCTmGdCmGmCmC

ARC532

(SEQ ID NO: 53)
Biotin-AGfCmGfCfCGfCmGmGfUfCfUfCmAmGmGfCGfCfUmGmAm
GfUfCfUmGmAmGfUfUfUAfCfCfUmGfCmG

ARC543

(SEQ ID NO: 54)
mGmGfCmGfCfCGfCmGmGfUdCTdCmAmGmGdCGfCfUmGmAmGTdCTm
GmAmGfUfUfUAfCfCfUmGfCmGmCmC

ARC544

(SEQ ID NO: 55)
mGmGfCmGfCfCGfCmGmGfUmCmUmCmAmGmGfCGfCfUmGmAmGmUmC
mUmGmAmGfUfUfUAfCfCfUmGfCmGmCmC

ARC550

(SEQ ID NO: 56)
fCmGfCGCGfCmGmGfUfCfUfCmAmGmGfCGfCfUmGmAmGfUfCfUmG
mAmGfUfUfUmAfCfCfUmGfCmG-3T

ARC551

(SEQ ID NO: 57)
fCmGfCfCGfCmGmGfUfCfUfCmAmGmGfCGmCmUmGmAmGfUfCfUmG
mAmGfUfUfUAfCfCfUmGfCmG-3T

ARC552

(SEQ ID NO: 58)
fCmGfCfCGfCmGmGfUfCfUfCmAmGmGfCGfCfUmGmAmGfUfCfUmG
mAmGTfUfUAfCfCfUmGfCmG-3T

ARC553

(SEQ ID NO: 59)
fCmGfCfCGfCmGmGfUfCfUfCmAmGmGfCGmCmUmGmAmGfUCfUmGm
AmGfUfUfUmAfCfCfUmGfCmG-3T

ARC554

(SEQ ID NO: 60)
fCmGfCfCGfCmGmGfUfCfUfCmAmGmGfCGmCmUmGmAmGfUfCfUmG
mAmGTfUfUmAfCfCfUmGfCmG-3T

ARC 657

(SEQ ID NO: 61)
20 kDa PEG-NH-fCmGfCfCGfCmGmGfUfCfUfCmAmGmGfCGfCfU
mGmAmGfUfCfUmGmAmGfUfUfUAfCfCfUmGfCmG-3T

ARC 658

(SEQ ID NO: 62)
30 kDa PEG-NH-fCmGfCfCGfCmGmGfUfCfUfCmAmGmGfCGfCfU
mGmAmGfUfCfUmGmAmGfUfUfUAfCfCfUmGfCmG-3T

TABLE 1-continued

ARC 672

(SEQ ID NO: 63)
NH2-fCmGfCfCGfCmGmGfUfCfUfCmAmGmGfCGfCfUmGmAmGfUfC
fUmGmAmGfUfUfUAfCfCfUmGfCmG-3T

ARC706

(SEQ ID NO: 64)
10 kDa PEG-NH-fCmGfCfCGfCmGmGfUfCfUfCmAmGmGfCGfCfU
mGmAmGmfCfUmGmAmGfUfUfUAfCfCmmGfCmG-3T

ARC1537

(SEQ ID NO: 65)
40kDa PEG-NH-fCmGfCfCGfCmGmGfUfCfUfCmAmGmGfCGfCfUm
GmAmGfUfCfUmGmAmGfUfUfUAfCfCfUmGfCmG-3T

ARC1730

(SEQ ID NO: 66)
PEG20K-NH-fCmGfCfCGfCmGmGfUfCfUfCmAmGmGfCGfCfUmGmA
mGfUfCfUmGmAmGfUfUfUAfCfCfUmGfCmG-NH-PEG20K

ARC1905

(SEQ ID NO: 67)
40K PEG-NH- -fCmGfCGfCmGmGfUfCfUfCmAmGmGfCGfCfUmGm
AmGfUfCfUmGmAmGfUfUfUAfCfCfUmGfCmG-3T

ARC243

(SEQ ID NO: 68)
GGfCGAfUfUAfCfUGGGAfCGGAfCfUfCGCGAUGfUGAGfCfCfCAGA
CGAfCfUfCGfCfC

ARC244

(SEQ ID NO: 69)
GGfCfUfUfCfUGAAGAfUfUAfUfUfUfCGfCGAfUGfUGAAfCfUfCf
CAGAfCfCfCfC

```
where:
X1  = fC or mC
X2  = rG orgy
X3  = rG or mG
X4  = rG or mG
X5  = fC or dC
X6  = fU or dT
X7  = fC or dC
X8  = rA or mA
X9  = rG or mG
X10 = rG or mG
X11 = fC or dC
X12 = fC or mC
X13 = fU or mU
X14 = rG or mG
X15 = rA or mA
X16 = rG or mG
X17 = fU or dT
X18 = fC or dC
X19 = fU or dT
X20 = rG or mG
X21 = rA or mA
X22 = rG or mG
X23 = fU or dT
X24 = rA or mA
X25 = fC or dC
X26 = fC or dC
X27 = fU or dT
X28 = rG or mG
X29 = rG or mG
Where the branched 40 kDa PEG is ,3-bis(mPEG-[20
kDa])-propyl-2-(4'-butamide)
Where the branched 40 kDa PEG is 2,3-bis(mPEG-[20
kDa])-propyl-1-carbamoyl
```

Other aptamers of the invention that bind complement protein C5 are described below in Example 3.

In some embodiments aptamer therapeutics of the present invention have great affinity and specificity to their targets while reducing the deleterious side effects from non-naturally occurring nucleotide substitutions if the aptamer therapeutics break down in the body of patients or subjects. In some embodiments, the therapeutic compositions containing the aptamer therapeutics of the present invention are free of or have a reduced amount of fluorinated nucleotides.

The aptamers of the present invention can be synthesized using any oligonucleotide synthesis techniques known in the art including solid phase oligonucleotide synthesis techniques well known in the art (see, e.g., Froehler et al., Nucl. Acid Res. 14:5399-5467 (1986) and Froehler et al., Tet. Lett. 27:5575-5578 (1986)) and solution phase methods such as triester synthesis methods (see, e.g., Sood et al., Nucl. Acid Res. 4:2557 (1977) and Hirose et al., Tet. Lett., 28:2449 (1978)).

Pharmaceutical Compositions

The invention also includes pharmaceutical compositions containing aptamer molecules that bind to complement protein C5. In some embodiments, the compositions are suitable for internal use and include an effective amount of a pharmacologically active compound of the invention, alone or in combination, with one or more pharmaceutically acceptable carriers. The compounds are especially useful in that they have very low, if any toxicity.

Compositions of the invention can be used to treat or prevent a pathology, such as a disease or disorder, or alleviate the symptoms of such disease or disorder in a patient. For example, compositions of the present invention can be used to treat or prevent a pathology associated with complement-related heart disorders (e.g., myocardial injury; C5 mediated complement complications relating to coronary artery bypass graft (CABG) surgery such as post-operative bleeding, systemic neutrophil and leukocyte activation, increased risk of myocardial infarction and increased cognitive dysfunction; restenosis; and C5 mediated complications relating to percutaneous coronary intervention); ischemia-reperfusion injury (e.g., myocardial infarction, stroke, frostbite); complement-related inflammatory disorders (e.g., asthma, arthritis, sepsis, and rejection after organ transplantation); and complement-related autoimmune disorders (e.g., myasthenia gravis, systemic lupus erythematosus (SLE, or lupus); lung inflammation; extracorporeal complement activation; antibody-mediated complement activation; and ocular indications such as diabetic retinopathy. Compositions of the invention are useful for administration to a subject suffering from, or predisposed to, a disease or disorder which is related to or derived from complement protein C5 to which the aptamers of the invention specifically bind.

Compositions of the invention can be used in a method for treating a patient or subject having a pathology. The methods of the invention involve administering to the patient or subject an aptamer or a composition comprising aptamers that bind to complement protein C5, so that binding of the aptamer to complement protein C5 alters its biological function, thereby treating the pathology.

The patient or subject having a pathology, i.e., the patient or subject treated by the methods of this invention can be a vertebrate, more particularly a mammal, or more particularly a human.

In practice, the aptamers or their pharmaceutically acceptable salts, are administered in amounts which will be sufficient to exert their desired biological activity, e.g., inhibiting the binding of the aptamer target to its receptor, preventing cleavage of a target protein.

One aspect of the invention comprises an aptamer composition of the invention in combination with other treatments for C5 mediated complement disorders. The aptamer composition of the invention may contain, for example, more than one aptamer. In some examples, an aptamer composition of the invention, containing one or more compounds of the invention, is administered in combination with another useful composition such as an anti-inflammatory agent, an immunosuppressant, an antiviral agent, or the like. Furthermore, the compounds of the invention may be administered in combination with a cytotoxic, cytostatic, or chemotherapeutic agent such as an alkylating agent, anti-metabolite, mitotic inhibitor or cytotoxic antibiotic, as described above. In general, the currently available dosage forms of the known therapeutic agents for use in such combinations will be suitable.

"Combination therapy" (or "co-therapy") includes the administration of an aptamer composition of the invention and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected).

"Combination therapy" may, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents.

Sequential or substantially simultaneous administration of each therapeutic agent can be effected by any appropriate route including, but not limited to, topical routes, oral routes, intravenous routes, intramuscular routes, and direct absorption through mucous membrane tissues. The therapeutic agents can be administered by the same route or by different routes. For example, a first therapeutic agent of the combination selected may be administered by injection while the other therapeutic agents of the combination may be administered topically.

Alternatively, for example, all therapeutic agents may be administered topically or all therapeutic agents may be administered by injection. The sequence in which the therapeutic agents are administered is not narrowly critical unless noted otherwise. "Combination therapy" also can embrace the administration of the therapeutic agents as described above in further combination with other biologically active ingredients. Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Therapeutic or pharmacological compositions of the present invention will generally comprise an effective amount of the active component(s) of the therapy, dissolved or dispersed in a pharmaceutically acceptable medium. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the therapeutic compositions of the present invention.

The preparation of pharmaceutical or pharmacological compositions will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including eye drops, creams, lotions, salves, inhalants and the like. The use of sterile formulations, such as saline-based washes, by surgeons, physicians or health care workers to treat a particular area in the operating field may also be particularly useful. Compositions may also be delivered via microdevice, microparticle or sponge.

Upon formulation, therapeutics will be administered in a manner compatible with the dosage formulation, and in such amount as is pharmacologically effective. The formulations are easily administered in a variety of dosage forms, such as the type of injectable solutions described above, but drug release capsules and the like can also be employed.

In this context, the quantity of active ingredient and volume of composition to be administered depends on the host animal to be treated. Precise amounts of active compound required for administration depend on the judgment of the practitioner and are peculiar to each individual.

A minimal volume of a composition required to disperse the active compounds is typically utilized. Suitable regimes for administration are also variable, but would be typified by initially administering the compound and monitoring the results and then giving further controlled doses at further intervals.

For instance, for oral administration in the form of a tablet or capsule (e.g., a gelatin capsule), the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, magnesium aluminum silicate, starch paste, gelatin, methylcellulose, sodium carboxymethylcellulose and/or polyvinylpyrrolidone, natural sugars such as glucose or beta-lactose, corn sweeteners, natural and synthetic gums such as acacia, tragacanth or sodium alginate, polyethylene glycol, waxes and the like. Lubricants used in these dosage forms include sodium oleate, sodium stearate, magnesium stearate, sodium benzoate, sodium acetate, sodium chloride, silica, talcum, stearic acid, its magnesium or calcium salt and/or polyethyleneglycol and the like. Disintegrators include, without limitation, starch, methyl cellulose, agar, bentonite, xanthan gum starches, agar, alginic acid or its sodium salt, or effervescent mixtures, and the like. Diluents, include, e.g., lactose, dextrose, sucrose, mannitol, sorbitol, cellulose and/or glycine.

Injectable compositions are preferably aqueous isotonic solutions or suspensions, and suppositories are advantageously prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and typically contain about 0.1 to 75%, preferably about 1 to 50%, of the active ingredient.

The compounds of the invention can also be administered in such oral dosage forms as timed release and sustained release tablets or capsules, pills, powders, granules, elixirs, tinctures, suspensions, syrups and emulsions.

Liquid, particularly injectable compositions can, for example, be prepared by dissolving, dispersing, etc. The active compound is dissolved in or mixed with a pharmaceutically pure solvent such as, for example, water, saline, aqueous dextrose, glycerol, ethanol, and the like, to thereby form the injectable solution or suspension. Additionally, solid forms suitable for dissolving in liquid prior to injection can be formulated.

The compounds of the present invention can be administered in intravenous (both bolus and infusion), intraperitoneal, subcutaneous or intramuscular form, all using forms well known to those of ordinary skill in the pharmaceutical arts. Injectables can be prepared in conventional forms, either as liquid solutions or suspensions.

Parenteral injectable administration is generally used for subcutaneous, intramuscular or intravenous injections and infusions. Additionally, one approach for parenteral administration employs the implantation of a slow-release or sustained-released systems, which assures that a constant level of dosage is maintained, according to U.S. Pat. No. 3,710,795, incorporated herein by reference.

Furthermore, preferred compounds for the present invention can be administered in intranasal form via topical use of suitable intranasal vehicles, inhalants, or via transdermal routes, using those forms of transdermal skin patches well known to those of ordinary skill in that art. To be administered in the form of a transdermal delivery system, the dosage administration will, of course, be continuous rather than intermittent throughout the dosage regimen. Other preferred topical preparations include creams, ointments, lotions, aerosol sprays and gels, wherein the concentration of active ingredient would typically range from 0.01% to 15%, w/w or w/v.

For solid compositions, excipients include pharmaceutical grades of mannitol, lactose, starch, magnesium stearate, sodium saccharin, talcum, cellulose, glucose, sucrose, magnesium carbonate, and the like may be used. The active compound defined above, may be also formulated as suppositories using for example, polyalkylene glycols, for example, propylene glycol, as the carrier. In some embodiments, suppositories are advantageously prepared from fatty emulsions or suspensions.

The compounds of the present invention can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564. For example, the aptamer molecules described herein can be provided as a complex with a lipophilic compound or non-immunogenic, high molecular weight compound constructed using methods known in the art. An example of nucleic-acid associated complexes is provided in U.S. Pat. No. 6,011,020.

The compounds of the present invention may also be coupled with soluble polymers as targetable drug carriers. Such polymers can include polyvinylpyrrolidone, pyran copolymer, polyhydroxypropyl-methacrylamide-phenol, polyhydroxyethylaspanamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, poly-epsilon caprolactone, polyhydroxy butyric acid, polyorthoesters, polyacetals, polydihydropyrans, polycyanoacrylates and cross-linked or amphipathic block copolymers of hydrogels.

If desired, the pharmaceutical composition to be administered may also contain minor amounts of non-toxic auxiliary substances such as wetting or emulsifying agents, pH buffering agents, and other substances such as for example, sodium acetate, and triethanolamine oleate.

The dosage regimen utilizing the aptamers is selected in accordance with a variety of factors including type, species, age, weight, sex and medical condition of the patient; the severity of the condition to be treated; the route of administration; the renal and hepatic function of the patient; and the particular aptamer or salt thereof employed. An ordinarily skilled physician or veterinarian can readily determine and prescribe the effective amount of the drug required to prevent, counter or arrest the progress of the condition.

Oral dosages of the present invention, when used for the indicated effects, will range between about 0.05 to 7500 mg/day orally. The compositions are preferably provided in the form of scored tablets containing 0.5, 1.0, 2.5, 5.0, 10.0, 15.0, 25.0, 50.0, 100.0, 250.0, 500.0 and 1000.0 mg of active ingredient. Compounds of the present invention may be administered in a single daily dose, or the total daily dosage may be administered in divided doses of two, three or four times daily.

Infused dosages, intranasal dosages and transdermal dosages will range between 0.05 to 7500 mg/day. Subcutaneous, intravenous and intraperineal dosages will range between 0.05 to 3800 mg/day.

Effective plasma levels of the compounds of the present invention range from 0.002 mg/mL to 50 mg/mL.

Modulation of Pharmacokinetics and Biodistribution of Aptamer Therapeutics

It is important that the pharmacokinetic properties for all oligonucleotide-based therapeutics, including aptamers, be tailored to match the desired pharmaceutical application. While aptamers directed against extracellular targets do not suffer from difficulties associated with intracellular delivery (as is the case with antisense and RNAi-based therapeutics), such aptamers must still be able to be distributed to target organs and tissues, and remain in the body (unmodified) for a period of time consistent with the desired dosing regimen.

Thus, the present invention provides materials and methods to affect the pharmacokinetics of aptamer compositions, and, in particular, the ability to tune aptamer pharmacokinetics. The tunability of (i.e., the ability to modulate) aptamer pharmacokinetics is achieved through conjugation of modifying moieties (e.g., PEG polymers) to the aptamer and/or the incorporation of modified nucleotides (e.g., 2'-fluoro or 2'-OMe) to alter the chemical composition of the nucleic acid. The ability to tune aptamer pharmacokinetics is used in the improvement of existing therapeutic applications, or alternatively, in the development of new therapeutic applications. For example, in some therapeutic applications, e.g., in anti-neoplastic or acute care settings where rapid drug clearance or turn-off may be desired, it is desirable to decrease the residence times of aptamers in the circulation. Alternatively, in other therapeutic applications, e.g., maintenance therapies where systemic circulation of a therapeutic is desired, it may be desirable to increase the residence times of aptamers in circulation.

In addition, the tunability of aptamer pharmacokinetics is used to modify the biodistribution of an aptamer therapeutic in a subject. For example, in some therapeutic applications, it may be desirable to alter the biodistribution of an aptamer therapeutic in an effort to target a particular type of tissue or a specific organ (or set of organs). In these applications, the aptamer therapeutic preferentially accumulates in a specific tissue or organ(s). In other therapeutic applications, it may be desirable to target tissues displaying a cellular marker or a symptom associated with a given disease, cellular injury or other abnormal pathology, such that the aptamer therapeutic preferentially accumulates in the affected tissue. For example, as described in copending provisional application U.S. Ser. No. 60/550,790, filed on Mar. 5, 2004, and entitled "Controlled Modulation of the Pharmacokinetics and Biodistribution of Aptamer Therapeutics), PEGylation of an aptamer therapeutic (e.g., PEGylation with a 20 kDa PEG polymer) is used to target inflamed tissues, such that the PEGylated aptamer therapeutic preferentially accumulates in inflamed tissue.

To determine the pharmacokinetic and biodistribution profiles of aptamer therapeutics (e.g., aptamer conjugates or aptamers having altered chemistries, such as modified nucleotides) a variety of parameters are monitored. Such parameters include, for example, the half-life ($t_{1/2}$), the plasma clearance (Cl), the volume of distribution (Vss), the area under the concentration-time curve (AUC), maximum observed serum or plasma concentration ($C_{max}$), and the mean residence time (MRT) of an aptamer composition. As used herein, the term "AUC" refers to the area under the plot of the plasma concentration of an aptamer therapeutic versus the time after aptamer administration. The AUC value is used to estimate the bioavailability (i.e., the percentage of administered aptamer therapeutic in the circulation after aptamer administration) and/or total clearance (Cl) (i.e., the rate at which the aptamer therapeutic is removed from circulation) of a given aptamer therapeutic. The volume of distribution relates the plasma concentration of an aptamer therapeutic to the amount of aptamer present in the body. The larger the Vss, the more an aptamer is found outside of the plasma (i.e., the more extravasation).

The present invention provides materials and methods to modulate, in a controlled manner, the pharmacokinetics and biodistribution of stabilized aptamer compositions in vivo by conjugating an aptamer to a modulating moiety such as a small molecule, peptide, or polymer terminal group, or by incorporating modified nucleotides into an aptamer. As described herein, conjugation of a modifying moiety and/or altering nucleotide(s) chemical composition alters fundamental aspects of aptamer residence time in circulation and distribution to tissues.

In addition to clearance by nucleases, oligonucleotide therapeutics are subject to elimination via renal filtration. As such, a nuclease-resistant oligonucleotide administered intravenously typically exhibits an in vivo half-life of <10 min, unless filtration can be blocked. This can be accomplished by either facilitating rapid distribution out of the blood stream into tissues or by increasing the apparent molecular weight of the oligonucleotide above the effective size cut-off for the glomerulus. Conjugation of small therapeutics to a PEG polymer (PEGylation), described below, can dramatically lengthen residence times of aptamers in circulation, thereby decreasing dosing frequency and enhancing effectiveness against vascular targets.

Aptamers can be conjugated to a variety of modifying moieties, such as high molecular weight polymers, e.g., PEG; peptides, e.g., Tat (a 13-amino acid fragment of the HIV Tat protein (Vives, et al. (1997), J. Biol. Chem. 272(25): 16010-7)), Ant (a 16-amino acid sequence derived from the third helix of the *Drosophila antennapedia* homeotic protein (Pietersz, et al. (2001), Vaccine 19(11-12): 1397-405)) and $Arg_7$ (a short, positively charged cell-permeating peptides composed of polyarginine ($Arg_7$) (Rothbard, et al. (2000), Nat. Med. 6(11): 1253-7; Rothbard, J et al. (2002), J. Med. Chem. 45(17): 3612-8)); and small molecules, e.g., lipophilic compounds such as cholesterol. Among the various conjugates described herein, in vivo properties of aptamers are altered most profoundly by complexation with PEG groups. For example, complexation of a mixed 2'F and 2'-OMe modified aptamer therapeutic with a 20 kDa PEG polymer hinders renal filtration and promotes aptamer distribution to both healthy and inflamed tissues. Furthermore, the 20 kDa PEG polymer-aptamer conjugate proves nearly as effective as a 40 kDa PEG polymer in preventing renal filtration of aptamers. While one effect of PEGylation is on aptamer clearance, the prolonged systemic exposure afforded by presence of the 20 kDa moiety also facilitates distribution of aptamer to tissues, particularly those of highly perfused organs and those at the site of inflammation. The aptamer-20 kDa PEG polymer conjugate directs aptamer distribution to the site of inflammation, such that the PEGylated aptamer preferentially accumulates in inflamed tissue. In some instances, the 20 kDa PEGylated aptamer conjugate is able to access the interior of cells, such as, for example, kidney cells.

Overall, effects on aptamer pharmacokinetics and tissue distribution produced by low molecular weight modifying moieties, including cholesterol and cell-permeating peptides are less pronounced than those produced as a result of PEGylation or modification of nucleotides (e.g., an altered chemical composition). While not intending to be bound by theory, it is suggested that cholesterol-mediated associations with plasma lipoproteins, postulated to occur in the case of the antisense conjugate, are precluded in the particular context of the aptamer-cholesterol conjugate folded structure, and/or relate to aspect of the lipophilic nature of the cholesterol group. Like cholesterol, the presence of a Tat peptide tag promotes clearance of aptamer from the blood stream, with comparatively high levels of conjugate appearing in the kidneys at 48 hrs. Other peptides (e.g., Ant, $Arg_7$) that have been reported in the art to mediate passage of macromolecules across cellular membranes in vitro, do not appear to promote aptamer clearance from circulation. However, like Tat, the Ant conjugate significantly accumulates in the kidneys relative to other aptamers. While not intending to be bound by theory, it is possible that unfavorable presentation of the Ant and $Arg_7$ peptide modifying moieties in the context of three dimensionally folded aptamers in vivo impairs the ability of these peptides to influence aptamer transport properties.

Modified nucleotides can also be used to modulate the plasma clearance of aptamers. For example, an unconjugated aptamer which incorporates both 2'-F and 2'-OMe stabilizing chemistries, which is typical of current generation aptamers as it exhibits a high degree of nuclease stability in vitro and in vivo, displays rapid loss from plasma (i.e., rapid plasma clearance) and a rapid distribution into tissues, primarily into the kidney, when compared to unmodified aptamer.

PEG-Derivatized Nucleic Acids

As described above, derivatization of nucleic acids with high molecular weight non-immunogenic polymers has the potential to alter the pharmacokinetic and pharmacodynamic properties of nucleic acids making them more effective therapeutic agents. Favorable changes in activity can include increased resistance to degradation by nucleases, decreased filtration through the kidneys, decreased exposure to the immune system, and altered distribution of the therapeutic through the body.

The aptamer compositions of the invention may be derivatized with polyalkylene glycol ("PAG") moieties. Examples of PAG-derivatized nucleic acids are found in U.S. patent application Ser. No. 10/718,833, filed on Nov. 21, 2003 (abandoned), which is herein incorporated by reference in its entirety. Typical polymers used in the invention include poly (ethylene glycol) ("PEG'), also known as poly(ethylene oxide) ("PEO") and polypropylene glycol (including poly isopropylene glycol). Additionally, random or block copolymers of different alkylene oxides (e.g., ethylene oxide and propylene oxide) can be used in many applications. In its most common form, a polyalkylene glycol, such as PEG, is a linear polymer terminated at each end with hydroxyl groups: $HO-CH_2CH_2O-(CH_2CH_2O)_n-CH_2CH_2-OH$. This polymer, alpha-, omega-dihydroxylpoly(ethylene glycol), can also be represented as HO-PEG-OH, where it is understood that the -PEG-symbol represents the following structural unit: $-CH_2CH_2O-(CH_2CH_2O)_n-CH_2CH_2-$ where n typically ranges from about 4 to about 10,000.

As shown, the PEG molecule is di-functional and is sometimes referred to as "PEG diol." The terminal portions of the PEG molecule are relatively non-reactive hydroxyl moieties, the —OH groups, that can be activated, or converted to functional moieties, for attachment of the PEG to other compounds at reactive sites on the compound. Such activated PEG diols are referred to herein as bi-activated PEGs. For example, the terminal moieties of PEG diol have been functionalized as active carbonate ester for selective reaction with amino moieties by substitution of the relatively nonreactive hydroxyl moieties, —OH, with succinimidyl active ester moieties from N-hydroxy succinimide.

In many applications, it is desirable to cap the PEG molecule on one end with an essentially non-reactive moiety so that the PEG molecule is mono-functional (or mono-activated). In the case of protein therapeutics which generally display multiple reaction sites for activated PEGs, bi-functional activated PEGs lead to extensive cross-linking, yielding poorly functional aggregates. To generate mono-activated PEGs, one hydroxyl moiety on the terminus of the PEG diol molecule typically is substituted with non-reactive methoxy end moiety, $-OCH_3$. The other, un-capped terminus of the PEG molecule typically is converted to a reactive end moiety that can be activated for attachment at a reactive site on a surface or a molecule such as a protein.

PAGs are polymers which typically have the properties of solubility in water and in many organic solvents, lack of toxicity, and lack of immunogenicity. One use of PAGs is to covalently attach the polymer to insoluble molecules to make the resulting PAG-molecule "conjugate" soluble. For example, it has been shown that the water-insoluble drug paclitaxel, when coupled to PEG, becomes water-soluble. Greenwald, et al., *J. Org. Chem.*, 60:331-336 (1995). PAG conjugates are often used not only to enhance solubility and stability but also to prolong the blood circulation half-life of molecules.

Polyalkylated compounds of the invention are typically between 5 and 80 kD in size however any size can be used, the choice dependent on the aptamer and application. Other PAG compounds of the invention are between 10 and 80 kD in size. Still other PAG compounds of the invention are between 10 and 60 kD in size. For example, a PAG polymer may be at least 10, 20, 30, 40, 50, 60, or 80 kD in size. Such polymers can be linear or branched.

Figure 4:
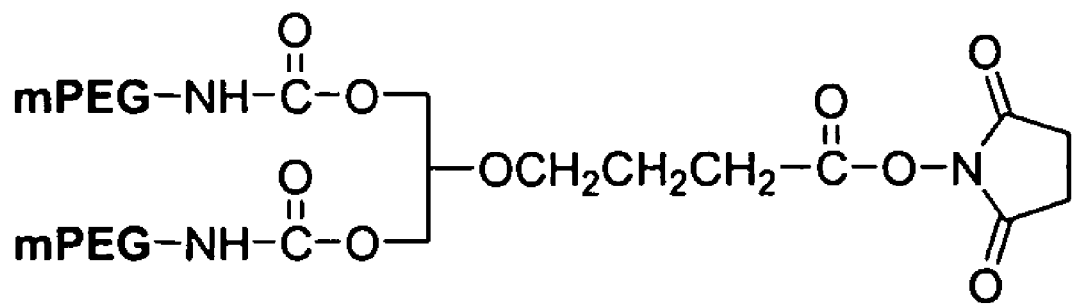
FIG. 4 is an illustration of a 40 kD branched PEG (1,3-bis (mPEG-[20 kDa])-propyl-2-(4'-butamide).
Figure 5:
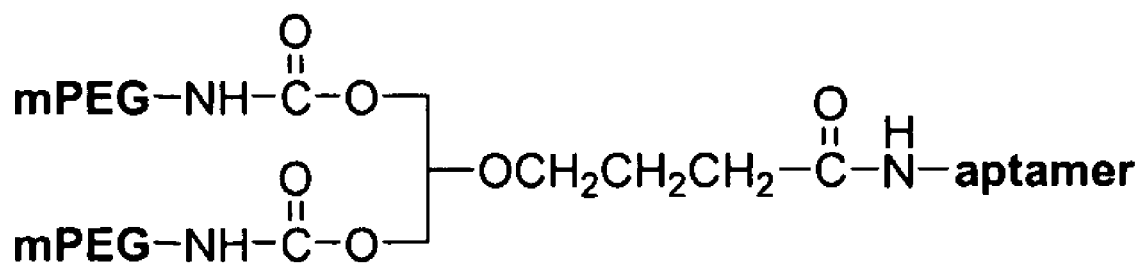
FIG. 5 is an illustration of a 40 kD branched PEG (1,3-bis (mPEG-[20 kDa])-propyl-2-(4'-butamide) attached to the 5'end of an aptamer.

In contrast to biologically-expressed protein therapeutics, nucleic acid therapeutics are typically chemically synthesized from activated monomer nucleotides. PEG-nucleic acid conjugates may be prepared by incorporating the PEG using the same iterative monomer synthesis. For example, PEGs activated by conversion to a phosphoramidite form can be incorporated into solid-phase oligonucleotide synthesis. Alternatively, oligonucleotide synthesis can be completed with site-specific incorporation of a reactive PEG attachment site. Most commonly this has been accomplished by addition of a free primary amine at the 5'-terminus (incorporated using a modified phosphoramidite in the last coupling step of solid phase synthesis). Using this approach, a reactive PEG (e.g., one which is activated so that it will react and form a bond with an amine) is combined with the purified oligonucleotide and the coupling reaction is carried out in solution. In some embodiment the polymers are branched PEG molecules. In still other embodiments the polymers are 40 kDa branched PEG, see, e.g. (1,3-bis(mPEG-[20 kDa])-propyl-2-(4'-butamide) depicted in FIG. 4. In some embodiments the 40 kD branched PEG (1,3-bis(mPEG-[20 kDa])-propyl-2-(4'-butamide) is attached to the 5' end of the aptamer as depicted in FIG. 5.

The ability of PEG conjugation to alter the biodistribution of a therapeutic is related to a number of factors including the apparent size (e.g., as measured in terms of hydrodynamic radius) of the conjugate. Larger conjugates (>10 kDa) are known to more effectively block filtration via the kidney and to consequently increase the serum half-life of small macromolecules (e.g., peptides, antisense oligonucleotides). The ability of PEG conjugates to block filtration has been shown to increase with PEG size up to approximately 50 kDa (further increases have minimal beneficial effect as half life becomes defined by macrophage-mediated metabolism rather than elimination via the kidneys).

Production of high molecular weight PEGs (>10 kDa) can be difficult, inefficient, and expensive. As a route towards the synthesis of high molecular weight PEG-nucleic acid conjugates, previous work has been focused towards the generation of higher molecular weight activated PEGs. One method for generating such molecules involves the formation of a branched activated PEG in which two or more PEGs are attached to a central core carrying the activated group. The terminal portions of these higher molecular weight PEG molecules, i.e., the relatively non-reactive hydroxyl (—OH) moieties, can be activated, or converted to functional moieties, for attachment of one or more of the PEGs to other compounds at reactive sites on the compound. Branched activated PEGs will have more than two termini, and in cases where two or more termini have been activated, such activated higher molecular weight PEG molecules are referred to herein as, multi-activated PEGs. In some cases, not all termini in a branch PEG molecule are activated. In cases where any two termini of a branch PEG molecule are activated, such PEG molecules are referred to as bi-activated PEGs. In some cases where only one terminus in a branch PEG molecule is activated, such PEG molecules are referred to as mono-activated. As an example of this approach, activated PEG prepared by the attachment of two monomethoxy PEGs to a lysine core which is subsequently activated for reaction has been described (Harris et al., Nature, vol. 2: 214-221, 2003).

The present invention provides another cost effective route to the synthesis of high molecular weight PEG-nucleic acid (preferably, aptamer) conjugates including multiply PEGylated nucleic acids. The present invention also encompasses PEG-linked multimeric oligonucleotides, e.g., dimerized aptamers. The present invention also relates to high molecular weight compositions where a PEG stabilizing moiety is a linker which separates different portions of an aptamer, e.g., the PEG is conjugated within a single aptamer sequence, such that the linear arrangement of the high molecular weight aptamer composition is, e.g., nucleic acid-PEG-nucleic acid (-PEG-nucleic acid)$_n$, where n is greater than or equal to 1.

High molecular weight compositions of the invention include those having a molecular weight of at least 10 kD. Compositions typically have a molecular weight between 10 and 80 kD in size. High molecular weight compositions of the invention are at least 10, 20, 30, 40, 50, 60, or 80 kD in size.

A stabilizing moiety is a molecule, or portion of a molecule, which improves pharmacokinetic and pharmacodynamic properties of the high molecular weight aptamer compositions of the invention. In some cases, a stabilizing moiety is a molecule or portion of a molecule which brings two or more aptamers, or aptamer domains, into proximity, or provides decreased overall rotational freedom of the high molecular weight aptamer compositions of the invention. A stabilizing moiety can be a polyalkylene glycol, such a polyethylene glycol, which can be linear or branched, a homopolymer or a heteropolymer. Other stabilizing moieties include polymers such as peptide nucleic acids (PNA). Oligonucleotides can also be stabilizing moieties; such oligonucleotides can include modified nucleotides, and/or modified linkages, such as phosphorothioates. A stabilizing moiety can be an integral part of an aptamer composition, i.e., it is covalently bonded to the aptamer.

Compositions of the invention include high molecular weight aptamer compositions in which two or more nucleic acid moieties are covalently conjugated to at least one polyalkylene glycol moiety. The polyalkylene glycol moieties serve as stabilizing moieties. In compositions where a polyalkylene glycol moiety is covalently bound at either end to an aptamer, such that the polyalkylene glycol joins the nucleic acid moieties together in one molecule, the polyalkylene glycol is said to be a linking moiety. In such compositions, the primary structure of the covalent molecule includes the linear arrangement nucleic acid-PAG-nucleic acid. One example is a composition having the primary structure nucleic acid-PEG-nucleic acid. Another example is a linear arrangement of: nucleic acid -PEG-nucleic acid-PEG-nucleic acid.

To produce the nucleic acid-PEG-nucleic acid conjugate, the nucleic acid is originally synthesized such that it bears a single reactive site (e.g., it is mono-activated). In a preferred embodiment, this reactive site is an amino group introduced at the 5'-terminus by addition of a modified phosphoramidite as the last step in solid phase synthesis of the oligonucleotide. Following deprotection and purification of the modified oligonucleotide, it is reconstituted at high concentration in a solution that minimizes spontaneous hydrolysis of the activated PEG. In a preferred embodiment, the concentration of oligonucleotide is 1 mM and the reconstituted solution contains 200 mM NaHCO$_3$-buffer, pH 8.3. Synthesis of the conjugate is initiated by slow, step-wise addition of highly purified bi-functional PEG. In a preferred embodiment, the PEG diol is activated at both ends (bi-activated) by derivatization with succinimidyl propionate. Following reaction, the PEG-nucleic acid conjugate is purified by gel electrophoresis or liquid chromatography to separate fully-, partially-, and un-conjugated species. Multiple PAG molecules concatenated (e.g., as random or block copolymers) or smaller PAG chains can be linked to achieve various lengths (or molecular weights). Non-PAG linkers can be used between PAG chains of varying lengths.

The 2'-OMe, 2'-fluoro and other modified nucleotide modifications stabilize the aptamer against nucleases and increase its half life in vivo. The 3'-3'-dT cap also increases exonuclease resistance. See, e.g., U.S. Pat. Nos. 5,674,685; 5,668,264; 6,207,816; and 6,229,002, each of which is incorporated by reference herein in its entirety.

Pag-derivatization of a Reactive Nucleic Acid

High molecular weight PAG-nucleic acid-PAG conjugates can be prepared by reaction of a mono-functional activated PEG with a nucleic acid containing more than one reactive site. In one embodiment, the nucleic acid is bi-reactive, or bi-activated, and contains two reactive sites: a 5'-amino group and a 3'-amino group introduced into the oligonucleotide through conventional phosphoramidite synthesis, for example: 3'-5'-di-PEGylation as illustrated in FIG. 6. In alternative embodiments, reactive sites can be introduced at internal positions, using for example, the 5-position of pyrimidines, the 8-position of purines, or the 2'-position of ribose as sites for attachment of primary amines. In such embodiments, the nucleic acid can have several activated or reactive sites and is said to be multiply activated. Following synthesis and purification, the modified oligonucleotide is combined with the mono-activated PEG under conditions that promote selective reaction with the oligonucleotide reactive sites while minimizing spontaneous hydrolysis. In the preferred embodiment, monomethoxy-PEG is activated with succinimidyl propionate and the coupled reaction is carried out at pH 8.3. To drive synthesis of the bi-substituted PEG, stoichiometric excess PEG is provided relative to the oligonucleotide. Following reaction, the PEG-nucleic acid conjugate is purified by gel electrophoresis or liquid chromatography to separate fully-, partially-, and un-conjugated species.

The linking domains can also have one or more polyalkylene glycol moieties attached thereto. Such PAGs can be of varying lengths and may be used in appropriate combinations to achieve the desired molecular weight of the composition.

The effect of a particular linker can be influenced by both its chemical composition and length. A linker that is too long, too short, or forms unfavorable steric and/or ionic interactions with the target will preclude the formation of complex between aptamer and target. A linker, which is longer than necessary to span the distance between nucleic acids, may reduce binding stability by diminishing the effective concentration of the ligand. Thus, it is often necessary to optimize linker compositions and lengths in order to maximize the affinity of an aptamer to a target.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLE 1

Anti-C5 Aptamer Activity in the Classical and Alternative Complement Pathways

Example 1A

Hemolysis Assay

The CH50 test measures the ability of the complement system in a serum test sample to lyse 50% of cells in a standardized suspension of antibody-coated sheep erythrocytes. A solution of 0.2% human serum was mixed with antibody-coated sheep erythrocytes (Diamedix EZ Complement CH50 Kit, Diamedix Corp., Miami, Fla.) in the presence or absence of various anti-C5 aptamers. The assay was run according to the kit protocol in veronal-buffered saline containing calcium, magnesium and 1% gelatin ($GVB^{++}$ complement buffer) and incubated for 30 minutes at 37° C. After incubation, the samples were centrifuged to pellet intact erythrocytes. The optical density at 412 nm ($OD_{412}$) of the supernatant was read to quantify the release of soluble hemoglobin, which is proportional to the extent of hemolysis (Green et al., (1995) Chem. Biol. 2:683-95). To verify that the aptamers blocked C5 activation, some hemolysis supernatants were analyzed for the presence of C5a and C5b-9 by ELISA (C5b-9 ELISA kit, Quidel, San Diego, Calif.; C5a ELISA kit, BD Biosciences, San Diego, Calif.) following the ELISA kit protocols.

Figures 7A, 7B:
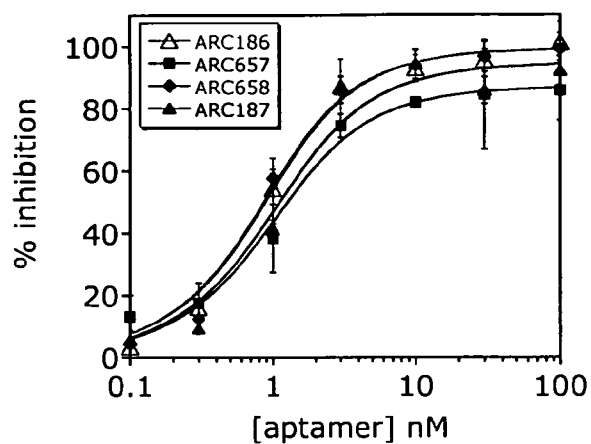
FIG. 7A is a graph comparing dose dependent inhibition of hemolysis by PEGylated anti-C5 aptamers (ARC657 (SEQ ID NO: 61), ARC658 (SEQ ID NO: 62), and ARC187 (SEQ ID NO: 5)), to a non-PEGylated anti-C5 aptamer (ARC186 (SEQ ID NO: 4))
FIG. 7B is a table of the $IC_{50}$ values of the aptamers used in the hemolysis assay depicted in FIG. 7A.
Figures 7C, 7D:
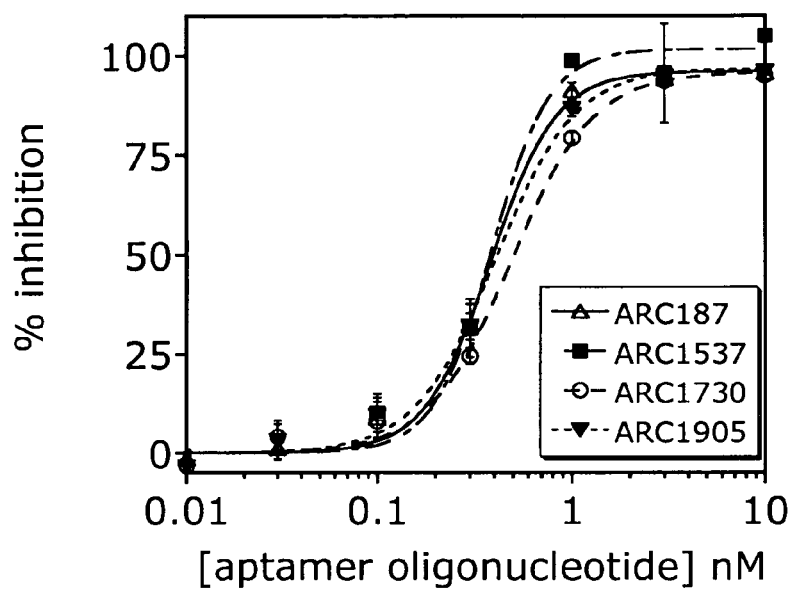
FIG. 7C is a graph comparing dose dependent inhibition of hemolysis by PEGylated anti-C5 aptamers ARC187 (SEQ ID NO: 5), ARC1537 (SEQ ID NO: 65), ARC1730 (SEQ ID NO: 66), and ARC1905 (SEQ ID NO: 67)
FIG. 7D is a table of the $IC_{50}$ values of the aptamers used in the hemolysis assay depicted in FIG. 7C.

The addition of a non-PEGylated anti-C5 aptamer (ARC186) (SEQ ID NO: 4) to the reaction mixture inhibited hemolysis in a dose-dependent manner, as shown in the graph of FIG. 7A, with an $IC_{50}$ of 0.5±0.1 nM, (see FIG. 7B), a value that is consistent with the $K_D$ determined by nitrocellulose filtration. At very high aptamer concentrations (>10 nM), the extent of hemolysis was essentially indistinguishable from background (no serum added), indicating that ARC186 (SEQ ID NO: 4) was able to completely block complement activity. Conjugation of the ARC186 (SEQ ID NO: 4) aptamer with 20 kDa (ARC657; SEQ ID NO: 61), 30 kDa (ARC658; SEQ ID NO: 62), branched 40 kDa (1,3-bis(mPEG-[20 kDa])-propyl-2-(4'-butamide) (ARC187; SEQ ID NO: 5), branched 40 kDa (2,3-bis(mPEG-[20 kDa])-propyl-1-carbamoyl) (ARC1905; SEQ ID NO: 67), linear 40 kDa (ARC1537; SEQ ID NO: 65), and linear 2×20 kDa (ARC1730; SEQ ID NO: 66) PEG groups had little effect on the aptamer inhibitory activity in the CH50 hemolysis assay (FIG. 7A-FIG. 7D).

Figure 58:
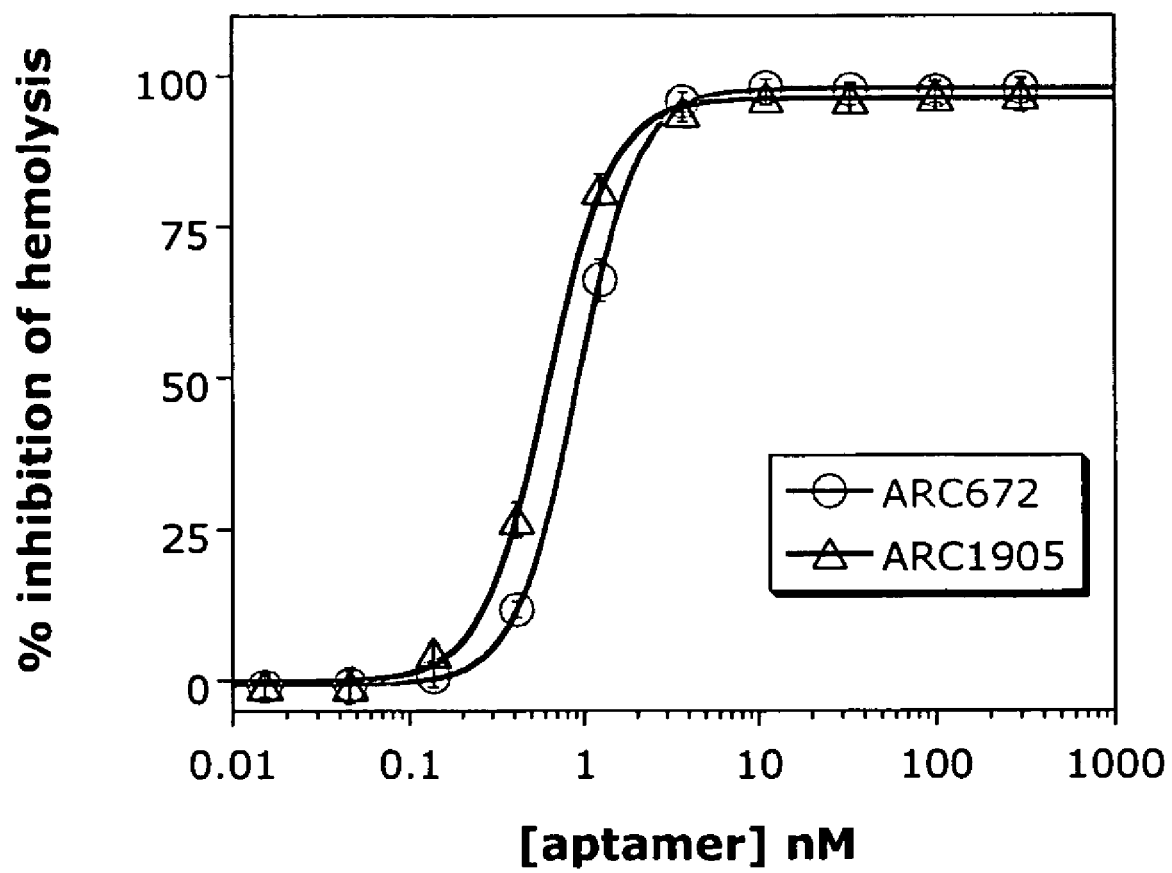
FIG. 58 is a graph depicting the percent inhibition of sheep erythrocyte hemolysis in the presence of human serum as a function of concentration of anti-C5 aptamers ARC1905 (SEQ ID NO 67) or ARC672 (SEQ ID NO 63).

In an additional study, the inhibitory activity of the PEGylated anti-C5 aptamer ARC1905 (branched 40 kDa (2,3-bis(mPEG-[20 kDa])-propyl-1-carbamoyl); SEQ ID NO: 67) was compared to its non-PEGylated precursor, ARC672 (SEQ ID NO 63) which contains a terminal 5'-amine, in the CH50 hemolysis assay described above. A solution of human serum (Innovative Research, Southfield, Mich.) was mixed with antibody-coated sheep erythrocytes (Diamedix EZ Complement CH50 Kit, Diamedix Corp., Miami, Fla.) in the presence or absence of various concentrations of ARC1905 and ARC627 respectively such that the final concentration of serum in each assay was 0.1%, and the assay was run according to manufacturer's recommended protocol. The hemolysis reactions were incubated for 1 hour at 37° C. with agitation to ensure that cells remained in suspension. At the end of the incubation, intact cells were pelleted by centrifugation (2000 rpm, 2 min, room temperature), 200 μL supernatant was transferred to a flat-bottomed polystyrene plate (VWR, cat#62409-003). The optical density at 415 nm ($OD_{415}$) of the supernatant was read to quantify the release of soluble hemoglobin. The % inhibition at each aptamer concentration measured was calculated using the equation % inh=100-100×($A_{sample}$-$A_{no\ serum}$)/($A_{no\ aptamer}$-$A_{no\ serum}$), where $A_{sample}$ is the sample absorbance at varying concentrations of aptamer, $A_{no\ serum}$ is the absorbance due to background hemolysis in the absence of serum (100% inhibition control) and $A_{no\ aptamer}$ is the absorbance due to basal complement activity in the absence of aptamer (0% inhibition control). $IC_{50}$ values were determined from a plot of % inhibition versus [inhibitor] using the equation % inh=(% inh)$_{maximum}$×[inhibitor]$^n$/($IC_{50}^n$+[inhibitor]$^n$)+background. $IC_{90}$ and $IC_{99}$ values were calculated from $IC_{50}$ values using the equations $IC_{90}$=$IC_{50}$×[90/(100-90)]$^{1/n}$ and $IC_{90}$=$IC_{50}$×[99/(100-99)]$^{1/n}$. The $IC_{50}$ values for ARC1905 and ARC627 in this parallel study were 0.648+/−0.0521 and 0.913+/−0.0679 respectively (see also FIG. 58) further confirming that PEGylation had little, if any, effect on aptamer function.

ELISA analysis of hemolysis supernatants indicated that this functional inhibition correlated with blockade of C5a release. Thus, the hemolysis data show that ARC186 (SEQ ID NO: 4), and its PEGylated conjugates, are highly potent complement inhibitors that function by blocking the convertase-catalyzed activation of C5.

Figure 8:
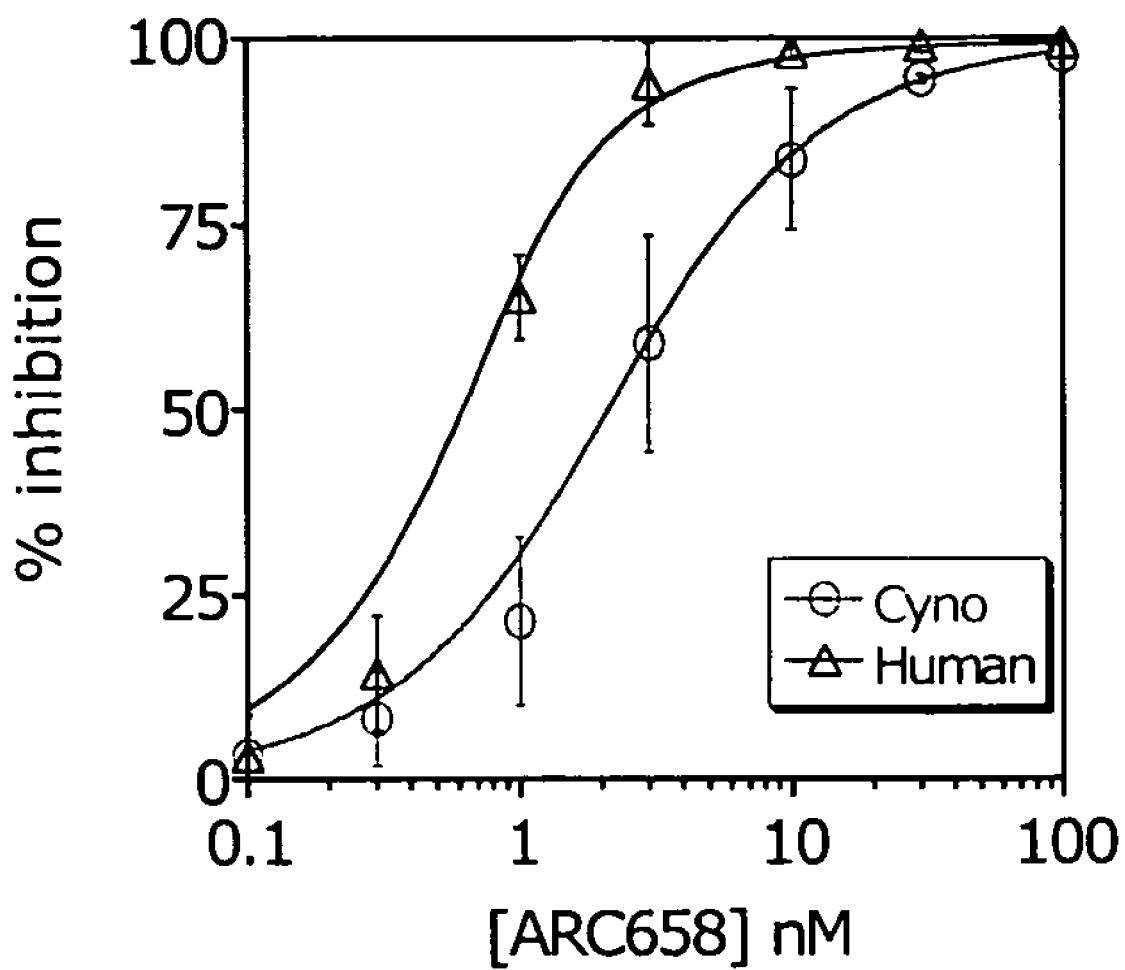
FIG. 8 is a graph of percent inhibition of hemolysis by the anti-C5 aptamer, ARC658 (SEQ ID NO: 62), of cynomolgus serum complement versus human serum complement.

Hemolysis assays with non-PEGylated material indicated that the anti-C5 aptamer does not cross-react with C5 from a number of non-primate species, including rat, guinea pig, dog and pig. However, significant inhibitory activity was observed in screens of primate serum, including serum from cynomolgus macaque, rhesus macaque and chimpanzee. The in vitro efficacy of the anti-C5 aptamer was further investigated in cynomolgus serum using ARC658 (SEQ ID NO: 62), the 30 kDa-PEG analogue of ARC186 (SEQ ID NO: 4). In a side-by-side comparison (n=3), ARC658 inhibited human complement activity with an $IC_{50}$ of 0.21±0.0 nM and cynomolgus complement activity with an $IC_{50}$ of 1.7±0.4 nM (FIG. 8). Thus ARC658 (SEQ ID NO: 62) is 8±3 fold less potent in cynomolgus serum compared to human by this measure.

Figures 59A, 59B:
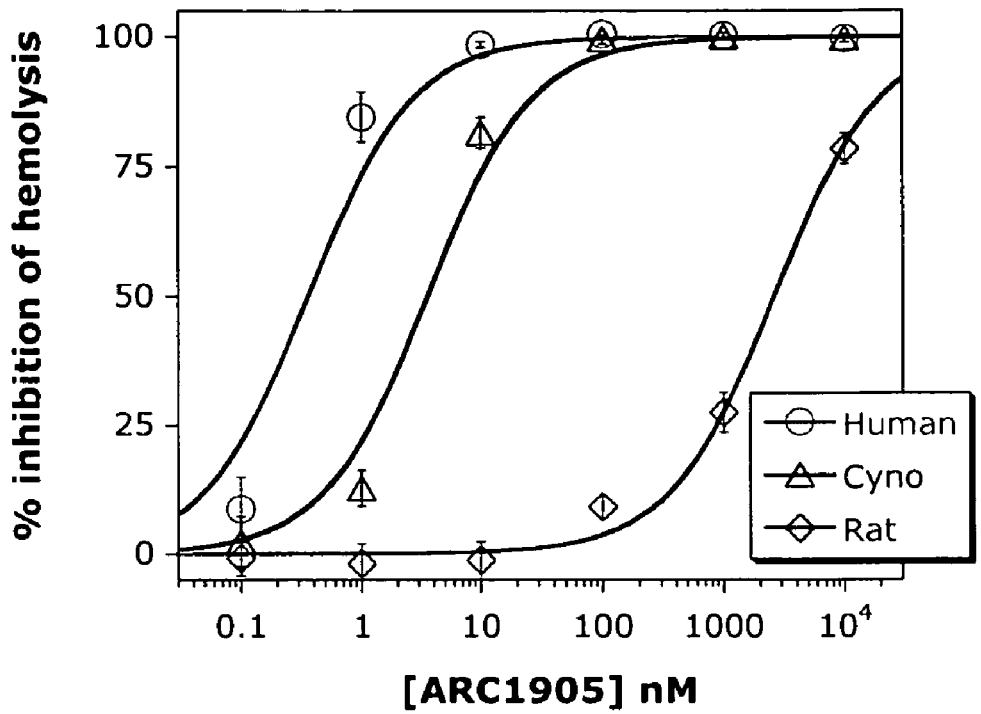
FIG. 59A is a graph depicting the percent inhibition of hemolysis in the presence of human, cynomolgus monkey and rat serum by ARC1905 (SEQ ID NO 67)
FIG. 59B is a table summarizing the mean $IC_{50}$ values for inhibition of complement activation in human, cynomolgus monkey and rat serum by ARC1905, an anti-C5 aptamer or ARC127, an irrelevant aptamer which does not bind C5 (negative control).

In a related study, the effects of the branched 40 kDa (2,3-bis(mPEG-[20 kDa])-propyl-1-carbamoyl) PEGylated anti-C5 aptamer, ARC1905 (SEQ ID NO: 67) on classical complement pathway activation as assayed by sheep erythrocyte hemolysis was investigated in the presence of human (Innovative Research, Southfield, Mich.), cynomolgus monkey (Bioreclamation, Hicksville, N.Y.), or rat serum (Bioreclamation, Hicksville, N.Y.). These assays were performed in highly diluted serum, 0.1% for human and cynomolgus monkey, and 0.3% for rat, under the same conditions as those used to compare the inhibitory effects of ARC1905 against ARC672 on sheep erythrocyte hemolysis as described directly above. In a side by side comparison, complete inhibition (90-99%) of in vitro complement activity was achievable with ARC1905 in both human and cynomolgus monkey sera whereas ARC1905 displayed little to no specific inhibitory activity in the rat complement sample (FIG. 59A). Similar to ARC658, ARC1905 was ~10-fold less potent against cynomolgus complement activity under the conditions of the assay, as reflected in the $IC_{90}$ and $IC_{99}$ values reported in FIG. 59B.

Nitrocellulose Filter Binding Assays. Individual aptamers were $^{32}$P-labeled at the 5' end by incubation with γ-$^{32}$P-ATP and polynucleotide kinase (New England Biolabs, Beverly, Mass.). Radiolabeled aptamer was purified away from free ATP by gel-filtration followed by polyacrylamide gel electrophoresis. To measure anti-C5 aptamer affinity, radiolabeled aptamer (≦10 pM) was incubated with increasing concentrations (0.05-100 nM) of purified C5 protein (Quidel, San Diego, Calif.) in phosphate-buffered saline containing 1 mM MgCl$_2$ at room temperature (23° C.) and 37° C., for 15 min and 4 hr time intervals. The binding reactions were analyzed by nitrocellulose filtration using a Minifold I dot-blot, 96-well vacuum filtration manifold (Schleicher & Schuell, Keene, N.H.). A three-layer filtration medium was used, consisting (from top to bottom) of Protran nitrocellolose (Schleicher & Schuell), Hybond-P nylon (Amersham Biosciences, Piscataway, N.J.) and GB002 gel blot paper (Schleicher & Schuell). The nitrocellulose layer, which selectively binds protein over nucleic acid, preferentially retained the anti-C5 aptamer in complex with a protein ligand, while non-complexed anti-C5 aptamer passed through the nitrocellulose and adhered to the nylon. The gel blot paper was included simply as a supporting medium for the other filters. Following filtration, the filter layers were separated, dried and exposed on a phosphor screen (Amersham Biosciences) and quantified using a Storm 860 Phosphorimager® blot imaging system (Amersham Biosciences).

Figure 9:
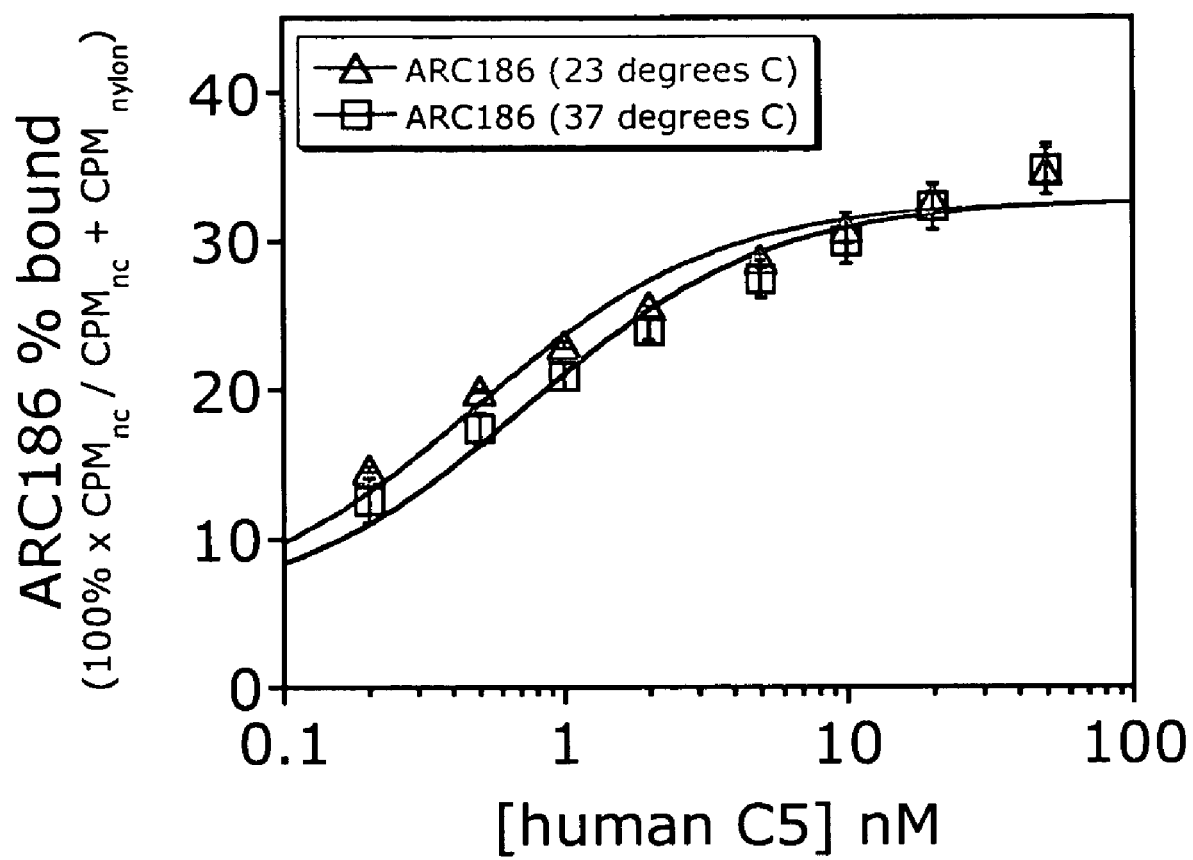
FIG. 9 is a graph depicting the binding of ARC186 (SEQ ID NO: 4) to purified C5 protein at both 37° C. and room temperature (23° C.) following a 15 minute incubation.
Figure 10:
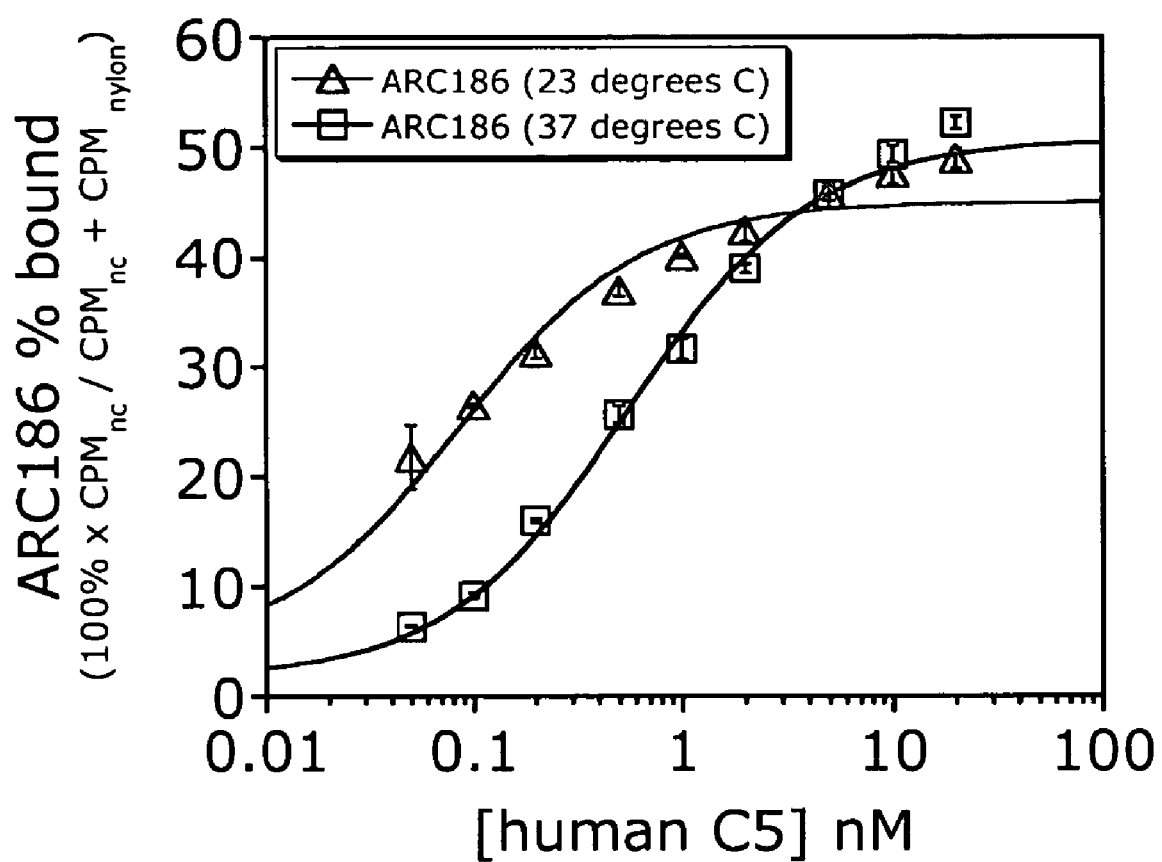
FIG. 10 is another graph depicting the binding of ARC186 (SEQ ID NO: 4) to purified C5 protein at both 37° C. and room temperature (23° C.) following a 4 hour incubation.

As shown in shown in FIG. 9 and FIG. 10, increasing C5 concentrations enhance the proportion of ARC186 captured on the nitrocellulose membrane. The dependence of bound ARC186 on increasing C5 concentrations is well-described by a single-site binding model (C5+ARC186↔C5•ARC186; % bound=$C_{max}$/(1+$K_D$/[C5]); $C_{max}$ is the maximum % bound at saturating [C5]; $K_D$ is the dissociation constant). ARC186 binding curves at two temperatures following either a 15 min or a 4 hr incubation are shown in FIGS. 9 and 10, respectively. Following a 15 min incubation, the ARC186 binding curves at 23 and 37° C. are essentially indistinguishable within error, fitting with $K_D$ values of 0.5-0.6 nM (FIG. 9). Differences between binding curves at 23 and 37° C. become more pronounced when the incubation time is extended. Following a 4 hr incubation (FIG. 10), the $K_D$ observed at 23° C. decreases to 0.08±0.01 nM, while the $K_D$ observed at 37° C. remains unchanged (0.6±0.1 nM).

To demonstrate the basis for the long incubation requirement at room temperature, the affinity at this temperature was further explored using kinetic methods. The rate of the reverse reaction describing the dissociation of C5•ARC186 is $v_{rev}$=$k_{-1}$[C5•ARC186], where $v_{rev}$ is the rate (units of M min$^{-1}$) and $k_{-1}$ is the first order dissociation rate constant (units of min$^{-1}$). The rate of the forward reaction describing the formation of the C5•ARC186 complex is $v_{for}$=$k_1$[C5][ARC186], where $v_{for}$ is the rate (units of M min$^{-1}$) and $k_1$ is the second order association rate constant (units of M$^{-1}$min$^{-1}$). The data were analyzed using the pseudo-first order assumption, where the concentration of one reactant (C5 in this case) is held in vast excess over the other ([C5]>>[ARC186], and thus remains essentially unchanged over the course of the reaction. Under these conditions, the forward reaction is described by the rate equation for a first order process, $v_{for}$=$k_1'$[ARC186], where $k_1'$=$k_1$[C5].

Figure 11:
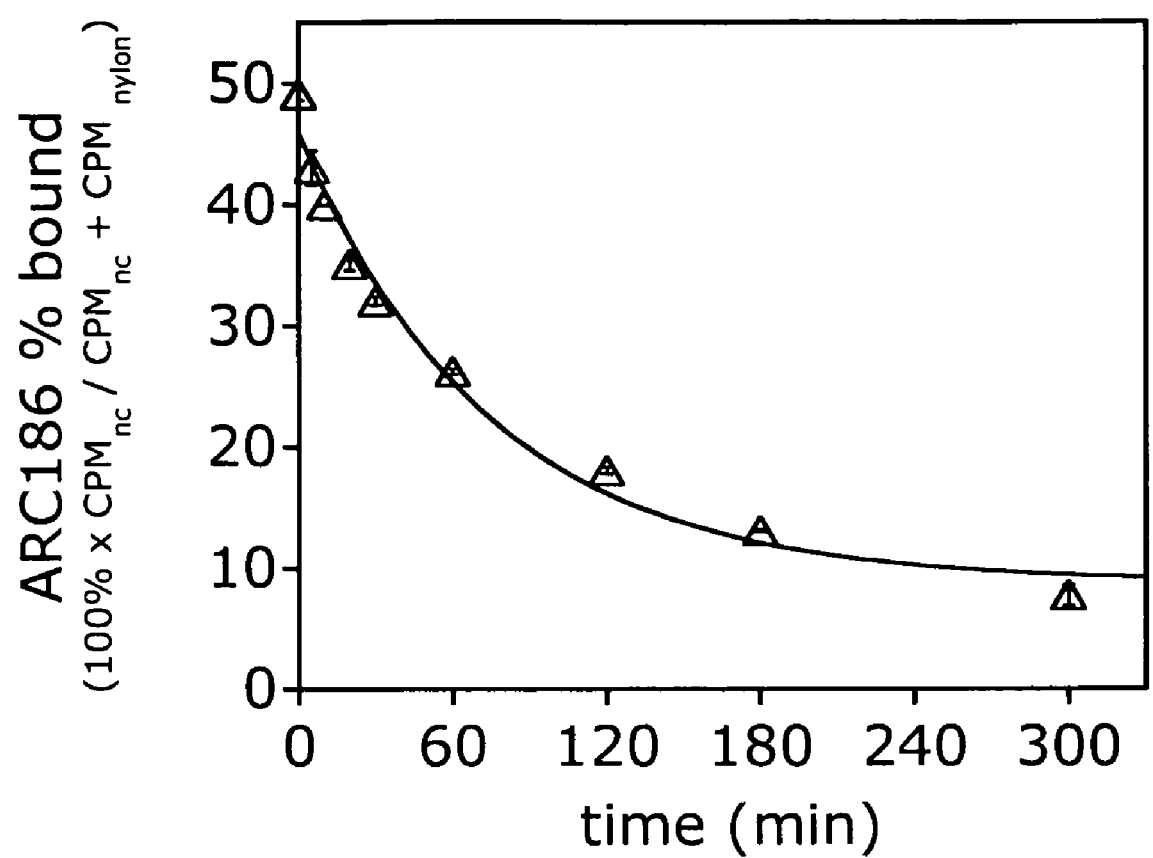
FIG. 11 is graph showing a time course of dissociation of C5•ARC186 complex at 23° C.

To analyze dissociation of C5•ARC186, radiolabeled ARC186 (≦10 pM) was pre-equilibrated with 5 nM C5 protein in phosphate-buffered saline containing 1 mM MgCl$_2$ at room temperature (23° C.). The dissociation reaction was initiated by the addition of non-labeled ARC186 (1 μM), which acts as a trap for free C5, and stopped by nitrocellulose filtration partitioning of bound and free radiolabeled ARC186. A timecourse of ARC186 dissociation was obtained by varying the duration between initiation of the dissociation reaction and filtration. The timecourse of dissociation, observed as a decrease in the percentage of radiolabeled ARC186 captured on the nitrocellulose filter (equal to the percent bound to C5), is well-described by a single-exponential decay where % ARC186 bound=100×e$^{-k_{-1}t}$ (see FIG. 11). The value of the dissociation rate constant, $k_{-1}$, determined by this method is 0.013±0.02 min$^{-1}$, corresponding to a half-life ($t_{1/2}$=ln 2/$k_{-1}$) of 53±8 min.

Figure 12:
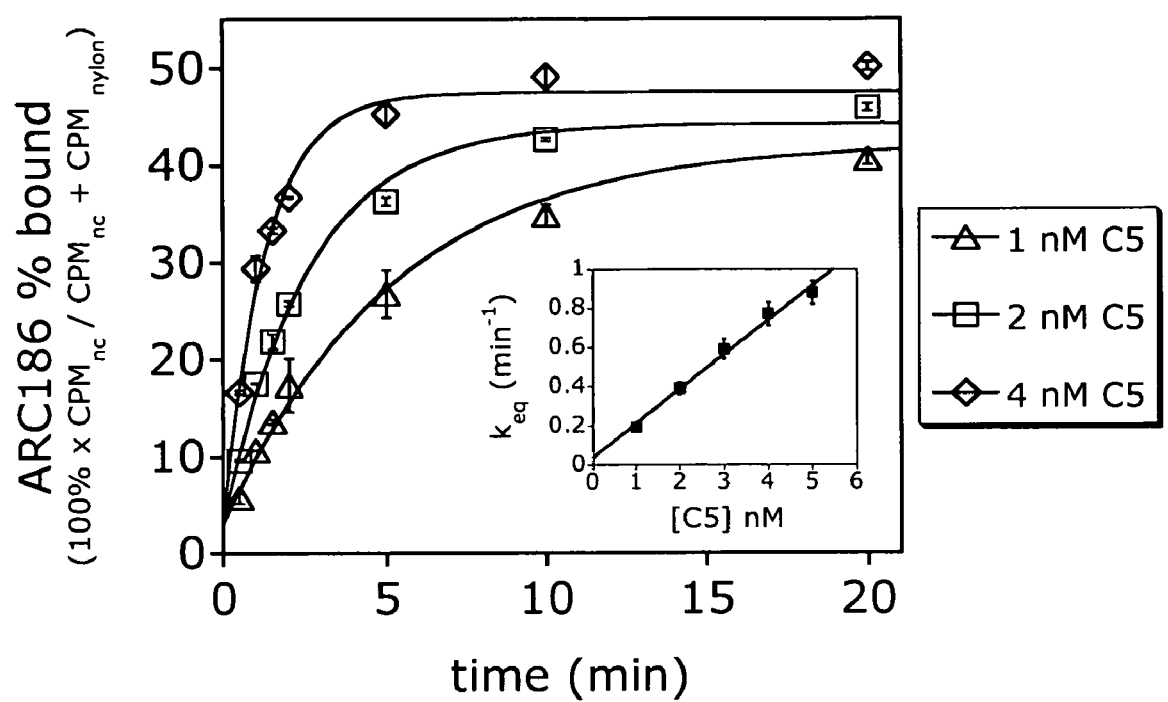
FIG. 12 is a graph showing a time course of equilibration in the formation of C5•ARC186 complex at 23° C.

To analyze the association reaction, the equilibration rate constant ($k_{eq}$) for the formation of C5•ARC186 was measured in the presence of varying concentrations of C5 protein (1-5 nM). Complex formation was initiated by mixing together C5 protein and radiolabeled ARC186 in PBS containing 1 mM MgCl$_2$ at room temperature (23° C.), and stopped by nitrocellulose filtration partitioning. As described for the dissociation reactions, a timecourse of complex formation was obtained by varying the duration between the initiation of the reaction and filtration. The timecourse of equilibration, observed as an increase in the percentage of radiolabeled ARC186 captured on the nitrocellulose filter, is well described by a single-exponential decay where % ARC186 bound=100×(1−e$^{-k_1t}$). The timecourses of equilibration for 1, 2 and 4 nM C5 are displayed in FIG. 12. As expected, the value of $k_{eq}$ increases linearly with [C5] ($k_{eq}$ (1 nM)=0.19±0.02 min$^{-1}$; $k_{eq}$ (2 nM)=0.39±0.03 min$^{-1}$; $k_{eq}$ (3 nM)=0.59±0.05 min$^{-1}$; $k_{eq}$ (4 nM)=0.77±0.06 min$^{-1}$; $k_{eq}$ (5 nM)=0.88±0.06 min$^{-1}$). Under the conditions of the experiment, the relationship between $k_{eq}$, $k_1$ and $k_{-1}$ is $k_{eq}$=$k_1$[C5]+$k_{-1}$. Thus, an estimate of $k_1$ is derived from the slope of a plot of $k_{eq}$ versus [C5] (see FIG. 12 inset), in this case 0.18±0.01 nM$^{-1}$min$^{-1}$.

These data indicate that, under conditions of low C5 concentration (e.g., 0.1 nM), an extended incubation is required in order for the mixture of C5 and radiolabeled ARC186 to reach equilibrium. Under these conditions, $k_{eq}$=(0.18±0.01 nM$^{-1}$min$^{-1}$) (0.1 nM)+0.013 min$^{-1}$=0.03 min$^{-1}$, corresponding to a half-life of 22 min. Thus, nearly 2 hours of room temperature incubation (~5 half-lives) are required for complete (>95%) equilibration. A short incubation time (e.g., 15 min) will significantly underestimate the actual affinity of the complex, as shown above by the difference in affinities observed for a 15 min ($K_D$=0.5 nM) versus a 4 hour ($K_D$=0.08 nM) incubation. An alternative estimate of the room temperature $K_D$ can be calculated from the kinetic data according to the relationship $K_D$=$k_{-1}$/$k_1$. In this case, the calculated $K_D$ is 0.07±0.01 nM, which is completely consistent with the $K_D$ determined above by thermodynamic methods.

The specificity of ARC186 (SEQ ID NO: 4) for C5 was also assessed in nitrocellulose filtration assays by comparison with complement components both upstream and downstream from C5 in the complement cascade. Purified human proteins and protein complexes were purchased from Complement Technologies (Tyler, Tex.) including: C1q (cat. # A099.18; 2.3 μM), C3 (cat. # A113c.8; 27 μM), C5 (cat. # A120.14; 5.4 μM), C5a des Arg (cat. # A145.6; 60 μM), sC5b-9 (cat. # A127.6; 1 μM), factor B (cat. # A135.12; 11 μM) and factor H (cat. # A137.13P; 6.8 μM). Binding reactions were established by performing serial dilutions of protein in PBS plus 1 mM MgCl$_2$, 0.02 mg/mL BSA and 0.002 mg/mL tRNA, incubating for 1-4 hours at 25° C. or 37° C., and then applied to the nitrocellulose filtration apparatus as described above. Dissociation constants $K_D$ were determined from semi-log plots of % nitrocellulose binding versus [C5] by a fit of the data to the equation: % nitrocellulose binding=amplitude×[C5]/($K_D$+[C5]).

Figure 13:
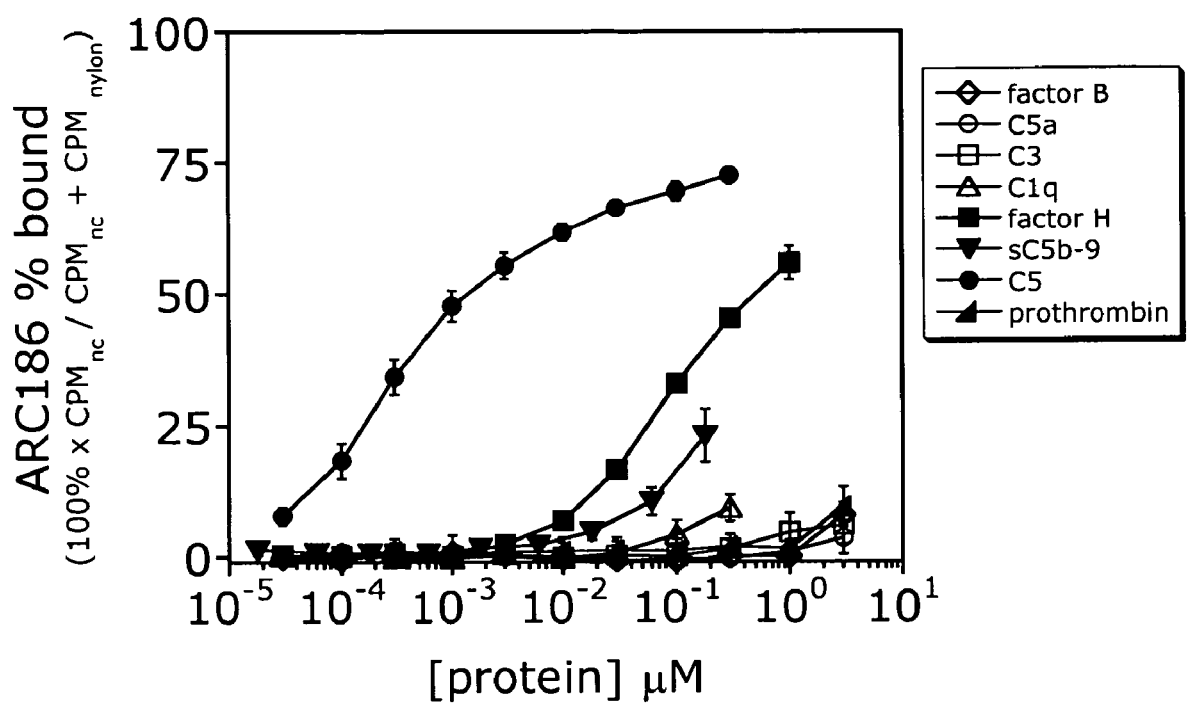
FIG. 13 is a graph depicting ARC186 (SEQ ID NO: 4) binding to C5 protein versus protein components upstream and downstream in the complement cascade.

The results depicted in FIG. 13 show the aptamer essentially does not recognize C5a ($K_D$>>3 μM), although it does display weak affinity for soluble C5b-9 ($K_D$>0.2 μM), presumably due to interactions with the C5b component. Other complement components display moderate to weak affinity for the aptamer. Non-activated C3 essentially does not bind to the aptamer; however, factor H ($K_D$~100 nM) and, to a much lesser extent, C1q ($K_D$>0.3 μM) do bind. Taken together, the data indicate that ARC186 (SEQ ID NO: 4) binds with high affinity to human C5, mainly via recognition of the C5b domain. Thus, ARC186 and its PEGylated derivatives e.g., ARC1905 should not interfere with generation of C3b, which is important for bacterial opsonization, or with innate control of C' activation by regulatory factors.

Figure 14:
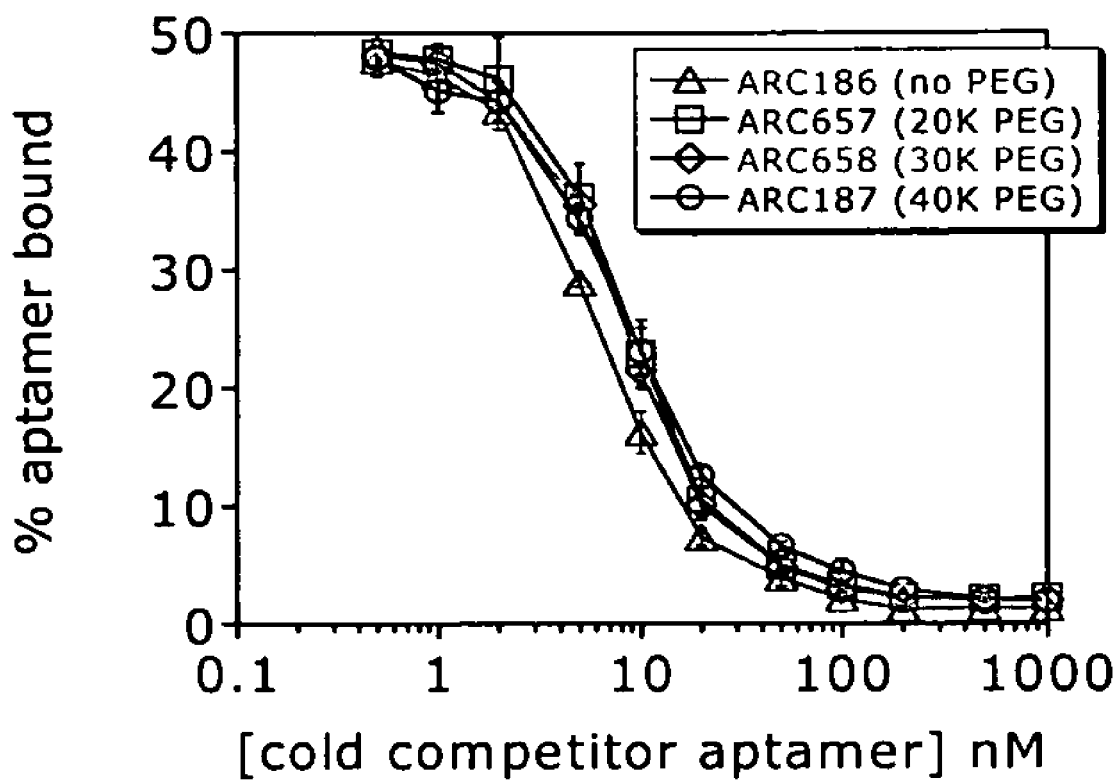
FIG. 14 is a graph depicting the percentage of radiolabeled ARC186 (SEQ ID NO: 4) that bound C5 in the presence of unlabeled competitor ARC186 (SEQ ID NO: 4), ARC657 (SEQ ID NO: 61), ARC658 (SEQ ID NO: 62) or ARC187 (SEQ ID NO: 5).

Conjugation of aptamers with high molecular weight PEG moieties introduces the possibility of steric hindrance leading to reduced affinity. PEG-modified aptamers are not readily evaluated for direct binding by nitrocellulose filtration assays due to the tendency of these aptamers to adhere to nitrocellulose even in the absence of target protein. However, the relative affinities of these aptamers can be assessed from their comparative ability to compete with radiolabeled, non-PE-Gylated aptamer (≦10 pM) for binding to target as measured by nitrocellulose filtration known as a competition binding assay, run at 37° C. As the concentration of cold (i.e., non-radiolabeled) competitor increases, the percent of radiolabeled aptamer bound to target protein decreases. As shown in FIG. 14, increasing concentrations of cold ARC186 (SEQ ID NO: 4) or PEGylated aptamer (ARC657 (SEQ ID NO: 61), ARC658 (SEQ ID NO: 62), and ARC187 (SEQ ID NO: 5)) (0.05-1000 nM) readily compete with radiolabeled ARC186 (SEQ ID NO: 4) for binding in the presence of 2 nM C5 protein. Additionally, the titration curves for all four aptamers nearly overlap, indicating that PEG-conjugation in the case of ARC657, ARC658 and ARC187 has little or no effect on the affinity of the aptamer for C5.

In a similar study, the effect of PEG conjugation on binding to C5 was tested by comparing ARC672 (ARC186 with a 5'-terminal amine; SEQ ID NO 63) with ARC1905 (ARC627 conjugated with a branched 40 kDa (2,3-bis(mPEG-[20 kDa])-propyl-1-carbamoyl) PEG) using the competition binding assay. 10 μM stocks of each aptamer were prepared in PBS plus 1 mM $MgCl_2$, 0.01 mg/mL BSA, 0.002 mg/mL tRNA, and serially diluted to generate a 10× sample series covering a >100-fold range of aptamer concentration. 12 μL aliquots of each sample were then added in a 96-well plate to 96 μL $^{32}$P-radiolabeled ARC186 to generate a 1.1×solution of label and cold competitor. 90 μL of label/competitor solution was then added to 10 μL of 10× C5 protein to initiate the reactions. The final concentration of radiolabeled ARC186 in each reaction was held constant. Binding reactions were equilibrated for 15-30 min at 37° C., and then filtered onto nitrocellulose filter apparatus described above. For the purposes of data analysis, cold competitor aptamers were treated as competitive inhibitors of the ARC186/C5 interaction; % inhibition was calculated by normalizing the data to control reactions lacking competitor (0% inhibition control). $IC_{50}$ values were determined from semi-log plots of % inhibition versus [ARC672] or [ARC1905] by a fit of the data to the equation: % inhibition=amplitude×[competitor]$^n$/($IC_{50}^n$+[competitor]$^n$).

Figure 60:
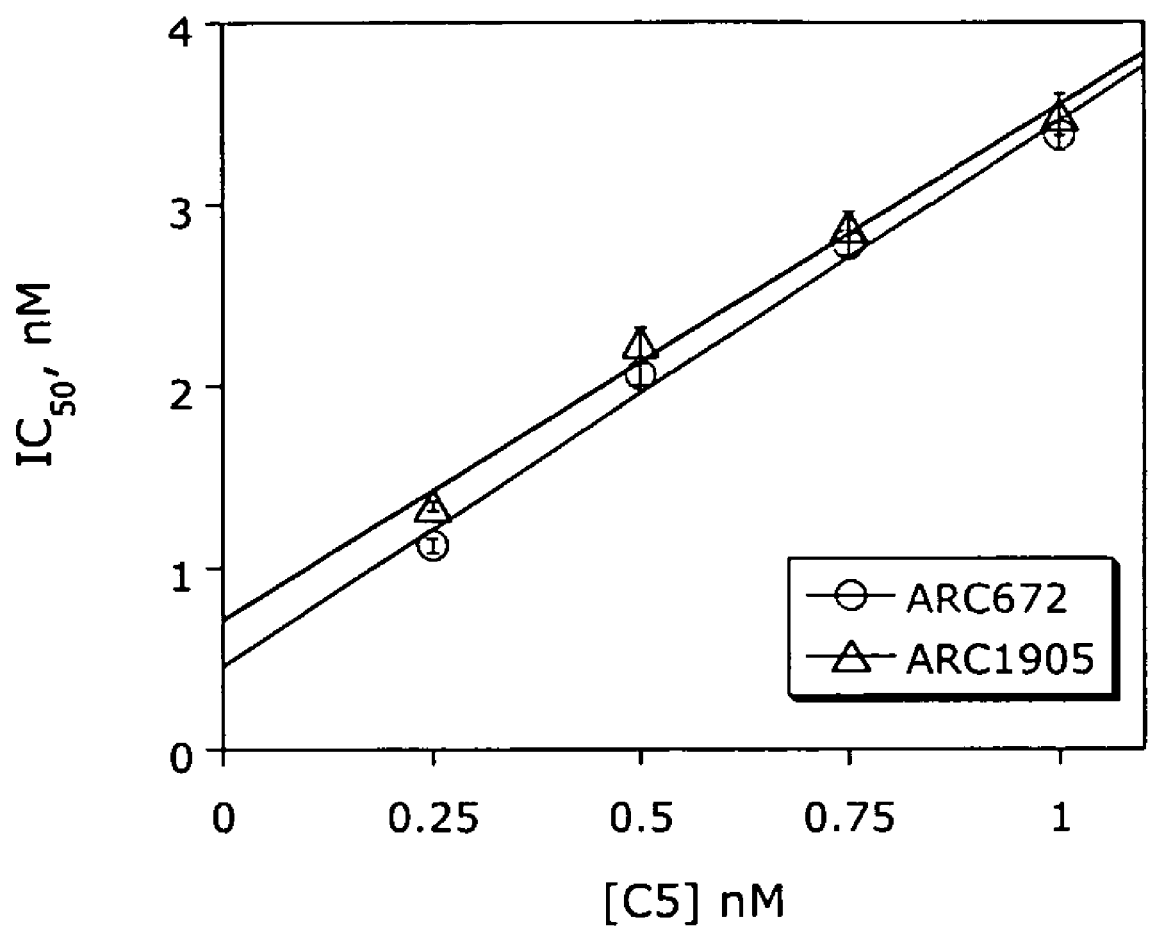
FIG. 60 is a graph depicting the $IC_{50}$ value for inhibition of radiolabeled ARC186 (SEQ ID NO: 4) (vertical axis) as a function of concentration of unlabeled competitor ARC1905 (SEQ ID NO 67) or ARC672 (SEQ ID NO 63) (horizontal axis), in a competition binding assay.

As shown in FIG. 60, the addition of a branched 40 kDa (2,3-bis(mPEG-[20 kDa])-propyl-1-carbamoyl) PEG had little or no effect on aptamer affinity as measured by competitive binding. $K_D$ values of 0.46+/−0.149 nM and 0.71+/−0.130 nM were approximated for ARC672 and ARC1905 respectively by the y-intercept of the line fit to the $IC_{50}$ versus C5 data in FIG. 60. Both values are close to the $K_D$ determined for ARC186 at 37° C.

Figure 61:
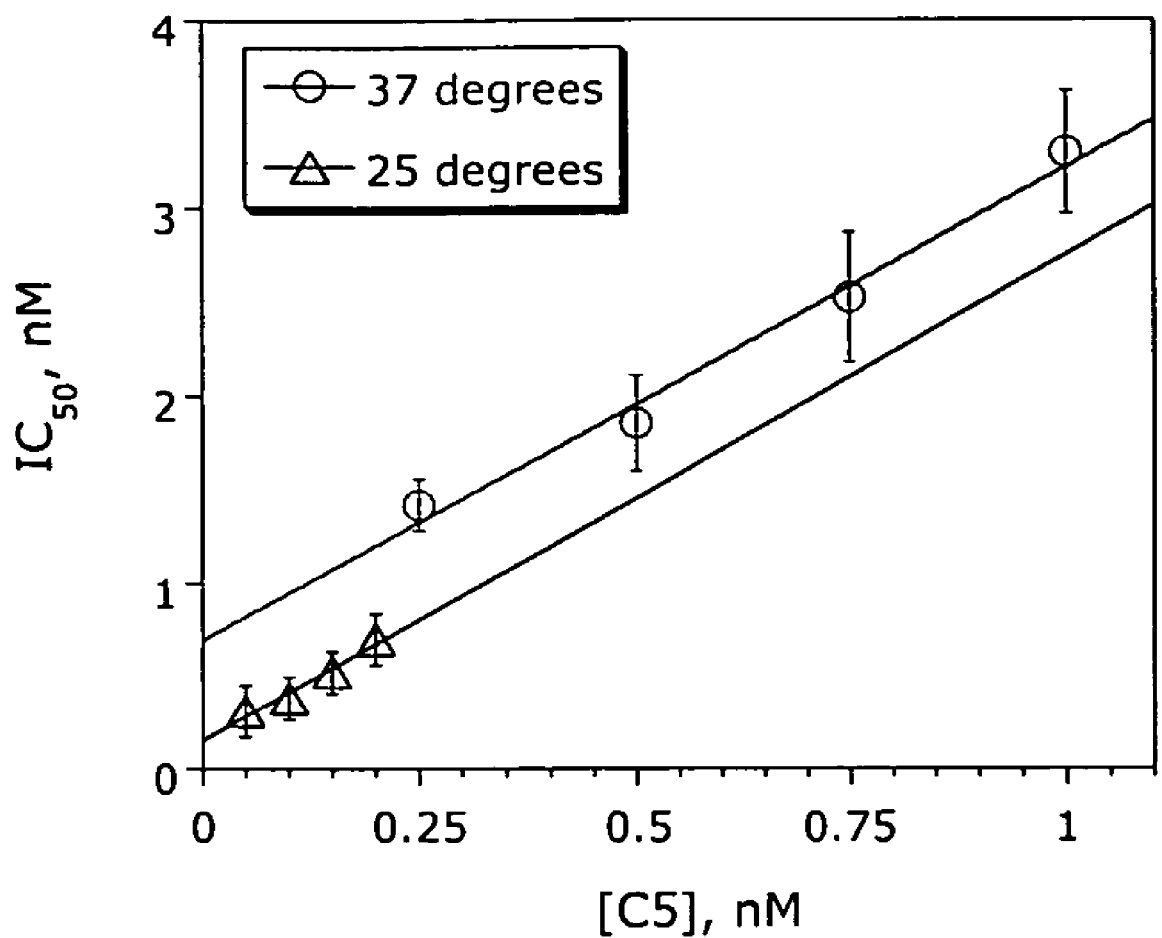
FIG. 61 is a graph depicting the $IC_{50}$ value for inhibition of radiolabeled ARC186 (SEQ ID NO: 4) (vertical axis) as a function of concentration of unlabeled competitor ARC1905 (SEQ ID NO 67) (horizontal axis) at 37° C. and 25° C. in a competition binding assay.

The temperature dependence of the interaction between ARC1905 and C5 was also estimated by competition assay. ARC1905 was serially diluted to generate 10× sample series as described above. Binding reactions were equilibrated for 1-4 hours at 25° C. or 37° C., and then filtered onto the nitrocellulose filter apparatus. Percent inhibition was calculated by normalizing the data to control reactions lacking competitor (0% inhibition control) or lacking C5 protein (100% inhibition control). $IC_{50}$ values were determined from semi-log plots of % inhibition versus [ARC672] or [ARC1905] by a fit of the data to the equation: % inhibition=amplitude×[competitor]$^n$/($IC_{50}^n$+[competitor]$^n$). As shown in FIG. 61 ARC1905 binds to C5 with high affinity at both 25° C. and 37° C. $K_D$ values of 0.15±0.048 nM and 0.69±0.148 nM were obtained at 25° C. and 37° C., respectively, from the y-intercept of the $IC_{50}$ versus C5 data. Both values are consistent with the $K_D$ values determined for the ARC186/C5 interaction described above.

Example 1B

Whole Blood Assay.

Figure 15:
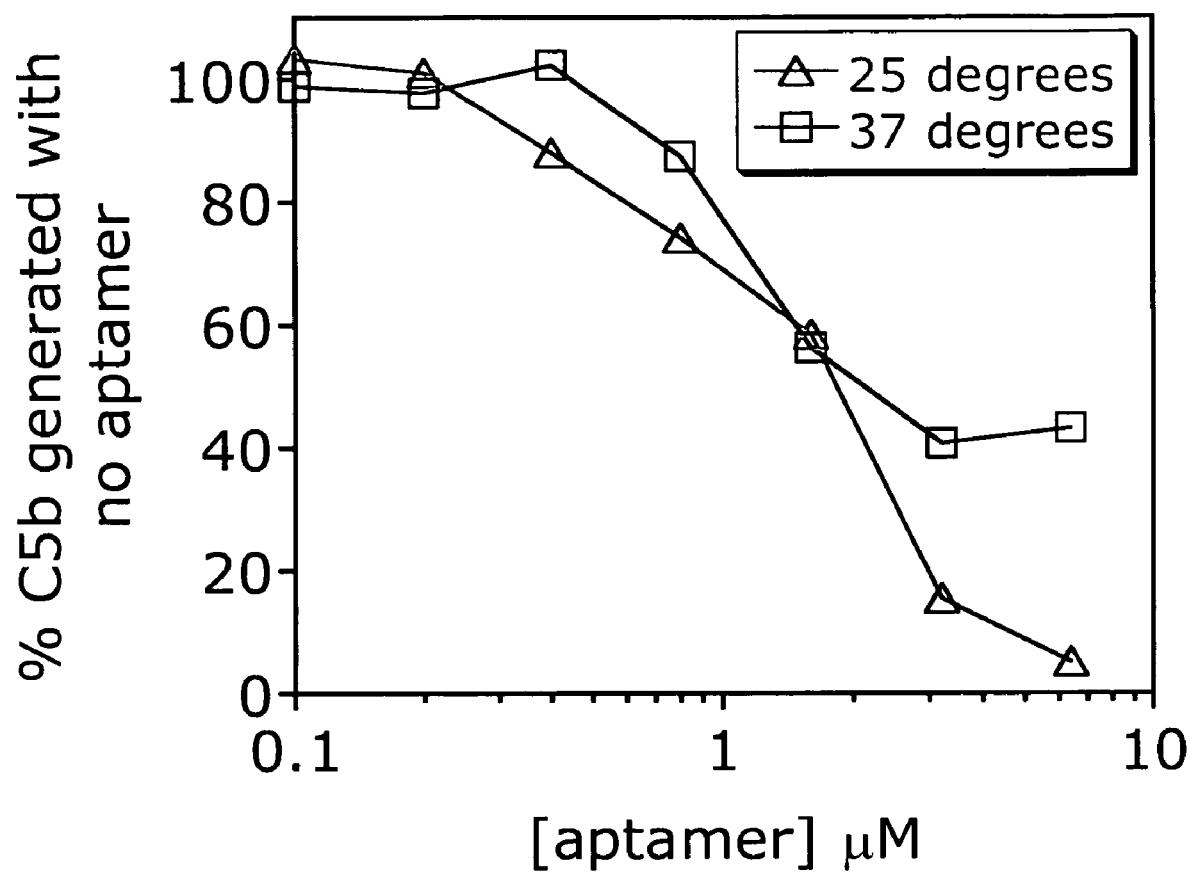
FIG. 15 is a graph depicting the amount of C5b complement protein produced in blood samples incubated for 5 hours at 25° C. and 37° C. in the presence of varying concentrations of the ARC186 (SEQ ID NO: 4) aptamer.

The effect of the anti-C5 aptamer on the alternative pathway of the complement system was analyzed using the following whole blood assay. In the absence of an anticoagulant, blood was drawn from normal human volunteers. Aliquots of blood (containing no anticoagulant) were incubated with increasing concentrations of ARC186 (SEQ ID NO: 4) for 5 hours at room temperature or 37° C. Samples were centrifuged to isolate serum and the presence of C5b in the serum was detected by sC5b-9 ELISA (C5b-9 ELISA kit, Quidel, San Diego, Calif.). As shown in FIG. 15, the anti-complement activity, as reflected in production of C5b-9, between samples incubated at different temperatures diverged at 3 μM. The room temperature data indicated that the concentration of aptamer required for quantitative inhibition is in the range of 3-6 μM, whereas the reported concentration of C5 is approximately 400 nM. These results suggest that greater than 10-fold molar excess of anti-C5 aptamer (ARC186; SEQ ID NO: 4) may be required for complete inhibition of C5 activity.

Example 1C

Complement Activation by Zymosan

Zymosan is a polysaccharide component of the yeast cell wall, and a potent activator of the alternative complement cascade. Addition of zymosan to ex vivo samples of blood, plasma or serum results in the accumulation of complement activation products, including C5a and the soluble version of C5b-9 (sC5b-9). Samples of undiluted human serum (Center for Blood Research, Boston, Mass.), citrated human whole blood (Center for Blood Research, Boston, Mass.) or cynomolgus serum (Charles River Labs, Wilmington, Mass.) were spiked with increasing concentrations of ARC658 (SEQ ID NO: 62), the 30K PEG analog of ARC186 (SEQ ID NO: 4). To activate complement, zymosan (Sigma, St. Louis, Mo.) in a 10× suspension was added to samples to a final concentration of 5 mg/mL. Following a 15 minute incubation at 37° C., zymosan particles were removed by centrifugation and the extent of complement activation was determined by C5a and/or sC5b-9 ELISA (C5b-9 ELISA kit, Quidel, San Diego, Calif.; C5a ELISA kit, BD Biosciences, San Diego, Calif.).

Figure 16:
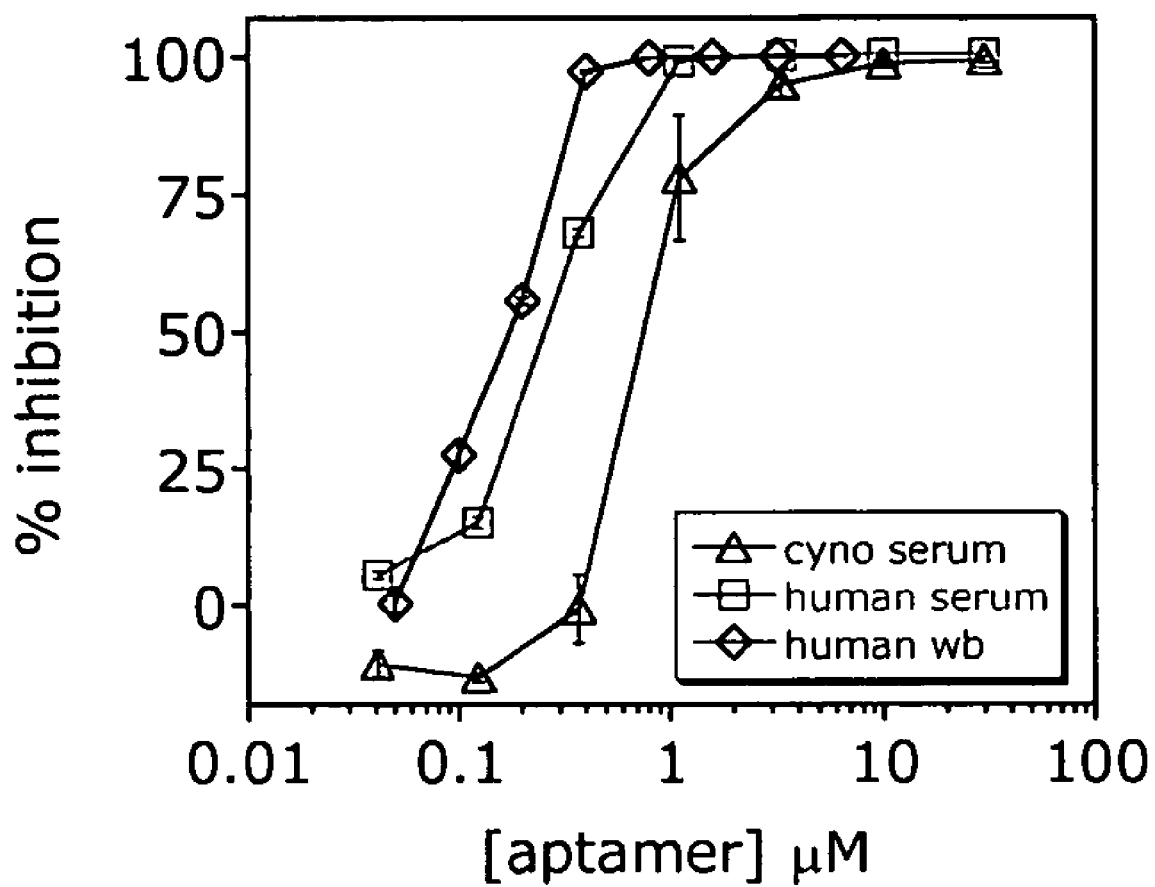
FIG. 16 is a graph depicting percent complement inhibition by ARC187 (SEQ ID NO: 5) in the presence of zymosan in undiluted human serum, citrated human whole blood or cynomolgus serum.

In the absence of aptamer, zymosan treatment activates ~50% of serum or whole blood C5, compared to ~1% activation in untreated sample. Addition of anti-C5 aptamer up to 50 nM (~10% of C5 concentration in blood) had little effect on sC5b-9 formation. However, further titration of C5 with increasing concentrations of ARC658 (SEQ ID NO: 62) inhibited C5 activation in a dose-dependent manner as seen in FIG. 16. In human serum or whole blood, quantitative (~99%)

inhibition was observed at 0.8-1 µM ARC658 (SEQ ID NO: 62), corresponding to ~2 molar equivalents of aptamer to C5. Higher concentrations of aptamer were required to achieve comparable inhibition in cynomolgus serum. In this case, 99% inhibition was achieved only in the presence of 10 µM aptamer, or ~20 molar equivalents of aptamer to C5.

In a similar study, the inhibitory effects of ARC1905 (the branched 40 kDa (2,3-bis(mPEG-[20 kDa])-propyl-1-carbamoyl) PEGylated version of ARC186) was tested on human and cynomolgus monkey samples using the zymosan to activate complement via the alternative pathway as follows. Zymosan A from *Saccharomyces cerevisiae* was supplied by Sigma-Aldrich, Inc. (cat. no. Z4250-1G, St. Louis, Mo.). The zymosan A was supplied as a powder and was resuspended in Dulbecco's PBS (Gibco, Carlsbad, Calif., cat. no. 14190-144) to yield a 50 mg/mL suspension. Frozen, pooled normal human serum (cat. no. IPLA-SER) was purchased from Innovative Research (Southfield, Mich.). Frozen, pooled cynomolgus macaque serum (cat. no. CYNSRM) was purchased from Bioreclamation (Hicksville, N.Y.). Vials of 5-10 mL serum provided by the supplier were thawed at 37° C., aliquoted (~1 mL) and stored at –20° C. Aliquots were thawed as needed just prior to use by incubation at 37° C. and stored on ice during experiments. The final concentration of serum in each assay was ~100%. A 20 µM stock of ARC1905 was prepared in 0.9% saline and serially diluted to generate a 10× sample series covering a ~90-fold range of aptamer concentrations. A no-aptamer (saline only) sample was also included as a negative (0% inhibition) control.

90 µL of serum was pipetted into wells of a 96-well PCR plate (VWR, cat. no. 1442-9596). 10 µL of aptamer sample was diluted directly into the serum at room temperature and mixed. 8 µL of 50 mg/mL zymosan was pipetted into wells of a separate 96-well PCR plate. Both plates were simultaneously pre-incubated at 37° C. for 15 minutes. Immediately following the pre-incubation, 80 µL of the serum/aptamer mixture was added directly to 8 µL of zymosan and mixed, yielding 5 mg/mL zymosan final concentration. The reaction plate was sealed and incubated for 15 minutes at 37° C. At the end of the incubation, the reaction was quenched by pipetting 8 µL 0.5M EDTA into the wells and mixing. The zymosan was pelleted by centrifugation (3700 rpm, 5 min, room temperature) and ~80 µL quenched supernatant was transferred to a new 96-well PCR plate and sealed. Supernatants were flash frozen in liquid nitrogen and stored at –20° C. To control for zymosan-independent background activation, serum samples were prepared and treated exactly as described above, except that 8 µL of saline was added instead of zymosan.

Figures 62, 63:
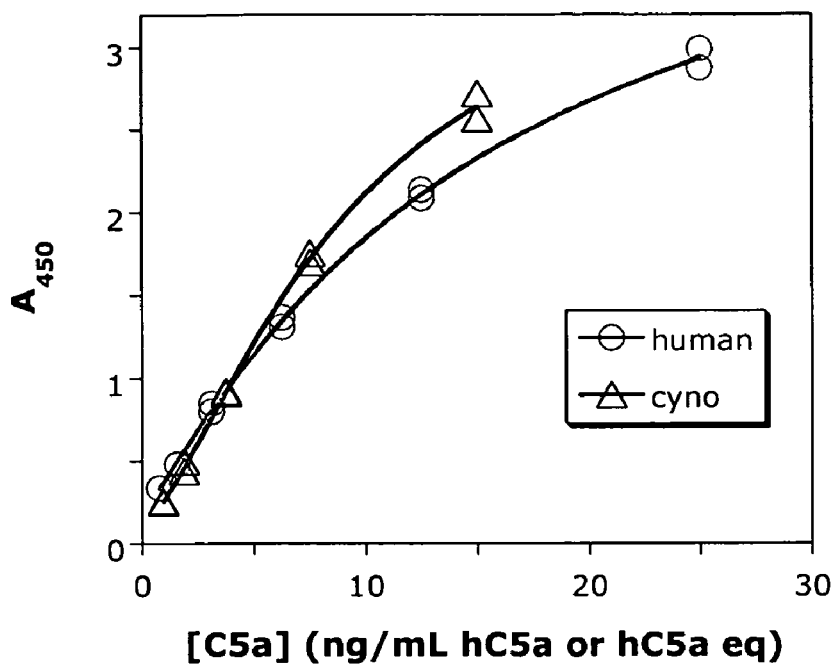
FIG. 62 is a graph depicting standard curves for human C5a (hC5a) and cynomolgus monkey C5a (hC5a eq).
FIG. 63 is a table summarizing the $IC_{50}$, $IC9_0$ and $IC_{99}$ values for inhibition of C5 activation in human and cynomolgus monkey serum by ARC1905 (SEQ ID NO 67), as measured in a zymosan-induced complement activation assay.

The extent of C5 activation was determined from the relative levels of C5a generated in each zymosan-activated sample, as measured by C5a ELISA (ALPCO Diagnostics, Windham, N.H., cat. no. EIA-3327) following the C5a ELISA kit protocol. The C5a ELISA kit includes human specific reagents and is formatted for analysis of human C5a (hC5a) in plasma or serum samples. It was therefore necessary to characterize the response of the ELISA to cynomolgus monkey C5a using cynomolgus concentration standards. To prepare a set of custom standards, 0.5 mL aliquots of human or cynomolgus monkey serum were incubated with 5 mg/mL zymosan for 15 min at 37° C., quenched with 12.5 µL 0.5M EDTA and centrifuged to remove the zymosan. The concentration of C5a in the zymosan-activated human serum sample was determined to be approximately 2 µg/mL hC5a by comparison to hC5a standard plasmas provided with the kit. The concentration of C5a in the cynomolgus monkey sample, expressed in human C5a equivalents (hC5a eq), was determined to be approximately 0.6 µg/mL hC5a eq. Series of standards covering a range from 0.4-400 ng/mL hC5a or 0.12-120 ng/mL hC5a eq were prepared by dilution into rat serum (which does not interfere with the ELISA). Standards were pre-treated with a protein-precipitating reagent as directed in the ELISA kit protocol and applied without further dilution to the ELISA plate. The ELISA plate was read at an aborbance maximum of 450 nm ($A_{450}$) using a VersaMax UV/vis absorbance plate reader (Molecular Dynamics, Sunnyvale, Calif.). The $A_{450}$ varied with C5a concentration from a low of 0.1-0.2 at low C5a, plateauing ~3.5 at high C5a. For the purposes of quantifying C5a in assay samples, the upper and lower limits of quantification were, respectively, 25 and 0.78 ng/mL hC5a for human, and 15 and 0.94 ng/mL hC5a eq for cynomolgus monkey. $A_{450}$ versus ng/mL hC5a or hC5a eq was plotted as shown in FIG. 62, and a standard curve was obtained from a 4-parameter fit to the data using the equation $y=((A-D)/(1+(x/C)^B))+D$.

Just prior to C5a analysis, assay samples (including the saline-only and no-zymosan controls) were pre-treated with protein-precipitating reagent as directed in the ELISA kit protocol, then serially diluted in 0.9% saline. C5a levels in undiluted assay samples (including some of the no-zymosan controls) typically exceeded the upper limit of quantitation (ULOQ). Therefore, dilutions of 1/5, 1/50 and 1/250 were tested to accommodate the full range of assay sample C5a concentrations. C5a levels were quantified by comparison with the appropriate (human or cynomolgus monkey) standard curve and corrected for dilution. The % inhibition at each aptamer concentration was calculated using the equation % inh.=$100-100\times(C5a_{sample}-C5a_{no-zymosan})/(C5a_{saline-only}-C5a_{no-zymosan})$. $IC_{50}$ values were determined from a plot of % inhibition versus [ARC1905] using the equation % inh=(% inh.$)_{maximum}\times[ARC1905]^n/(IC_{50}^n+[ARC1905]^n)$+background. $IC_{90}$ and $IC_{99}$ values were calculated from $IC_{50}$ values using the equations $IC_{90}=IC_{50}\times[90/(100-90)]^{1/n}$ and $IC_{99}=IC_{50}\times[99/(100-99)]^{1/n}$.

The extent of C3 activation (the step in the common complement pathway just upstream of C5) was determined from the relative levels of C3a generated in each zymosan-activated sample, as measured by C3a ELISA (Becton-Dickinson OptiEIA C3a ELISA kit, cat. no. 550499, Franklin Lakes, N.J.) following the C3a ELISA kit protocol.

Just prior to C3a analysis, samples (including the saline-only and no-zymosan controls) were serially diluted in 0.9% saline. The C3a ELISA is more sensitive than that for C5a; therefore, dilutions of 1/500, 1/5000 and 1/25,000 were necessary to accommodate the full range of sample C3a concentrations. Kit standards, derived from human serum, were used instead of the custom standards prepared for C5a analysis. Since C3a levels did not vary greatly, the human-specific standards provided a sufficient indication of their relative levels.

Figure 64:
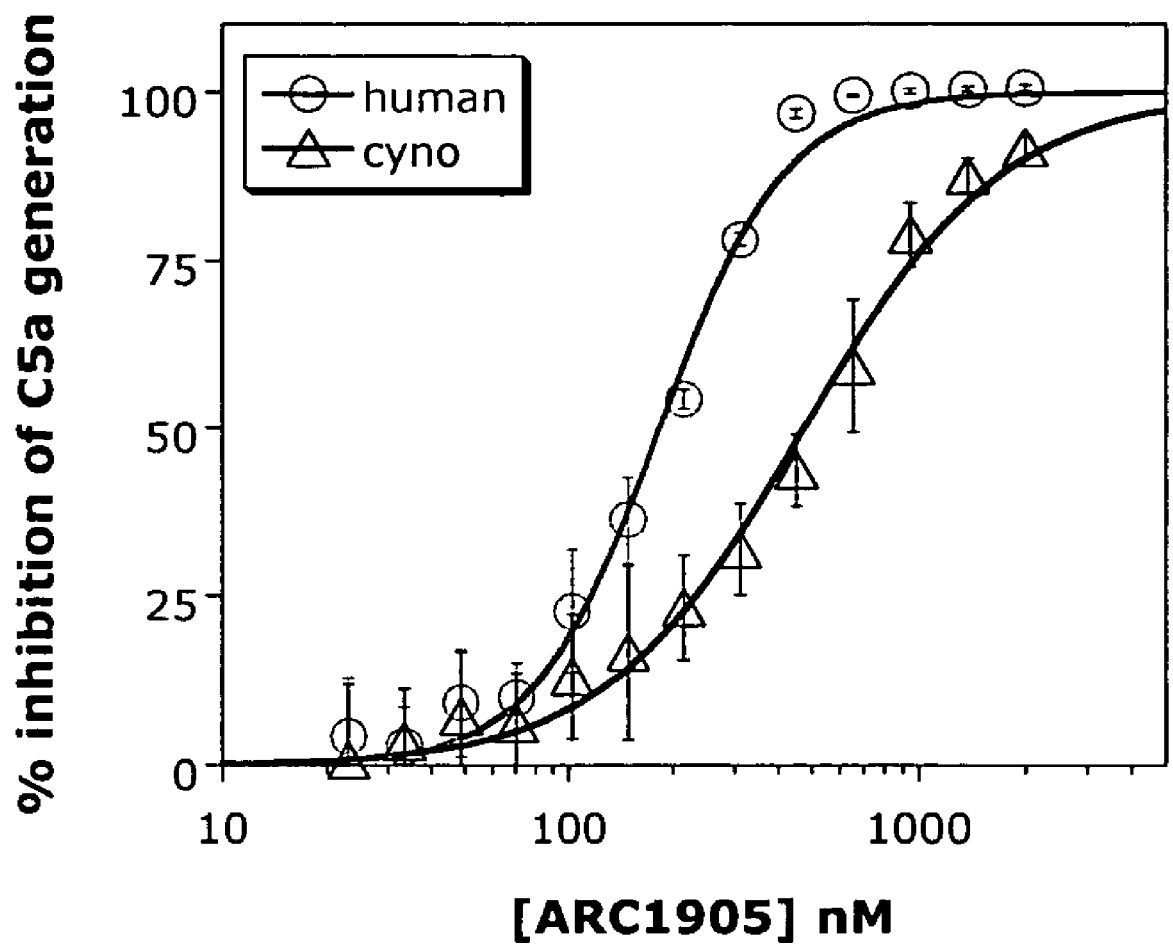
FIG. 64 is a graph depicting the percent inhibition of C5a generation as a function of ARC1905 (SEQ ID NO 67) concentration in human and cynomolgus monkey sera as measured in a zymosan-induced complement activation assay.

The data generated from both the C5a and C3 ELISAs were analyzed using Microsoft Excel, and the mean % inhibition values were plotted using Kaleidagraph (v. 3.51, Synergy Software). $IC_{50}$, $IC_{90}$ and $IC_{99}$ values were determined using the XLfit 4.1 plug-in to Excel. The comparative effects of ARC1905 on human and cynomolgus monkey complement activation, as measured by this approach, are summarized in FIG. 63 and FIG. 64. As can be seen from these Figures, complete inhibition of C5 activation via the alternate pathway is achievable in vitro with ARC1905 in both human and cynomolgus monkey sera. In human serum, the concentration of ARC1905 required for 90% inhibition of C5 activation in an undiluted sample was 442±23 nM, approximately equivalent to the average molar concentration of C5. However, ARC1905 was 4-6-fold less potent against cynomolgus monkey complement activity under the conditions of the assay, as reflected in the $IC_{90}$ and $IC_{99}$ values.

Figures 65, 66:
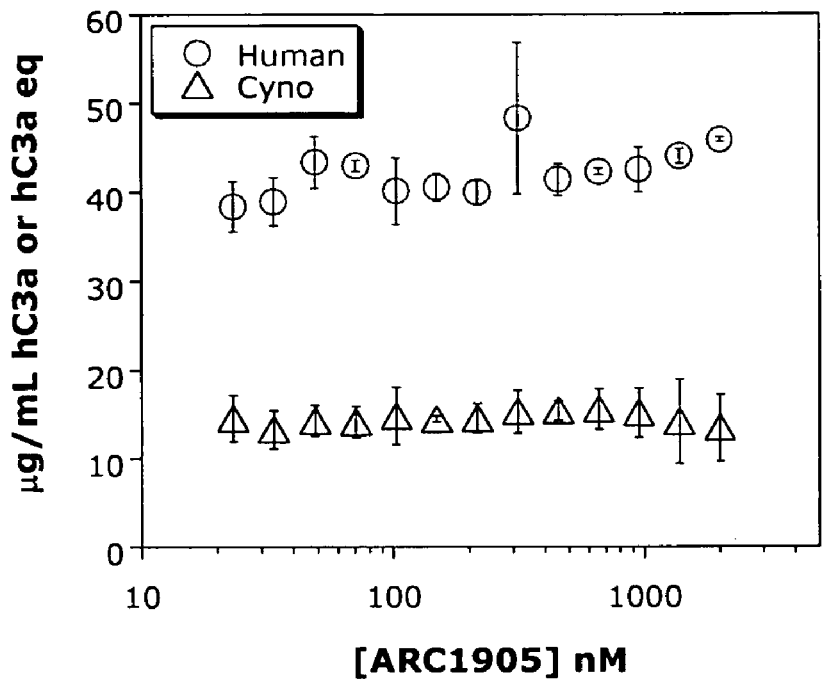
FIG. 65 is a graph depicting the effect of ARC1905 (SEQ ID NO 67) on C3a generation in human or cynomolgus monkey serum, as measured in a zymosan-induced complement activation assay.
FIG. 66 is a table summarizing the mean $IC_{50}$, $IC_{90}$ and $IC_{99}$ values for ARC1905 inhibition of complement activation (SEQ ID NO 67) in human serum from 5 donors, as measured in a tubing loop model of complement activation.

The effects of ARC1905 C3 activation, as measured by C3a levels, are summarized in FIG. 65. The rationale for specifically targeting the tail end of the complement pathway is to block the pro-inflammatory functions of C5a and the membrane attack complex (MAC) without compromising the pathogen-fighting functions of upstream factors culminating in C3a and C3b generation. The data in FIG. 65 demonstrates that ARC1905, up to 2 µM, does not inhibit C3a generation and indicates that upstream complement activation is not negatively impacted by ARC1905. Essentially complete blockade of alternate pathway C5 activation was achieved in both human and cynomolgus monkey serum samples using ARC1905. ARC1905 was approximately an order of magnitude less potent in inhibiting cynomolgus monkey C5 activation than human C5 activation under the conditions of this assay. While not wishing to be bound by theory, the inhibitory effect of ARC1905 on complement activation is specific to C5 since activation of C3 was not inhibited.

Example 1D

Tubing Loop Model of Complement Activation

To test the ability of anti-C5 aptamer to block complement activation induced by exposure to foreign materials, as found in a cardiopulmonary bypass circuit, we used the tubing loop model described by Nilsson and colleagues (Gong et al, (1996) Journal of Clinical Immunology 16, 222-9; Nilsson et al, (1998) Blood 92, 1661-7). Tygon S-50-HL medical/surgical tubing (¼" inner diameter) (United States Plastic Corp. ((Lima, Ohio), cat. # 00542) was cut into lengths of approximately 300 mm (approximately 9 mL volume) and filled with 5 mL human donor blood containing 0.4 units/mL heparin (Celsus) and varying concentrations of ARC658 (SEQ ID NO: 62) (0-5 µM). Each length of Tygon tubing was closed into a loop with short sections (~50 mm) of non-surgical silicone linker tubing (⅜" inner diameter) (United States Plastic Corp. (formulation R-3603, cat. # 00271) as described in Gong et al. Tubing loops were rotated for 1 hour at approximately 30 rpm in a 37° C. water bath. The loop contents were then poured into polypropylene conical tubes containing EDTA (10 mM final concentration) to quench complement activation. Platelet-poor plasma was isolated by centrifugation and analyzed for C5a and C3a by ELISA (C3a ELISA kit, Quidel, San Diego, Calif.; C5a ELISA kit, BD Biosciences, San Diego, Calif.).

Figure 17:
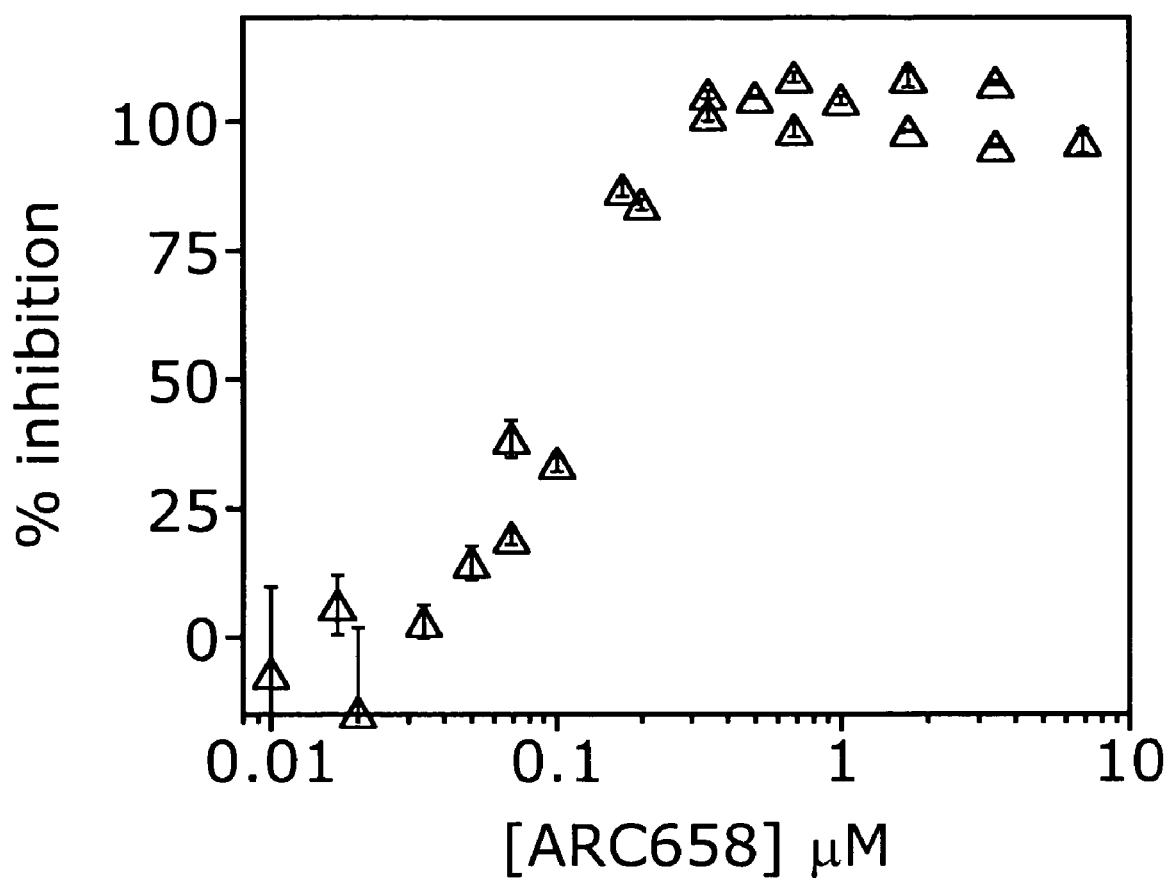
FIG. 17 is a graph showing ARC658 (SEQ ID NO: 62) fully inhibits complement activation (C5a) in the tubing loop model described in Example 1D.

The total complement activation in the absence of aptamer was small compared to the zymosan assay. Typically, C5a levels increased by approximately 6 ng/mL following the 1 hour incubation, corresponding to activation of <1% of the available C5. Nevertheless, this increase was reproducible and inhibited by titration with ARC658 (SEQ ID NO: 62). As shown in FIG. 17, 300-400 nM ARC658 (SEQ ID NO: 62) was sufficient to achieve 99% inhibition of C5 activation, a level that is approximately equivalent or slightly less than the molar concentration of C5 in blood. While not wishing to be bound by any theory, although less aptamer is required to obtain 99% inhibition of C5 activation in this model than in the zymosan model, this observation could reflect the substantial differences in the complement-activating stimulus used in the two assays. C3a generation was also monitored as a control to verify that ARC658 (SEQ ID NO: 62) did not block activation steps earlier than C5 in the complement cascade. C3a levels increased by approximately 4000 ng/mL following the 1 hour incubation, corresponding to activation of around 10% of the available C3. In contrast to C5a generation, little dose dependent inhibition of C3a generation was observed upon titration with ARC658 (SEQ ID NO: 62) demonstrating that ARC658 (SEQ ID NO: 62) specifically blocks C5 cleavage.

The tubing loop model study was repeated with the anti-C5 aptamer ARC1905 (SEQ ID NO 67). ARC1905 was serially diluted in 0.9% saline to generate a 20× sample series covering a 100-fold range of aptamer concentrations (10-1000 nM final in the assay). Samples containing irrelevant aptamer (ARC127) were included to control for non-specific oligonucleotide effects. A no-aptamer (saline only) sample was also included as a negative control Single-donor blood samples were drawn by standard phlebotomy methods from in-house volunteers. Whole blood was drawn from 5 separate donors directly into a 60 mL syringe (Becton-Dickinson, (Franklin Lakes, N.J.), cat. # 309653) and immediately aliquoted into bivalirudin (20 µM final) (Prospec-Tany Technogene Ltd., (Israel), lot # 105BIV01)+/-aptamer. The anticoagulant bivalirudin, a direct thrombin inhibitor, was used instead of heparin which interferes with complement activation.

The tubing loop model was performed essentially as described immediately above. ~300 mm sections of tube (diameter ¼", volume ~9 mL) were filled with 5 mL of blood/aptamer/bivalirudin samples immediately after the blood had been drawn from the donor. The tubes were then securely fastened into loops with short sections (~50 mm) of silicone linker tubing, yielding a gas volume of ~4 mL. The tubing loops were rotated vertically at 32 rpm during incubation in a 37° C. water bath for 1 hour. After incubation, all 5 mL of sample was transferred to a 15 mL conical tube (Corning, (Corning, N.Y.), cat. # 430766) containing 100 µL of 0.5M EDTA, giving a final EDTA concentration of 10 mM. 1 mL of plasma supernatant was collected from each quenched sample following centrifugation (Eppendorf Centrifuge 5804) at 4° C. (3,300 rpm, 20 minutes). Supernatants were flash frozen in liquid nitrogen and stored at −20° C. To control for background activation, a pre-CPB sample was prepared by adding 5 mL of fresh blood directly to a 15 mL conical tube on ice containing 100 µL 0.5M EDTA. This sample was processed for plasma and stored as described above.

The extent of C5 activation was determined from the relative levels of C5a generated in each activated sample, as measured by C5a ELISA as described immediately above. The C5a ELISA was performed on undiluted plasma samples according the ELISA kit protocol and sample C5a levels were quantified by comparison with the C5a standards provided by the manufacturer. The % inhibition of C5a generation at each aptamer concentration was calculated using the equation % inh=$100-100\times(C5a_{sample}-C5a_{pre-CPB})/(C5a_{saline-only}-C5a_{pre-CPB})$. $IC_{50}$ values were determined from a plot of % inhibition versus [ARC1905] using the equation % inh=(% inh.)$_{maximum}\times[ARC1905]^n/(IC_{50}^n+[ARC1905]^n)$+background. $IC_{90}$ and $IC_{99}$ values were calculated from $IC_{50}$ values using the equations $IC_{90}=IC_{50} \times[90/(100-90)]^{1/n}$ and $IC_{99}=IC_{50}\times[99/(100-99)]^{1/n}$.

The extent of C3 activation was determined from the relative levels of C3a generated in each activated sample, as measured by C3a ELISA as described immediately above. Just prior to C3a analysis, samples (including the saline-only and pre-CPB controls) were serially diluted in 0.9% saline. The C3a ELISA is more sensitive than that for C5a; therefore, a dilution of 1/5000 was necessary to accommodate the range of sample C3a concentrations. Sample C3a levels were quantified by comparison to kit standards, and % inhibition was calculated as described for C5a. The data were analyzed using Microsoft Excel, and the mean % inhibition values were plotted using Kaleidagraph (v3.5 Synergy Software). $IC_{50}$, $IC_{90}$ and $IC_{99}$ values were determined using the XLfit 4.1 plug-in to Excel.

Figure 67:
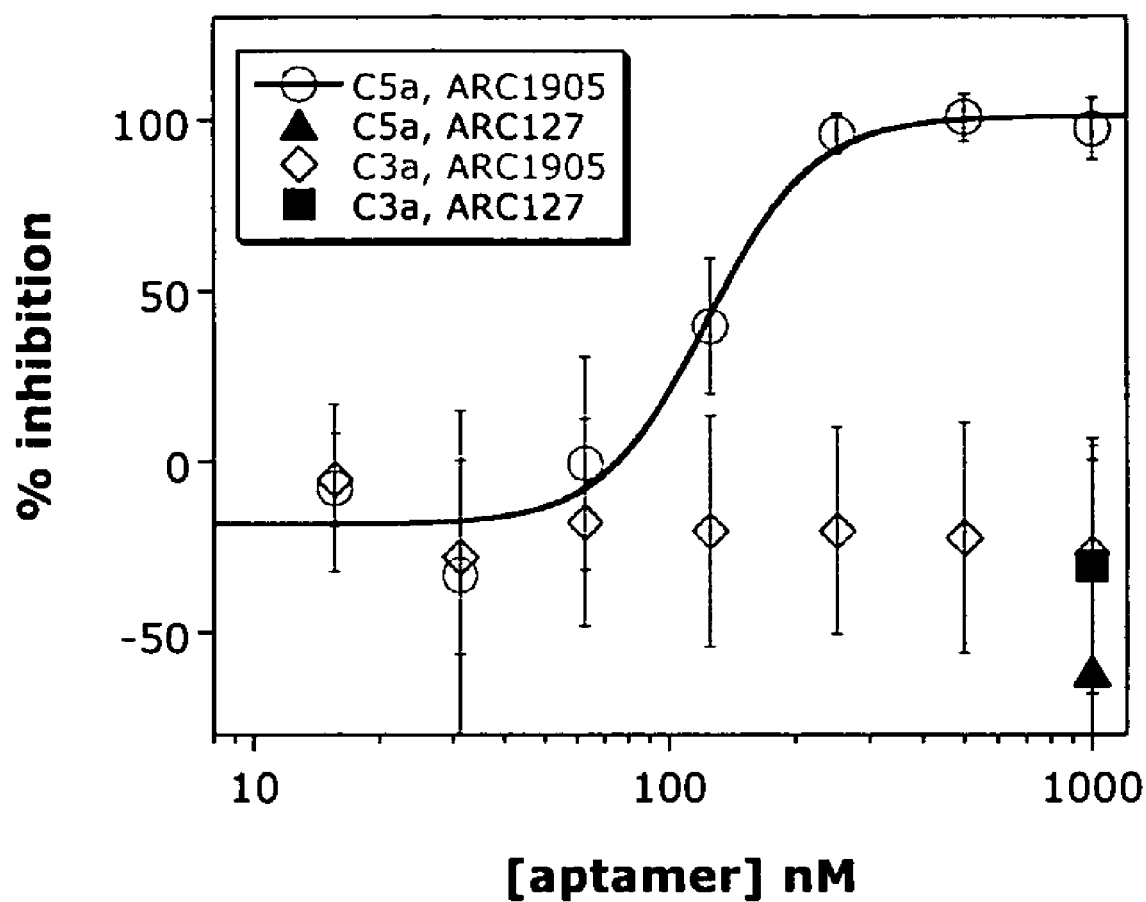
FIG. 67 is a graph depicting the percent inhibition of C5a and C3a generation as a function of concentration of ARC1905, an anti-C5 aptamer, or ARC127, an irrelevant aptamer which does not bind C5 (negative control) in a tubing loop model of complement activation.

The mean effects of ARC1905 and irrelevant aptamer, ARC127, on complement activation in the five donors is summarized in FIG. 66. As shown in FIG. 67 complete blockade of C5 activation, as reflected in the generation of C5a, was achieved with <500 nM ARC1905, while the irrelevant aptamer had no inhibitory effect up to 1 µM. The mean whole blood $IC_{50}$, $IC_{90}$ and $IC_{99}$ values were 119±28.6 nM, 268±39.2 nM and 694±241 nM, respectively (FIG. 66). While not wishing to be bound by theory, it is reasonable to assume that ARC1905 is excluded from the cellular blood volume, which comprises approximately 45% of the total. The $IC_{50}$, $IC_{90}$ and $IC_{99}$ values, adjusted to reflect C5 inhibition in plasma, therefore, were 216±52.0 nM, 487±71 nM and 1261±438 nM. These values are consistent with the parameters calculated for ARC1905 inhibition of zymosan-induced complement activation in serum suggesting that cellular blood components do not interfere significantly with ARC1905 anti-C5 activity. C3a generation was not inhibited by ARC1905 or irrelevant aptamer up to 1 µM. While not wishing to be bound by theory, this suggests that ARC1905 neither inhibits the C3 convertase reaction, nor blocks other steps that contribute to alternate cascade activation such as C3 deposition and convertase assembly.

EXAMPLE 2

De Novo Selections and Sequences

C5 Selection with dRmY pool

Two selections were performed to identify dRmY aptamers to human full length C5 protein. The C5 protein (Quidel Corporation, San Diego, Calif. or Advanced Research Technologies, San Diego, Calif.) was used in full length ("FL") and partially trypsinized ("TP") form and both selections were direct selections against the protein targets which had been immobilized on a hydrophobic plate. Both selections yielded pools significantly enriched for full length C5 binding versus naïve, unselected pool. All sequences shown in this example are shown 5' to 3'.

Pool Preparation: a DNA template with the sequence TAATACGACTCACTATAGGGAGAG-GAGAGAACGTTCTACN$_{(30)}$GGTCGATC GATCGAT-CATCGATG (ARC520; SEQ ID NO: 70) was synthesized using an ABI EXPEDITE™ DNA synthesizer, and deprotected by standard methods. The templates were amplified with 5' primer TAATACGACTCACTATAGGGAGAG-GAGAGAACGTTCTAC (SEQ ID NO: 71) and 3' primer CATCGATGATCGATCGATCGACC (SEQ ID NO: 72) and then used as a template for in vitro transcription with Y639F single mutant T7 RNA polymerase. Transcriptions were done using 200 mM HEPES, 40 mM DTT, 2 mM spermidine, 0.01% TritonX-100, 10% PEG-8000, 9.5 mM $MgCl_2$, 2.9 mM $MnCl_2$, 2 mM NTPs, 2 mM GMP, 2 mM spermine, 0.01 units/µl inorganic pyrophosphatase, and Y639F single mutant T7 polymerase.

Selection: In round 1, a positive selection step was conducted on nitrocellulose filter binding columns. Briefly, $1 \times 10^{15}$ molecules (0.5 nmoles) of pool RNA were incubated in 100 µL binding buffer (1× DPBS) with 3 uM full length C5 or 2.6 uM partially trypsinized C5 for 1 hour at room temperature. RNA:protein complexes and free RNA molecules were separated using 0.45 um nitrocellulose spin columns from Schleicher & Schuell (Keene, N.H.). The columns were pre-washed with 1 mL 1× DPBS, and then the RNA:protein containing solutions were added to the columns and spun in a centrifuge at 1500 g for 2 min. Three buffer washes of 1 mL were performed to remove nonspecific binders from the filters, then the RNA:protein complexes attached to the filters were eluted twice with 200 µl washes of elution buffer (7 M urea, 100 mM sodium acetate, 3 mM EDTA, pre-heated to 95° C.). The eluted RNA was precipitated (2 µL glycogen, 1 volume isopropanol, ½ volume ethanol). The RNA was reverse transcribed with the ThermoScript RT-PCR™ system (Invitrogen, Carlsbad, Calif.) according to the manufacturer's instructions, using the 3' primer described above SEQ ID NO: 72, followed by PCR amplification (20 mM Tris pH 8.4, 50 mM KCl, 2 mM $MgCl_2$, 0.5 uM primers SEQ ID NO: 71 and SEQ ID NO: 72, 0.5 mM each dNTP, 0.05 units/µL Taq polymerase (New England Biolabs, Beverly, Mass.)). The PCR templates were purified using Centricep columns (Princeton Separations, Princeton, N.J.) and used to transcribe the next round pool.

In subsequent rounds of selection, separation of bound and free RNA was done on Nunc Maxisorp hydrophobic plates (Nunc, Rochester, N.Y.). The round was initiated by immobilizing 20 pmoles of both the full length C5 and partially trypsinized C5 to the surface of the plate for 1 hour at room temperature in 100 µL of 1× DPBS. The supernatant was then removed and the wells were washed 4 times with 120 µL wash buffer (1× DPBS). The protein wells were then blocked with a 1× DPBS buffer containing 0.1 mg/mL yeast tRNA and 0.1 mg/mL salmon sperm DNA as competitors. The pool concentration used was always at least in five fold excess of the protein concentration. The pool RNA was also incubated for 1 hour at room temperature in empty wells to remove any plastic binding sequences, and then incubated in a blocked well with no protein to remove any competitor binding sequences from the pool before the positive selection step. The pool RNA was then incubated for 1 hour at room temperature and the RNA bound to the immobilized C5 was reverse transcribed directly in the selection plate by the addition of RT mix (3' primer, SEQ ID NO:72 and Thermoscript RT, Invitrogen) followed by incubation at 65° C. for 1 hour. The resulting cDNA was used as a template for PCR (Taq polymerase, New England Biolabs). Amplified pool template DNA was desalted with a Centrisep column (Princeton Separations) according to the manufacturer's recommended conditions and used to program transcription of the pool RNA for the next round of selection. The transcribed pool was gel purified on a 10% polyacrylamide gel every round.

The selection progress was monitored using a sandwich filter binding (dot blot) assay. The 5'-$^{32}$P-labeled pool RNA (trace concentration) was incubated with C5, 1× DPBS plus 0.1 mg/mL tRNA and 0.1 mg/mL salmon sperm DNA, for 30 minutes at room temperature, and then applied to a nitrocellulose and nylon filter sandwich in a dot blot apparatus (Schleicher and Schuell). The percentage of pool RNA bound to the nitrocellulose was calculated and monitored approximately every 3 rounds with a single point screen (+/−300 nM C5). Pool $K_d$ measurements were measured using a titration of protein and the dot blot apparatus as described above.

Figure 18:
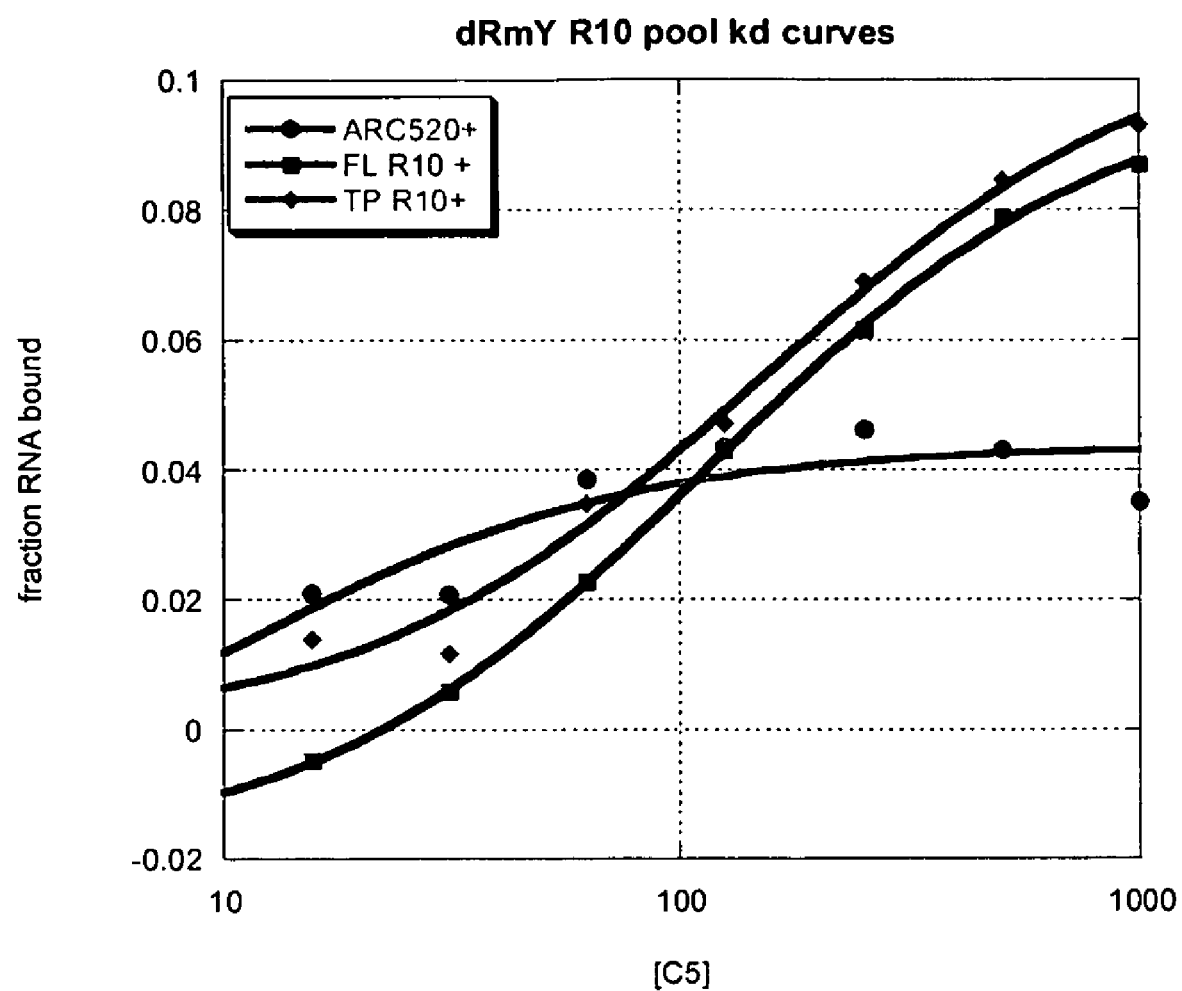
FIG. 18 is a graph depicting the dissociation constants for Round 10 of the C5 selection pools. Dissociation constants ($K_d$s) were estimated by fitting the data to the equation: fraction RNA bound=amplitude*$K_d$/($K_d$+[C5]). "ARC520" (SEQ ID NO: 70) refers to the naïve unselected dRmY pool and the "+" indicates the presence of competitor (0.1 mg/ml tRNA, 0.1 mg/ml salmon sperm DNA).

Selection data: Both selections were enriched after 10 rounds over the naïve pool. See FIG. 18. At round 10, the pool $K_d$ was approximately 115 nM for the full length and 150 nM for the trypsinized selection, but the extent of binding was only about 10% at the plateau in both. The R10 pools were cloned using TOPO TA cloning kit (Invitrogen) and sequenced.

Figure 19:
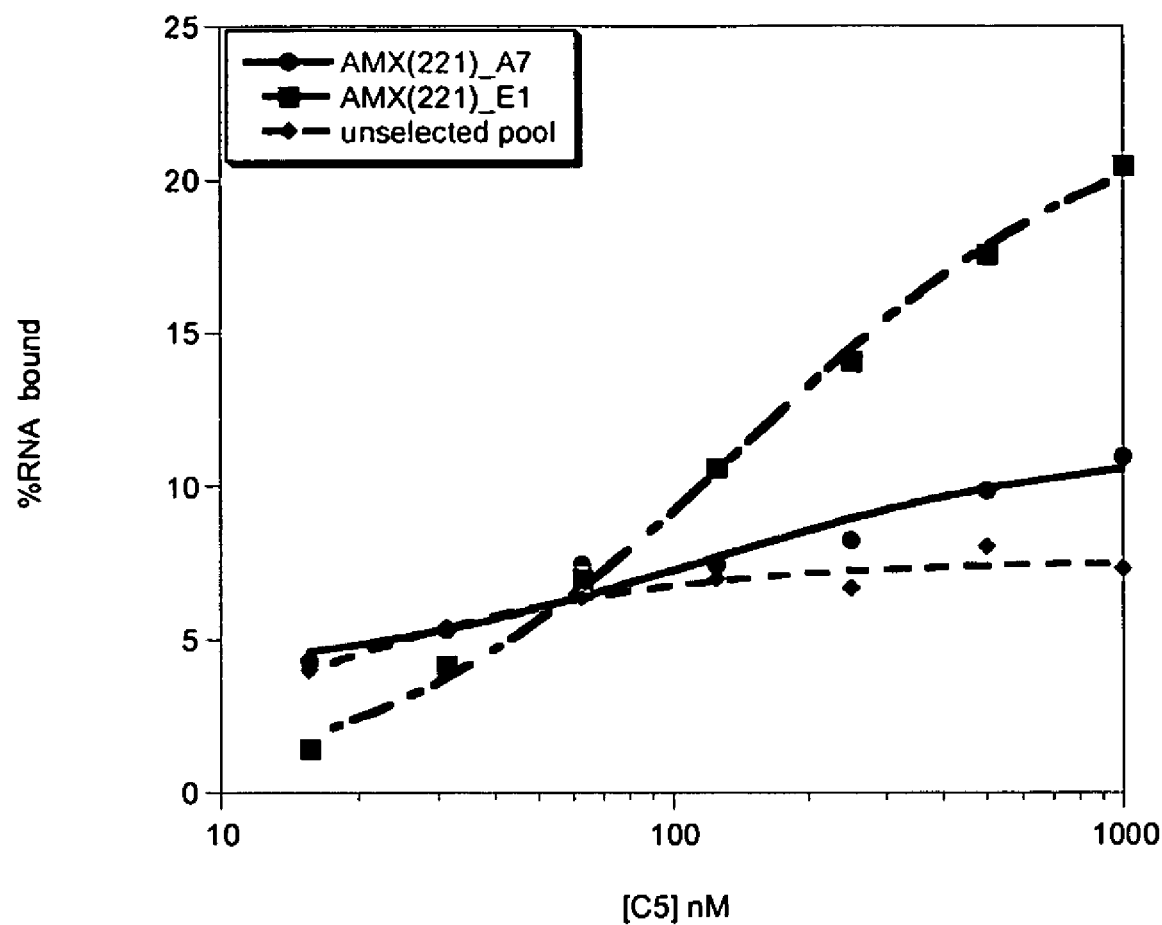
FIG. 19 is a graph depicting C5 clone dissociation constant curves. Dissociation constants ($K_d$s) were estimated by fitting the data to the equation: fraction RNA bound=amplitude*$K_d$/($K_d$+[C5]).

Sequence Information: 45 clones from each pool were sequenced. R10 full length pool was dominated by one single clone ARC913 (SEQ ID NO: 75) which made up 24% of the pool, 2 sets of duplicates and single sequences made up the remainder. The R10 trypsinized pool contained 8 copies of the same sequence ARC913 (SEQ ID NO: 75), but the pool was dominated by another sequence (AMX221.A7; 46%). The clone ARC913 (SEQ ID NO: 75) had a $K_d$ about 140 nM and the extent of binding went to 20%. See FIG. 19.

The individual sequence listed in Table 5 is listed in the 5' to 3' direction, and represents the ribonucleotide sequence of the aptamer that was selected under the dRmY SELEX™ conditions provided. In the embodiments of the invention derived from this selection (and as reflected in the sequence listing) the purines (A and G) are deoxy and the pyrimidines (U and C) are 2'-OMe. The sequence listed in Table 5 may or may not contain capping (e.g., a 3'-inverted dT). The unique sequence of the aptamer below begins at nucleotide 23, immediately following the fixed sequence GGGAGAG-GAGAGAACGUUCUAC (SEQ ID NO: 73), and runs until it meets the 3'fixed nucleic acid sequence GGUCGAUC-GAUCGAUCAUCGAUG (SEQ ID NO: 74)

TABLE 5

Nucleotide sequence of fhe C5 dRmY aptamer

ARC913
(SEQ ID NO: 75)
GGGAGAGGAGAGAACGUUCUACCUUGGUUUGGCACAGGCAUACAUACGCA

GGGGUCGAUCGAUCGAUCAUCGAUG

Figure 20:
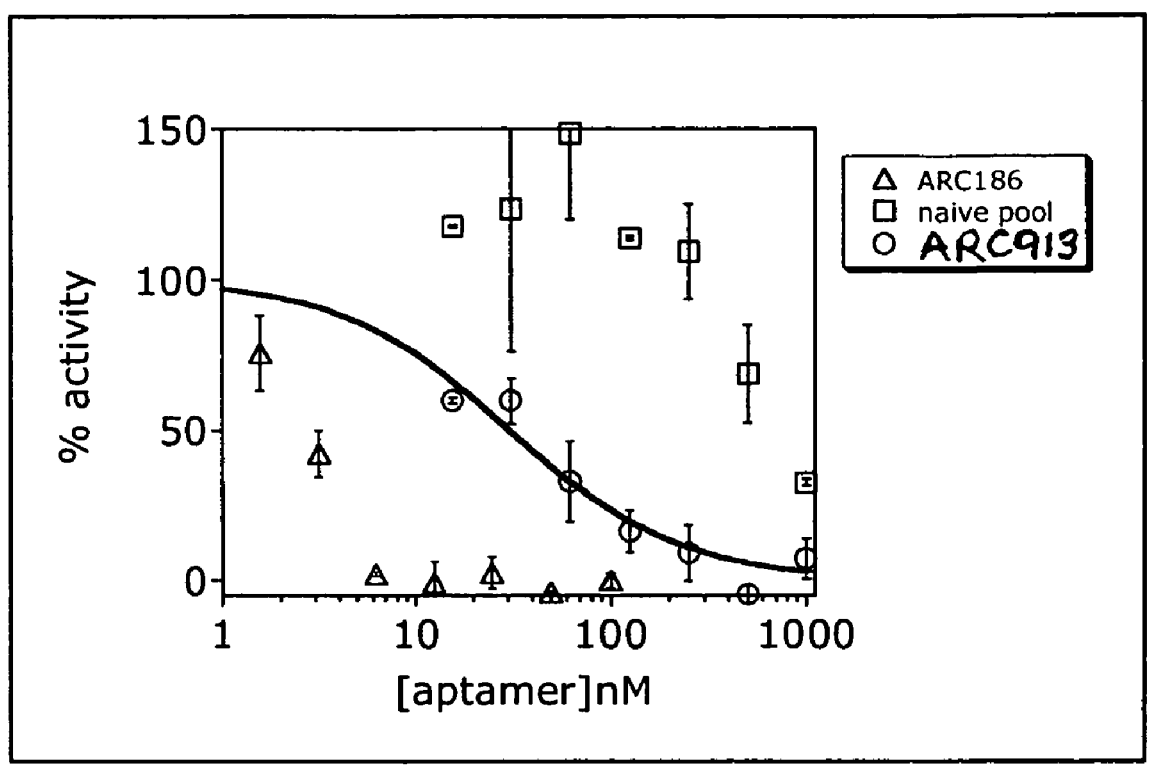
FIG. 20 is a graph depicting an $IC_{50}$ curve that illustrates the inhibitory effect on hemolysis activity of varying concentrations of anti-C5 aptamer clone ARC913 (SEQ ID NO: 75) as compared to ARC186 (SEQ ID NO: 4).

Hemolysis Assay: The effect of ARC913 (SEQ ID NO: 75) on the classical pathway of the complement system was analyzed using a hemolysis assay previously described, compared to both ARC186 (SEQ ID NO: 4) (Anti-C5 aptamer, positive control) and unselected dRmY pool (negative control). In the assay of hemolytic inhibition, a solution of 0.2% whole human serum was mixed with antibody-coated sheep erythrocytes (Diamedix EZ Complement CH50 Test, Diamedix Corporation, Miami, Fla.) in the presence of titrated ARC913 (SEQ ID NO: 75). The assay was run in veronal-buffered saline containing calcium, magnesium and 1% gelatin (GVB++ complement buffer) and incubated for 1 hr at 25° C. After incubation the samples were centrifuged. The optical density at 415 nm ($OD_{415}$) of the supernatant was read. The inhibition of hemolysis activity is expressed as % hemolysis activity compared to control. See FIG. 20. The $IC_{50}$ of the aptamer was calculated to be about 30 nM.

EXAMPLE 3

Composition and Sequence Optimization

Example 3A

Minimization of ARC913

Six constructs based on ARC913 (SEQ ID NO: 75) were transcribed, gel purified, and tested in dot blots for binding to C5. ARC954 was similar to the parent clone with a $K_d$ of 130 nM and extent of binding at 20%, while ARC874 (SEQ ID NO: 76) was the only other clone that bound to C5 with a $K_d$ of 1 uM.

The individual sequences listed in Table 6 are listed in the 5' to 3' direction and were derived from aptamers that were selected under the dRmY SELEX conditions provided. In the embodiments of the invention derived from this selection (and as reflected in the sequence listing) the purines (A and G) are deoxy and the pyrimidines (U and C) are 2'-OMe. Each of the sequences listed in Table 6 may or may not contain capping (e.g., a 3'-inverted dT).

TABLE 6

Nucleotide sequences of ARC913 minimized clones

ARC874
(SEQ ID NO: 76)
CCUUGGUUUGGCACAGGCAUACAUACGCAGGG

ARC875
(SEQ ID NO: 77)
CCUUGGUUUGGCACAGGCAUACAAACGCAGGG

ARC876
(SEQ ID NO: 78)
GGGUUUGGCACAGGCAUACAUACCC

ARC877
(SEQ ID NO: 79)
GGGUUUGGCACAGGCAUACAAACCC

ARC878
(SEQ ID NO: 80)
GGCGGCACAGGCAUACAUACGCAGGGGUCGCC

ARC954
(SEQ ID NO: 81)
CGUUCUACCUUGGUUUGGCACAGGCAUACAUACGCAGGGGUCGAUCG

Example 3B

Optimization of ARC913: Doped Reselection

In order to both optimize clone ARC913 (SEQ ID NO: 75) for C5 binding affinity and to determine the key binding elements, a doped reselection was conducted. Doped reselections are used to explore the sequence requirements within an active clone or minimer. Selections are carried out with a synthetic, degenerate pool that has been designed based on a single sequence. The level of degeneracy usually varies from 70% to 85% wild type nucleotide. In general, neutral mutations are observed but in some cases sequence changes can result in improvements in affinity. The composite sequence information can then be used to identify the minimal binding motif and aid in optimization efforts.

Pool preparation: The template sequence taatacgactcactat-aGGGAGAGGAGAGAACGTTCTACN$_{(30)}$GTTACGAC-TAGCATCGATG (SEQ ID NO: 82) was based on ARC913 (SEQ ID NO: 75) and was synthesized with each residue originating from the random region doped at a 15% level, i.e. at each random ("N") position, the residue has a 85% chance of being the nucleotide found in the wild type sequence CTTGGTTTGGCACAGGCATACATACG-CAGGGGTCGATCG (SEQ ID NO: 83) and a 15% chance of being one of the other three nucleotides.

The template and RNA pool for the doped reselection were prepared essentially as described above. The templates were amplified with the primers taatacgactcactataGGGAGAG-GAGAGAACGTTCTAC (SEQ ID NO: 84) and CATCGAT-GCTAGTCGTAAC (SEQ ID NO: 85). Two selections were done with full length C5, one selection using a higher concentration of salt in the wash step. The selection protocol was carried out as described above, with two exceptions: 1) Round 1 was done on hydrophobic plates (as well as all subsequent rounds) with only a positive step; and 2) no competitor was used at all during the selection. The C5 concentration and RNA pool concentration were kept constant at 200 nM and 1 uM respectively.

Doped reselection data. Both the normal and high salt selections were enriched after 5 rounds over the naïve pool. At round 5 the pool $K_d$ was approximately 165 nM for the high salt selection and 175 nM for the normal salt selection. The extent of binding was about 20% at the plateau in both. The R4 pools were cloned using TOPO TA cloning kit (Invitrogen, Carlsbad, Calif.), and 48 clones from each pool were sequenced. 12 clones from each pool were transcribed and assayed in a single point dot blot assay at 500 nM C5. Dissociation constants ($K_d$s) were again measured using the dot blot assay previously described. $K_d$s were estimated for the 11 best clones identified in the single point screen, by fitting the data to the equation: fraction RNA bound=amplitude*$K_d$/($K_d$+[C5]). The clones with the three best $K_d$s were SEQ ID NO: 91 (73 nM), SEQ ID NO: 96 (84 nM) and SEQ ID NO: 95 (92 nM). The sequences for these 11 clones are listed below in Table 7.

The sequences listed in Table 7 are listed in the 5' to 3' direction and represent the nucleotide sequences of the aptamers that were selected under the dRmY SELEX conditions provided. In the embodiments of the invention derived from this selection (and as reflected in the sequence listing), the corresponding sequences comprising the dRmY combinations of residues, as indicated in the text, wherein the purines (A and G) are deoxy and the pyrimidines (U and C) are 2'-OMe. Each of the sequences listed in Table 7 may or may not contain capping (e.g., a 3'-inverted dT). The unique sequences of each of aptamer below begins at nucleotide 23, immediately following the 5' fixed sequence GGGAGAGGAGAGAACGUUCUAC (SEQ ID NO: 86), and runs until it meets the 3'fixed nucleic acid sequence GUUACGACUAGCAUCGAUG (SEQ ID NO: 87).

TABLE 7

Nucleotide sequences of clones from doped reselection (SEQ ID NO: 88)
GGGAGAGGAGAGAACGUUGUACCUUGGUUUGGCACAGGCAUACAUACGCA
GGGGUCGAUCGGUUACGACUAGCAUCGAUG (SEQ ID NO: 89)
GGGAGAGGAGAGAACGUUCUACCUUGGUUUGGCACAGGCAUACAUACGCA
GGUGUCGAUCUGUUACGACUAGCAUCGAUG (SEQ ID NO: 90)
GGGAGAGGAGAGAACGUUCUACCUUGGUUUGGCACAGGCAUAAAUACGCA
GGGCUCGAUCGGUUACGACUAGCAUCGAUG (SEQ ID NO: 91)
GGGAGAGGAGAGAACGUUCUACCUUGGUUUGGCCCAGGCAUAUAUACGCA
GGGAUUGAUCCGUUACGACUAGCAUCGAUG (SEQ ID NO: 92)
GGGAGAGGAGAGAACGUUCUACCUUGGUUUGGCGCAGGCAUACAUACGCA
GGUCGAUCGGUUACGACUAGCAUCGAUG (SEQ ID NO: 93)
GGGAGAGGAGAGAACGUUCUACCUUGUUGUGGCACAGCCAACCCUACGCA
CGGAUCGCCCGGUUACGACUAGCAUCGAUG (SEQ ID NO: 94)
GGGAGAGGAGAGAACGUUCUACCUUGGUUUGGCACAGGCAUACAUACGCA
GGUCGAUCGGUUACGACUA TABLE 7-continued Nucleotide sequences of clones from doped reselection (SEQ ID NO: 95)
GGGAGAGGAGAGAACGUUCUACCUUAGGUUCGCACUGUCAUACAUACACA
CGGGCAAUCGGUUACGACUAGCAUCGAUG (SEQ ID NO: 96)
GGGAGAGGAGAGAACGUUCUACCUUGGUUUGGCNCAGGCAUANAUACGCA
CGGGUCGAUCGGUUACGACUAGCAU (SEQ ID NO: 97)
GGGAGAGGAGAGAACGUUCUACCUUUCUCUGCCACAAGCAUACCUUCGCG
GGGUUCUAUUGGUUACGACUAGCAUCGAUG (SEQ ID NO: 98)
GGGAGAGGAGAGAACGUUCUACCUUGGUUUGGCACAGGCAUAUAUACGCA
GGGUCGAUCCGUUACGACUAGCAUCGAUG Example 3C 40 kDa Branched PEG Modification of ARC186

The oligonucleotide 5' NH$_2$-fCmGfCfCGfCmGmGfUfC-fUfCmAmGmGfCGfCfUmGmAmGfUfC-fUmGmAmGfUfUfUAfCfCfUmGf CmG-3T-3' (ARC672, SEQ ID NO: 63) was synthesized on an Expedite DNA synthesizer (ABI, Foster City, Calif.) according to the recommended manufacturer's procedures using standard commercially available 2'-OMe RNA and 2'-F RNA and TBDMS-protected RNA phosphoramidites (Glen Research, Sterling, Va.) and a inverted deoxythymidine CPG support. Terminal amine function was attached with a 5'-amino-modifier, 6-(Trifluoroacetylamino)hexyl-(2-cyanoethyl)-(N,N-diisopropyl)-phosphoramidite, C6-TFA (Glen Research, Sterling, Va.). After deprotection, the oligonucleotides were purified by ion exchange chromatography on Super Q 5PW (30) resin (Tosoh Biosciences) and ethanol precipitated.

Figure 21:
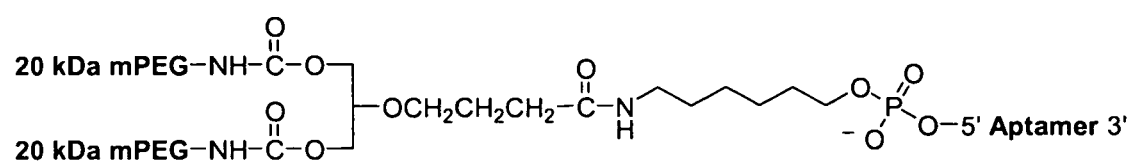
FIG. 21 is an illustration depicting the structure of ARC187 (SEQ ID NO: 5).
Figure 22:
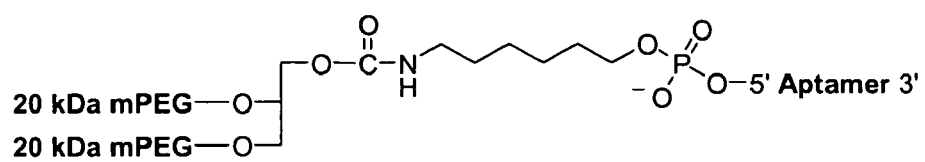
FIG. 22 is an illustration depicting the structure of ARC1905 (SEQ ID NO: 67).

The amine-modified aptamer was conjugated to different PEG moieties post-synthetically. The aptamer was dissolved in a water/DMSO (1:1) solution to a concentration between 1.5 and 3 mM. Sodium carbonate buffer, pH 8.5, was added to a final concentration of 100 mM, and the oligo was reacted overnight with a 1.7 molar excess of the desired PEG reagent (e.g. ARC1905 40 kDa Sunbright GL2-400NP p-nitrophenyl carbonate ester [NOF Corp, Japan], or ARC187 40 kDa mPEG2-NHS ester [Nektar, Huntsville Ala.]) dissolved in an equal volume of acetonitrile. The resulting products were purified by ion exchange chromatography on Super Q 5PW (30) resin (Tosoh Biosciences), and desalted using reverse phase chromatography performed on Amberchrom CG300-S resin (Rohm and Haas), and lyophilized. The structure of ARC187 (SEQ ID NO: 5) is shown in FIG. 21 while the structure of ARC1905 (SEQ ID NO: 67) is shown in FIG. 22.

EXAMPLE 4

Isolated Perfused Heart Model

Example 4A

Proof of Principle with ARC186

The average concentration of complement component C5 in human plasma is approximately 500 nM. Upon exposure of isolated mouse hearts perfused with Krebs Heinseleit buffer to 6% human plasma, the human complement cascade is activated, leading to cleavage of C5 into C5a and C5b. Component C5b subsequently forms a complex with complement components C6, C7, C8 and C9 also known as the "membrane attack complex" ("MAC" or C5b-9) which damages heart blood vessels and cardiac myocytes, thus leading to myocardial dysfunction (increased end diastolic pressure, arrhythmias) and asystole (Evans et. al., Molecular Immunology, 32, 1183-1195 (1995)). Previously, monoclonal and single chain antibodies that block human C5 cleavage (Pexelizumab or a single-chain scFv version of Pexelizumab) were tested in this model and shown to inhibit myocardial damage and dysfunction (Evans et al, 1995).

This model was used to establish that the C5-blocking aptamer ARC186 (SEQ ID NO: 4), like Pexeluzimab, inhibited human C5-mediated complement damage to isolated perfused mouse hearts. C57 Bl/6 mice were purchased from Charles River Laboratories, (Wilmington, Mass.). Briefly, following induction of deep anesthesia, each mouse heart was removed and mounted on a blunt needle inserted into the aorta, through which the heart was continuously perfused with Krebs Heinseleit buffer. A pressure transducer (Mouse Specifics, Boston, Mass.) was inserted into the left ventricle allowing continuous measurement of the heart rate and intraventricular pressure. After a 15-minute period of equilibration during which baseline measurements were taken, hearts were subsequently perfused with buffer and 6% human plasma+/−aptamer at various concentrations (See FIG. 23). During these studies and as described in Evans et al., we demonstrated that hearts which were perfused with Krebs Heinseleit buffer+6% human plasma experienced failure within 5 minutes of adding the plasma to the perfusate, whereas hearts that were continuously perfused with buffer alone continued to beat in excess of two hours. Hence, the length of each experiment was arbitrarily defined as 15 minutes. The outline of this study with ARC186 is presented in FIG. 23.

Figure 24:
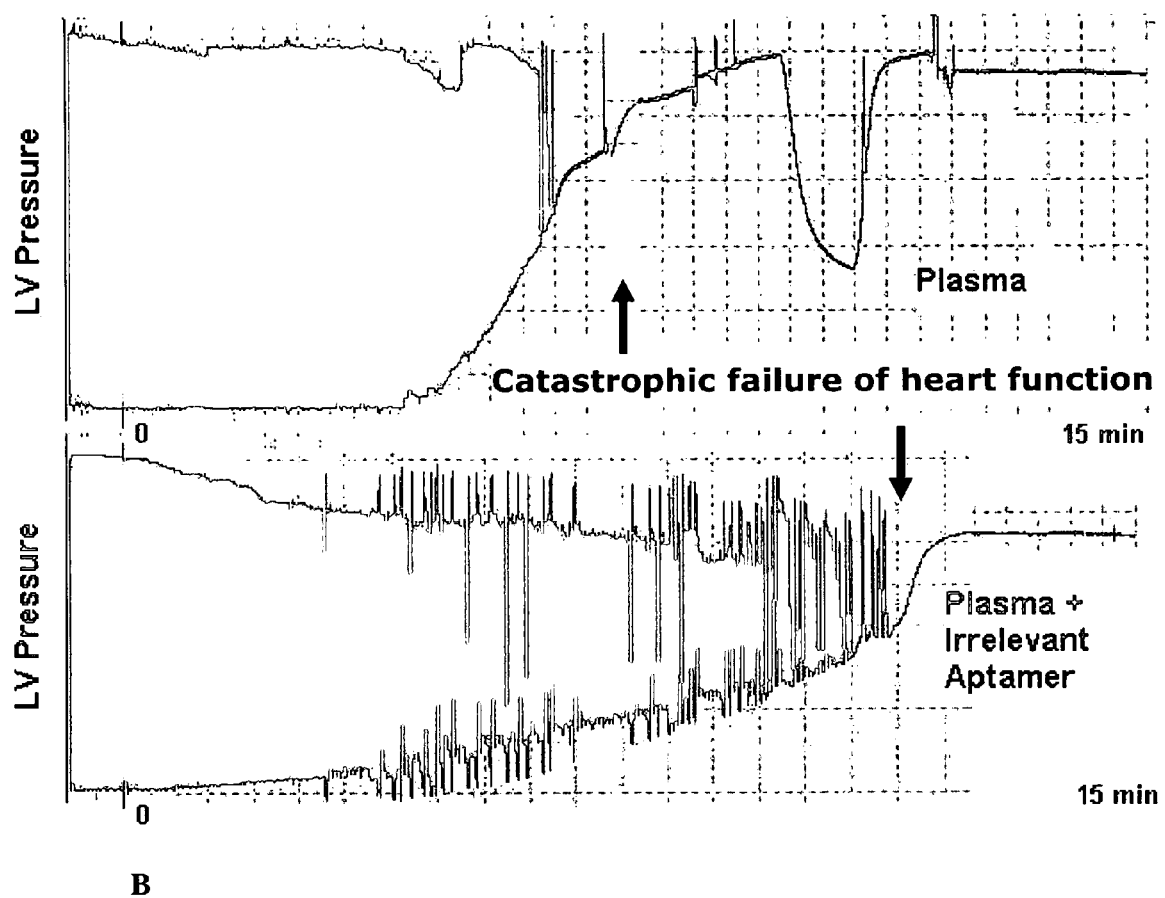
FIG. 24 is a graph comparing the pressure tracings for the intraventricular pressure in the left ventricle (LV) of an isolated heart exposed to human plasma (A) with the LVP pressure tracings of an isolated heart exposed to the control aptamer solution (B).
Figure 25:
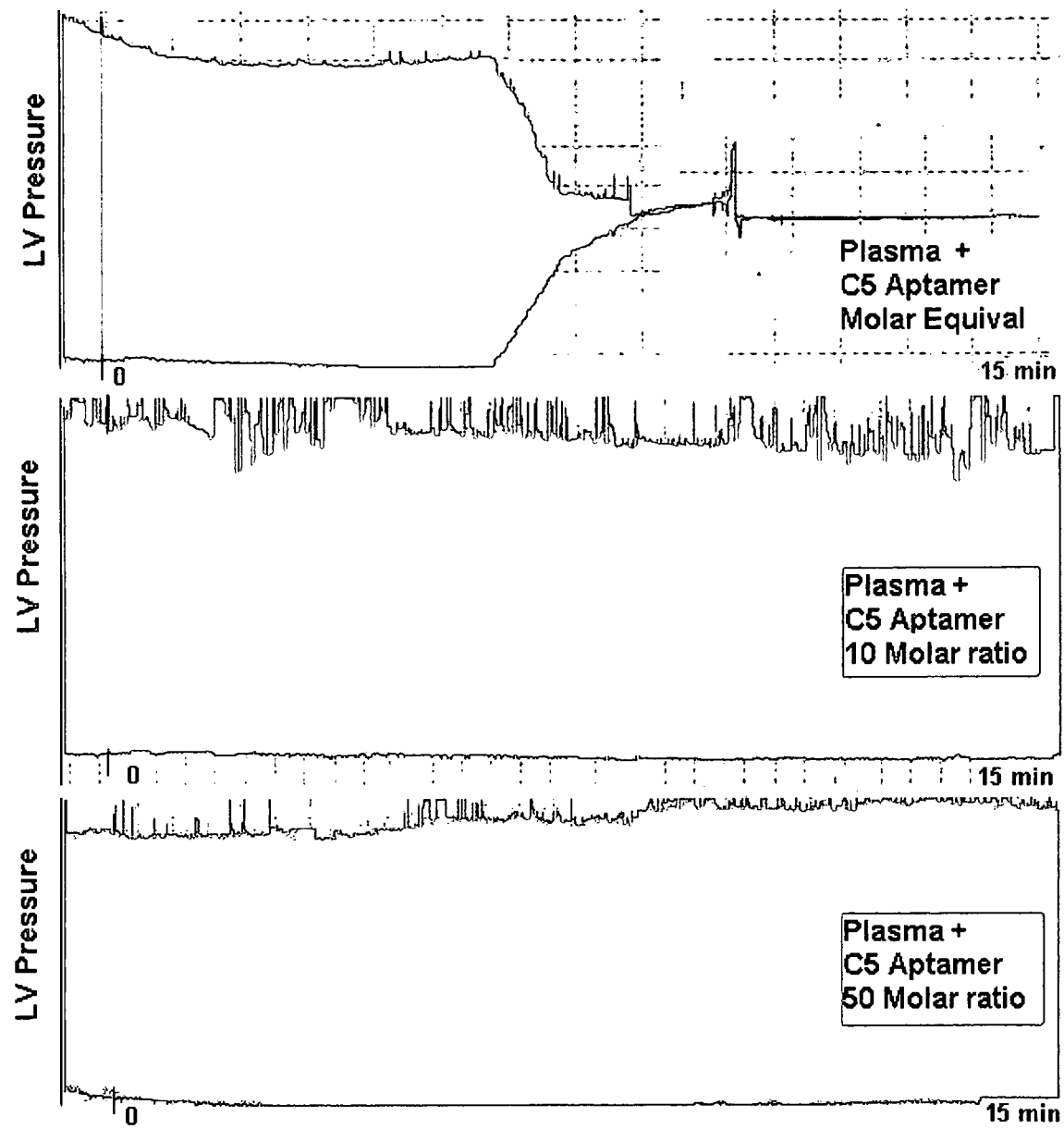
FIG. 25 is a graph comparing the pressure tracings for the intraventricular pressure in the left ventricle (LV) of the isolated hearts exposed to the molar equivalent, 10× and 50× aptamer/C5 solutions (where a concentration of approximately 500 nM is assumed for C5 in normal, undiluted human plasma).

Intraventricular pressure was monitored and recorded continuously resulting in a pressure wave tracing (FIGS. 24 and 25). The lowest deflection point represents the end diastolic pressure ("EDP") and the highest deflection point represents the systolic pressure ("SP"). Baseline pressure waves appear to the left of the vertical black line marked "0" shown on each tracing. As previously published (Evans et al, 1995), hearts perfused with 6% human plasma experienced a rapid increase in left ventricular end diastolic pressure, ultimately culminating in asystole (the heart stops) within 5 minutes (FIG. 24). When irrelevant aptamer was added to the human plasma at 50-fold molar excess, increased EDP and asystole were also observed (FIG. 24).

When ARC186 was added to the system at molar equivalence, there was also a precipitous increase in EDP, culminating in asystole (FIG. 25). In all three groups of hearts that experienced complement-mediated damage, increased EDP and asystole, the heart was visibly edematous and turgid by the end of the experiment. When ARC186 was added to plasma in 10-fold or 50-fold (FIG. 25) molar excess, ventricular pressure waves remained normal and asystole was not observed. In addition, the previously described edema and turgidity were not apparent in these groups.

Figure 26:
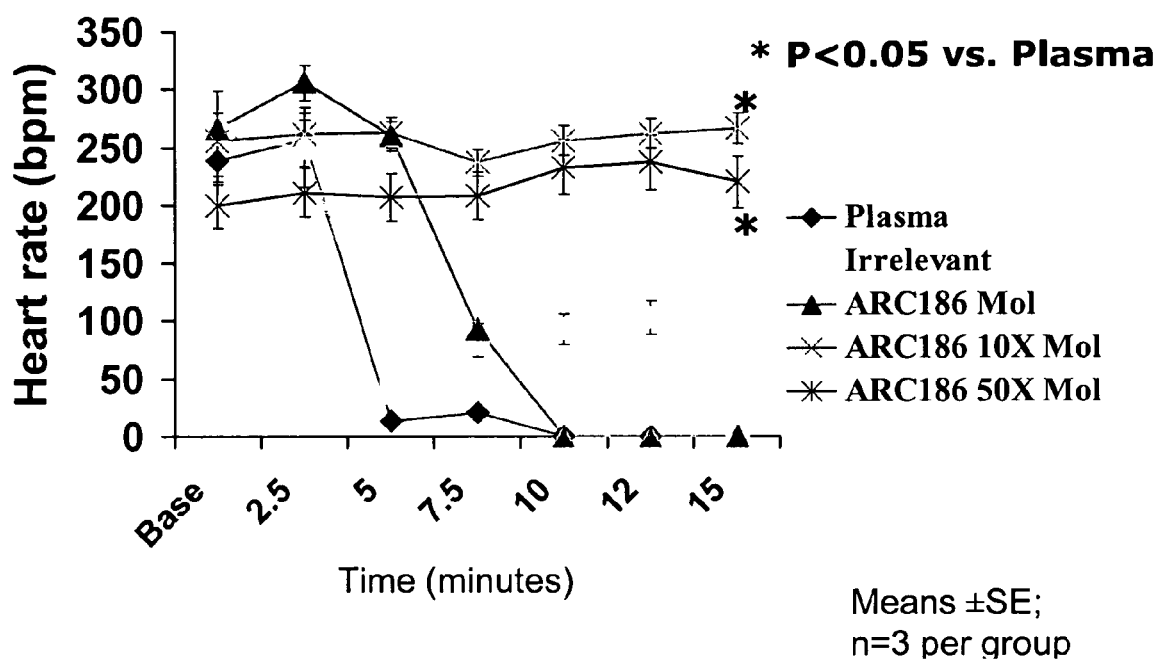
FIG. 26 is a graph comparing the heart rate changes in beats per minute (bpm) in isolated mouse hearts after exposure to human plasma and various plasma/aptamer solutions.

During each experiment, the heart rate was recorded at 5-minute intervals, and the average heart rate for the group during each interval was graphed. As shown in FIG. 26 hearts perfused without aptamer or with irrelevant aptamer developed asystole quickly, usually within 5 minutes. ARC186 added to the system at molar equivalence slightly delayed the onset of asystole. Hearts in this group ultimately failed, however. ARC186 added to the plasma at 10-fold or 50-fold molar excess preserved the heart rate for the duration of each experiment.

Figure 27:
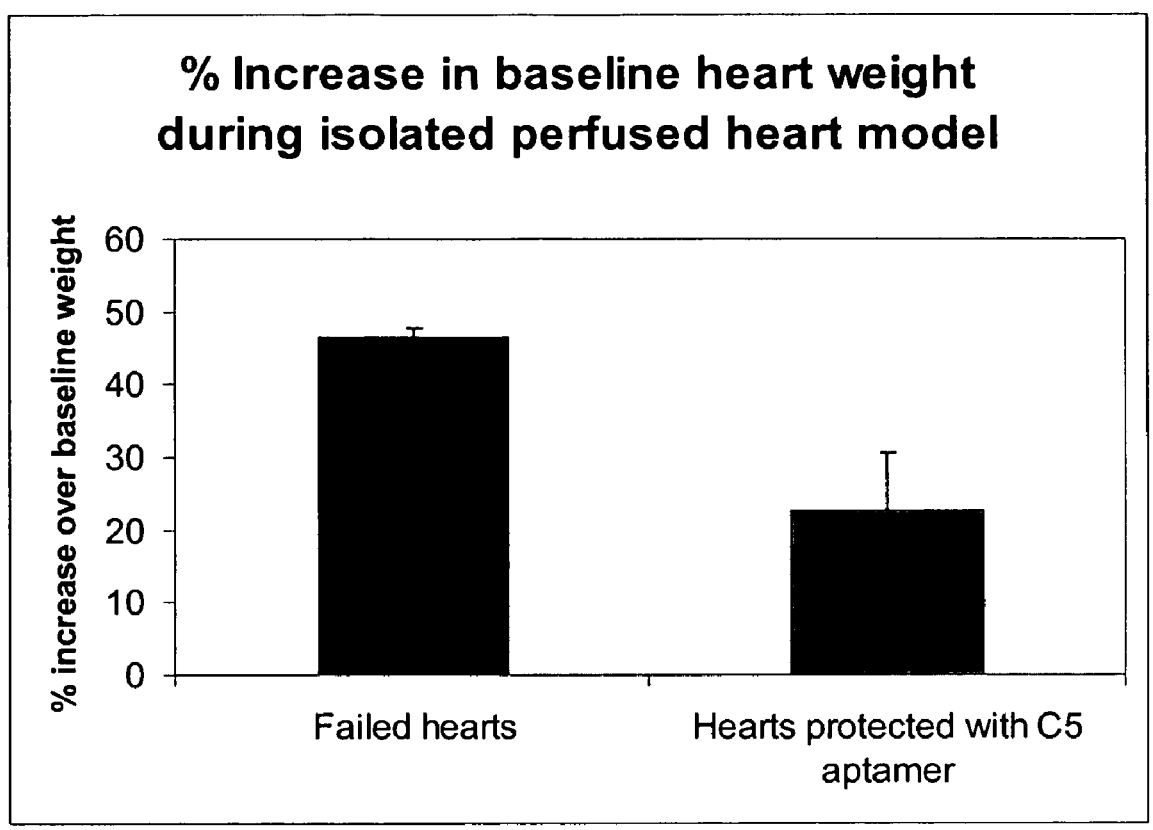
FIG. 27 is a graph comparing the changes in the heart weight in isolated mouse hearts before and after exposure to human plasma containing 0-1× molar ratio ARC186 (SEQ ID NO: 4) (failed hearts), or 10-50× molar ratio (hearts protected with C5 aptamer).

The percent increase in heart weight over baseline was calculated for a representative sample of failed hearts (no aptamer or 50-fold molar excess of irrelevant aptamer) and compared to ARC186-protected hearts (10-fold and 50-fold molar excess of ARC186). As shown in FIG. 27, ARC186 protected hearts gained significantly less weight than the failed hearts in the control groups.

Figure 28:
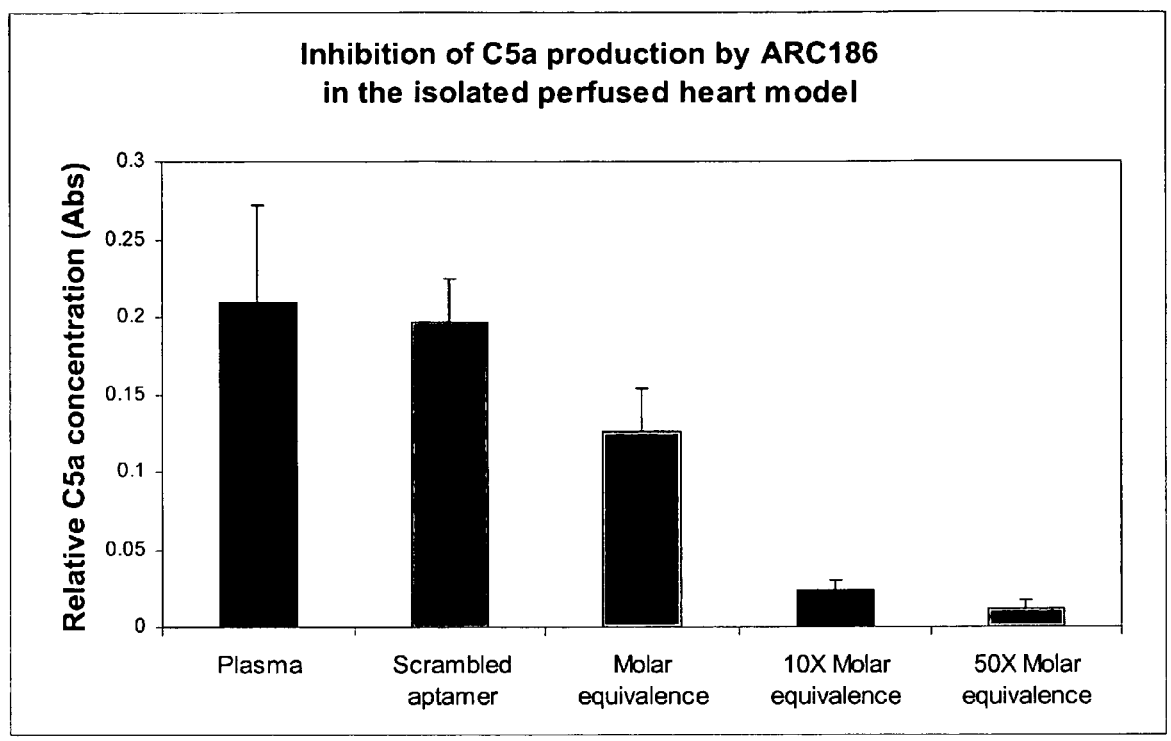
FIG. 28 is a graph comparing the relative C5a production in human plasma, containing varying aptamer concentrations, following perfusion through isolated mouse hearts. Relative C5a concentrations are plotted as absorbance units (Abs), where higher readings reflect the presence of higher C5a levels.
Figure 29:
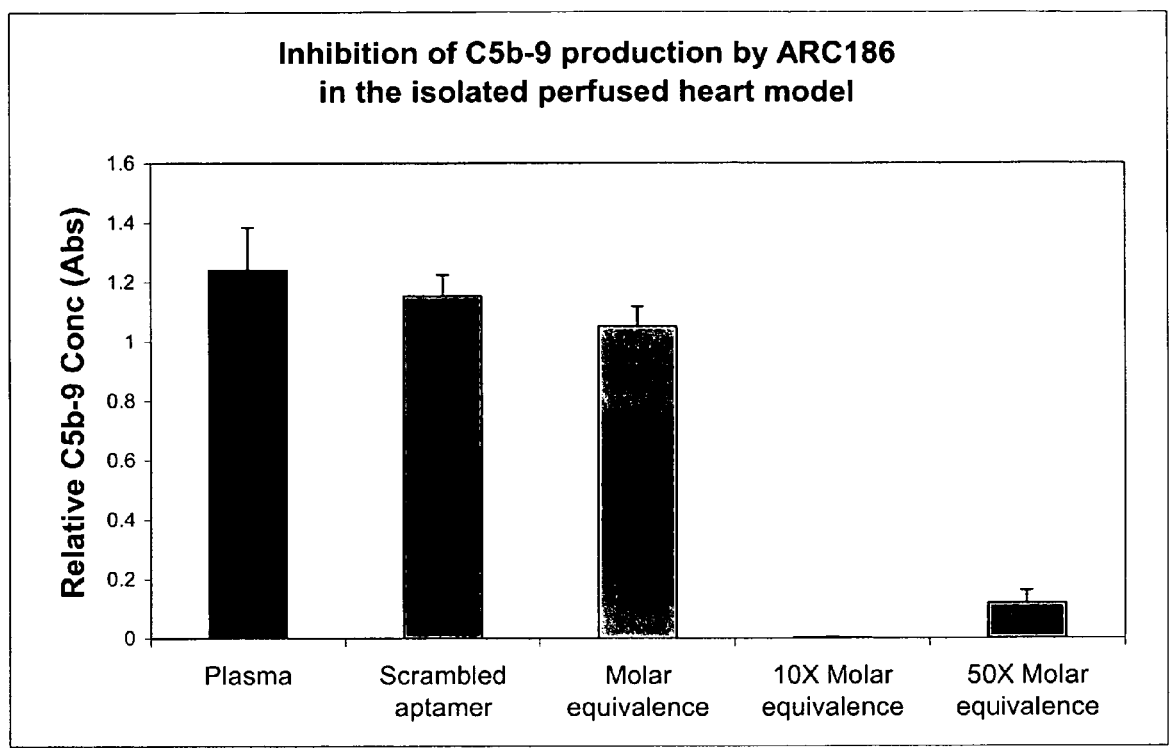
FIG. 29 is a graph comparing the relative soluble C5b-9 production in human plasma containing varying aptamer concentrations, following perfusion through isolated mouse hearts.
Figure 30:
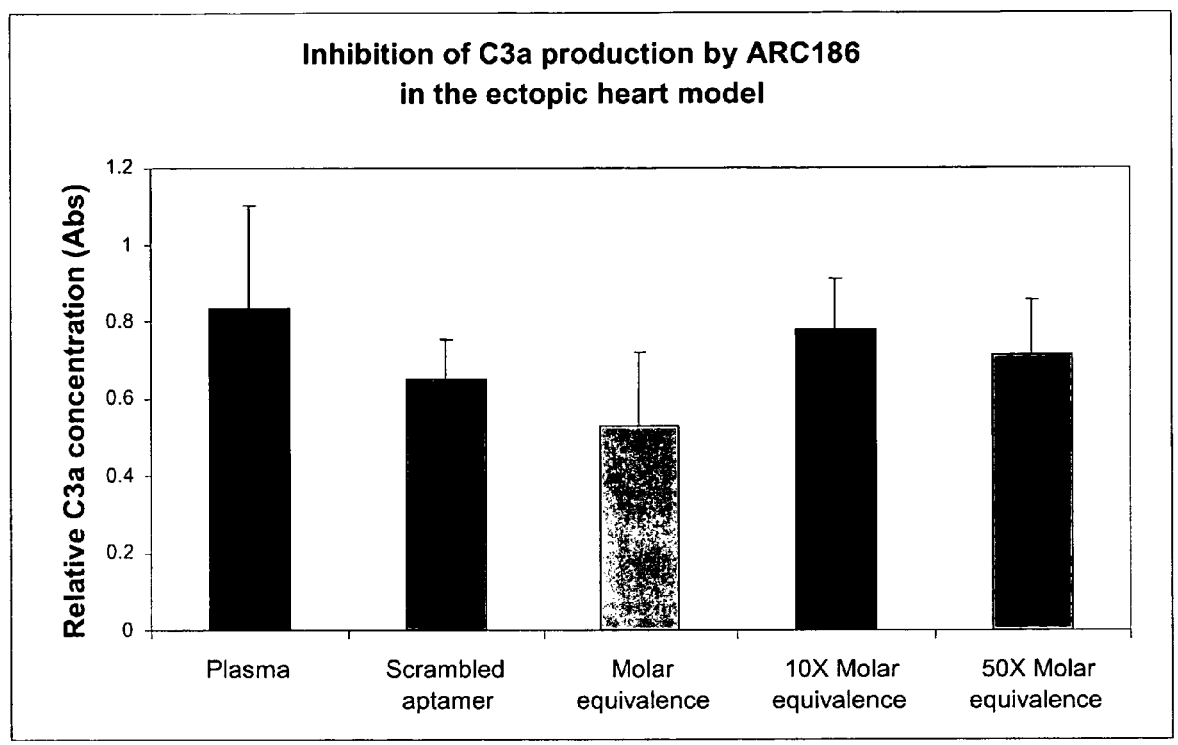
FIG. 30 is a graph showing the effect of ARC186 (SEQ ID NO: 4) on C3 cleavage in mouse heart effluent.

Because ARC186 inhibits C5 but not C3 cleavage, C3 cleavage products (C3a) but not C5 cleavage products (C5a or C5b) should be found in the effluent flowing from the isolated hearts protected by ARC186. To directly show that ARC186 inhibited cleavage of human plasma C5, the relative levels of human complement proteins C5a and C5b (C5 cleavage products) and C3a (a C3 cleavage product) were measured in the buffer effluent from the various groups by commercially available ELISA kits (C5b-9 ELISA kit, Quidel, San Diego, Calif.; C5a and C3a ELISA kit, BD Biosciences, San Diego, Calif.). ARC186 inhibited human plasma C5 cleavage and the production of C5a (FIG. 28) and C5b-9 (FIG. 29) in a dose-dependent manner. In contrast, ARC186 had no effect on cleavage of human C3 into C3a and C3b (FIG. 30) further demonstrating the C5 specificity of the molecule.

Once generated, complement C3b and C5b fragments are deposited locally on tissues in the vicinity of the site of complement activation. Following completion of the experiments, mouse hearts were frozen in OCT media (Sakura Finetek, Torrance, Calif.), sectioned and then stained using standard immunohistochemistry for the presence of human C3b (clone H11, Chemicon, Temecula, Calif.), human C5b-9 (clone aE11, DAKO, Carpinteria, Calif.) or control mouse IgG (Vector Laboratories, Burlingame, Calif.). Results of the study are presented in FIG. 31.

As described in this study, the C5-blocking aptamer ARC186 was tested in an ex vivo model of complement component C5-mediated tissue damage which uses isolated mouse hearts perfused with Krebs Heinseleit buffer and 6% heparinized human plasma, based on a model described in a previously published study that tested the effects of the anti-C5 antibody, Pexeluzimab on the complement system (Evans, Molecular Immunol 32:1183, (1995). Using this model, it was demonstrated that the C5-blocking aptamer (a) inhibited cleavage of human plasma C5 (but not C3), (b) inhibited deposition of human C5b (but not C3b) on mouse heart tissue and (c) inhibited human C5b-9 mediated myocardial dysfunction at clinically relevant concentrations (5 µM, a 10-fold molar excess of aptamer vs. C5). These data show that when the human complement cascade is activated in a physiologically relevant manner, C5-blocking aptamers are able to inhibit cleavage of plasma C5 and prevent myocardial damage and dysfunction.

Example 4B

Efficacy of PEGylated Aptamer

The material and methods used in this study were exactly the same as described in Example 4A above. The experimental design and results are presented in FIG. 32. The first half of the experiment used human heparinized plasma (Center for Blood Research, Harvard Medical School, Boston, Mass.) as a source of complement and the second half used heparinized cynomolgus macaque plasma (Charles River Laboratories, Wilmington, Mass.) as a source of complement. A PEGylated aptamer (ARC658; SEQ ID NO:62) was added to the system at increasing molar ratios. Although all of the relevant ventricular pressure tracings were collected, the table lists the presence or absence of an increase in end diastolic pressure (EDP), whether or not asystole occurred and the time until heart failure (defined as the presence of an elevated EDP and asystole).

During experiments with human plasma, the optimal dose of AR658 (SEQ ID NO: 62) was determined to be molar equivalence (500 nM) whereas during experiments with non-human primate plasma, a 50-fold molar excess (25 µM) was necessary to protect the heart from C5b-mediated damage (see FIG. 32).

These data are consistent with the difference in the affinity of the anti-C5 aptamer for human v. non-human primate C5 indicated by the in vitro data. While not wishing to be bound by any theory, during our subsequent cynomolgus macaque PK/PD studies described in Example 5, we additionally demonstrated that a 30-fold molar excess of aptamer was necessary to inhibit zymosan-mediated plasma C5 cleavage, further supporting the notion that the aptamer binds primate C5 with lower affinity than human C5.

Collectively, these studies indicate that both C5-blocking aptamers ARC186 (SEQ ID NO: 4) and to a greater extent ARC658 (SEQ ID NO: 62) are efficacious in the mouse isolated, perfused heart model. This model also demonstrated that significantly more ARC658 (SEQ ID NO: 62) had to be used to inhibit cynomolgus macaque plasma C5-mediated heart damage (30+molar excess), compared with human C5-mediated heart damage (molar equivalence), further supporting in vitro data which indicated that the aptamer had lower affinity for primate C5. Finally, these data indicated that cynomolgus macaques would need to be dosed beyond a 30-fold molar excess in order to demonstrate in vivo C5 blockade during PK/PD studies.

EXAMPLE 5

Drug Metabolism & Pharmacokinetics of Anti-C5 Aptamers in Animals

In Examples 5A-5G, all mass based concentration data refers only to the molecular weight of the oligonucleotide portion of the aptamer, irrespective of the mass conferred by PEG conjugation.

Example 5A

Metabolic Stability of the C5 Inhibitor ARC186 in Primate and Rat Plasma

The non-PEGylated oligonucleotide precursor of the aptamers (i.e., ARC186; SEQ ID NO: 4) was tested in rat and cynomolgus macaque plasma (Charles River Labs, Wilmington, Mass.) in order to assess its stability, rate kinetics, and pathways of degradation. Testing was performed using 5' end-radiolabeled ($^{32}$P) aptamer incubated at 37° C. in 95% pooled plasma (citrated) over the course of 50 hrs. At selected time points, aliquots of aptamer-containing plasma were withdrawn, immediately flash frozen in liquid nitrogen, and stored at −80° C. Detection and analysis of the aptamer and its metabolites in plasma was accomplished using liquid-liquid (phenol-chloroform) extraction followed by gel electrophoresis (on a 10% denaturing polyacrylamide sequencing gel) and high-resolution autoradiography.

Figure 33:
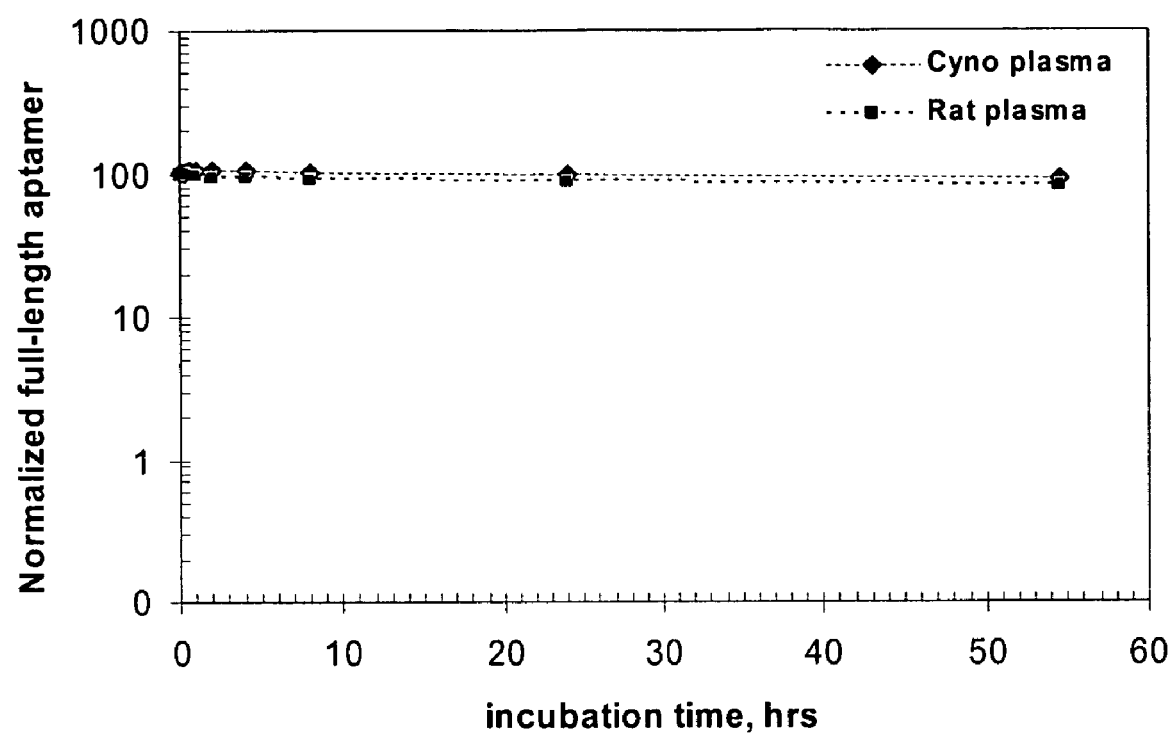
FIG. 33 is a graph showing a log-linear plot of remaining percent of full-length ARC186 as a function of incubation time in both rat and cynomolgus macaque plasma.

FIG. 33 shows a log-linear plot of remaining percent of full-length aptamer as a function of incubation time in both rat and cynomolgus macaque plasma. The degradation profile in both species appears to be essentially monophasic, with a rate constant of approximately $k \sim 0.002$ $hr^{-1}$.

Example 5B

Pharmacokinetics of ARC657, ARC658 and ARC187 in the Rat Following Intravenous Administration To assess the pharmacokinetic profile of ARC657 (SEQ ID NO: 61), ARC658 (SEQ ID NO: 62) and ARC187 (SEQ ID NO: 5), and to estimate the required dosing level and frequency in primates and humans, a pharmacokinetic study was conducted in catheterized Sprague-Dawley rats (Charles River Labs, Wilmington, Mass.). Aptamers were formulated for injection at 10 mg/mL (oligo weight) in standard saline and sterile-filtered (0.2 µm) into a pre-sterilized dosing vial under aseptic conditions. The route of administration used for the rat study was an intravenous bolus via the tail vein at a dose of 10 mg/kg. Study arms consisted of 3 animals per group, from which serial bleeds were taken pre-dose and at specified time points over the course of 48 hours. The study design is outlined in FIG. 34. Blood samples were obtained from the surgically implanted jugular vein catheters, transferred directly to EDTA-coated tubes, mixed by inversion, and placed on ice until processing for plasma.

Plasma was harvested by centrifugation of blood-EDTA tubes at 5000 rpm for 5 minutes and supernatant (plasma) was transferred to a fresh pre-labeled tube. Plasma samples were stored at −80° C. until the time of analysis. Analysis of plasma samples for ARC187 was accomplished using a homogeneous assay format utilizing the direct addition of plasma aliquots to assay wells containing the commercially available fluorescent nucleic acid detection reagent Oligreen™ (Molecular Probes, Eugene, Oreg.). After a brief incubation period (5 min) at room temperature, protected from light, the assay plates were read by a fluorescence plate reader (SpectraMax Gemini XS, Molecular Devices, Sunnyvale, Calif.). The fluorescence signal from each well was proportional to the concentration of aptamer in the well, and sample concentrations were calculated by interpolation of fluorescence values from a fluorescence-concentration standard curve (mean values from duplicate or triplicate curves). Mean plasma concentrations were obtained at each time point from the three animals in each group. Plasma concentration versus time data was subjected to noncompartmental analysis (NCA) using the industry standard pharmacokinetic modeling software WinNonLin™ v.4.0 (Pharsight Corp., Mountain View, Calif.). Estimates were obtained for the following primary pharmacokinetic parameters: maximum plasma concentration, $C_{max}$; area under the concentration-time curve, AUC; terminal half-life, $t_{1/2}$; terminal clearance, Cl; and volume of distribution at steady state, $V_{SS}$.

Figure 36:
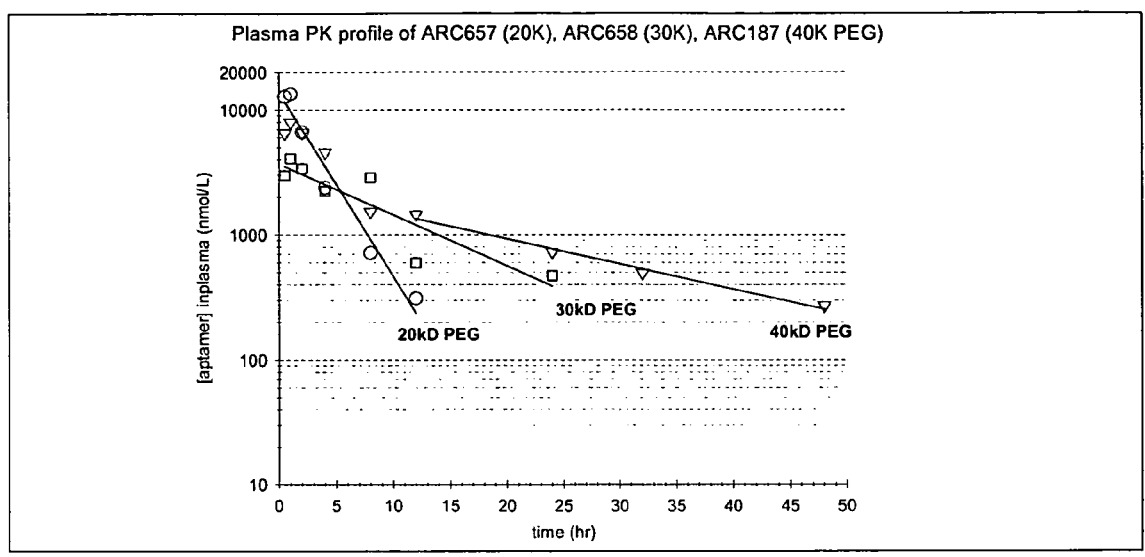
FIG. 36 is a graph depicting mean plasma concentration of ARC657 (SEQ ID NO: 61), ARC658 (SEQ ID NO: 62) and ARC187 (SEQ ID NO: 5) over time following intravenous administration of aptamer in rats.

Mean plasma concentration versus time data are shown in FIG. 35 and are plotted in FIG. 36. The concentration versus time data was subjected to noncompartmental analysis (NCA) using WinNonLin™ v.4.0. This analysis yielded the values presented in FIG. 37.

As anticipated, the 40 kDa aptamer ARC187 (SEQ ID NO: 5) had the longest half-life and the 20 kDa aptamer, ARC657 (SEQ ID NO: 61), the shortest. The observed Vss relative to the known plasma volume (~40 mL/kg) suggested a moderate degree of binding/sequestration of ARC187 (SEQ ID NO: 5) to proteins and/or tissue matrix in the extravascular space. Assuming a need to maintain a 5-fold molar excess of aptamer, the results of this study suggested that ARC187 (SEQ ID NO: 5) provides a significant advantage in terms of the dosing frequency and total amount of aptamer needed to maintain the desired plasma levels.

Previous studies (data not shown) in rodents and primates with aptamers of similar composition have shown dose proportionality/linearity at doses up to 30 mg/kg, so it is not anticipated that this dosing level will result in nonlinear pharmacokinetic behavior.

Example 5C

Figures 38A, 38B:
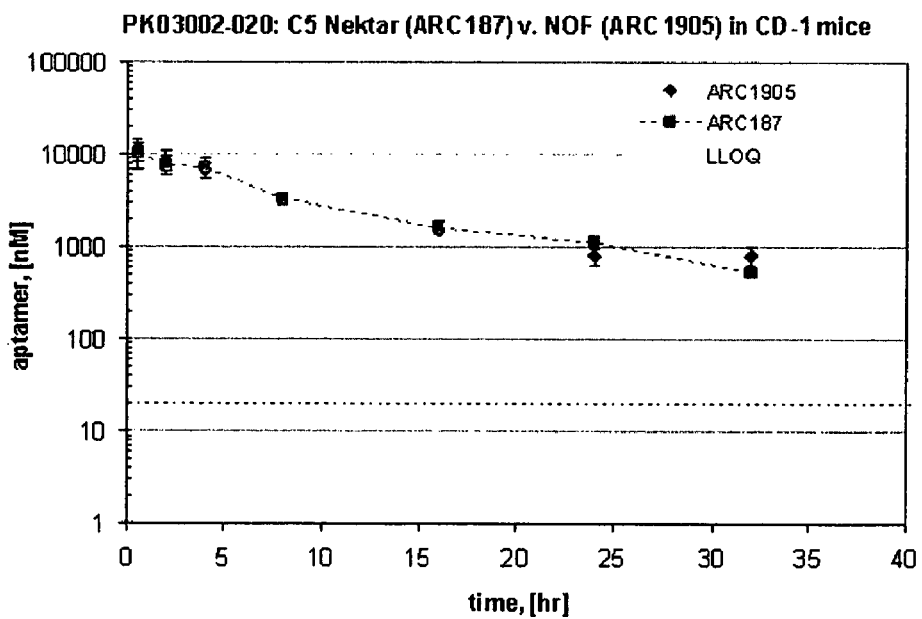
FIG. 38A is a table showing the design for the pharmacokinetic study of ARC187 (SEQ ID NO: 5) and ARC1905 (SEQ ID NO: 67) in mice.
FIG. 38B is a graph depicting the pharmacokinetic profile of ARC187 (SEQ ID NO: 5) and ARC1905 (SEQ ID NO: 67) in CD-1 mice after a single IV bolus administration.

Pharmacokinetics of ARC 187 and ARC1905 in the Mouse Following Intravenous Administration To assess the pharmacokinetic profile of the ARC186 (SEQ ID NO: 4) oligonucleotide backbone conjugated to a different 40 kDa branched PEG than that of ARC187 (SEQ ID NO:5), a pharmacokinetic study was conducted in female CD-1 mice (obtained from Charles River Labs, Wilmington, Mass.). Aptamers were formulated for injection at 2.5 mg/mL (oligo weight) in standard saline and sterile-filtered (0.2 µm) into a pre-sterilized dosing vial under aseptic conditions. The route of administration used for the mouse study was an intravenous bolus via the tail vein at a dose of 10 mg/kg. Study arms consisted of 3 animals per group, from which terminal bleeds were taken pre-dose (i.e., the non-dosed control group) and at specified time points over the course of 72 hours. The study design is outlined in FIG. 38A.

Blood samples were obtained by terminal cardiac puncture, transferred directly to EDTA-coated tubes, mixed by inversion, and placed on ice until processing for plasma. Plasma was harvested by centrifugation of blood-EDTA tubes at 5000 rpm for 5 minutes and supernatant (plasma) was transferred to a fresh pre-labeled tube. Plasma samples were stored at −80° C. until the time of analysis. Analysis of plasma samples for ARC187 and 1905 was accomplished using a homogeneous assay format utilizing the direct addition of plasma aliquots to assay wells containing the commercially available fluorescent nucleic acid detection reagent Oligreen™ (Molecular Probes, Eugene, Oreg.). After a brief incubation period (5 min) at room temperature, protected from light, the assay plates were read by a fluorescence plate reader (SpectraMax Gemini XS, Molecular Devices, Sunnyvale, Calif.). The fluorescence signal from each well was proportional to the concentration of aptamer in the well, and sample concentrations were calculated by interpolation of fluorescence values from a fluorescence-concentration standard curve (mean values from duplicate or triplicate curves). Mean plasma concentrations were obtained at each time point from the three animals in each group. Plasma concentration versus time data was subjected to noncompartmental analysis (NCA) using the industry standard pharmacokinetic modeling software WinNonLin™ v.4.0 (Pharsight Corp., Mountain View, CA.). Estimates were obtained for the following primary pharmacokinetic parameters: maximum plasma concentration, $C_{max}$; area under the concentration-time curve, AUC; terminal half-life, $t_{1/2}$; terminal clearance, Cl; and volume of distribution at steady state, $V_{ss}$. Mean plasma concentration versus time data are plotted in FIG. 38B.

The concentration versus time data was subjected to noncompartmental analysis (NCA) using WinNonLin™ v.4.0. This analysis yielded the values presented in FIG. 38C. As anticipated, the 40 kDa PEGs from both vendors showed pharmacokinetic equivalence in mice.

The same plasma samples for ARC187 and 1905 used for the oligreen analysis described directly above were analyzed using a validated high performance liquid chromatography (HPLC) assay with UV detection Mean plasma concentration values for ARC187 and ARC1905 were calculated using Microsoft Excel 2003. When plasma concentration values were below the LLOQ of the bioanalytical assay at pre-dose (time 0), a zero value was assigned. Values below the LLOQ from samples taken post-dose were omitted from mean plasma concentration calculations. Mean plasma concentration data were used in a model-independent PK analysis using WinNonlin, version 5.1 (Pharsight Corporation, Mountainview, Calif.). The area under the plasma concentration-time curve ($AUC_{0-last}$) was estimated using the linear trapezoidal rule. For calculations, any value that was below the LLOQ of the assay, except the pre-dose sample, was excluded from calculations for PK parameter estimates. The apparent terminal half-life was calculated using the formula $t_{1/2}=0.693/\lambda_z$ where $\lambda_z$ is the elimination rate constant estimated from the regression of the terminal slope of the concentration versus time curve. At least three plasma concentration values after the peak concentration on the terminal phase were used to determine $\lambda_z$ and the coefficient of determination ($r^2$) was required to be $\geq 0.85$.

Overall, the HPLC analysis confirms the oligreen analysis described immediately above showing that ARC1905 and ARC187 were found to be bioequivalent based on comparisons of mean $C_{max}$, $AUC_{0-last}$ and $AUC_{0-\infty}$ parameter estimates. Differences in $AUC_{0-last}$ and $AUC_{0-\infty}$ values for ARC1905 relative to ARC187 (as measured by HPLC) were well within bioequivalence acceptability criteria of ±20%.

Example 5D

Tissue Uptake Study of the C5 Inhibitors ARC657, ARC658 and ARC187 in the Mouse Following Intravenous Bolus Administration Female CD-1 mice were obtained from Charles River Labs (Wilmington, Mass.). Formulation of ARC657 (SEQ ID NO: 61), ARC658 (SEQ ID NO: 62) and ARC187 (SEQ ID NO: 5) for injection was in saline at 5 mg/ml. Dosing formulations were sterile-filtered (0.2 µm) into pre-sterilized dosing vials under aseptic conditions and animals were given an intravenous bolus via the tail vein at a dose of 25 mg/kg. The study consisted of groups of 3 animals for each of four time-points, t=pre-dose, 3, 6, 12 hrs. Following exsanguination, the vasculature of each animal was flushed extensively (V~30 mL) with saline to remove any blood left in the vasculature. Tissues (heart, liver, kidney) were harvested, weighed, then homogenized at 50% w/v in standard saline, and stored at −80° C. until the time of analysis.

Analysis of tissue for ARC657 (SEQ ID NO: 61), ARC658 (SEQ ID NO: 62), and ARC187 (SEQ ID NO: 5) was accomplished using a hybridization-based ELISA-type assay. In this assay, a biotinylated capture probe was pre-immobilized in the wells of a 96-well microplate at a binding solution concentration of 125 nM for 3 hrs. The plate wells were washed 5 times with 1× PBS. The plates were then blocked with 150 µl/well of a 1× SuperBlock in TBS (Pierce Chemical, Rockford, Ill.). Plates were washed again, covered, and stored at 4° C. until use. In separate tubes, the samples(s) were annealed in a buffer containing a FAM-labeled (5'-Fluorescein) sample-detection probe at 200 nM at 90° C. for 10 min, then quenched on ice. Concentration standards and control samples of plasma/tissue were also pre-annealed with sample-detection probe solutions and then pipetted into assay plate wells containing immobilized biotin capture probe, and annealed at 45° C. for 2.5 hrs. Plates were then washed again, and filled with 100 µl/well of a solution containing 1× PBS containing 1 µg/mL of anti-fluorescein monoclonal antibody conjugated to horse radish peroxidase (anti-FITC MAb-HRP, Molecular Probes, Eugene, Oreg.) in 1× PBS, and incubated for approximately 1 hr. Plates were washed again as above. Assay plate wells are were then filled with 100 µl of a solution containing a fluorogenic HRP substrate (QuantaBlu, Pierce Chemical, Rockford, Ill.), and incubated for 20-30 min protected from light. After 45 minute incubation, 100 µl/well of a stop solution was added to quench the fluorescent precipitate-producing reaction. Plates were read immediately on a fluorescence microplate reader (SpectraMax Gemini XS, Molecular Devices, Sunnyvale, Calif.) with fluorescence excitation at 325 nm and emission detected at 420 nm. Each well was read 10 times. All three aptamers were detectable in the heart tissue at the three timepoints (FIG. 39).

Example 5E

Pharmacokinetics and Pharmacodynamics of the C5 Inhibitors ARC657, ARC658 and ARC187 in the Cynomolgus Macaque Following Intravenous Administration Study 1

Formulation of ARC657 (SEQ ID NO: 61), ARC658 (SEQ ID NO: 62) and ARC187 (SEQ ID NO: 5) for injection was in standard saline at 10 mg/mL and dosing formulations were sterile-filtered (0.2 µm) into pre-sterilized dosing vials under aseptic conditions. The route of administration used for the macaque study was an intravenous bolus via a surgically implanted femoral vein catheter at a dose of 30 mg/kg (approximately 50-fold molar excess). The study design is outlined in FIG. 40. Blood samples were obtained from the femoral vein catheters, transferred directly to sodium citrate-coated tubes, mixed by inversion, and placed on ice until they were centrifuged to separate plasma (3000 rpm for 5 minutes). Plasma was then divided into 250 µl aliquots which were stored at −80° C. and one aliquot of each sample was evaluated for aptamer concentration using the fluorescence-based Oligreen™ assay previously described in the rat PK section above.

The primary plasma concentration versus time data is presented in tabular form in FIG. 41. As anticipated, the 40 kDa PEG aptamer ARC187 (SEQ ID NO: 5) persisted in plasma for the longest period of time whereas the 20 kDa PEG aptamer ARC657 (SEQ ID NO: 61) persisted for the shortest amount of time. Inspection of the data shown in FIG. 41 suggested that the data would best be fit by a two-compartment model. Thus, the pharmacokinetic parameter estimates reported in FIG. 42 were derived from the two-compartment model using the industry standard pharmacokinetic modeling software WinNonLin™ v.4.0 (Pharsight Corp., Mountain View, Calif.).

As shown in FIG. 42, all of the aptamers had a similar Cmax value, between 23 and 30 µM, indicating that the aptamer dose (30 mg/kg) was sufficient to achieve a 50-fold molar excess of plasma aptamer vs C5 concentration (50 fold molar excess, about 25 µM). Although they differ by 10,000 molecular weight, ARC657 (20 kDa PEG) (SEQ ID NO: 61) and ARC658 (30 kDa PEG) (SEQ ID NO: 62) had similar exposure (AUC), $t_{1/2}$ (α) and $t_{1/2}$ (β) values. In contrast, ARC187 (SEQ ID NO: 5) had significantly higher exposure (AUC) values, a prolonged $t_{1/2}$ (α) and a slightly longer $t_{1/2}$ (β) than the other molecules.

Additional aliquots of the plasma samples collected during the pharmacokinetics study were subsequently analyzed in vitro to determine the efficacy of primate C5 blockade. The zymosan activation assay was run as described above to determine the amount of primate C5b-9 and C5a, generated, respectively. The data were plotted in several different formats including C5b-9 concentration versus sample time (FIG. 43a), C5b-9 concentration versus aptamer concentration (FIG. 43b), C5a concentration versus sample time (FIG. 43c), and C5a concentration versus aptamer concentration (FIG. 43d).

The 40 kDa PEG aptamer ARC 187 (SEQ ID NO: 5) inhibited primate C5 cleavage (C5b-9 and C5a concentration) for the longest period of time (FIGS. 43a and 43c). When the C5b-9 and C5a data were plotted versus aptamer concentration, it indicated that the concentration of C5 blocking aptamer had to exceed 30-fold molar excess, regardless of the size of the PEG molecules, in order for C5 cleavage to be completely inhibited (FIGS. 43b and 43d).

In summary, the data from the cynomolgus macaque PK/PD study demonstrate that (a) as anticipated, at least a 30-fold molar excess of aptamer (about 15 µM plasma aptamer concentration) was necessary to inhibit C5 cleavage in vivo in the cynomolgus macaque, regardless of the size of the PEG group, (b) C5-blocking aptamers did not cause overt toxicity in this species, and (c) when animals were dosed at a relatively high levels (50-fold molar excess), plasma aptamer levels were well within the appropriate assay range during the period of sampling to allow calculation of pharmacokinetic parameters Example 5F Pharmacokinetics and Pharmacodynamics of the C5 Inhibitors ARC658 and ARC187 in the Cynomolgus Macaque Following Intravenous Administration-Study 2

Study 2 was similar in design to study 1 described above, with the following exceptions a) only two compounds were evaluated (ARC658 (SEQ ID NO: 62) and ARC 187 (SEQ ID NO: 5); b) the number of animals was increased to four per group; and c) the 1-minute plasma sample was deleted and replaced with a 144 hour sample to ensure that the terminal half-life calculation was based upon more data points. The formulation and dosing of these two aptamers, blood sampling and plasma isolation techniques was identical to the methods described above in study 1. The design for study 2 is summarized in FIG. 44.

Following completion of study 2, plasma aliquots were analyzed as described in study 1 to determine the a) the concentration of aptamer in plasma at various timepoints following intravenous administration, and b) the efficacy of C5 blockade.

Figure 45:
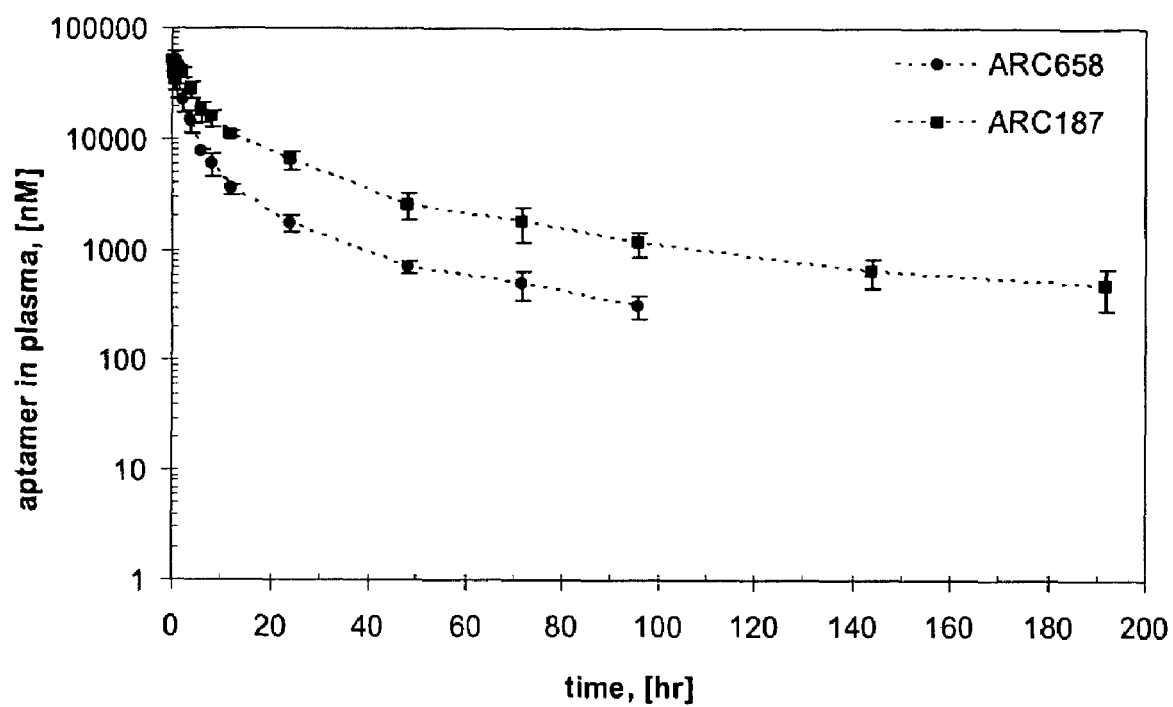
FIG. 45 is a graph showing the mean aptamer plasma concentration at various time points following intravenous administration of ARC658 (SEQ ID NO: 62), or ARC187 (SEQ ID NO: 5) to cynomolgus macaques.

Plasma aptamer concentration was plotted as a function of time (FIG. 45) and the primary data for ARC658 (SEQ ID NO: 62) and ARC187 (SEQ ID NO: 5) are presented in tabular form in FIGS. 39 and 40, respectively. The 40 kDa PEG aptamer ARC187 (SEQ ID NO: 5) persisted in plasma for the longest period of time. Inspection of FIG. 45 indicated that the data would be best fit by a two-compartment model. Thus, the pharmacokinetic parameter estimates reported in FIG. 46 were derived from the two-compartment model using WinNonLin™ v.4.0 (Pharsight Corp., Mountain View, Calif.).

Comparing the pharmacokinetic parameters generated during the PK/PD study 1 and study 2 above, the data for ARC658 (SEQ ID NO: 62) and ARC187 (SEQ ID NO: 5) were similar with the exception of the $t_{1/2}$ (α) measurement for ARC187. While not wishing to be bound by any theory, the discrepancy in the $t_{1/2}$ (α) measurements for ARC187 between the two studies is likely due to the small sample size in the pilot study.

As demonstrated in FIG. 46, the Cmax values were similar for ARC658 (SEQ ID NO: 62) and ARC187 (SEQ ID NO: 5). In contrast, drug exposure (AUC) was significantly greater in animals treated with ARC187 (SEQ ID NO: 5). Also, ARC187 had prolonged $t_{1/2}$ (α) and $t_{1/2}$ (β) values as compared to ARC658 (SEQ ID NO: 62). These data, along with the data generated during the PK/PD study 1 indicate that of the C5-blocking aptamers ARC187 may provide the most effective in vivo C5 blockade for a given dose.

Additional aliquots of the plasma samples collected during the pharmacokinetics study were subsequently analyzed in vitro to determine the efficacy of primate C5 blockade. As before, the zymosan activation assay was run to determine the amount of primate C5b-9 and C5a, respectively, generated. The data were plotted as C5b-9 concentration versus aptamer concentration (FIG. 47) and C5a concentration versus aptamer concentration (FIG. 48). As previously demonstrated during PK/PD study 1, the concentration of C5 blocking aptamer must exceed a 30-fold molar excess (aptamer to plasma C5 concentration), or approximately 15 μM, regardless of the size of the PEG molecule, in order for primate C5 cleavage to be completely inhibited (FIGS. 41 and 42).

By inspecting the data in the tables of FIGS. 39 and 40, it is apparent that after a 30 mg/kg I.V. bolus, ARC658 (SEQ ID NO: 62) remains above 15 μM for approximately 4 hours whereas ARC187 remains above 15 μM for approximately 8 hours. Thus, given a similar dose of drug, the 40 K aptamer ARC 187 provides clinical efficacy for approximately twice as long as the 30K aptamer ARC658 (SEQ ID NO: 62).

In summary, cynomolgus macaques must be treated with at least a 30-fold molar excess of aptamer vs plasma C5 in order to block C5 conversion in vivo. These data are consistent with previous in vitro (hemolysis) and ex-vivo (isolated perfused mouse heart) studies which suggested that the C5-binding aptamers had a lower affinity for primate C5 versus human C5. It has been shown that C5-blocking aptamers can safely be delivered as an intravenous bolus at a dose of up to 30 mg/kg, which equates to approximately a 50-fold molar excess of aptamer vs C5 concentration.

Example 5G

ARC1905 in the Cynomolgus Macaque Following Bolus IV Administration

The pharmacodynamics of the C5 inhibitors ARC1905 was evaluated in the cynomolgus macaque following intravenous administration. Formulation of ARC1905 for injection was in standard saline at 7.5 mg/mL and dosing formulations were sterile-filtered (0.2 μm) into pre-sterilized dosing vials under aseptic conditions. Cynomolgus monkeys (n=4) were dosed at 0 (saline control) or 30 mg/kg via intravenous bolus administration. Blood samples were obtained from a peripheral vein or the arterial access port and blood samples (0.5 mL) were transferred into dipotassium ($K_2$) EDTA tubes, placed on wet ice, and centrifuged within 30 minutes of collection at approximately 4° C.

The plasma samples were analyzed in vitro to determine the efficacy of ARC1905 in primate C5 blockade. The zymosan assay previously described with respect to ARC1905 in Example 1C was used to determine the amount of primate C5a generated. The decrease in post-zymosan C5a values at 0.5 and 2 hours after dosing indicates that ARC1905 inhibits C5 cleavage in vivo in the cynomolgus macaque in a similar manner as ARC187 when dosed at approximately the same concentration and the same route of administration as measured in vitro using the zymosan activation assay.

Example 5H

Pharmacokinetics and Pharmacodynamics of the C5 Inhibitor ARC187 in the Cynomolgus Macaque Following Bolus IV Administration and Infusion The pharmacokinetic (PK) and pharmacodynamic (PD) profiles of ARC187 (SEQ ID NO: 5) were also evaluated in cynomolgus macaques after an intravenous loading bolus followed immediately by the initiation of an intravenous infusion. This study design is shown in FIG. 49.

The loading bolus dose and infusion rate necessary to achieve the target steady state plasma concentration of 1 uM were calculated using the pharmacokinetic parameters derived from the IV bolus-only study listed in FIG. 50.

A total of three cynomolgus macaques were administered an IV bolus of ARC187 at 1 mg/kg, followed immediately by the initiation of an IV infusion at a rate of 0.0013 mg/kg/min for a period of 48 hrs. Samples of whole blood were collected from 0 to 192 hours post-treatment, stored on wet ice, processed for plasma, and then stored frozen at −80 C. The concentration of ARC187 in plasma samples was determined using both a fluorescent nucleic acid stain assay (described in Example 5B) and a GLP-validated performance liquid chromatography (HPLC) assay. The HPLC assay method for the determination of ARC187 in monkey plasma was validated by ClinTrials Bio-Research (Montreal, Canada). The validation study complied with the United States Food and Drug Administration (FDA) Good Laboratory Practice (GLP) regulations (21 CFR §58). The HPLC assay method was validated with respect to: selectivity, linearity, lower limit of quantitation (LLOQ), carry-over, intra-assay precision and accuracy, inter-assay precision and accuracy, stock solution stability, injection medium stability, short-term matrix stability, freeze-thaw stability, long-term matrix stability and dilution integrity. The usable linear dynamic concentration range of assay was determined to be 0.080 to 50.0 μM.

Figure 51:
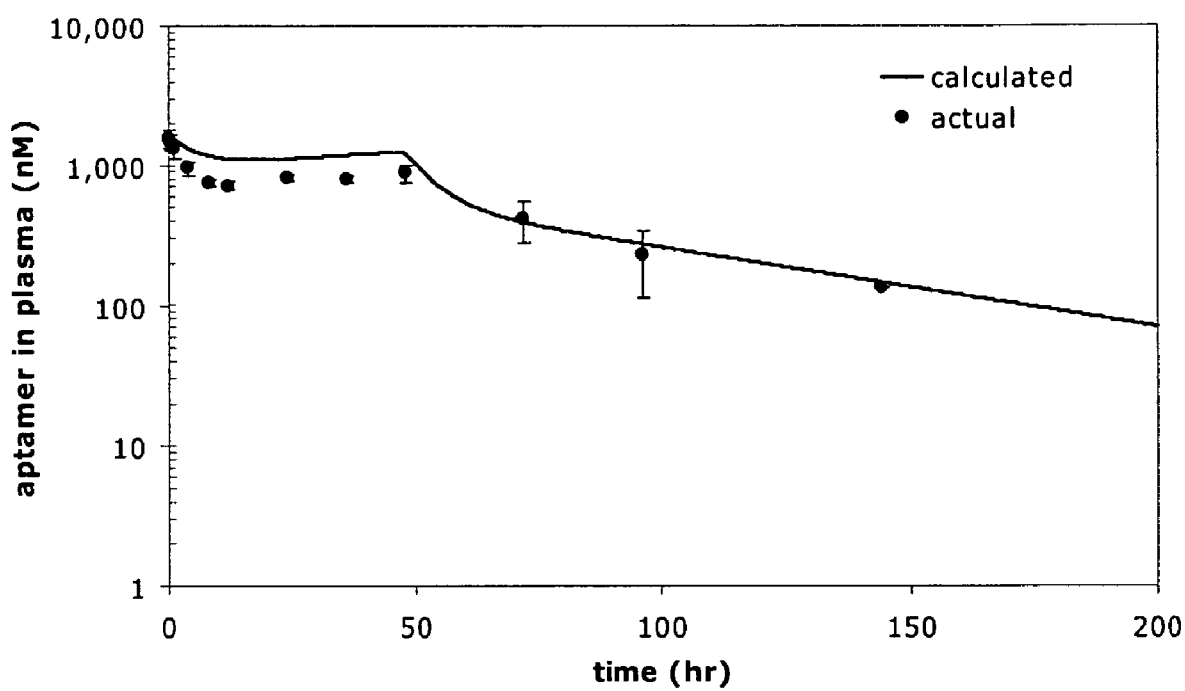
FIG. 51 is a graph depicting the calculated and actual measured pharmacokinetic profiles of ARC187 (SEQ ID NO: 5) during and after IV bolus plus infusion administration to cynomolgus macaques.

The measured PK profile of ARC187 under these conditions conformed well to the calculated profile generated using only the IV bolus PK parameters (see FIG. 51). The target plasma concentration of 1 uM was established in <5 min post-dose and maintained for the entire duration of infusion. After cessation of the infusion, the aptamer showed a terminal clearance half-life, $t_{1/2}$ (β) ~40-60 hr.

Figures 52, 53:
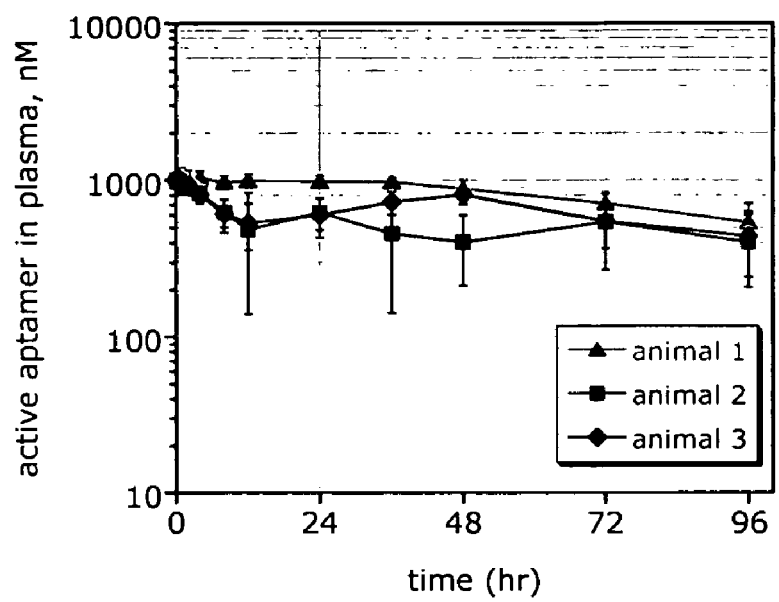
FIG. 52 is a graph showing the plasma levels of active ARC187 (SEQ ID NO: 5) remain constant during and after IV bolus plus infusion administration to cynomolgus macaques.
FIG. 53 is a table showing the predicted human dosing requirements for anti-C5 aptamers in CABG surgery.

The pharmacodynamic activity of ARC187 (SEQ ID NO: 5) in the cynomolgus macaque was evaluated ex-vivo by using plasma samples collected during PK study in the zymosan activation assay previously described with the modification that cynomolgous sample plasma was diluted 10-fold into 10% human plasma and then treated with 5 mg/mL zymosan. C5 activation, as reflected by the appearance of the C5a cleavage product, was measured by ELISA specific to human C5a (C5a ELISA kit, BD Biosciences, San Diego, Calif.). The concentration of active ARC187 in each sample was then quantified by comparison with a standard curve derived from zymosan assays using samples prepared with known ARC187 levels (see FIG. 52). This study indicates that ARC 187 maintains its anti-complement activity throughout the duration of and following infusion, at levels substantially consistent with the pharmacokinetic profile described above.

Example 5I

Prediction of Human Dosing Requirement

Human dosing requirements for prevention, amelioration, or treatment of complications related to CABG surgery are based on the following assumptions: first, CABG patients will be administered a single intravenous bolus dose of the anti-C5 aptamer prior to initiating surgery, followed by continuous infusion to establish and maintain a steady-state plasma concentration of 1.5 µM for 24-48 hours post CABG surgery. The bolus dose and infusion rate estimates are based upon calculations using the pharmacokinetic parameters derived from the previously described IV bolus-only and bolus plus infusion studies in cynomolgus macaques. The estimated bolus dose of ARC187 is 1 mg/kg, and the associated infusion rate is 0.0013 mg/kg/min. For this bolus plus 48 hr infusion regimen, the anticipated total drug requirement is 0.4 g for ARC187, where mass refers to oligonucleotide weight only (see column 7 in the table of FIG. 53). Column 2 of the table shown in FIG. 53 refers to the weight of the PEG group conjugated to oligonucleotide portion of ARC187, column three refers to the molecular weight of the oligonucleotide portion of ARC187 (and will be the same for all aptamers herein that comprise ARC186 (SEQ ID NO: 4) as its oligonucleotide sequence), column 4 refers to the molecular weight of 40 kDA PEG conjugated to ARC186 (SEQ ID NO: 4) via amine reactive chemistry as described in Example 3C above, column 5 refers to ARC187's α phase half life in a two compartment model, and column six refers to ARC187's β phase half life in a two compartment model.

EXAMPLE 6

Anti-C5 Aptamers and Heparin/Protamine Interaction

One anticipated application of the anti-C5 aptamer is as a prophylactic for the prevention or mitigation of inflammatory side effects associated with coronary artery bypass graft (CABG) surgery. High concentrations of the anticoagulant heparin (3-5 units/mL or 1-2 µM) are typically administered during CABG to prevent thrombosis and maintain patency within components of the bypass pump; reversal of heparin's effect after the procedure, and restoration of normal hemostasis, is achieved by the administration of similarly high concentrations of protamine (~5 µM). Given the potential dangers to patients of any interference in the effectiveness of either of these drugs, it was necessary to demonstrate that anti-C5 aptamers (1) do not alter the activities of either drug and (2) do not display inherent effects on hemostasis that could complicate patient anticoagulation treatment.

Heparin is a sulfated polysaccharide with a net negative charge and a mean molecular mass of approximately 15 kDa that exerts an inhibitory effect on a number of proteases in the coagulation cascade by promoting interactions with antithrombin. Protamine, a highly positively charged polypeptide, is able to block heparin activity via a poorly characterized interaction that is at least partially electrostatic in nature. The functional core of ARC187 (SEQ ID NO: 5), like heparin, is highly anionic. Thus, it is conceivable that ARC187 could nonspecifically bind to heparin-binding sites or protamine and interfere with the activities of these molecules. The following studies investigated the inherent (i.e., heparin-like) anticoagulant properties of ARC187, the effects of ARC187 on heparin function, the effects of ARC187 on heparin-neutralization by protamine, and the effects of protamine on the complement inhibiting properties of ARC187.

Example 6A

In Vitro Effects of ARC187 on Coagulation

Figure 54:
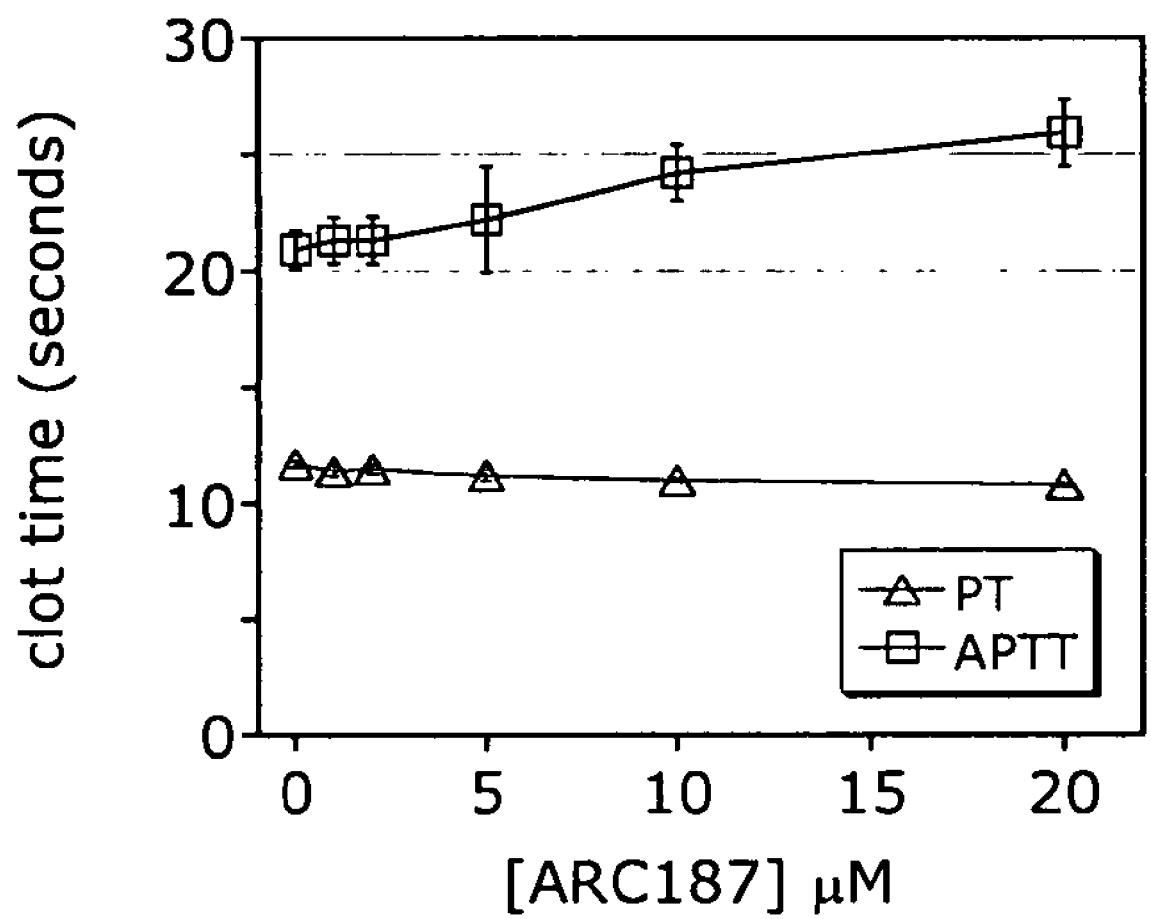
FIG. 54 is a graph depicting ARC187 (SEQ ID NO: 5) has relatively no in vitro effect on coagulation as measured by the prothrombin time (PT) and activated partial thromboplastin time (APTT).

The inherent effects of ARC187 (SEQ ID NO: 5) on plasma coagulability were investigated using standard clinical tests of the extrinsic and intrinsic arms of the coagulation cascade, the prothrombin time (PT) and activated partial thromboplastin time (aPTT), respectively. As shown in FIG. 54, titration of citrated human plasma with concentrations well in excess of projected doses (up to 20 µM) resulted in no change in the PT, and only a slight elevation in the aPTT.

To assess the in vitro effects of ARC187 on heparin and protamine functions, blood from 3 individuals was drawn into 4-5 units/mL heparin, doses associated with heparin levels used in CABG surgery. The coagulability of these samples was assessed using the activated clot time (ACT), a whole blood coagulation test routinely used to monitor heparin activity during surgery. At these concentrations of heparin, in the absence of other additives, the ACT was significantly prolonged from a baseline value of ~150 seconds to ~500 seconds in the presence of 4 U/mL heparin or ~800 seconds in the presence of 5 U/mL heparin. Addition of 10 µM ARC187 to these samples had little effect on clot time, demonstrating that ARC187 does not interfere with the anticoagulant activity of heparin.

The heparin anticoagulant effect was readily neutralized by titration with protamine up to 6-8 µM (4 U/mL heparin) or 12 µM (5 U/mL heparin). ACT values in the presence of heparin and neutralizing concentrations of protamine were essentially indistinguishable from baseline. Since the nucleic acid core of ARC187 (12 kDa) is of larger molecular weight than protamine (5 kDa), one might expect that equimolar concentrations of ARC187 added to protamine would be sufficient to completely reverse the neutralizing activity of protamine. However, preincubation of protamine with approximately equivalent concentrations of ARC187 had little effect on the ACT. Blood samples containing neutralizing concentrations of protamine displayed similar ACT values in the presence or absence of 10 µM ARC187, indicating that ARC187 has only a slight if any effect on the procoagulant activity of protamine. These results are summarized in FIG. 55.

Example 6B

In Vivo Effects of ARC187 on Coagulation

Figure 56:
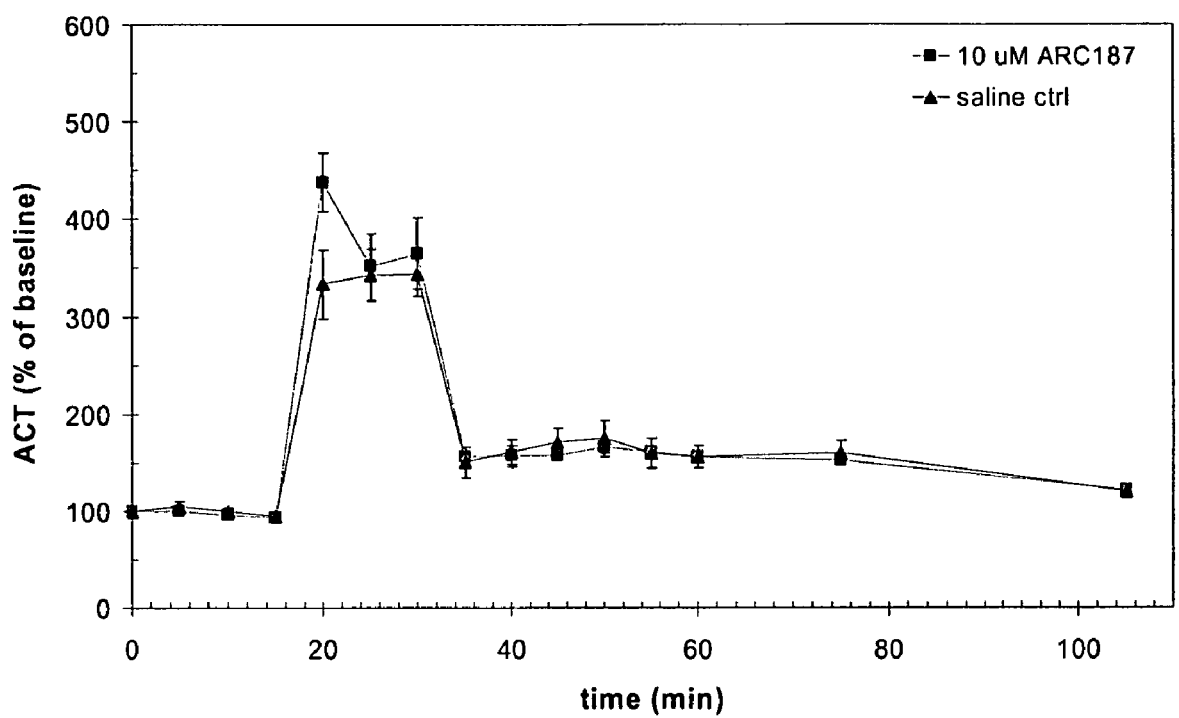
FIG. 56 is a graph showing ARC187 (SEQ ID NO: 5) does not effect the reversal of heparin anticoagulation in vivo.

The interactions between the function of heparin and protamine during concurrent administration of anti-C5 aptamer ARC187 (SEQ ID NO: 5), at clinical doses of heparin and clinical/subclinical/superclinical doses of protamine were investigated to determine whether the presence of subclinical/superclinical plasma concentrations of ARC187 would interfere with the reversal of heparin anticoagulation by protamine. The results of the study are summarized in FIG. 56. Briefly, the baseline ACT values were unaffected by 10 uM (i.e., 10-fold molar excess of the clinical dose) of ARC187 at all heparin doses tested. Similarly, the extent of anticoagulation by heparin was unaffected by 10 uM ARC187. In the absence of ARC187, the minimum efficacious dose of protamine was ~30% (clinical dose=100%). Furthermore, the reversal of heparin anticoagulation by 30% protamine was unaffected by 10-fold molar excess of the clinical dose (i.e., 10 uM) of ARC187. Thus, the use of ARC187 for complement inhibition in a clinical setting (e.g., CABG) should be unaffected by concurrent use of heparin and protamine at typical doses.

Example 6C

Effect of Heparin and Protamine on ARC187 Anti-complement Function

Figure 57:
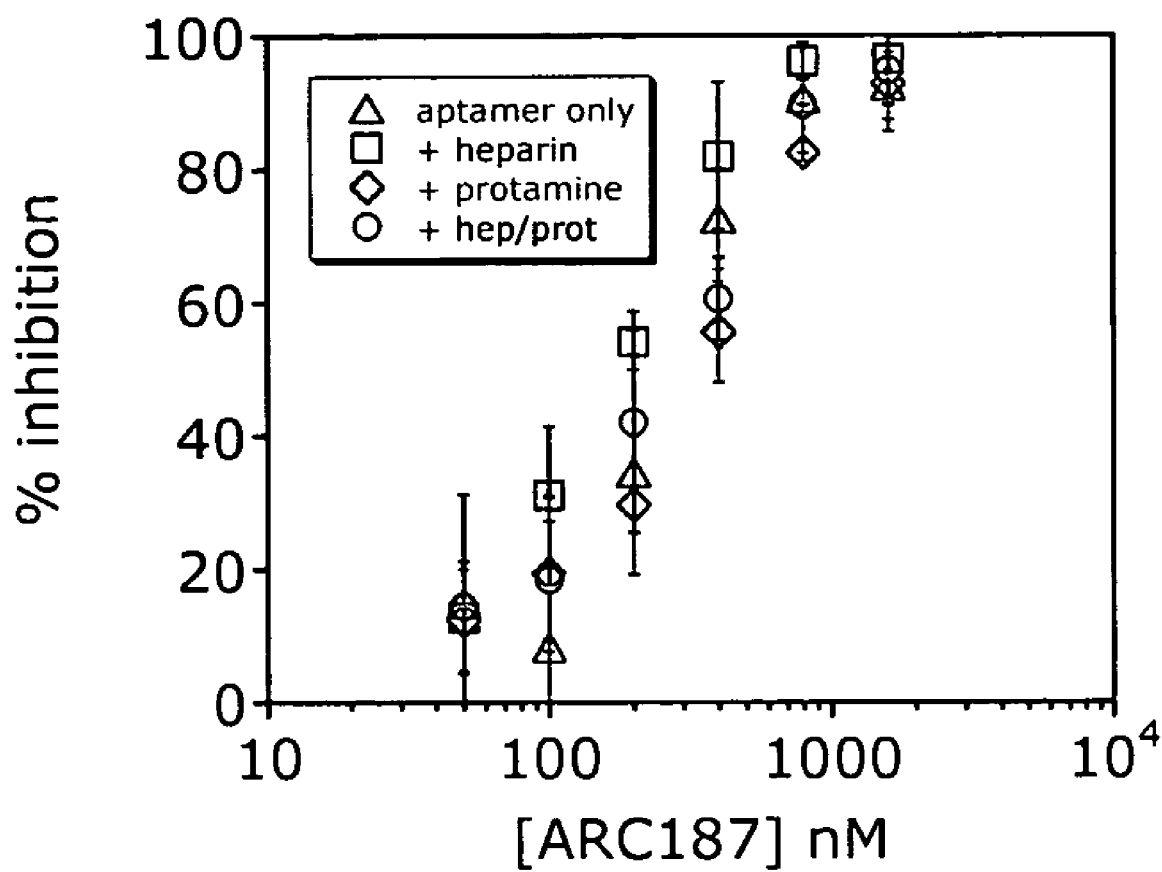
FIG. 57 is graph showing heparin and protamine both have no effect on ARC187 (SEQ ID NO: 5) anti-complement function, measured by inhibition of complement activation of zymosan.

The effects of heparin and protamine on the anti-complement activity of ARC187 (SEQ ID NO: 5) were examined in citrated whole blood samples activated with zymosan, as described in Example 1. Just prior to zymosan activation, ARC187 was titrated into samples of citrated blood treated under four conditions: 1) no treatment (no heparin or protamine); 2) 4 U/mL heparin; 3) 6 µM protamine; 4) 4 U/mL heparin+6 µM protamine. Following activation with zymosan, C5 activation was quantified by ELISA measurement of sC5b-9 in plasma (C5b-9 ELISA kit, Quidel, San Diego, Calif.). For each condition, the results, expressed as percent inhibition of C5 activation versus ARC187 concentration, were indistinguishable within error (see FIG. 57). In all cases complete inhibition was achieved with 1-2 µM ARC187. Thus, heparin and protamine, separately or combined at concentrations relevant to their use in CABG surgery, do not appear to affect the anti-complement activity of ARC187.

The invention having now been described by way of written description and example, those of skill in the art will recognize that the invention can be practiced in a variety of embodiments and that the description and examples above are for purposes of illustration and not limitation of the following claims.

What is claimed is:

1. A composition comprising a therapeutically effective amount of an aptamer comprising:

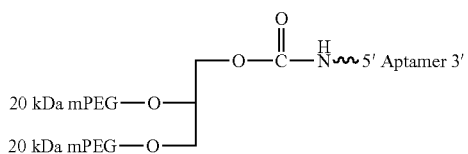

where,

⁓⁓⁓⁓⁓ indicates a linker

Aptamer=
the nucleic acid sequence
fCmGfCfCGfCmGmGfUfCfUfCmAmG-
mGfCGfCfUmGmAmGfUfCfUmGmAmG-
fUfUfUAfCfCfUmGfCmG-3T as set forth in SEQ ID NO: 4,
wherein fC and fU=2'-fluoro nucleotides, and mG and mA=2'-OMe nucleotides and all other nucleotides are 2'-OH and 3T indicates an inverted deoxy thymidine,
or a salt thereof.

2. The composition of claim 1, wherein the aptamer linker is an alkyl linker.

3. The composition of claim 2, wherein the alkyl linker comprises 2 to 18 consecutive $CH_2$ groups.

4. The composition of claim 1, wherein the aptamer comprises the structure set forth below:

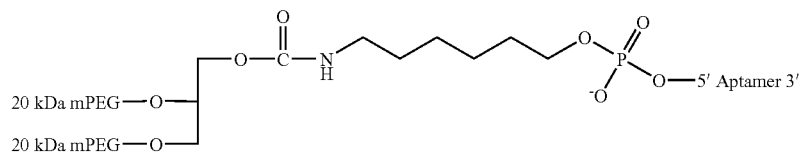

where Aptamer=
the nucleic acid sequence fCmGfCfCGfCmGmGfUfCfUfCmAmG-mGfCGfCfUmGmAmGfUfCfUmGmAmG-fUfUfUAfCfCfUmGfCmG-3T as set forth in SEQ ID NO: 4 wherein fC and fU=2'-fluoro nucleotides, and mG and mA=2'-OMe nucleotides and all other nucleotides are 2'-OH and 3T indicates an inverted deoxy thymidine.

5. The composition of claim 4, comprising a pharmaceutically acceptable carrier or diluent.

6. The composition of claim 2, wherein the alkyl linker comprises 6 consecutive $CH_2$ groups.

* * * * *

UNITED STATES PATENT AND TRADEMARK OFFICE
CERTIFICATE OF CORRECTION

PATENT NO. : 7,579,456 B2
APPLICATION NO. : 11/354657
DATED : August 25, 2009
INVENTOR(S) : Benedict et al.

It is certified that error appears in the above-identified patent and that said Letters Patent is hereby corrected as shown below:

Column 154, lines 53-54, Claim 4, "The composition of claim 1, wherein the aptamer comprises the structure set forth below" should read --The composition of claim 1, wherein the compound has the structure set forth below--.

Signed and Sealed this

Thirtieth Day of March, 2010

David J. Kappos
*Director of the United States Patent and Trademark Office*

UNITED STATES PATENT AND TRADEMARK OFFICE
CERTIFICATE OF CORRECTION

PATENT NO. : 7,579,456 B2  Page 1 of 1
APPLICATION NO. : 11/354657
DATED : August 25, 2009
INVENTOR(S) : Benedict et al.

It is certified that error appears in the above-identified patent and that said Letters Patent is hereby corrected as shown below:

Column 153, lines 39-40, Claim 1, "A composition comprising a therapeutically effective amount of an aptamer comprising:" should read -- A composition comprising a therapeutically effective amount of a compound having the formula: --.

Column 154, lines 49-50, Claim 2, "The composition of claim 1, wherein the aptamer linker is an alkyl linker" should read -- The composition of claim 1, wherein the linker is an alkyl linker --.

Signed and Sealed this

Eighteenth Day of May, 2010

David J. Kappos
*Director of the United States Patent and Trademark Office*

SEQUENCE LISTING

```
<160> NUMBER OF SEQ ID NOS: 102

<210> SEQ ID NO 1
<211> LENGTH: 38
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<223> OTHER INFORMATION: cytosine at positions 3, 4, 6 and 37 are
      2'-fluoro
<220> FEATURE:
<221> NAME/KEY: misc_feature
<223> OTHER INFORMATION: uridine at positions 9, 30 and 31 are 2'-fluoro
<220> FEATURE:
<221> NAME/KEY: misc_feature
<222> LOCATION: (1)..(1)
<223> OTHER INFORMATION: n at position 1 is 2'-fluoro cytidine or
      2'-O-methyl cytidine
<220> FEATURE:
<221> NAME/KEY: misc_feature
<222> LOCATION: (2)..(2)
<223> OTHER INFORMATION: n at position 2 is 2'-OH guanosine or
      2'-O-methyl guanosine
<220> FEATURE:
<221> NAME/KEY: misc_feature
<222> LOCATION: (7)..(7)
<223> OTHER INFORMATION: n at position 7 is 2'-OH guanosine or
      2'-O-methyl guanosine
<220> FEATURE:
<221> NAME/KEY: misc_feature
<222> LOCATION: (8)..(8)
<223> OTHER INFORMATION: n at position 8 is 2'-OH guanosine or
      2'-O-methyl guanosine
<220> FEATURE:
<221> NAME/KEY: misc_feature
<222> LOCATION: (10)..(10)
<223> OTHER INFORMATION: n at position 10 is 2'-fluoro cytosine or deoxy
      cytidine
<220> FEATURE:
<221> NAME/KEY: misc_feature
<222> LOCATION: (11)..(11)
<223> OTHER INFORMATION: n at position 11 is 2'-fluoro uridine or deoxy
      thymidine
<220> FEATURE:
<221> NAME/KEY: misc_feature
<222> LOCATION: (12)..(12)
<223> OTHER INFORMATION: n at position 12 is is 2'-fluoro cytosine or
      deoxy cytidine
<220> FEATURE:
<221> NAME/KEY: misc_feature
<222> LOCATION: (13)..(13)
<223> OTHER INFORMATION: n at position 13 is 2'-OH adenosine or
```

2'-O-methyl adenosine
<220> FEATURE:
<221> NAME/KEY: misc_feature
<222> LOCATION: (14)..(14)
<223> OTHER INFORMATION: n at position 14 is 2'-OH guanosine or
      2'-O-methyl guanosine
<220> FEATURE:
<221> NAME/KEY: misc_feature
<222> LOCATION: (15)..(15)
<223> OTHER INFORMATION: n at position 15 is 2'-OH guanosine or
      2'-O-methyl guanosine
<220> FEATURE:
<221> NAME/KEY: misc_feature
<222> LOCATION: (16)..(16)
<223> OTHER INFORMATION: n at position 16 is 2'-fluoro cytosine or deoxy
      cytidine
<220> FEATURE:
<221> NAME/KEY: misc_feature
<222> LOCATION: (18)..(18)
<223> OTHER INFORMATION: n at position 18 is 2'-fluoro cytosine or
      2'-O-methyl cytosine
<220> FEATURE:
<221> NAME/KEY: misc_feature
<222> LOCATION: (19)..(19)
<223> OTHER INFORMATION: n at position 19 is 2'-fluoro uridine or
      2'-O-methyl uridine
<220> FEATURE:
<221> NAME/KEY: misc_feature
<222> LOCATION: (20)..(20)
<223> OTHER INFORMATION: n at position 20 is 2'-OH guanosine or
      2'-O-methyl guanosine
<220> FEATURE:
<221> NAME/KEY: misc_feature
<222> LOCATION: (21)..(21)
<223> OTHER INFORMATION: n at position 21 is 2'-OH adenosine or
      2'-O-methyl adenosine
<220> FEATURE:
<221> NAME/KEY: misc_feature
<222> LOCATION: (22)..(22)
<223> OTHER INFORMATION: n at position 22 is 2'-OH guanosine or
      2'-O-methyl guanosine
<220> FEATURE:
<221> NAME/KEY: misc_feature
<222> LOCATION: (23)..(23)
<223> OTHER INFORMATION: n at position 23 is 2'-fluoro uridine or deoxy
      thymidine
<220> FEATURE:
<221> NAME/KEY: misc_feature
<222> LOCATION: (24)..(24)
<223> OTHER INFORMATION: n at position 24 is 2'-fluoro cytosine or deoxy
      cytidine
<220> FEATURE:
<221> NAME/KEY: misc_feature
<222> LOCATION: (25)..(25)
<223> OTHER INFORMATION: n at position 25 is 2'-fluoro uridine or deoxy
      thymidine
<220> FEATURE:
<221> NAME/KEY: misc_feature
<222> LOCATION: (26)..(26)
<223> OTHER INFORMATION: n at position 26 is 2'-OH guanosine or
      2'-O-methyl guanosine
<220> FEATURE:
<221> NAME/KEY: misc_feature
<222> LOCATION: (27)..(27)
<223> OTHER INFORMATION: n at position 27 is 2'-OH adenosine or
      2'-O-methyl adenosine
<220> FEATURE:
<221> NAME/KEY: misc_feature
<222> LOCATION: (28)..(28)
<223> OTHER INFORMATION: n at position 28 is 2'-OH guanosine or
      2'-O-methyl guanosine
<220> FEATURE:
<221> NAME/KEY: misc_feature
<222> LOCATION: (29)..(29)
<223> OTHER INFORMATION: n at position 29 is 2'-fluoro uridine or deoxy
      thymidine
<220> FEATURE:
<221> NAME/KEY: misc_feature
<222> LOCATION: (32)..(32)

<223> OTHER INFORMATION: n at position 32 is 2'-OH adenosine or
      2'-O-methyl adenosine
<220> FEATURE:
<221> NAME/KEY: misc_feature
<222> LOCATION: (33)..(33)
<223> OTHER INFORMATION: n at position 33 is 2'-fluoro cytosine or deoxy
      cytidine
<220> FEATURE:
<221> NAME/KEY: misc_feature
<222> LOCATION: (34)..(34)
<223> OTHER INFORMATION: n at position 34 is 2'-fluoro cytosine or deoxy
      cytidine
<220> FEATURE:
<221> NAME/KEY: misc_feature
<222> LOCATION: (35)..(35)
<223> OTHER INFORMATION: n at position 35 is 2'-fluoro uridine or deoxy
      thymidine
<220> FEATURE:
<221> NAME/KEY: misc_feature
<222> LOCATION: (36)..(36)
<223> OTHER INFORMATION: n at position 36 is 2'-OH guanosine or
      2'-O-methyl guanosine
<220> FEATURE:
<221> NAME/KEY: misc_feature
<222> LOCATION: (38)..(38)
<223> OTHER INFORMATION: n at position 38 is 2'-OH guanosine or
      2'-O-methyl guanosine

<400> SEQUENCE: 1
nnccgcnnun nnnnnngnnn nnnnnnnnnu unnnnncn                            38

<210> SEQ ID NO 2
<211> LENGTH: 38
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(38)
<223> OTHER INFORMATION: all pyrimidines are 2'-fluoro; except at
      positions 10, 12, 16 and 24, wherein cytidine is deoxy, and at
      positions 11, 23 and 25, which are deoxy thymidine
<220> FEATURE:
<221> NAME/KEY: misc_feature
<222> LOCATION: (1)..(38)
<223> OTHER INFORMATION: all purines are 2'-O-methyl; except at
      positions 5 and 17, wherein guanosine is 2'-OH, and position 32,
      wherein adenosine is 2'-OH

<400> SEQUENCE: 2
cgccgcgguc tcaggcgcug agtctgaguu uaccugcg                            38

<210> SEQ ID NO 3
<211> LENGTH: 42
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(42)
<223> OTHER INFORMATION: all pyrimidines are 2'-fluoro

<400> SEQUENCE: 3
gacgaugcgg ucucaugcgu cgagugugag uuuaccuucg uc                       42

<210> SEQ ID NO 4
<211> LENGTH: 39
<212> TYPE: DNA
<213> ORGANISM: artificial sequence
<220> FEATURE:
<223> OTHER INFORMATION: synthetic aptamer

```
<220> FEATURE:
<221> NAME/KEY: misc_feature
<222> LOCATION: (1)..(38)
<223> OTHER INFORMATION: all pyrimidines are 2'-fluoro
<220> FEATURE:
<221> NAME/KEY: misc_feature
<222> LOCATION: (1)..(38)
<223> OTHER INFORMATION: all purines are 2'-O-methyl; except at
      positions 5 and 17, wherein guanosine is 2'-OH, and at position
      32, wherein adenosine is 2'-OH
<220> FEATURE:
<221> NAME/KEY: misc_feature
<222> LOCATION: (39)..(39)
<223> OTHER INFORMATION: thymidine at position 39 is a 3' inverted deoxy
      thymidine (3'-3'linked)

<400> SEQUENCE: 4
cgccgcgguc ucaggcgcug agucugaguu uaccugcgt                              39

<210> SEQ ID NO 5
<211> LENGTH: 39
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(1)
<223> OTHER INFORMATION: cytosine at position 1 is a modified by a
      40 kDa branched (1,3-bis(mPEG-[20 kDa])-propyl-2-(4'-butamide))
      PEG attached to the nucleotide via an amine linker
<220> FEATURE:
<221> NAME/KEY: misc_feature
<222> LOCATION: (1)..(38)
<223> OTHER INFORMATION: all pyrimidines are 2'-fluoro
<220> FEATURE:
<221> NAME/KEY: misc_feature
<222> LOCATION: (1)..(38)
<223> OTHER INFORMATION: all purines are 2'-O-methyl; except at
      positions 5 and 17, wherein guanosine is 2'-OH, and at position
      32, wherein adenosine is 2'-OH
<220> FEATURE:
<221> NAME/KEY: misc_feature
<222> LOCATION: (39)..(39)
<223> OTHER INFORMATION: thymidine at position 39 is a 3' inverted deoxy
      thymidine (3'-3' linked)

<400> SEQUENCE: 5
cgccgcgguc ucaggcgcug agucugaguu uaccugcgt                              39

<210> SEQ ID NO 6
<211> LENGTH: 44
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(44)
<223> OTHER INFORMATION: all pyrimidines are 2'-fluoro

<400> SEQUENCE: 6
aggacgaugc ggucucaugc gucgagugug aguuuaccuu cguc                        44

<210> SEQ ID NO 7
<211> LENGTH: 40
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(40)
```

```
<223> OTHER INFORMATION: all pyrimidines are 2'-fluoro
<220> FEATURE:
<221> NAME/KEY: misc_feature
<222> LOCATION: (1)..(40)
<223> OTHER INFORMATION: all purines are 2'-O-methyl; except at
      positions 2, 7 and 19, wherein guanosine is 2'-OH, and positions 1
      and 34, wherein adenosine is 2'-OH

<400> SEQUENCE: 7
agcgccgcgg ucucaggcgc ugagucugag uuuaccugcg                            40

<210> SEQ ID NO 8
<211> LENGTH: 40
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(40)
<223> OTHER INFORMATION: all pyrimidines are 2'-fluoro

<400> SEQUENCE: 8
ggcgccgcgg ucucaggcgc ugagucugag uuuaccugcg                            40

<210> SEQ ID NO 9
<211> LENGTH: 39
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(38)
<223> OTHER INFORMATION: all purines are 2'-O-methyl; except at
      positions 5 and 17, wherein guanosine is 2'-OH, and position 32,
      wherein adenosine is 2'-OH
<220> FEATURE:
<221> NAME/KEY: misc_feature
<222> LOCATION: (1)..(38)
<223> OTHER INFORMATION: all pyrimidines are 2'-fluoro; except at
      positions 10, 12, 16, 24, 33 and 34, wherein cytidine is deoxy,
      and at positions 11, 23, and 25, which are deoxy thymidine
<220> FEATURE:
<221> NAME/KEY: misc_feature
<222> LOCATION: (39)..(39)
<223> OTHER INFORMATION: thymidine at position 39 is a 3' inverted deoxy
      thymidine (3'-3' linked)

<400> SEQUENCE: 9
cgccgcgguc tcaggcgcug agtctgaguu uaccugcgt                             39

<210> SEQ ID NO 10
<211> LENGTH: 39
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(38)
<223> OTHER INFORMATION: all purines are 2'-O-methyl, except at
      positions 5 and 17, wherein guanosine is 2'-OH, and position 32,
      wherein adenosine is 2'-OH
<220> FEATURE:
<221> NAME/KEY: misc_feature
<222> LOCATION: (1)..(38)
<223> OTHER INFORMATION: all pyrimidines are 2'-fluoro, except at
      positions 10, 12, 16, 24, 33 and 34, wherein cytidine is deoxy; at
      positions 1, 3, and 37, wherein cytosine is 2'-O-methyl; and at
      postions 11, 23, and 25, which are deoxy thymidine
<220> FEATURE:
<221> NAME/KEY: misc_feature
```

```
<222> LOCATION: (39)..(39)
<223> OTHER INFORMATION: thymidine at position 39 is a 3' inverted deoxy
      thymidine (3'-3' linked)

<400> SEQUENCE: 10
cgccgcgguc tcaggcgcug agtctgaguu uaccugcgt                         39

<210> SEQ ID NO 11
<211> LENGTH: 38
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(38)
<223> OTHER INFORMATION: all purines are 2'-O-methyl, except at
      positions 5 and 17, wherein guanosine is 2'-OH, and position 32,
      wherein adenosine is 2'-OH
<220> FEATURE:
<221> NAME/KEY: misc_feature
<222> LOCATION: (1)..(38)
<223> OTHER INFORMATION: all pyrimidines are 2'-fluoro; except at
      positions 1, 3, 10, 12, 16, 24 and 37, wherein cytidine is deoxy;
      and at positions 11, 23 and 25, which are deoxy thymidine

<400> SEQUENCE: 11
cgccgcgguc tcaggcgcug agtctgaguu uaccugcg                          38

<210> SEQ ID NO 12
<211> LENGTH: 38
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(38)
<223> OTHER INFORMATION: all purines are 2'-O-methyl; except at
      positions 5 and 17, wherein guanosine is 2'-OH, and position 32,
      wherein adenosine is 2'-OH
<220> FEATURE:
<221> NAME/KEY: misc_feature
<222> LOCATION: (1)..(38)
<223> OTHER INFORMATION: all pyrmidines are 2'-fluoro; except at
      positions 1, 10, 12, 16 and 24, wherein cytidine is deoxy, and at
      positions 11, 23 and 25, which are deoxy thymidine

<400> SEQUENCE: 12
cgccgcgguc tcaggcgcug agtctgaguu uaccugcg                          38

<210> SEQ ID NO 13
<211> LENGTH: 38
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(38)
<223> OTHER INFORMATION: all purines are 2'-O-methyl; except at
      positions 5 and 17, wherein guanosine is 2'-OH, and position 32,
      wherein adenosine is 2'-OH
<220> FEATURE:
<221> NAME/KEY: misc_feature
<222> LOCATION: (1)..(38)
<223> OTHER INFORMATION: all  pyrimidines are 2'-fluoro; except at
      positions 3, 10, 12, 16 and 24, wherein cytidine is deoxy; and
      positions 11, 23, and 25, which are deoxy thymidine

<400> SEQUENCE: 13
cgccgcgguc tcaggcgcug agtctgaguu uaccugcg                          38
```

<210> SEQ ID NO 14
<211> LENGTH: 38
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(38)
<223> OTHER INFORMATION: all purines are 2'-O-methyl; except at
      positions 5 and 17, wherein guanosine is 2'-OH, and position 32,
      wherein adenosine is 2'-OH
<220> FEATURE:
<221> NAME/KEY: misc_feature
<222> LOCATION: (1)..(38)
<223> OTHER INFORMATION: all pyrimidines are 2'-fluoro; except at
      positions 10, 12, 16, 24 and 37, wherein cytidine is deoxy; and at
      positions 11, 23, and 25, which are deoxy thymidine

<400> SEQUENCE: 14
cgccgcgguc tcaggcgcug agtctgaguu uaccugcg                            38

<210> SEQ ID NO 15
<211> LENGTH: 38
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(38)
<223> OTHER INFORMATION: all purines are 2'-O-methyl; except at
      positions 5 and 17, wherein guanosine is 2'-OH, and position 32,
      wherein adenosine is 2'-OH
<220> FEATURE:
<221> NAME/KEY: misc_feature
<222> LOCATION: (1)..(38)
<223> OTHER INFORMATION: all pyrimidines are 2'-fluoro; except at
      positions 10, 12, 16, and 24, wherein cytidine is deoxy; at
      position 3, wherein cytosine is 2'-O-methyl; and at positions 11,
      23, and 25, which are deoxy thymidine

<400> SEQUENCE: 15
cgccgcgguc tcaggcgcug agtctgaguu uaccugcg                            38

<210> SEQ ID NO 16
<211> LENGTH: 38
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(38)
<223> OTHER INFORMATION: all purines are 2'-O-methyl; except at
      positions 5 and 17, wherein guanosine is 2'-OH, and position 32,
      wherein adenosine is 2'-OH
<220> FEATURE:
<221> NAME/KEY: misc_feature
<222> LOCATION: (1)..(38)
<223> OTHER INFORMATION: all pyrimidines are 2'-fluoro; except at
      positions 10, 12, 16 and 24, wherein cytidine is deoxy; at
      position 37, wherein cytosine is 2'-O-methyl; and at positions 11,
      23 and 25, which are deoxy thymidine

<400> SEQUENCE: 16
cgccgcgguc tcaggcgcug agtctgaguu uaccugcg                            38

<210> SEQ ID NO 17
<211> LENGTH: 38
<212> TYPE: DNA

```
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(38)
<223> OTHER INFORMATION: all purines are 2'-O-methyl; except at
      positions 5 and 17, wherein guanosine is 2'-OH, and position 32,
      wherein adenosine is 2'-OH
<220> FEATURE:
<221> NAME/KEY: misc_feature
<222> LOCATION: (1)..(38)
<223> OTHER INFORMATION: all pyrimidines are 2'-fluoro; except at
      positions 10, 12, 16 and 24, wherein cytidine is deoxy; at
      position 1, wherein cytosine is 2'-O-methyl; and at positions 11,
      23 and 25, which are deoxy thymidine

<400> SEQUENCE: 17
cgccgcgguc tcaggcgcug agtctgaguu uaccugcg                             38

<210> SEQ ID NO 18
<211> LENGTH: 38
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(38)
<223> OTHER INFORMATION: all purines are 2'-O-methyl; except at
      positions 5 and 17, wherein guanosine is 2'-OH, and position 32,
      wherein adenosine is 2'-OH
<220> FEATURE:
<221> NAME/KEY: misc_feature
<222> LOCATION: (1)..(38)
<223> OTHER INFORMATION: all pyrimidines are 2'-fluoro; except at
      positions 10, 12, 16 and 24, wherein cytidine is deoxy; at
      positions 1, 3 and 37, wherein cytosine is 2'-O-methyl; and at
      positions 11, 23 and 25, which are deoxy thymidine

<400> SEQUENCE: 18
cgccgcgguc tcaggcgcug agtctgaguu uaccugcg                             38

<210> SEQ ID NO 19
<211> LENGTH: 38
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(38)
<223> OTHER INFORMATION: all purines are 2'-O-methyl; except at
      positions 5 and 17, wherein guanosine is 2'-OH, and position 32,
      wherein adenosine is 2'-OH
<220> FEATURE:
<221> NAME/KEY: misc_feature
<222> LOCATION: (1)..(38)
<223> OTHER INFORMATION: all pyrimidines are 2'-fluoro; except a
      positions 4, 10, 12, 16 and 24, wherein cytidine is deoxy; and at
      positions 11, 23, and 25, which are deoxy thymidine

<400> SEQUENCE: 19
cgccgcgguc tcaggcgcug agtctgaguu uaccugcg                             38

<210> SEQ ID NO 20
<211> LENGTH: 38
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
```

```
<222> LOCATION: (1)..(38)
<223> OTHER INFORMATION: all purines are 2'-O-methyl; except at
      positions 5 and 17, wherein guanosine is 2'-OH, and position 32,
      wherein adenosine is 2'-OH
<220> FEATURE:
<221> NAME/KEY: misc_feature
<222> LOCATION: (1)..(38)
<223> OTHER INFORMATION: all pyrimidines are 2'-fluoro; except a
      positions 6, 10, 12, 16 and 24, wherein cytidine is deoxy; and at
      positions 11, 23 and 25, which are deoxy thymidine

<400> SEQUENCE: 20
cgccgcgguc tcaggcgcug agtctgaguu uaccugcg                            38

<210> SEQ ID NO 21
<211> LENGTH: 38
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(38)
<223> OTHER INFORMATION: all purines are 2'-O-methyl; except at
      positions 5 and 17, wherein guanosine is 2'-OH, and position 32,
      wherein adenosine is 2'-OH
<220> FEATURE:
<221> NAME/KEY: misc_feature
<222> LOCATION: (1)..(38)
<223> OTHER INFORMATION: all pyrimidines are 2'-fluoro;  except at
      positions 4, 6, 10, 12, 16 and 24, wherein cytidine is deoxy; and
      at positions 11, 23 and 25, which are deoxy thymidine

<400> SEQUENCE: 21
cgccgcgguc tcaggcgcug agtctgaguu uaccugcg                            38

<210> SEQ ID NO 22
<211> LENGTH: 38
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(38)
<223> OTHER INFORMATION: all purines are 2'-O-methyl; except at
      positions 5 and 17, wherein guanosine is 2'-OH, and position 32,
      wherein adenosine is 2'-OH
<220> FEATURE:
<221> NAME/KEY: misc_feature
<222> LOCATION: (1)..(38)
<223> OTHER INFORMATION: all pyrimidines are 2'-fluoro; except at
      positions 10, 12, 16, 18 and 24, wherein cytidine is deoxy; and at
      positions 11, 23 and 25, which are deoxy thymidine

<400> SEQUENCE: 22
cgccgcgguc tcaggcgcug agtctgaguu uaccugcg                            38

<210> SEQ ID NO 23
<211> LENGTH: 38
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(38)
<223> OTHER INFORMATION: all purines are 2'-O-methyl; except at
      positions 5 and 17, wherein guanosine is 2'-OH, and position 32,
      wherein adenosine is 2'-OH
<220> FEATURE:
<221> NAME/KEY: misc_feature
<222> LOCATION: (1)..(38)
```

```
<223> OTHER INFORMATION: all all pyrimidines are 2'-fluoro; except at
      positions 10, 12, 16 and 24, wherein cytidine is deoxy; and at
      positions 11, 19, 23 and 25, which are deoxy thymidine

<400> SEQUENCE: 23
cgccgcgguc tcaggcgctg agtctgaguu uaccugcg                              38

<210> SEQ ID NO 24
<211> LENGTH: 38
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(38)
<223> OTHER INFORMATION: all purines are 2'-O-methyl; except at
      positions 5 and 17, wherein guanosine is 2'-OH, and position 32,
      wherein adenosine is 2'-OH
<220> FEATURE:
<221> NAME/KEY: misc_feature
<222> LOCATION: (1)..(38)
<223> OTHER INFORMATION: all pyrimidines are 2'-fluoro; except at
      positions 10, 12, 16, 18 and 24, wherein cytidine is deoxy; and at
      positions 11, 19, 23 and 25, which are deoxy thymidine

<400> SEQUENCE: 24
cgccgcgguc tcaggcgctg agtctgaguu uaccugcg                              38

<210> SEQ ID NO 25
<211> LENGTH: 38
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(38)
<223> OTHER INFORMATION: all purines are 2'-O-methyl except at
      positions 5 and 17, wherein guanosine is 2'-OH, and position 32,
      wherein adenosine is 2'-OH
<220> FEATURE:
<221> NAME/KEY: misc_feature
<222> LOCATION: (1)..(38)
<223> OTHER INFORMATION: all pyrimidines are 2'-fluoro; except at
      positions 10, 12, 16 and 24, wherein cytidine is deoxy; and at
      positions 11, 23, 25 and 29, which are deoxy thymidine

<400> SEQUENCE: 25
cgccgcgguc tcaggcgcug agtctgagtu uaccugcg                              38

<210> SEQ ID NO 26
<211> LENGTH: 38
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(38)
<223> OTHER INFORMATION: all purines are 2'-O-methyl except at
      positions 5 and 17, wherein guanosine is 2'-OH, and position 32,
      wherein adenosine is 2'-OH
<220> FEATURE:
<221> NAME/KEY: misc_feature
<222> LOCATION: (1)..(38)
<223> OTHER INFORMATION: all pyrimidines are 2'-fluoro; except at
      positions 10, 12, 16 and 24, wherein cytidine is deoxy; and at
      positions 11, 23, 25 and 30, which are deoxy thymidine

<400> SEQUENCE: 26
cgccgcgguc tcaggcgcug agtctgagut uaccugcg                              38
```

<210> SEQ ID NO 27
<211> LENGTH: 38
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (1)..(38)
<223> OTHER INFORMATION: all purines are 2'-O-methyl except at
      positions 5 and 17, wherein guanosine is 2'-OH, and position 32,
      wherein adenosine is 2'-OH
<220> FEATURE:
<221> NAME/KEY: misc_feature
<222> LOCATION: (1)..(38)
<223> OTHER INFORMATION: all pyrimidines are 2'-fluoro; except at
      positions 10, 12, 16 and 24, wherein cytidine is deoxy; and at
      positions 11, 23, 25 and 31, which are deoxy thymidine

<400> SEQUENCE: 27
cgccgcgguc tcaggcgcug agtctgaguu taccugcg                              38

<210> SEQ ID NO 28
<211> LENGTH: 38
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(38)
<223> OTHER INFORMATION: all purines are 2'-O-methyl except at
      positions 5 and 17, wherein guanosine is 2'-OH, and position 32,
      wherein adenosine is 2'-OH
<220> FEATURE:
<221> NAME/KEY: misc_feature
<222> LOCATION: (1)..(38)
<223> OTHER INFORMATION: all pyrimidines are 2'-fluoro; except at
      positions 10, 12, 16 and 24, wherein cytidine is deoxy; and at
      positions 11, 23, 25, 29, 30 and 31, which are deoxy thymidine

<400> SEQUENCE: 28
cgccgcgguc tcaggcgcug agtctgagtt taccugcg                              38

<210> SEQ ID NO 29
<211> LENGTH: 38
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(38)
<223> OTHER INFORMATION: all purines are 2'-O-methyl except at
      positions 5 and 17, wherein guanosine is 2'-OH, and position 32,
      wherein adenosine is 2'-OH
<220> FEATURE:
<221> NAME/KEY: misc_feature
<222> LOCATION: (1)..(38)
<223> OTHER INFORMATION: all pyrimidines are 2'-flouro; except at
      positions 10, 12, 16 and 24, wherein cytidine is deoxy; and at
      positions 11, 23, 25 and 35, which are deoxy thymidine

<400> SEQUENCE: 29
cgccgcgguc tcaggcgcug agtctgaguu uacctgcg                              38

<210> SEQ ID NO 30
<211> LENGTH: 38
<212> TYPE: DNA
<213> ORGANISM: artificial sequence
<220> FEATURE:

```
<223> OTHER INFORMATION: synthetic aptamer
<220> FEATURE:
<221> NAME/KEY: misc_feature
<222> LOCATION: (1)..(38)
<223> OTHER INFORMATION: all purines are 2'-O-methyl except at
      positions 5 and 17, wherein guanosine is 2'-OH, and position 32,
      wherein adenosine is 2'-OH
<220> FEATURE:
<221> NAME/KEY: misc_feature
<222> LOCATION: (1)..(38)
<223> OTHER INFORMATION: all pyrimidines are 2'-fluoro; except at
      positions 10, 12, 16, 24, 33 and 34, wherein cytidine is deoxy; at
      position 9, wherein uridine is 2'-O-methyl; and at positions 11,
      23 and 25, which are deoxy thymidine

<400> SEQUENCE: 30
cgccgcgguc tcaggcgcug agtctgaguu uaccugcg                              38

<210> SEQ ID NO 31
<211> LENGTH: 38
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(38)
<223> OTHER INFORMATION: all purines are 2'-O-methyl except at
      positions 5 and 17, wherein guanosine is 2'-OH, and position 32,
      wherein adenosine is 2'-OH
<220> FEATURE:
<221> NAME/KEY: misc_feature
<222> LOCATION: (1)..(38)
<223> OTHER INFORMATION: all pyrimidines are 2'-fluoro; except at
      positions 10, 12, 16 and 24, wherein cytidine is deoxy; at
      position 4, wherein cytosine is 2'-O-methyl; and at positions 11,
      23, and 25, which are deoxy thymidine

<400> SEQUENCE: 31
cgccgcgguc tcaggcgcug agtctgaguu uaccugcg                              38

<210> SEQ ID NO 32
<211> LENGTH: 38
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(38)
<223> OTHER INFORMATION: all purines are 2'-O-methyl except at
      positions 5 and 17, wherein guanosine is 2'-OH, and position 32,
      wherein adenosine is 2'-OH
<220> FEATURE:
<221> NAME/KEY: misc_feature
<222> LOCATION: (1)..(38)
<223> OTHER INFORMATION: all pyrimidines are 2'-fluoro; except at
      positions 10, 12, 16 and 24, wherein cytidine is deoxy; at
      position 6, wherein cytosine is 2'-O-methyl; and at positions 11,
      23, and 25, which are deoxy thymidine

<400> SEQUENCE: 32
cgccgcgguc tcaggcgcug agtctgaguu uaccugcg                              38

<210> SEQ ID NO 33
<211> LENGTH: 38
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(38)
```

```
<223> OTHER INFORMATION: all purines are 2'-O-methyl except at
      positions 5 and 17, wherein guanosine is 2'-OH, and position 32,
      wherein adenosine is 2'-OH
<220> FEATURE:
<221> NAME/KEY: misc_feature
<222> LOCATION: (1)..(38)
<223> OTHER INFORMATION: all pyrimidines are 2'-fluoro; except at
      positions 10, 12, 16 and 24, wherein cytidine is deoxy; at
      position 4 and 6, wherein cytosine is 2'-O-methyl; and at
      positions 11, 23, and 25, which are deoxy thymidine

<400> SEQUENCE: 33
cgccgcgguc tcaggcgcug agtctgaguu uaccugcg                                38

<210> SEQ ID NO 34
<211> LENGTH: 38
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(38)
<223> OTHER INFORMATION: all purines are 2'-O-methyl except at
      positions 5 and 17, wherein guanosine is 2'-OH, and position 32,
      wherein adenosine is 2'-OH
<220> FEATURE:
<221> NAME/KEY: misc_feature
<222> LOCATION: (1)..(38)
<223> OTHER INFORMATION: all pyrimidines are 2'-fluoro; except at
      positions 10, 12, 16 and 24, wherein cytidine is deoxy; and at
      position 18, wherein cytosine is 2'-O-methyl

<400> SEQUENCE: 34
cgccgcgguc ucaggcgcug agucugaguu uaccugcg                                38

<210> SEQ ID NO 35
<211> LENGTH: 38
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(38)
<223> OTHER INFORMATION: all purines are 2'-O-methyl except at
      positions 5 and 17, wherein guanosine is 2'-OH, and position 32,
      wherein adenosine is 2'-OH
<220> FEATURE:
<221> NAME/KEY: misc_feature
<222> LOCATION: (1)..(38)
<223> OTHER INFORMATION: all pyrimidines are 2'-fluoro; except at
      positions 10, 12, 16 and 24, wherein cytidine is deoxy; and at
      position 19, wherein uridine is 2'-O-methyl

<400> SEQUENCE: 35
cgccgcgguc ucaggcgcug agucugaguu uaccugcg                                38

<210> SEQ ID NO 36
<211> LENGTH: 38
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(38)
<223> OTHER INFORMATION: all purines are 2'-O-methyl except at
      positions 5 and 17, wherein guanosine is 2'-OH, and position 32,
      wherein adenosine is 2'-OH
<220> FEATURE:
<221> NAME/KEY: misc_feature
<222> LOCATION: (1)..(38)
```

```
<223> OTHER INFORMATION: all pyrimidines are 2'-fluoro; except at
      positions 10, 12, 16 and 24, wherein cytidine is deoxy; at
      position 18, wherein cytosine is 2'-O-methyl; and at position 19,
      wherein uridine is 2'-O-methyl

<400> SEQUENCE: 36
cgccgcgguc ucaggcgcug agucugaguu uaccugcg                                 38

<210> SEQ ID NO 37
<211> LENGTH: 38
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(38)
<223> OTHER INFORMATION: all purines are 2'-O-methyl except at
      positions 5 and 17, wherein guanosine is 2'-OH, and position 32,
      wherein adenosine is 2'-OH
<220> FEATURE:
<221> NAME/KEY: misc_feature
<222> LOCATION: (1)..(38)
<223> OTHER INFORMATION: all pyrimidines are 2'-fluoro; except at
      positions 10, 12, 16 and 24, wherein cytidine is deoxy; at
      position 29, wherein uridine is 2'-O-methyl; and at positions 11,
      23 and 25, which are deoxy thymidine

<400> SEQUENCE: 37
cgccgcgguc tcaggcgcug agtctgaguu uaccugcg                                 38

<210> SEQ ID NO 38
<211> LENGTH: 38
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(38)
<223> OTHER INFORMATION: all purines are 2'-O-methyl except at
      positions 5 and 17, wherein guanosine is 2'-OH, and position 32,
      wherein adenosine is 2'-OH
<220> FEATURE:
<221> NAME/KEY: misc_feature
<222> LOCATION: (1)..(38)
<223> OTHER INFORMATION: all pyrimidines are 2'-fluoro; except at
      positions 10, 12, 16 and 24, wherein cytidine is deoxy; at
      position 30, wherein uridine is 2'-O-methyl; and at positions 11,
      23 and 25, which are deoxy thymidine

<400> SEQUENCE: 38
cgccgcgguc tcaggcgcug agtctgaguu uaccugcg                                 38

<210> SEQ ID NO 39
<211> LENGTH: 38
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(38)
<223> OTHER INFORMATION: all purines are 2'-O-methyl except at
      positions 5 and 17, wherein guanosine is 2'-OH, and position 32,
      wherein adenosine is 2'-OH
<220> FEATURE:
<221> NAME/KEY: misc_feature
<222> LOCATION: (1)..(38)
<223> OTHER INFORMATION: all pyrimidines are 2'-fluoro; except at
      positions 10, 12, 16 and 24, wherein cytidine is deoxy; at
      position 31, wherein uridine is 2'-O-methyl; and at positions 11,
      23 and 25, which are deoxy thymidine
```

<400> SEQUENCE: 39
cgccgcgguc tcaggcgcug agtctgaguu uaccugcg                    38

<210> SEQ ID NO 40
<211> LENGTH: 38
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(38)
<223> OTHER INFORMATION: all purines are 2'-O-methyl except at
      positions 5 and 17, wherein guanosine is 2'-OH, and position 32,
      wherein adenosine is 2'-OH
<220> FEATURE:
<221> NAME/KEY: misc_feature
<222> LOCATION: (1)..(38)
<223> OTHER INFORMATION: all pyrimidines are 2'-fluoro; except at
      positions 10, 12, 16 and 24, wherein cytidine is deoxy; at
      positions 29, 30 and 31, wherein uridine is 2'-O-methyl; and at
      positions 11, 23 and 25, which are deoxy thymidine

<400> SEQUENCE: 40
cgccgcgguc tcaggcgcug agtctgaguu uaccugcg                    38

<210> SEQ ID NO 41
<211> LENGTH: 38
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(38)
<223> OTHER INFORMATION: all purines are 2'-O-methyl except at
      positions 5 and 17, wherein guanosine is 2'-OH, and position 32,
      wherein adenosine is 2'-OH
<220> FEATURE:
<221> NAME/KEY: misc_feature
<222> LOCATION: (1)..(38)
<223> OTHER INFORMATION: all pyrimidines are 2'-fluoro; except at
      positions 10, 12, 16 and 24, wherein cytidine is deoxy; at
      position 35, wherein uridine is 2'-O-methyl; and at positions 11,
      23 and 25, which are deoxy thymidine

<400> SEQUENCE: 41
cgccgcgguc tcaggcgcug agtctgaguu uaccugcg                    38

<210> SEQ ID NO 42
<211> LENGTH: 38
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(38)
<223> OTHER INFORMATION: all purines are 2'-O-methyl except at position
      5, wherein guanosine is deoxy; at position 17, wherein guanosine
      is 2'-OH; and position 32, wherein adenosine is 2'-OH
<220> FEATURE:
<221> NAME/KEY: misc_feature
<222> LOCATION: (1)..(38)
<223> OTHER INFORMATION: all pyrimidines are 2'-fluoro; except at
      positions 10, 12, 16 and 24, wherein cytidine is deoxy; and at
      positions 11, 23 and 25, which are deoxy thymidine

<400> SEQUENCE: 42
cgccgcgguc tcaggcgcug agtctgaguu uaccugcg                    38

<210> SEQ ID NO 43
<211> LENGTH: 38
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(38)
<223> OTHER INFORMATION: all purines are 2'-O-methyl; except at
      position 5, wherein guanosine is 2'-OH; at position 17, wherein
      guanosine is deoxy; and position 32, wherein adenosine is 2'-OH
<220> FEATURE:
<221> NAME/KEY: misc_feature
<222> LOCATION: (1)..(38)
<223> OTHER INFORMATION: all pyrimidines are 2'-fluoro; except at
      positions 10, 12, 16 and 24, wherein cytidine is deoxy; and at
      positions 11, 23 and 25, which are deoxy thymidine

<400> SEQUENCE: 43
cgccgcgguc tcaggcgcug agtctgaguu uaccugcg                              38

<210> SEQ ID NO 44
<211> LENGTH: 38
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(38)
<223> OTHER INFORMATION: all purines are 2'-O-methyl; except at
      positions 5 and 17, wherein guanosine is 2'-OH; and position 32,
      wherein adenosine is deoxy
<220> FEATURE:
<221> NAME/KEY: misc_feature
<222> LOCATION: (1)..(38)
<223> OTHER INFORMATION: all pyrimidines are 2'-fluoro; except at
      positions 10, 12, 16 and 24, wherein cytidine is deoxy; and at
      positions 11, 23 and 25, which are deoxy thymidine

<400> SEQUENCE: 44
cgccgcgguc tcaggcgcug agtctgaguu uaccugcg                              38

<210> SEQ ID NO 45
<211> LENGTH: 40
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(40)
<223> OTHER INFORMATION: all purines are 2'-O-methyl; except at
      positions 6 and 18, wherein guanosine is 2'-OH; and position 33,
      wherein adenosine is 2'-OH
<220> FEATURE:
<221> NAME/KEY: misc_feature
<222> LOCATION: (1)..(40)
<223> OTHER INFORMATION: all pyrimidines are 2'-fluoro; except at
      positions 11, 13, 17 and 25, wherein cytidine is deoxy; at
      position 40, wherein cytosine is 2'-O-methyl; and at positions 12,
      24 and 26, which are deoxy thymidine

<400> SEQUENCE: 45
gcgucgcggu ctcaggcgcu gagtctgagu uuaccuacgc                            40

<210> SEQ ID NO 46
<211> LENGTH: 38
<212> TYPE: DNA
<213> ORGANISM: artificial sequence
<220> FEATURE:

<223> OTHER INFORMATION: synthetic aptamer
<220> FEATURE:
<221> NAME/KEY: misc_feature
<222> LOCATION: (1)..(38)
<223> OTHER INFORMATION: all purines are 2'-O-methyl; except at
      positions 5 and 17, wherein guanosine is 2'-OH; and position 32,
      wherein adenosine is deoxy
<220> FEATURE:
<221> NAME/KEY: misc_feature
<222> LOCATION: (1)..(38)
<223> OTHER INFORMATION: all pyrimidines are 2'-fluoro; except at
      positions 10, 12, 16 and 24, wherein cytidine is deoxy; at
      positions 36, 37 and 38 wherein cytosine is 2'-O-methyl; and at
      positions 11, 23 and 25, which are deoxy thymidine

<400> SEQUENCE: 46
gggcgcgguc tcaggcgcug agtctgaguu uaccuccc                              38

<210> SEQ ID NO 47
<211> LENGTH: 40
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(40)
<223> OTHER INFORMATION: all purines are 2'-O-methyl; except at
      positions 6 and 18, wherein guanosine is 2'-OH; and position 33,
      wherein adenosine is 2'-OH
<220> FEATURE:
<221> NAME/KEY: misc_feature
<222> LOCATION: (1)..(40)
<223> OTHER INFORMATION: all pyrimidines are 2'-fluoro; except at
      positions 11, 13, 17 and 25, wherein cytidine is deoxy; at
      position 40, wherein cytosine is 2'-O-methyl; and at positions 12,
      24 and 26, which are deoxy thymidine

<400> SEQUENCE: 47
gcgccgcggu ctcaggcgcu gagtctgagu uuaccugcgc                            40

<210> SEQ ID NO 48
<211> LENGTH: 45
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(44)
<223> OTHER INFORMATION: all purines are 2'-O-methyl; except at
      positions 8 and 20, wherein guanosine is 2'-OH; and position 35
      wherein adenosine is 2'-OH
<220> FEATURE:
<221> NAME/KEY: misc_feature
<222> LOCATION: (1)..(44)
<223> OTHER INFORMATION: all pyrimidines are 2'-fluoro
<220> FEATURE:
<221> NAME/KEY: misc_feature
<222> LOCATION: (45)..(45)
<223> OTHER INFORMATION: thymidine at position 45 is a 3' inverted deoxy
      thymidine (3'-3'linked)

<400> SEQUENCE: 48
ggacgccgcg gucucaggcg cugagucuga guuuaccugc gucut                      45

<210> SEQ ID NO 49
<211> LENGTH: 42
<212> TYPE: DNA
<213> ORGANISM: artificial sequence
<220> FEATURE:
<223> OTHER INFORMATION: synthetic aptamer
<220> FEATURE:

```
<221> NAME/KEY: misc_feature
<222> LOCATION: (1)..(42)
<223> OTHER INFORMATION: all purines are 2'-O-methyl; except at
      positions 7 and 19, wherein guanosine is 2'-OH; and at position
      34, wherein adenosine is 2'-OH
<220> FEATURE:
<221> NAME/KEY: misc_feature
<222> LOCATION: (1)..(42)
<223> OTHER INFORMATION: all cytosines are 2'-fluoro; except at
      positions 12, 14, 18, 26, 35 and 36, which are deoxy cytidine; and
      at positions 20, 41 and 42, wherein cytosine is 2'-O-methyl
<220> FEATURE:
<221> NAME/KEY: misc_feature
<222> LOCATION: (1)..(42)
<223> OTHER INFORMATION: all uridines are 2'-fluoro; except at position
      21, wherein uridine is 2'-O-methyl; and at positions 13, 25, 27,
      31 and 37, which are deoxy thymidine

<400> SEQUENCE: 49
ggcgccgcgg uctcaggcgc ugagtctgag tuuacctgcg cc                          42

<210> SEQ ID NO 50
<211> LENGTH: 42
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(42)
<223> OTHER INFORMATION: all purines are 2'-O-methyl; except at
      positions 7 and 19, wherein guanosine is 2'-OH; and at
      position 34, wherein adenosine is 2'-OH
<220> FEATURE:
<221> NAME/KEY: misc_feature
<222> LOCATION: (1)..(42)
<223> OTHER INFORMATION: all cytosines are 2'-fluoro; except at
      positions 12, 14, 18, 26, 35, 36 and 39, which are deoxy cytidine;
      and at positions 3, 20, 41 and 42, wherein cytosine is 2'-O-methyl
<220> FEATURE:
<221> NAME/KEY: misc_feature
<222> LOCATION: (1)..(42)
<223> OTHER INFORMATION: uridine at position 11 is 2'-fluoro;
      uridine at position 21 is 2'-O-methyl; positions 13, 25, 27, 31,
      32, 33 and 37 are deoxy thymidine

<400> SEQUENCE: 50
ggcgccgcgg uctcaggcgc ugagtctgag tttacctgcg cc                          42

<210> SEQ ID NO 51
<211> LENGTH: 42
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(42)
<223> OTHER INFORMATION: all purines are 2'-O-methyl; except at
      positions 7 and 19, wherein guanosine is 2'-OH
<220> FEATURE:
<221> NAME/KEY: misc_feature
<222> LOCATION: (1)..(42)
<223> OTHER INFORMATION: cytosine at positions 5, 6, 8, 12, 14, 18, 26,
      35, 36 and 39 are deoxy cytidine; and cystosine at positions 3,
      20, 41 and 42 are 2'-O-methyl
<220> FEATURE:
<221> NAME/KEY: misc_feature
<222> LOCATION: (1)..(42)
<223> OTHER INFORMATION: uridine at position 21 is 2'-O-methyl;
      positions 11, 13, 25, 27, 31, 32, 33 and 37 are deoxy thymidine

<400> SEQUENCE: 51
ggcgccgcgg tctcaggcgc ugagtctgag tttacctgcg cc                          42
```

<210> SEQ ID NO 52
<211> LENGTH: 42
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(42)
<223> OTHER INFORMATION: all purines are 2'-O-methyl; except at
      positions 7 and 19, wherein guanosine is 2'-OH
<220> FEATURE:
<221> NAME/KEY: misc_feature
<222> LOCATION: (1)..(42)
<223> OTHER INFORMATION: uridine at positions 13, 21, 25 and 27 are
      2'-O-methyl; positions 11, 31, 32, 33 and 37 are deoxy thymidine
<220> FEATURE:
<221> NAME/KEY: misc_feature
<222> LOCATION: (1)..(42)
<223> OTHER INFORMATION: cytosine at positions 5, 6, 8, 12, 18, 35, 36
      and 39 are deoxy cytidine; and cytosine at positions 3, 14, 20,
      26, 41 and 42 are 2'-O-methyl

<400> SEQUENCE: 52
ggcgccgcgg tcucaggcgc ugagucugag tttacctgcg cc          42

<210> SEQ ID NO 53
<211> LENGTH: 40
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(1)
<223> OTHER INFORMATION: adenosine at position 1 has biotin conjugated
      to the 5' end
<220> FEATURE:
<221> NAME/KEY: misc_feature
<222> LOCATION: (1)..(40)
<223> OTHER INFORMATION: all purines are 2'-O-methyl; except at
      positions 3, 8 and 20, wherein guanosine is 2'-OH; and at
      position 2, wherein adenosine is 2'-OH
<220> FEATURE:
<221> NAME/KEY: misc_feature
<222> LOCATION: (1)..(40)
<223> OTHER INFORMATION: all pyrimidines are 2'-fluoro

<400> SEQUENCE: 53
agcgccgcgg ucucaggcgc ugagucugag uuuaccugcg          40

<210> SEQ ID NO 54
<211> LENGTH: 42
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(42)
<223> OTHER INFORMATION: all purines are 2'-O-methyl; except at
      positions 7 and 19, wherein guanosine is 2'-OH; and at position
      34, wherein adenosine is 2'-OH
<220> FEATURE:
<221> NAME/KEY: misc_feature
<222> LOCATION: (1)..(42)
<223> OTHER INFORMATION: all cytosines are 2'-fluoro; except at
      positions 12, 14, 18 and 26, which are deoxy cytidine; and at
      positions 41 and 42, wherein cytosine is 2'-O-methyl
<220> FEATURE:
<221> NAME/KEY: misc_feature
<222> LOCATION: (1)..(42)
<223> OTHER INFORMATION: all uridines are 2'-fluoro; positions 13, 25, and 27 are deoxy thymidine

<400> SEQUENCE: 54
ggcgccgcgg uctcaggcgc ugagtctgag uuuaccugcg cc          42

<210> SEQ ID NO 55
<211> LENGTH: 42
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(42)
<223> OTHER INFORMATION: all purines are 2'-O-methyl; except at
      positions 7 and 19, wherein guanosine is 2'-OH; and at position
      34, wherein adenosine is 2'-OH
<220> FEATURE:
<221> NAME/KEY: misc_feature
<222> LOCATION: (1)..(42)
<223> OTHER INFORMATION: all cytosines are 2'-fluoro; except at
      positions 12, 14, 18, 26, 41 and 42, wherein cytosine is
      2'-O-methyl
<220> FEATURE:
<221> NAME/KEY: misc_feature
<222> LOCATION: (1)..(42)
<223> OTHER INFORMATION: all uridines are 2'-fluoro; except at positions
      13, 25, and 27, wherein uridine is 2'-O-methyl

<400> SEQUENCE: 55
ggcgccgcgg ucucaggcgc ugagucugag uuuaccugcg cc          42

<210> SEQ ID NO 56
<211> LENGTH: 39
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(38)
<223> OTHER INFORMATION: all pyrimidines are 2'-fluoro
<220> FEATURE:
<221> NAME/KEY: misc_feature
<222> LOCATION: (1)..(38)
<223> OTHER INFORMATION: all purines are 2'-O-methyl; except at
      positions 5 and 17, wherein guanosine is 2'-OH
<220> FEATURE:
<221> NAME/KEY: misc_feature
<222> LOCATION: (39)..(39)
<223> OTHER INFORMATION: thymidine at position 39 is a 3' inverted deoxy
      thymidine (3'-3' linked)

<400> SEQUENCE: 56
cgccgcgguc ucaggcgcug agucugaguu uaccugcgt             39

<210> SEQ ID NO 57
<211> LENGTH: 39
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(38)
<223> OTHER INFORMATION: all pyrimidines are 2'-fluoro; except at
      position 18, wherein cytosine is 2'-O-methyl; and at position 19
      wherein uridine is 2'-O-methyl
<220> FEATURE:
<221> NAME/KEY: misc_feature
<222> LOCATION: (1)..(38)
<223> OTHER INFORMATION: all purines are 2'-O-methyl; except at
      positions 5 and 17, wherein guanosine is 2'-OH; and at position

```
              32, wherein adenosine is 2'-OH
<220> FEATURE:
<221> NAME/KEY: misc_feature
<222> LOCATION: (39)..(39)
<223> OTHER INFORMATION: thymidine at position 39 is a 3' inverted deoxy
      thymidine (3'-3' linked)

<400> SEQUENCE: 57
cgccgcgguc ucaggcgcug agucugaguu uaccugcgt                              39

<210> SEQ ID NO 58
<211> LENGTH: 39
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(38)
<223> OTHER INFORMATION: all pyrimidines are 2'-fluoro; except at
      position 29, which is deoxy thymidine
<220> FEATURE:
<221> NAME/KEY: misc_feature
<222> LOCATION: (1)..(38)
<223> OTHER INFORMATION: all purines are 2'-O-methyl; except at
      positions 5 and 17, wherein guanosine is 2'-OH; and at position
      32, wherein adenosine is 2'-OH
<220> FEATURE:
<221> NAME/KEY: misc_feature
<222> LOCATION: (39)..(39)
<223> OTHER INFORMATION: thymidine at position 39 is a 3' inverted deoxy
      thymidine (3'-3' linked)

<400> SEQUENCE: 58
cgccgcgguc ucaggcgcug agucugagtu uaccugcgt                              39

<210> SEQ ID NO 59
<211> LENGTH: 39
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(38)
<223> OTHER INFORMATION: all purines are 2'-O-methyl; except at
      positions 5 and 17, wherein guanosine is 2'-OH
<220> FEATURE:
<221> NAME/KEY: misc_feature
<222> LOCATION: (1)..(38)
<223> OTHER INFORMATION: all pyrimidines are 2'-fluoro; except at
      position 18, wherein cytosine is 2'-O-methyl; and position 19,
      wherein uridine is 2'-O-methyl
<220> FEATURE:
<221> NAME/KEY: misc_feature
<222> LOCATION: (39)..(39)
<223> OTHER INFORMATION: thymidine at position 39 is a 3' inverted deoxy
      thymidine (3'-3' linked)

<400> SEQUENCE: 59
cgccgcgguc ucaggcgcug agucugaguu uaccugcgt                              39

<210> SEQ ID NO 60
<211> LENGTH: 39
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(38)
<223> OTHER INFORMATION: all purines are 2'-O-methyl; except at
      positions 5 and 17, wherein guanosine is 2'-OH
```

```
<220> FEATURE:
<221> NAME/KEY: misc_feature
<222> LOCATION: (1)..(38)
<223> OTHER INFORMATION: all pyrimidines are 2'-fluoro; except at
      position 18, wherein cytosine is 2'-O-methyl; at position 19,
      wherein uridine is 2'-O-methyl; and at position 29, which is
      deoxy thymidine
<220> FEATURE:
<221> NAME/KEY: misc_feature
<222> LOCATION: (39)..(39)
<223> OTHER INFORMATION: thymidine at position 39 is a 3' inverted deoxy
      thymidine (3'-3' linked)

<400> SEQUENCE: 60
cgccgcgguc ucaggcgcug agucugagtu uaccugcgt                             39

<210> SEQ ID NO 61
<211> LENGTH: 39
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(1)
<223> OTHER INFORMATION: cytosine at position 1 is modified by a 20 kDa
      PEG attached to the nucleotide via an amine linker
<220> FEATURE:
<221> NAME/KEY: misc_feature
<222> LOCATION: (1)..(38)
<223> OTHER INFORMATION: all pyrimidines are 2'-fluoro
<220> FEATURE:
<221> NAME/KEY: misc_feature
<222> LOCATION: (1)..(38)
<223> OTHER INFORMATION: all purines are 2'-O-methyl; except at
      positions 5 and 17, wherein guanosine is 2'-OH, and at position
      32, wherein adenosine is 2'-OH
<220> FEATURE:
<221> NAME/KEY: misc_feature
<222> LOCATION: (39)..(39)
<223> OTHER INFORMATION: thymidine at position 39 is a 3' inverted deoxy
      thymidine (3'-3' linked)

<400> SEQUENCE: 61
cgccgcgguc ucaggcgcug agucugaguu uaccugcgt                             39

<210> SEQ ID NO 62
<211> LENGTH: 39
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(1)
<223> OTHER INFORMATION: cytosine at position 1 is modified bya 30 kDa
      PEG attached to the nucleotide via an amine linker
<220> FEATURE:
<221> NAME/KEY: misc_feature
<222> LOCATION: (1)..(38)
<223> OTHER INFORMATION: all pyrimidines are 2'-fluoro
<220> FEATURE:
<221> NAME/KEY: misc_feature
<222> LOCATION: (1)..(38)
<223> OTHER INFORMATION: all purines are 2'-O-methyl; except at
      positions 5 and 17, wherein guanosine is 2'-OH, and at position
      32, wherein adenosine is 2'-OH
<220> FEATURE:
<221> NAME/KEY: misc_feature
<222> LOCATION: (39)..(39)
<223> OTHER INFORMATION: thymidine at position 39 is a 3' inverted deoxy
      thymidine (3'-3' linked)

<400> SEQUENCE: 62
```

-continued cgccgcgguc ucaggcgcug agucugaguu uaccugcgt          39

<210> SEQ ID NO 63
<211> LENGTH: 39
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(1)
<223> OTHER INFORMATION: cytosine at position 1 is modified by a 5'
      amine linker
<220> FEATURE:
<221> NAME/KEY: misc_feature
<222> LOCATION: (1)..(38)
<223> OTHER INFORMATION: all pyrimidines are 2'-fluoro
<220> FEATURE:
<221> NAME/KEY: misc_feature
<222> LOCATION: (1)..(38)
<223> OTHER INFORMATION: all purines are 2'-O-methyl; except at
      positions 5 and 17, wherein guanosine is 2'-OH, and at position
      32, wherein adenosine is 2'-OH
<220> FEATURE:
<221> NAME/KEY: misc_feature
<222> LOCATION: (39)..(39)
<223> OTHER INFORMATION: thymidine at position 39 is a 3' inverted deoxy
      thymidine (3'-3' linked)

<400> SEQUENCE: 63
cgccgcgguc ucaggcgcug agucugaguu uaccugcgt          39

<210> SEQ ID NO 64
<211> LENGTH: 39
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(1)
<223> OTHER INFORMATION: cytosine at position 1 is modified by a 10 kDa
      PEG attached to the nucleotide via an amine linker
<220> FEATURE:
<221> NAME/KEY: misc_feature
<222> LOCATION: (1)..(38)
<223> OTHER INFORMATION: all pyrimidines are 2'-fluoro
<220> FEATURE:
<221> NAME/KEY: misc_feature
<222> LOCATION: (1)..(38)
<223> OTHER INFORMATION: all purines are 2'-O-methyl; except at
      positions 5 and 17, wherein guanosine is 2'-OH, and at position
      32, wherein adenosine is 2'-OH
<220> FEATURE:
<221> NAME/KEY: misc_feature
<222> LOCATION: (39)..(39)
<223> OTHER INFORMATION: thymidine at position 39 is a 3' inverted deoxy
      thymidine (3'-3' linked)

<400> SEQUENCE: 64
cgccgcgguc ucaggcgcug agucugaguu uaccugcgt          39

<210> SEQ ID NO 65
<211> LENGTH: 39
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(1)
<223> OTHER INFORMATION: cytosine at position 1 is modified by a linear
      40 kDa PEG attached to the nucleotide via an amine linker
<220> FEATURE:

```
<221> NAME/KEY: misc_feature
<222> LOCATION: (1)..(38)
<223> OTHER INFORMATION: all pyrimidines are 2'-fluoro
<220> FEATURE:
<221> NAME/KEY: misc_feature
<222> LOCATION: (1)..(38)
<223> OTHER INFORMATION: all purines are 2'-O-methyl; except at
      positions 5 and 17, wherein guanosine is 2'-OH, and at position
      32, wherein adenosine is 2'-OH
<220> FEATURE:
<221> NAME/KEY: misc_feature
<222> LOCATION: (39)..(39)
<223> OTHER INFORMATION: thymidine at position 39 is a 3' inverted deoxy
      thymidine (3'-3' linked)

<400> SEQUENCE: 65
cgccgcgguc ucaggcgcug agucugaguu uaccugcgt                              39

<210> SEQ ID NO 66
<211> LENGTH: 38
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(1)
<223> OTHER INFORMATION: cytosine at position 1 is modified by a 20 kDa
      PEG attached to the nucleotide via an amine linker
<220> FEATURE:
<221> NAME/KEY: misc_feature
<222> LOCATION: (1)..(38)
<223> OTHER INFORMATION: all pyrimidines are 2'-fluoro
<220> FEATURE:
<221> NAME/KEY: misc_feature
<222> LOCATION: (1)..(38)
<223> OTHER INFORMATION: all purines are 2'-O-methyl; except at
      positions 5 and 17, wherein guanosine is 2'-OH, and at position
      32, wherein adenosine is 2'-OH
<220> FEATURE:
<221> NAME/KEY: misc_feature
<222> LOCATION: (38)..(38)
<223> OTHER INFORMATION: guanosine at position 38 is modified by a 20
      kDa PEG attached to the nucleotide via an amine linker

<400> SEQUENCE: 66
cgccgcgguc ucaggcgcug agucugaguu uaccugcg                               38

<210> SEQ ID NO 67
<211> LENGTH: 39
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(1)
<223> OTHER INFORMATION: cytosine at position 1 is modified by a 40 kDa
      branched (2,3-bis(mPEG-[20 kDa])-propyl-1-carbamoyl) PEG attached
      to the nucleotide via an amine linker
<220> FEATURE:
<221> NAME/KEY: misc_feature
<222> LOCATION: (1)..(38)
<223> OTHER INFORMATION: all pyrimidines are 2'-fluoro
<220> FEATURE:
<221> NAME/KEY: misc_feature
<222> LOCATION: (1)..(38)
<223> OTHER INFORMATION: all purines are 2'-O-methyl; except at
      positions 5 and 17, wherein guanosine is 2'-OH, and at position
      32, wherein adenosine is 2'-OH
<220> FEATURE:
<221> NAME/KEY: misc_feature
<222> LOCATION: (39)..(39)
<223> OTHER INFORMATION: thymidine at position 39 is a 3' inverted deoxy
      thymidine (3'-3' linked)
```

<400> SEQUENCE: 67
cgccgcgguc ucaggcgcug agucugaguu uaccugcgt          39

<210> SEQ ID NO 68
<211> LENGTH: 46
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(46)
<223> OTHER INFORMATION: all pyrimidines are 2'-fluoro

<400> SEQUENCE: 68
ggcgauuacu gggacggacu cgcgauguga gcccagacga cucgcc          46

<210> SEQ ID NO 69
<211> LENGTH: 40
<212> TYPE: RNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(40)
<223> OTHER INFORMATION: all pyrimidines are 2'-fluoro

<400> SEQUENCE: 69
ggcuucugaa gauuauuucg cgaugugaac uccagacccc          40

<210> SEQ ID NO 70
<211> LENGTH: 92
<212> TYPE: DNA
<213> ORGANISM: artificial sequence
<220> FEATURE:
<223> OTHER INFORMATION: synthetic template
<220> FEATURE:
<221> NAME/KEY: misc_feature
<222> LOCATION: (40)..(69)
<223> OTHER INFORMATION: n may be any nucleotide (a, c, g, or t)

<400> SEQUENCE: 70
taatacgact cactataggg agaggagaga acgttctacn nnnnnnnnn nnnnnnnnn          60 nnnnnnnnng gtcgatcgat cgatcatcga tg          92

<210> SEQ ID NO 71
<211> LENGTH: 39
<212> TYPE: DNA
<213> ORGANISM: artificial sequence
<220> FEATURE:
<223> OTHER INFORMATION: synthetic primer

<400> SEQUENCE: 71
taatacgact cactataggg agaggagaga acgttctac          39

<210> SEQ ID NO 72
<211> LENGTH: 23
<212> TYPE: DNA
<213> ORGANISM: artificial sequence
<220> FEATURE:
<223> OTHER INFORMATION: synthetic primer

<400> SEQUENCE: 72
catcgatgat cgatcgatcg acc          23

```
<210> SEQ ID NO 73
<211> LENGTH: 22
<212> TYPE: RNA
<213> ORGANISM: artificial sequence
<220> FEATURE:
<223> OTHER INFORMATION: synthetic fixed region

<400> SEQUENCE: 73
gggagaggag agaacguucu ac                                              22

<210> SEQ ID NO 74
<211> LENGTH: 23
<212> TYPE: RNA
<213> ORGANISM: artificial sequence
<220> FEATURE:
<223> OTHER INFORMATION: synthetic fixed region

<400> SEQUENCE: 74
ggucgaucga ucgaucaucg aug                                             23

<210> SEQ ID NO 75
<211> LENGTH: 75
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(75)
<223> OTHER INFORMATION: wherein all purines are deoxy, and all
      pyrimidines are 2'-O-methyl

<400> SEQUENCE: 75
gggagaggag agaacguucu accuuggutu ggcacaggca uacauacgca ggggucgauc    60
gaucgaucau cgaug                                                      75

<210> SEQ ID NO 76
<211> LENGTH: 32
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(32)
<223> OTHER INFORMATION: wherein all purines are deoxy, and all
      pyrimidines are 2'-O-methyl

<400> SEQUENCE: 76
ccuugguuug gcacaggcau acauacgcag gg                                   32

<210> SEQ ID NO 77
<211> LENGTH: 32
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(32)
<223> OTHER INFORMATION: wherein all purines are deoxy, and all
      pyrimidines are 2'-O-methyl

<400> SEQUENCE: 77
ccuugguuug gcacaggcau acaaacgcag gg                                   32

<210> SEQ ID NO 78
```

```
<211> LENGTH: 25
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(25)
<223> OTHER INFORMATION: wherein all purines are deoxy, and all
      pyrimidines are 2'-O-methyl

<400> SEQUENCE: 78
ggguuuggca caggcauaca uaccc                                              25

<210> SEQ ID NO 79
<211> LENGTH: 25
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(25)
<223> OTHER INFORMATION: wherein all purines are deoxy, and all
      pyrimidines are 2'-O-methyl

<400> SEQUENCE: 79
ggguuuggca caggcauaca aaccc                                              25

<210> SEQ ID NO 80
<211> LENGTH: 32
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(32)
<223> OTHER INFORMATION: wherein all purines are deoxy, and all
      pyrimidines are 2'-O-methyl

<400> SEQUENCE: 80
ggcggcacag gcauacauac gcagggucg cc                                       32

<210> SEQ ID NO 81
<211> LENGTH: 47
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(47)
<223> OTHER INFORMATION: wherein all purines are deoxy, and all
      pyrimidines are 2'-O-methyl

<400> SEQUENCE: 81
cguucuaccu ugguuuggca caggcauaca uacgcagggg ucgaucg                      47

<210> SEQ ID NO 82
<211> LENGTH: 88
<212> TYPE: DNA
<213> ORGANISM: artificial sequence
<220> FEATURE:
<223> OTHER INFORMATION: synthetic template
<220> FEATURE:
<221> NAME/KEY: misc_feature
<222> LOCATION: (40)..(69)
<223> OTHER INFORMATION: n may be any nucleotide (a, t, c, or g)

<400> SEQUENCE: 82
```

```
taatacgact cactataggg agaggagaga acgttctacn nnnnnnnnnn nnnnnnnnnn    60
nnnnnnnnng ttacgactag catcgatg                                      88

<210> SEQ ID NO 83
<211> LENGTH: 39
<212> TYPE: DNA
<213> ORGANISM: artificial sequence
<220> FEATURE:
<223> OTHER INFORMATION: synthetic template

<400> SEQUENCE: 83
cttggtttgg cacaggcata catacgcagg ggtcgatcg                          39

<210> SEQ ID NO 84
<211> LENGTH: 39
<212> TYPE: DNA
<213> ORGANISM: artificial sequence
<220> FEATURE:
<223> OTHER INFORMATION: synthetic primer

<400> SEQUENCE: 84
taatacgact cactataggg agaggagaga acgttctac                          39

<210> SEQ ID NO 85
<211> LENGTH: 19
<212> TYPE: DNA
<213> ORGANISM: artificial sequence
<220> FEATURE:
<223> OTHER INFORMATION: synthetic primer

<400> SEQUENCE: 85
catcgatgct agtcgtaac                                                19

<210> SEQ ID NO 86
<211> LENGTH: 22
<212> TYPE: RNA
<213> ORGANISM: artificial sequence
<220> FEATURE:
<223> OTHER INFORMATION: synthetic fixed region

<400> SEQUENCE: 86
gggagaggag agaacguucu ac                                            22

<210> SEQ ID NO 87
<211> LENGTH: 19
<212> TYPE: RNA
<213> ORGANISM: artificial sequence
<220> FEATURE:
<223> OTHER INFORMATION: synthetic fixed region

<400> SEQUENCE: 87
guuacgacua gcaucgaug                                                19

<210> SEQ ID NO 88
<211> LENGTH: 80
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(80)
<223> OTHER INFORMATION: wherein all purines are deoxy, and all
      pyrimidines are 2'-O-methyl

<400> SEQUENCE: 88
```

```
gggagaggag agaacguucu accuugguuu ggcacaggca uacauacgca ggggucgauc        60
gguuacgacu agcaucgaug                                                   80

<210> SEQ ID NO 89
<211> LENGTH: 80
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(80)
<223> OTHER INFORMATION: wherein all purines are deoxy, and all
      pyrimidines are 2'-O-methyl

<400> SEQUENCE: 89
gggagaggag agaacguucu accuugguuu ggcacaggca uacauacgca ggugucgauc        60
uguuacgacu agcaucgaug                                                   80

<210> SEQ ID NO 90
<211> LENGTH: 80
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(80)
<223> OTHER INFORMATION: wherein all purines are deoxy, and all
      pyrimidines are 2'-O-methyl

<400> SEQUENCE: 90
gggagaggag agaacguucu accuugguuu ggcacaggca uaaauacgca gggcucgauc        60
gguuacgacu agcaucgaug                                                   80

<210> SEQ ID NO 91
<211> LENGTH: 80
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(80)
<223> OTHER INFORMATION: wherein all purines are deoxy, and all
      pyrimidines are 2'-O-methyl

<400> SEQUENCE: 91
gggagaggag agaacguucu accuugguuu ggcccaggca uauauacgca gggauugauc        60
cguuacgacu agcaucgaug                                                   80

<210> SEQ ID NO 92
<211> LENGTH: 78
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(78)
<223> OTHER INFORMATION: wherein all purines are deoxy, and all
      pyrimidines are 2'-O-methyl

<400> SEQUENCE: 92
gggagaggag agaacguucu accuugguuu ggcgcaggca uacauacgca ggucgaucgg        60
```

-continued uuacgacuag caucgaug				78

<210> SEQ ID NO 93
<211> LENGTH: 80
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(80)
<223> OTHER INFORMATION: wherein all purines are deoxy, and all
      pyrimidines are 2'-O-methyl

<400> SEQUENCE: 93
gggagaggag agaacguucu accuuguugu ggcacagcca acccuacgca cggaucgccc		60 gguuacgacu agcaucgaug				80

<210> SEQ ID NO 94
<211> LENGTH: 69
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(69)
<223> OTHER INFORMATION: wherein all purines are deoxy, and all
      pyrimidines are 2'-O-methyl

<400> SEQUENCE: 94
gggagaggag agaacguucu accuugguuu ggcacaggca uacauacgca ggucgaucgg		60 uuacgacua				69

<210> SEQ ID NO 95
<211> LENGTH: 79
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(79)
<223> OTHER INFORMATION: wherein all purines are deoxy, and all
      pyrimidines are 2'-O-methyl

<400> SEQUENCE: 95
gggagaggag agaacguucu accuuagguu cgcacuguca uacauacaca cgggcaaucg		60 guuacgacua gcaucgaug				79

<210> SEQ ID NO 96
<211> LENGTH: 75
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(75)
<223> OTHER INFORMATION: wherein all purines are deoxy, and all
      pyrimidines are 2'-O-methyl
<220> FEATURE:
<221> NAME/KEY: misc_feature
<222> LOCATION: (34)..(34)
<223> OTHER INFORMATION: n may be any nucleotide (a, t, u, c, or g)
<220> FEATURE:
<221> NAME/KEY: misc_feature
<222> LOCATION: (43)..(43)
<223> OTHER INFORMATION: n may be any nucleotide (a, t, u, c, or g)

```
<400> SEQUENCE: 96
gggagaggag agaacguucu accuugguuu ggcncaggca uanauacgca cgggucgauc      60
gguuacgacu agcau                                                      75

<210> SEQ ID NO 97
<211> LENGTH: 80
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(80)
<223> OTHER INFORMATION: wherein all purines are deoxy, and all
      pyrimidines are 2'-O-methyl

<400> SEQUENCE: 97
gggagaggag agaacguucu accuucucu gccacaagca uaccuucgcg ggguucuauu       60
gguuacgacu agcaucgaug                                                 80

<210> SEQ ID NO 98
<211> LENGTH: 79
<212> TYPE: DNA
<213> ORGANISM: artificial sequence
<220> FEATURE:
<223> OTHER INFORMATION: synthetic aptamer
<220> FEATURE:
<221> NAME/KEY: misc_feature
<222> LOCATION: (1)..(79)
<223> OTHER INFORMATION: wherein all purines are deoxy, and all
      pyrimidines are 2'-O-methyl

<400> SEQUENCE: 98
gggagaggag agaacguucu accuugguuu ggcacaggca uauauacgca gggucgaucc      60
guuacgacua gcaucgaug                                                  79

<210> SEQ ID NO 99
<211> LENGTH: 93
<212> TYPE: DNA
<213> ORGANISM: artificial sequence
<220> FEATURE:
<223> OTHER INFORMATION: synthetic template
<220> FEATURE:
<221> NAME/KEY: misc_feature
<222> LOCATION: (25)..(54)
<223> OTHER INFORMATION: n may be any nucleotide (a, t, c, or g)

<400> SEQUENCE: 99
catcgatgct agtcgtaacg atccnnnnnn nnnnnnnnnn nnnnnnnnnn nnncgagaa       60 cgttctctcc tctccctata gtgagtcgta tta                                  93

<210> SEQ ID NO 100
<211> LENGTH: 92
<212> TYPE: DNA
<213> ORGANISM: artificial
<220> FEATURE:
<223> OTHER INFORMATION: synthetic template
<220> FEATURE:
<221> NAME/KEY: misc_feature
<222> LOCATION: (24)..(53)
<223> OTHER INFORMATION: n may be any nucleotide (a, t, c, or g)

<400> SEQUENCE: 100
catgcatcgc gactgactag ccgnnnnnnn nnnnnnnnnn nnnnnnnnnn nnngtagaac      60
```

```
gttctctcct ctccctatag tgagtcgtat ta                                    92
```

<210> SEQ ID NO 101
<211> LENGTH: 92
<212> TYPE: DNA
<213> ORGANISM: artificial
<220> FEATURE:
<223> OTHER INFORMATION: synthetic template
<220> FEATURE:
<221> NAME/KEY: misc_feature
<222> LOCATION: (24)..(53)
<223> OTHER INFORMATION: n  may be any nucleotide (a, t, c, or g)

<400> SEQUENCE: 101

```
catcgatcga tcgatcgaca gcgnnnnnnn nnnnnnnnnn nnnnnnnnnn nnngtagaac      60
gttctctcct ctccctatag tgagtcgtat ta                                    92
```

<210> SEQ ID NO 102
<211> LENGTH: 1676
<212> TYPE: PRT
<213> ORGANISM: artificial
<220> FEATURE:
<223> OTHER INFORMATION: synthetic C5

<400> SEQUENCE: 102

```
Met Gly Leu Leu Gly Ile Leu Cys Phe Leu Ile Phe Leu Gly Lys Thr
1               5                   10                  15

Trp Gly Gln Glu Gln Thr Tyr Val Ile Ser Ala Pro Lys Ile Phe Arg
            20                  25                  30

Val Gly Ala Ser Glu Asn Ile Val Ile Gln Val Tyr Gly Tyr Thr Glu
        35                  40                  45

Ala Phe Asp Ala Thr Ile Ser Ile Lys Ser Tyr Pro Asp Lys Lys Phe
    50                  55                  60

Ser Tyr Ser Ser Gly His Val His Leu Ser Ser Glu Asn Lys Phe Gln
65                  70                  75                  80

Asn Ser Ala Ile Leu Thr Ile Gln Pro Lys Gln Leu Pro Gly Gly Gln
                85                  90                  95

Asn Pro Val Ser Tyr Val Tyr Leu Glu Val Val Ser Lys His Phe Ser
            100                 105                 110

Lys Ser Lys Arg Met Pro Ile Thr Tyr Asp Asn Gly Phe Leu Phe Ile
        115                 120                 125

His Thr Asp Lys Pro Val Tyr Thr Pro Asp Gln Ser Val Lys Val Arg
    130                 135                 140

Val Tyr Ser Leu Asn Asp Asp Leu Lys Pro Ala Lys Arg Glu Thr Val
145                 150                 155                 160

Leu Thr Phe Ile Asp Pro Glu Gly Ser Glu Val Asp Met Val Glu Glu
                165                 170                 175

Ile Asp His Ile Gly Ile Ile Ser Phe Pro Asp Phe Lys Ile Pro Ser
            180                 185                 190

Asn Pro Arg Tyr Gly Met Trp Thr Ile Lys Ala Lys Tyr Lys Glu Asp
        195                 200                 205

Phe Ser Thr Thr Gly Thr Ala Tyr Phe Glu Val Lys Glu Tyr Val Leu
    210                 215                 220

Pro His Phe Ser Val Ser Ile Glu Pro Glu Tyr Asn Phe Ile Gly Tyr
225                 230                 235                 240

Lys Asn Phe Lys Asn Phe Glu Ile Thr Ile Lys Ala Arg Tyr Phe Tyr
                245                 250                 255

Asn Lys Val Val Thr Glu Ala Asp Val Tyr Ile Thr Phe Gly Ile Arg
```

-continued

```
                260                 265                 270
Glu Asp Leu Lys Asp Gln Lys Met Met Gln Thr Ala Met Gln
            275                 280                 285
Asn Thr Met Leu Ile Asn Gly Ile Ala Gln Val Thr Phe Asp Ser Glu
290                 295                 300
Thr Ala Val Lys Glu Leu Ser Tyr Tyr Ser Leu Glu Asp Leu Asn Asn
305                 310                 315                 320
Lys Tyr Leu Tyr Ile Ala Val Thr Val Ile Glu Ser Thr Gly Gly Phe
                325                 330                 335
Ser Glu Glu Ala Glu Ile Pro Gly Ile Lys Tyr Val Leu Ser Pro Tyr
            340                 345                 350
Lys Leu Asn Leu Val Ala Thr Pro Leu Phe Leu Lys Pro Gly Ile Pro
            355                 360                 365
Tyr Pro Ile Lys Val Gln Val Lys Asp Ser Leu Asp Gln Leu Val Gly
        370                 375                 380
Gly Val Pro Val Thr Leu Asn Ala Gln Thr Ile Asp Val Asn Gln Glu
385                 390                 395                 400
Thr Ser Asp Leu Asp Pro Ser Lys Ser Val Thr Arg Val Asp Asp Gly
                405                 410                 415
Val Ala Ser Phe Val Leu Asn Leu Pro Ser Gly Val Thr Val Leu Glu
            420                 425                 430
Phe Asn Val Lys Thr Asp Ala Pro Asp Leu Pro Glu Glu Asn Gln Ala
        435                 440                 445
Arg Glu Gly Tyr Arg Ala Ile Ala Tyr Ser Ser Leu Ser Gln Ser Tyr
    450                 455                 460
Leu Tyr Ile Asp Trp Thr Asp Asn His Lys Ala Leu Leu Val Gly Glu
465                 470                 475                 480
His Leu Asn Ile Ile Val Thr Pro Lys Ser Pro Tyr Ile Asp Lys Ile
                485                 490                 495
Thr His Tyr Asn Tyr Leu Ile Leu Ser Lys Gly Lys Ile Ile His Phe
            500                 505                 510
Gly Thr Arg Glu Lys Phe Ser Asp Ala Ser Tyr Gln Ser Ile Asn Ile
            515                 520                 525
Pro Val Thr Gln Asn Met Val Pro Ser Ser Arg Leu Leu Val Tyr Tyr
        530                 535                 540
Ile Val Thr Gly Glu Gln Thr Ala Glu Leu Val Ser Asp Ser Val Trp
545                 550                 555                 560
Leu Asn Ile Glu Glu Lys Cys Gly Asn Gln Leu Gln Val His Leu Ser
                565                 570                 575
Pro Asp Ala Asp Ala Tyr Ser Pro Gly Gln Thr Val Ser Leu Asn Met
            580                 585                 590
Ala Thr Gly Met Asp Ser Trp Val Ala Leu Ala Ala Val Asp Ser Ala
        595                 600                 605
Val Tyr Gly Val Gln Arg Gly Ala Lys Lys Pro Leu Glu Arg Val Phe
    610                 615                 620
Gln Phe Leu Glu Lys Ser Asp Leu Gly Cys Gly Ala Gly Gly Gly Leu
625                 630                 635                 640
Asn Asn Ala Asn Val Phe His Leu Ala Gly Leu Thr Phe Leu Thr Asn
                645                 650                 655
Ala Asn Ala Asp Asp Ser Gln Glu Asn Asp Glu Pro Cys Lys Glu Ile
            660                 665                 670
Leu Arg Pro Arg Arg Thr Leu Gln Lys Lys Ile Glu Glu Ile Ala Ala
        675                 680                 685
```

```
Lys Tyr Lys His Ser Val Val Lys Cys Cys Tyr Asp Gly Ala Cys
    690             695             700

Val Asn Asn Asp Glu Thr Cys Glu Gln Arg Ala Ala Arg Ile Ser Leu
705             710             715             720

Gly Pro Arg Cys Ile Lys Ala Phe Thr Glu Cys Cys Val Val Ala Ser
            725             730             735

Gln Leu Arg Ala Asn Ile Ser His Lys Asp Met Gln Leu Gly Arg Leu
        740             745             750

His Met Lys Thr Leu Leu Pro Val Ser Lys Pro Glu Ile Arg Ser Tyr
            755             760             765

Phe Pro Glu Ser Trp Leu Trp Glu Val His Leu Val Pro Arg Arg Lys
    770             775             780

Gln Leu Gln Phe Ala Leu Pro Asp Ser Leu Thr Thr Trp Glu Ile Gln
785             790             795             800

Gly Val Gly Ile Ser Asn Thr Gly Ile Cys Val Ala Asp Thr Val Lys
                805             810             815

Ala Lys Val Phe Lys Asp Val Phe Leu Glu Met Asn Ile Pro Tyr Ser
            820             825             830

Val Val Arg Gly Glu Gln Ile Gln Leu Lys Gly Thr Val Tyr Asn Tyr
        835             840             845

Arg Thr Ser Gly Met Gln Phe Cys Val Lys Met Ser Ala Val Glu Gly
    850             855             860

Ile Cys Thr Ser Glu Ser Pro Val Ile Asp His Gln Gly Thr Lys Ser
865             870             875             880

Ser Lys Cys Val Arg Gln Lys Val Glu Gly Ser Ser His Leu Val
            885             890             895

Thr Phe Thr Val Leu Pro Leu Glu Ile Gly Leu His Asn Ile Asn Phe
            900             905             910

Ser Leu Glu Thr Trp Phe Gly Lys Glu Ile Leu Val Lys Thr Leu Arg
        915             920             925

Val Val Pro Glu Gly Val Lys Arg Glu Ser Tyr Ser Gly Val Thr Leu
    930             935             940

Asp Pro Arg Gly Ile Tyr Gly Thr Ile Ser Arg Arg Lys Glu Phe Pro
945             950             955             960

Tyr Arg Ile Pro Leu Asp Leu Val Pro Lys Thr Glu Ile Lys Arg Ile
                965             970             975

Leu Ser Val Lys Gly Leu Leu Val Gly Glu Ile Leu Ser Ala Val Leu
            980             985             990

Ser Gln Glu Gly Ile Asn Ile Leu Thr His Leu Pro Lys Gly Ser Ala
        995             1000            1005

Glu Ala Glu Leu Met Ser Val Val Pro Val Phe Tyr Val Phe His
    1010            1015            1020

Tyr Leu Glu Thr Gly Asn His Trp Asn Ile Phe His Ser Asp Pro
    1025            1030            1035

Leu Ile Glu Lys Gln Lys Leu Lys Lys Lys Leu Lys Glu Gly Met
    1040            1045            1050

Leu Ser Ile Met Ser Tyr Arg Asn Ala Asp Tyr Ser Tyr Ser Val
    1055            1060            1065

Trp Lys Gly Gly Ser Ala Ser Thr Trp Leu Thr Ala Phe Ala Leu
    1070            1075            1080

Arg Val Leu Gly Gln Val Asn Lys Tyr Val Glu Gln Asn Gln Asn
    1085            1090            1095
```

-continued

```
Ser Ile Cys Asn Ser Leu Leu Trp Leu Val Glu Asn Tyr Gln Leu
1100                1105                1110

Asp Asn Gly Ser Phe Lys Glu Asn Ser Gln Tyr Gln Pro Ile Lys
1115                1120                1125

Leu Gln Gly Thr Leu Pro Val Glu Ala Arg Glu Asn Ser Leu Tyr
1130                1135                1140

Leu Thr Ala Phe Thr Val Ile Gly Ile Arg Lys Ala Phe Asp Ile
1145                1150                1155

Cys Pro Leu Val Lys Ile Asp Thr Ala Leu Ile Lys Ala Asp Asn
1160                1165                1170

Phe Leu Leu Glu Asn Thr Leu Pro Ala Gln Ser Thr Phe Thr Leu
1175                1180                1185

Ala Ile Ser Ala Tyr Ala Leu Ser Leu Gly Asp Lys Thr His Pro
1190                1195                1200

Gln Phe Arg Ser Ile Val Ser Ala Leu Lys Arg Glu Ala Leu Val
1205                1210                1215

Lys Gly Asn Pro Pro Ile Tyr Arg Phe Trp Lys Asp Asn Leu Gln
1220                1225                1230

His Lys Asp Ser Ser Val Pro Asn Thr Gly Thr Ala Arg Met Val
1235                1240                1245

Glu Thr Thr Ala Tyr Ala Leu Leu Thr Ser Leu Asn Leu Lys Asp
1250                1255                1260

Ile Asn Tyr Val Asn Pro Val Ile Lys Trp Leu Ser Glu Glu Gln
1265                1270                1275

Arg Tyr Gly Gly Gly Phe Tyr Ser Thr Gln Asp Thr Ile Asn Ala
1280                1285                1290

Ile Glu Gly Leu Thr Glu Tyr Ser Leu Leu Val Lys Gln Leu Arg
1295                1300                1305

Leu Ser Met Asp Ile Asp Val Ser Tyr Lys His Lys Gly Ala Leu
1310                1315                1320

His Asn Tyr Lys Met Thr Asp Lys Asn Phe Leu Gly Arg Pro Val
1325                1330                1335

Glu Val Leu Leu Asn Asp Asp Leu Ile Val Ser Thr Gly Phe Gly
1340                1345                1350

Ser Gly Leu Ala Thr Val His Val Thr Thr Val Val His Lys Thr
1355                1360                1365

Ser Thr Ser Glu Glu Val Cys Ser Phe Tyr Leu Lys Ile Asp Thr
1370                1375                1380

Gln Asp Ile Glu Ala Ser His Tyr Arg Gly Tyr Gly Asn Ser Asp
1385                1390                1395

Tyr Lys Arg Ile Val Ala Cys Ala Ser Tyr Lys Pro Ser Arg Glu
1400                1405                1410

Glu Ser Ser Ser Gly Ser Ser His Ala Val Met Asp Ile Ser Leu
1415                1420                1425

Pro Thr Gly Ile Ser Ala Asn Glu Glu Asp Leu Lys Ala Leu Val
1430                1435                1440

Glu Gly Val Asp Gln Leu Phe Thr Asp Tyr Gln Ile Lys Asp Gly
1445                1450                1455

His Val Ile Leu Gln Leu Asn Ser Ile Pro Ser Ser Asp Phe Leu
1460                1465                1470

Cys Val Arg Phe Arg Ile Phe Glu Leu Phe Glu Val Gly Phe Leu
1475                1480                1485

Ser Pro Ala Thr Phe Thr Val Tyr Glu Tyr His Arg Pro Asp Lys
```

-continued

```
                1490                1495                1500
Gln Cys Thr Met Phe Tyr Ser Thr Ser Asn Ile Lys Ile Gln Lys
    1505                1510                1515
Val Cys Glu Gly Ala Ala Cys Lys Cys Val Glu Ala Asp Cys Gly
    1520                1525                1530
Gln Met Gln Glu Glu Leu Asp Leu Thr Ile Ser Ala Glu Thr Arg
    1535                1540                1545
Lys Gln Thr Ala Cys Lys Pro Glu Ile Ala Tyr Ala Tyr Lys Val
    1550                1555                1560
Ser Ile Thr Ser Ile Thr Val Glu Asn Val Phe Val Lys Tyr Lys
    1565                1570                1575
Ala Thr Leu Leu Asp Ile Tyr Lys Thr Gly Glu Ala Val Ala Glu
    1580                1585                1590
Lys Asp Ser Glu Ile Thr Phe Ile Lys Lys Val Thr Cys Thr Asn
    1595                1600                1605
Ala Glu Leu Val Lys Gly Arg Gln Tyr Leu Ile Met Gly Lys Glu
    1610                1615                1620
Ala Leu Gln Ile Lys Tyr Asn Phe Ser Phe Arg Tyr Ile Tyr Pro
    1625                1630                1635
Leu Asp Ser Leu Thr Trp Ile Glu Tyr Trp Pro Arg Asp Thr Thr
    1640                1645                1650
Cys Ser Ser Cys Gln Ala Phe Leu Ala Asn Leu Asp Glu Phe Ala
    1655                1660                1665
Glu Asp Ile Phe Leu Asn Gly Cys
    1670                1675
```